United States Patent
Matsumoto et al.

(10) Patent No.: US 11,518,763 B2
(45) Date of Patent: Dec. 6, 2022

(54) MACROCYCLIC COMPOUND AND USE THEREOF

(71) Applicant: SCOHIA PHARMA, INC., Kanagawa (JP)

(72) Inventors: Shigemitsu Matsumoto, Kanagawa (JP); Ryoma Hara, Kanagawa (JP); Naoyoshi Noguchi, Kanagawa (JP); Hideto Fukushi, Kanagawa (JP); Ayumu Niida, Kanagawa (JP); Satoshi Sasaki, Kanagawa (JP); Minoru Ikoma, Kanagawa (JP); Toshitake Kobayashi, Kanagawa (JP); Tsuyoshi Maekawa, Kanagawa (JP)

(73) Assignee: SCOHIA PHARMA, INC., Kanagawa (JP)

( * ) Notice: Subject to any disclaimer, the term of this patent is extended or adjusted under 35 U.S.C. 154(b) by 0 days.

(21) Appl. No.: 17/299,659

(22) PCT Filed: Dec. 4, 2019

(86) PCT No.: PCT/JP2019/048593
§ 371 (c)(1),
(2) Date: Jun. 3, 2021

(87) PCT Pub. No.: WO2020/116660
PCT Pub. Date: Jun. 11, 2020

(65) Prior Publication Data
US 2022/0119391 A1    Apr. 21, 2022

(30) Foreign Application Priority Data
Dec. 5, 2018  (JP) .............................. JP2018-228234

(51) Int. Cl.
C07D 471/18    (2006.01)
C07D 491/22    (2006.01)
C07D 498/16    (2006.01)
C07D 498/22    (2006.01)

(52) U.S. Cl.
CPC ......... *C07D 471/18* (2013.01); *C07D 491/22* (2013.01); *C07D 498/16* (2013.01); *C07D 498/22* (2013.01)

(58) Field of Classification Search
CPC .. C07D 471/18; C07D 491/22; C07D 498/16; C07D 498/22
See application file for complete search history.

(56) References Cited

U.S. PATENT DOCUMENTS

| | | |
|---|---|---|
| 2012/0052094 A1 | 3/2012 | Villoslada et al. |
| 2015/0005239 A1 | 1/2015 | Villoslada et al. |
| 2016/0152596 A1 | 6/2016 | Baloglu et al. |
| 2017/0121367 A1 | 5/2017 | Villoslada et al. |
| 2018/0155317 A1 | 6/2018 | Baloglu et al. |
| 2018/0228776 A1 | 8/2018 | Saitoh et al. |
| 2020/0199099 A1 | 6/2020 | Baloglu et al. |

FOREIGN PATENT DOCUMENTS

| | | |
|---|---|---|
| EA | 29743 B1 | 5/2018 |
| RU | 2606622 | 1/2017 |
| WO | WO 2015/092713 A1 | 6/2015 |
| WO | WO 2016/202253 A1 | 12/2016 |
| WO | WO 2016/203400 A1 | 12/2016 |
| WO | WO 2016/203401 A1 | 12/2016 |
| WO | WO 2017/026516 A1 | 2/2017 |
| WO | WO 2017/060854 A1 | 4/2017 |
| WO | WO 2017/060855 A1 | 4/2017 |
| WO | WO 2018/109641 A1 | 6/2018 |
| WO | WO 2018/109642 A1 | 6/2018 |
| WO | WO 2018/109643 A1 | 6/2018 |
| WO | WO 2018/109646 A1 | 6/2018 |
| WO | WO 2018/109647 A1 | 6/2018 |
| WO | WO 2018/109648 A1 | 6/2018 |
| WO | WO 2018/109649 A1 | 6/2018 |
| WO | WO 2018/125880 A1 | 7/2018 |
| WO | WO 2018/140738 A1 | 8/2018 |
| WO | WO 2018/140876 A1 | 8/2018 |

(Continued)

OTHER PUBLICATIONS

Cho, Hye-Youn et al., Functional Polymorphisms in NRF2: Implications for Human Disease, *Free Radic Biol Med.* Nov. 2015; 88 (Pt B): pp. 362-372.

Lu, Meng-Chen et al., The Keap1-Nrf2-ARE Pathway As a Potential Preventive and Therapeutic Target: An Update, *Medicinal Research Reviews* 2016, pp. 924-963.

Al-Sawaf, Othman et al., Nrf2 in health and disease: current and future clinical implications, *Clinical Science* (2015) 129, pp. 989-999.

(Continued)

*Primary Examiner* — Susanna Moore
(74) *Attorney, Agent, or Firm* — Finnegan, Henderson, Farabow, Garrett & Dunner LLP

(57) ABSTRACT

A compound represented by the following formula (I): wherein each symbol in the formula is as described herein or a salt thereof has an NRF2 activating activity, and is expected to be useful as a preventive or therapeutic agent for diseases associated with oxidative stress, in particular, hepatic disease (for example, non-alcoholic steatohepatitis (NASH)), cardiovascular disease (for example, heart failure or pulmonary arterial hypertension), lung disease (for example, chronic obstructive pulmonary disease (COPD)), kidney disease (for example, chronic kidney disease (CKD) or acute kidney injury (AKI)), central nervous system disease (for example, Parkinson's disease), mitochondrial disease (for example, Friedreich motor ataxia, mitochondrial myopathy), inflammatory disease (for example, multiple sclerosis (MS), inflammatory bowel disease (IBD)), sickle cell disease, cancer, or the like.

14 Claims, No Drawings
Specification includes a Sequence Listing.

(56) References Cited

FOREIGN PATENT DOCUMENTS

WO   WO 2018/181345 A1   10/2018

OTHER PUBLICATIONS

De Zeeuw, Dick M.D., Ph.D., et al., Bardoxolone Methyl in Type 2 Diabetes and Stage 4 Chronic Kidney Disease, *The New England Journal of Medicine* 2013, pp. 2492-2503.
International Search Report, issued in PCT/JP2019/048593, dated Dec. 4, 2019 (four pages).
Written Opinion of the International Searching Authority issued in PCT/JP2019/048593, dated Feb. 25, 2020, (three pages).

SEQUENCE LISTING

```
<160> NUMBER OF SEQ ID NOS: 3

<210> SEQ ID NO 1
<211> LENGTH: 26
<212> TYPE: DNA
<213> ORGANISM: Artificial Sequence
<220> FEATURE:
<223> OTHER INFORMATION: Probe

<400> SEQUENCE: 1
tctgcgcttc tgtggcttcc aggtct                                        26

<210> SEQ ID NO 2
<211> LENGTH: 23
<212> TYPE: DNA
<213> ORGANISM: Artificial Sequence
<220> FEATURE:
<223> OTHER INFORMATION: Forward Primer

<400> SEQUENCE: 2
ggggacatga acgtcattct ctg                                           23

<210> SEQ ID NO 3
<211> LENGTH: 21
<212> TYPE: DNA
<213> ORGANISM: Artificial Sequence
<220> FEATURE:
<223> OTHER INFORMATION: Reverse Primer

<400> SEQUENCE: 3
gccaatgctg tacaccagtt g                                             21
```

MACROCYCLIC COMPOUND AND USE THEREOF

TECHNICAL FIELD

This application is a national stage filing under 35 U.S.C. § 371 of International Application No. PCT/JP2019/048593, filed on Dec. 4, 2019, which claims priority to Japanese Patent Application No. 2018-228234, filed on Dec. 5, 2018. The contents of each application are incorporated herein by reference in their entirety.

The present invention relates to a macrocyclic compound having an activity of activating nuclear factor erythroid 2-related factor 2 (herein, may be abbreviated as "NRF2") and is expected to be useful in treatment for diseases associated with oxidative stress.

BACKGROUND ART

Oxidative stress refers to a condition where oxidation and anti-oxidation is out of balance and excessive oxidation reaction adversely affects organisms, and it has been clear that oxidative stress is closely related to various pathogeneses. A living body provides a defense mechanism against oxidative stress, and NRF2 (nuclear factor erythroid 2-related factor 2) plays a central role in this mechanism. In the steady state, NRF2 is bound to KEAP1 (Kelch-like ECH-associated protein 1) and its intracellular concentration is kept low through degradation regulation by proteasome. However, when receiving some kind of oxidative stress, NRF2 dissociates from KEAP1, translocates to the inside of nucleus, and binds to a transcriptional region called ARE (anti-oxidant response element), thereby inducing gene expression of a variety of anti-oxidative substances (activation of NRF2). The NRF2-KEAP1 system is a biological defense mechanism for quickly responding to oxidative stress (Free Radical Biology and Medicine 2015 88: 362-372; Non Patent Literature 1). Accordingly, NRF2 activators are expected to provide a strong anti-oxidative activity by activating the NRF2-KEAP1 system. Among NRF2 activators, there is one type that modifies a Cys residue of KEAP1, and there is another type that inhibits the protein-protein interaction of NRF2-KEAP1, but both have been known to activate NRF2 (Med Res Rev. 2016 36(5): 924-63; Non Patent Literature 2).

NRF2 activators are believed to exhibit effectiveness in prevention or treatment for a variety of oxidative stress diseases. Specifically, examples of the diseases include hepatic disease (non-alcoholic steatohepatitis (NASH) or the like), bile duct disease (primary sclerosing cholangitis (PSC) or the like), lung disease (obstructive pulmonary disease (COPD) or the like), kidney disease (chronic kidney disease (CKD), acute kidney injury (AKI) or the like), heart disease (heart failure, pulmonary arterial hypertension or the like), central nervous system disease (Parkinson's disease, Alzheimer's disease, cerebral stroke or the like), mitochondrial disease (Friedreich motor ataxia, mitochondrial myopathy or the like), inflammatory disease (for example, multiple sclerosis (MS), inflammatory bowel disease (IBD)), sickle cell disease, cancer and the like (Clin Sci (Lond). 2015 129(12): 989-99; Non Patent Literature 3).

Bardoxolone methyl (CDDO-Me), which activates NRF2 by modifying a Cys residue of KEAP1, exhibited the effect of improving kidney function in a large scale clinical trial of CKD patients with type 2 diabetes; however, serious side effects, such as worsening of cardiovascular event and onset of heart failure, were confirmed, and therefore, the clinical trial was stopped in an early stage (N Engl J Med. 2013 26; 369(26): 2492-2503; Non Patent Literature 4). Low-molecular compounds inhibiting the protein-protein interaction of NRF2-KEAP1 are expected to exhibit effectiveness for the oxidative stress diseases described above by activating NRF2 through a mechanism different from that of CDDO-Me.

Up until now, compounds of monocyclic type, two-ring-bound type and fused ring type that have an NRF2 regulating activity are known.

(1) The following compounds are known as the monocyclic type compounds.

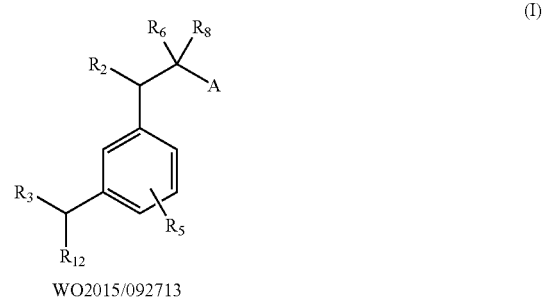

WO2015/092713

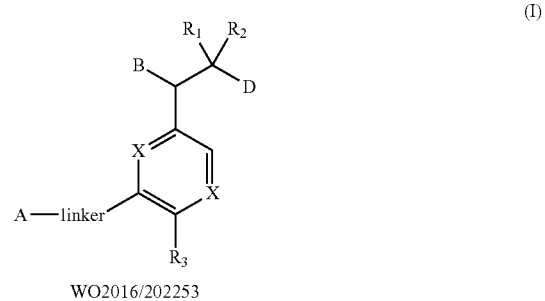

WO2016/202253

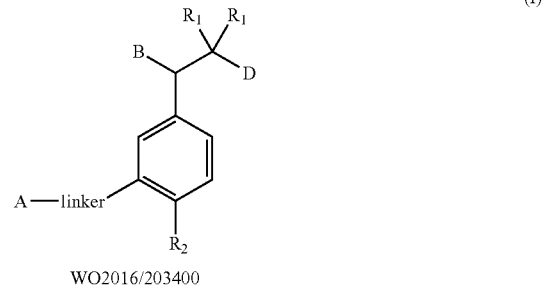

WO2016/203400

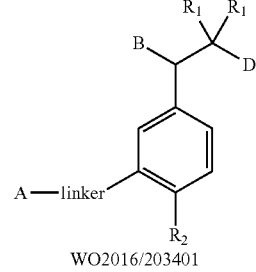

WO2016/203401

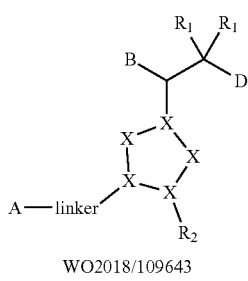
WO2018/109643
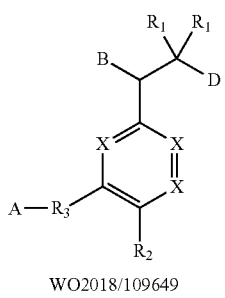
WO2018/109649
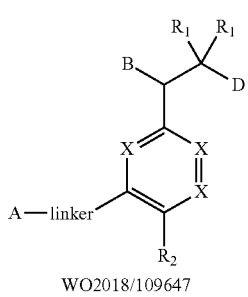
WO2018/109647
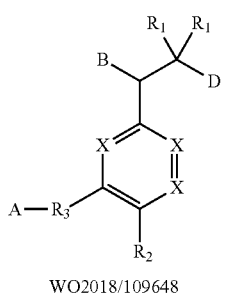
WO2018/109648
(2) The following compounds are known as the two-ring-bound type compounds.
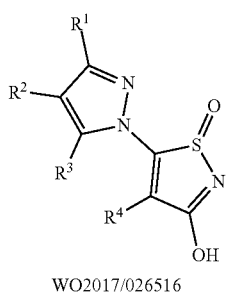
WO2017/026516
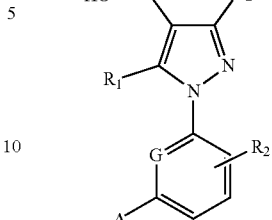
WO2017/060855
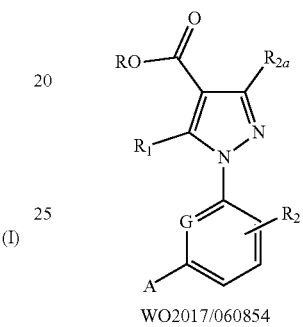
WO2017/060854
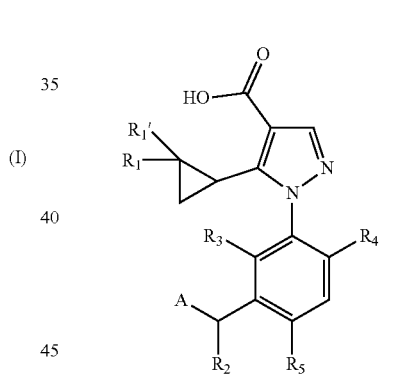
WO2018/109642
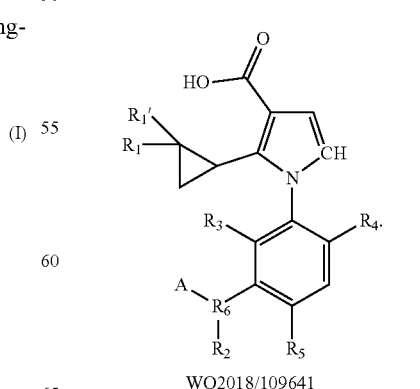
WO2018/109641

(3) The following compounds are known as the fused ring type compounds.

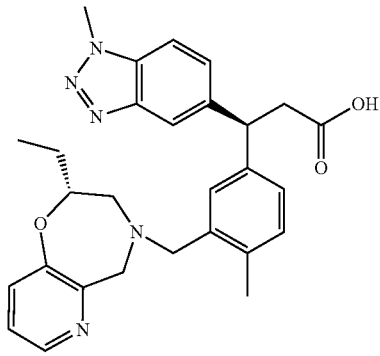

WO2018/109646

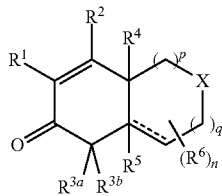

WO2018/125880

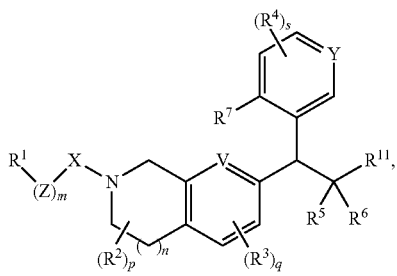

WO2018/140876

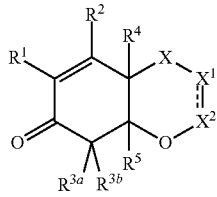

WO2018/140738

(For symbols in the formulas, see the relevant publications.)

An object of the present invention is to provide a compound having an NRF2 activating activity, having a novel structure, and being expected to be useful as a preventive or therapeutic agent for diseases associated with oxidative stress, in particular, hepatic disease (for example, non-alcoholic steatohepatitis (NASH)), bile duct disease (primary sclerosing cholangitis (PSC) or the like), cardiovascular disease (for example, heart failure or pulmonary arterial hypertension), lung disease (for example, chronic obstructive pulmonary disease (COPD)), kidney disease (for example, chronic kidney disease (CKD) or acute kidney injury (AKI)), central nervous system disease (for example, Parkinson's disease, Alzheimer's disease, cerebral stroke), mitochondrial disease (for example, Friedreich motor ataxia, mitochondrial myopathy), inflammatory disease (for example, multiple sclerosis (MS), inflammatory bowel disease (IBD)), sickle cell disease, cancer, or the like.

SUMMARY OF THE INVENTION

As a result of extensive studies in order to solve the problems described above, the present inventors have found that a macrocyclic compound represented by the following formula (I) has an NRF2 activating activity, and therefore, is expected to be useful as a preventive or therapeutic agent for diseases associated with oxidative stress, in particular, hepatic disease (for example, non-alcoholic steatohepatitis (NASH)), bile duct disease (primary sclerosing cholangitis (PSC) or the like), cardiovascular disease (for example, heart failure or pulmonary arterial hypertension), lung disease (for example, chronic obstructive pulmonary disease (COPD)), kidney disease (for example, chronic kidney disease (CKD) or acute kidney injury (AKI)), central nervous system disease (for example, Parkinson's disease, Alzheimer's disease, cerebral stroke), mitochondrial disease (for example, Friedreich motor ataxia, mitochondrial myopathy), inflammatory disease (for example, multiple sclerosis (MS), inflammatory bowel disease (IBD)), sickle cell disease, cancer, or the like, thereby completing the present invention.

That is, the present invention is as follows:

<1>

A compound represented by the following formula (I):

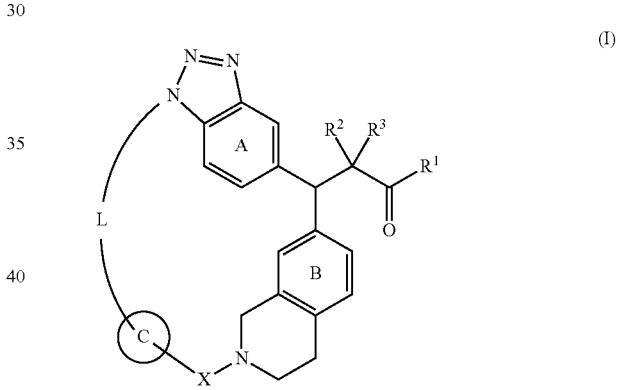

wherein
$R^1$ is OH, ORy or NHRy;
Ry is an optionally substituted $C_{1-6}$ alkyl group or an optionally substituted cyclic group;
$R^2$ and $R^3$, which may be the same or different, are a hydrogen atom or an optionally substituted $C_{1-6}$ alkyl group, or $R^2$ and $R^3$ are joined together to form a $C_{3-6}$ cycloalkyl group;
X is C(=O), $SO_2$ or $CR^{x1}R^{x2}$;
$R^{x1}$ and $R^{x2}$, which may be the same or different, are a hydrogen atom or an optionally substituted $C_{1-6}$ alkyl group;
ring A is a benzene ring which may have an additional substituent(s);
ring B is a benzene ring which may have an additional substituent(s);
ring C is an optionally substituted 5- or 6-membered aromatic ring which may contain a heteroatom(s) in the ring; and
L is optionally substituted, saturated or unsaturated linear $C_{4-8}$ alkylene optionally inserted by a heteroatom,
or a salt thereof.

<2>
The compound according to <1> above or a salt thereof, wherein in formula (I),
L is —(CR⁴R⁵)n-Y¹—(CR⁶R⁷)m-Y²—*
wherein * represents attachment to ring C;
n is an integer of 2 or more and 4 or less;
m is an integer of 1 or more and 4 or less;
R⁴ and R⁵ are the same as or different from each other, and are each a hydrogen atom, a halogen atom, OH, an optionally substituted $C_{1-6}$ alkyl group or an optionally substituted $C_{1-6}$ alkoxy group, or R⁴ and R⁵ are joined together to form an optionally substituted $C_{3-6}$ cycloalkyl group, and a plurality of R⁴ or a plurality of R⁵ may be the same as or different from each other, and the adjacent R⁴ or R⁵ may be joined together to form a double bond;
R⁶ and R⁷ are the same as or different from each other, and are each a hydrogen atom, a halogen atom, OH, an optionally substituted $C_{1-6}$ alkyl group or an optionally substituted $C_{1-6}$ alkoxy group, or R⁶ and R⁷ are joined together to form an optionally substituted $C_{3-6}$ cycloalkyl group, and when m is 2 or more, a plurality of R⁶ or a plurality of R⁷ may be the same as or different from each other, and the adjacent R⁶ or R⁷ may be joined together to form a double bond; Y¹ and Y², which may be the same or different, are a bond, an oxygen atom, a sulfur atom, SO, SO₂ or NR⁸, provided that when Y¹ is a bond, m is 1 or 4; and
R⁸ is a hydrogen atom, an optionally substituted $C_{1-6}$ alkyl group, or an optionally substituted $C_{1-6}$ alkoxy group, provided that when a plurality of R⁸ is present, the plurality of R⁸ may be the same as or different from each other.
<3>
The compound according to <1> or <2> above, or a salt thereof, wherein in formula (I), L is selected from the group consisting of the following formulas:
—CR⁴R⁵—CR⁴R⁵—CR⁶R⁷—CR⁶R⁷—CR⁶R⁷—CR⁶R⁷—*;
—CR⁴R⁵—CR⁴R⁵—CR⁴R⁵—CR⁴R⁵—CR⁶R⁷—*;
—CR⁴R⁵—CR⁴R⁵—CR⁴R⁵—CR⁶R⁷—O—*;
—CR⁴R⁵—CR⁴R⁵—CR⁴R⁵—O—CR⁶R⁷—*; and
—CR⁴R⁵—CR⁴R⁵—O—CR⁶R⁷—CR⁶R⁷—*.
<4-1>
The compound according to any one of <1> to <3> above, or a salt thereof, wherein in formula (I),
R¹ is OH or ORy;
Ry is an optionally substituted cyclic group;
R² and R³, which may be the same or different, are a hydrogen atom or an optionally substituted $C_{1-6}$ alkyl group;
X is C(=O);
ring A is a benzene ring which may have an additional substituent(s);
ring B is a benzene ring which may have an additional substituent(s); and
ring C is an optionally substituted benzene ring.
<4-2>
The compound according to any of <1> to <3> above, or a salt thereof, wherein in formula (I),
R¹ is OH or ORy;
Ry is a $C_{1-6}$ alkyl group;
R² and R³, which may be the same or different, are a hydrogen atom or a $C_{1-3}$ alkyl group;
X is C(=O);
ring A is a benzene ring which may have an additional substituent(s) of a fluorine atom, a chlorine atom, a $C_{1-3}$ alkyl group optionally substituted with 1 to 3 substituents (selected from a halogen atom and a $C_{1-3}$ alkoxy group), or a $C_{1-3}$ alkoxy group optionally substituted with 1 to 3 substituents (selected from a halogen atom and a $C_{1-3}$ alkoxy group);
ring B is a benzene ring which may have an additional substituent(s) of a fluorine atom, a chlorine atom, a cyano group, a $C_{1-3}$ alkyl group optionally substituted with 1 to 3 substituents (selected from a halogen atom and a $C_{1-3}$ alkoxy group), or a $C_{1-3}$ alkoxy group optionally substituted with 1 to 3 substituents (selected from a halogen atom and a $C_{1-3}$ alkoxy group); and ring C is a group represented by the following formula:

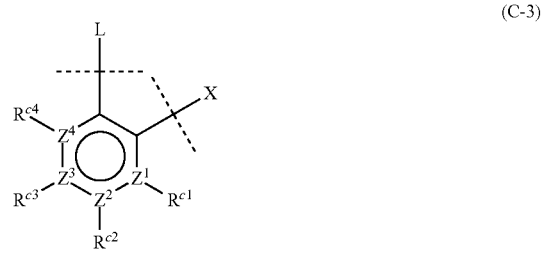

(C-3)

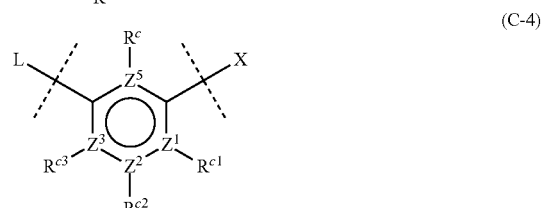

(C-4)

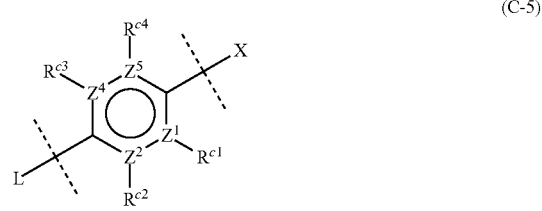

(C-5)

wherein $Z^1$, $Z^2$, $Z^3$, $Z^4$ and $Z^5$, which may be the same or different, represent a carbon atom or a nitrogen atom;
$R^c$ represents a hydrogen atom, a halogen atom, a nitro group, a cyano group, a hydroxy group, an optionally halogenated $C_{1-6}$ alkyl group, an optionally halogenated $C_{1-6}$ alkoxy group, or a $C_{3-10}$ cycloalkyl group; and
$R^{c1}$, $R^{c2}$, $R^{c3}$ and $R^{c4}$, which may be the same or different, are a hydrogen atom, a halogen atom, a nitro group, a cyano group, a hydroxy group, an optionally halogenated $C_{1-6}$ alkyl group, an optionally halogenated $C_{1-6}$ alkoxy group, or a $C_{3-10}$ cycloalkyl group; or adjacent two of $R^{c1}$, $R^{c2}$, $R^{c3}$ and $R^{c4}$ are joined together to form an optionally substituted ring, provided that when $Z^1$, $Z^2$, $Z^3$, $Z^4$ or $Z^5$ is a nitrogen atom, $R^c$, $R^{c1}$, $R^{c2}$, $R^{c3}$ or $R^{c4}$ is not present.
<5>
The compound according to any of <1> to <4> above, or a salt thereof, wherein in formula (I),
R¹ is OH;
R² and R³, which may be the same or different, are a hydrogen atom or a $C_{1-3}$ alkyl group;
X is C(=O);
ring A is a benzene ring which may have an additional substituent of a $C_{1-3}$ alkyl group;
ring B is a benzene ring which does not have an additional substituent; and ring C is a group represented by the following formula:

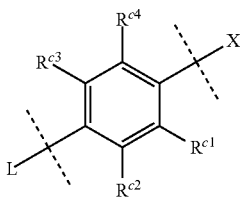

wherein
$R^{c1}$ and $R^{c4}$, which may be the same or different, are a hydrogen atom, an optionally halogenated $C_{1-6}$ alkyl group, an optionally halogenated $C_{1-6}$ alkoxy group, a chlorine atom, or a fluorine atom, and $R^{c2}$ and $R^{c3}$ are each a hydrogen atom; and
L is —CH$_2$—CH$_2$—CH$_2$—CH$_2$—CH$_2$—*,
—CH$_2$—CH$_2$—CH$_2$—CH$_2$—O—*,
—CH$_2$—CH$_2$—CH$_2$—O—CH$_2$—*, or
—CH$_2$—CH$_2$—O—CH$_2$—CH$_2$—*

<6>
The compound according to any of <1> to <5> above, or a salt thereof, wherein in formula (I),
$R^1$ is OH;
$R^2$ and $R^3$, which may be the same or different, are a hydrogen atom or a methyl group;
X is C(=O);
ring A is a substructure represented by the following formula:

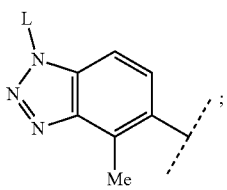

ring B is a benzene ring which does not have an additional substituent;
ring C is a group represented by the following formula:

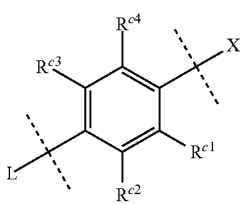

wherein
$R^{c1}$ and $R^{c4}$, which may be the same or different, are a hydrogen atom, a chlorine atom, or a methyl group, and $R^{c2}$ and $R^{c3}$ are each a hydrogen atom; and
L is —CH$_2$—CH$_2$—CH$_2$—CH$_2$—CH$_2$—*,
—CH$_2$—CH$_2$—CH$_2$—CH$_2$—O—*,
—CH$_2$—CH$_2$—CH$_2$—O—CH$_2$—*, or
—CH$_2$—CH$_2$—O—CH$_2$—CH$_2$—*.

<7>
A compound selected from the group consisting of the following:
[32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid:

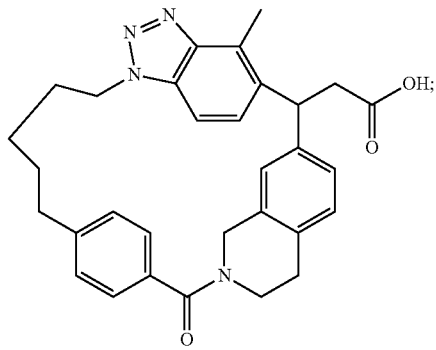

[32-methyl-20-oxo-14-oxa-8,9,10,21-tetraazahexacyclo[19.5.3.216,19.13,7.06,10.024,28] dotriaconta-1(26),3(32),4,6,8,16,18,24,27,30-decaen-2-yl]acetic acid:

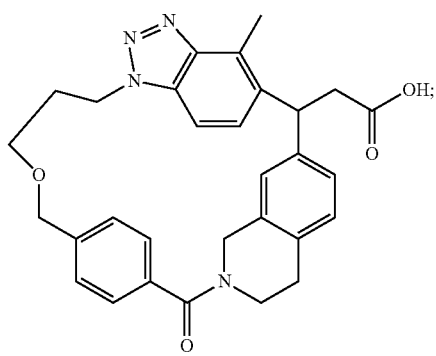 [SMILES: Cc1c2ccc3c1nnn3CCCCCc1ccc(cc1)C(=O)N1CCc3ccc(cc3C1)C2CC(=O)O]

2-methyl-2-[32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propionic acid:

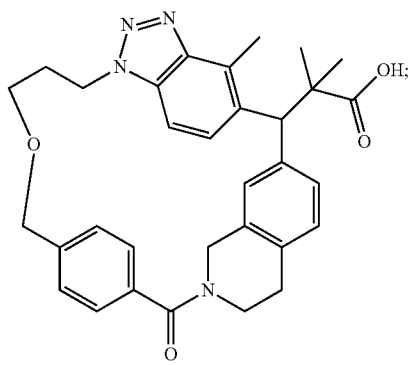

2-methyl-2-[18,30,32-trimethyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16(31),17,19(30),24(28),25-decaen-2-yl]propionic acid:

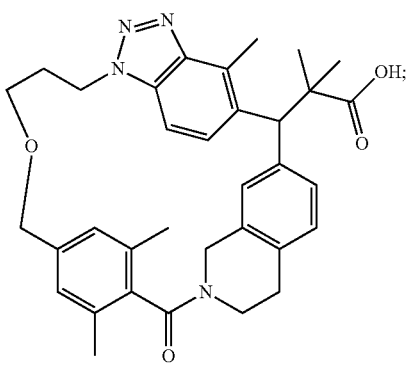 [SMILES: Cc1cc2cc(C)c1C(=O)N1CCc3ccc(cc3C1)C(C(C)(C)C(=O)O)c1ccc3c(nnn3CCCOC2)c1C]

2-methyl-2-[32-methyl-20-oxo-8,9,10,21-tetrazahexacyclo[19.5.3.2$^{16,19}$.1$^{3,7}$.0$^{6,10}$.0$^{24,28}$]dotriaconta-1(27),3(32),4,6,8,16(31),17,19(30),24(28),25-decaen-2-yl]propanoic acid or a salt thereof.

<7-2>

[32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid;

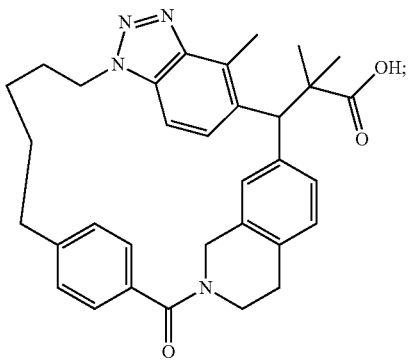 [SMILES: Cc1c2ccc3c1nnn3CCCCCc1ccc(cc1)C(=O)N1CCc3ccc(cc3C1)C2C(C)(C)C(=O)O]

or a salt thereof.

<7-3>

[32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid;

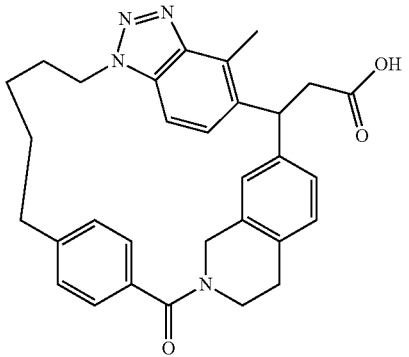 [SMILES: Cc1c2ccc3c1nnn3CCCCCc1ccc(cc1)C(=O)N1CCc3ccc(cc3C1)C2CC(=O)O]

or a salt thereof.

<8>

A medicament including the compound according to any of <1> to <7> above or a salt thereof.

<9>

The medicament according to <8> above, wherein the medicament is an NRF2 activator.

<10>

The medicament according to <9> above, wherein the medicament is a preventive or therapeutic agent for hepatic and bile duct disease, cardiovascular disease, lung disease, kidney disease, central nervous system disease, cancer, sickle cell disease, mitochondrial disease, or inflammatory disease.

<11>

A pharmaceutical composition comprising the compound according to any of <1> to <7> above or a pharmaceutically acceptable salt thereof for use in prevention or treatment for hepatic and bile duct disease, cardiovascular disease, lung disease, kidney disease, central nervous system disease, cancer, sickle cell disease, mitochondrial disease, or inflammatory disease.

<12>

A method of activating NRF2 in a mammal comprising administering the compound according to any of <1> to <7> above or a salt thereof to the mammal in an effective amount.

<13>

A method of preventing or treating hepatic and bile duct disease, cardiovascular disease, lung disease, kidney disease, central nervous system disease, cancer, sickle cell disease, mitochondrial disease, or inflammatory disease in a mammal, comprising administering the compound according to any of <1> to <7> or a salt thereof to the mammal.

<14>

Use of the compound according to any of <1> to <7> above or a salt thereof for producing a preventive or therapeutic agent for hepatic and bile duct disease, cardiovascular disease, lung disease, kidney disease, central nervous system disease, cancer, sickle cell disease, mitochondrial disease, or inflammatory disease.

The present invention can provide a compound that has an excellent NRF2 activating activity, and is expected to be useful as a preventive or therapeutic agent for diseases associated with oxidative stress, in particular, hepatic and bile duct disease such as hepatic disease (for example, non-alcoholic steatohepatitis (NASH)) and bile duct disease (primary sclerosing cholangitis (PSC) or the like), cardiovascular disease (for example, heart failure or pulmonary arterial hypertension), lung disease (for example, chronic obstructive pulmonary disease (COPD)), kidney disease (for example, chronic kidney disease (CKD) or acute kidney

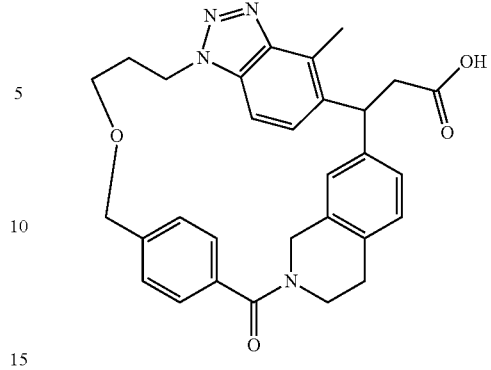

injury (AKI)), central nervous system disease (for example, Parkinson's disease, Alzheimer's disease, cerebral stroke), mitochondrial disease (for example, Friedreich motor ataxia, mitochondrial myopathy), inflammatory disease (for example, multiple sclerosis (MS), inflammatory bowel disease (IBD)), sickle cell disease, cancer, or the like.

DETAILED DESCRIPTION OF THE PREFERRED EMBODIMENTS (Detailed Description of the Invention)

Hereinafter, the present invention will be described in detail.

Hereinafter, the definition of each substituent as used herein will be described in detail. Unless noted otherwise, each substituent has the following definition.

Examples of the "halogen atom" as used herein include fluorine, chlorine, bromine and iodine. Examples of the "$C_{1-6}$ alkyl group" as used herein include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl.

Examples of the "cyclic group" in the "optionally substituted cyclic group" include a $C_{3-10}$ cycloalkyl group, a $C_{3-10}$ cycloalkenyl group, a $C_{6-14}$ aryl group, an aromatic heterocyclic group, and a non-aromatic heterocyclic group.

Note that the "optionally substituted ring" means a ring that does not have a bonding hand of the cyclic group defined as the "optionally substituted cyclic group."

Examples of the "$C_{3-10}$ cycloalkyl group" as used herein include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, and adamantyl.

The $C_{3-10}$ cycloalkyl group may be fused with a benzene ring, and examples of such a fused ring include tetrahydronaphthyl and dihydroindenyl.

Examples of the "$C_{3-10}$ cycloalkenyl group" include cyclopropenyl, cyclobutenyl, cyclopentenyl, cyclohexenyl, cycloheptenyl, and cyclooctenyl.

Examples of the "$C_{6-14}$ aryl group" include phenyl, 1-naphthyl, 2-naphthyl, 1-anthryl, 2-anthryl, and 9-anthryl.

The $C_{6-14}$ aryl group described above may be fused with a $C_{3-10}$ cycloalkane ring (preferably, a $C_{5-6}$ cycloalkane ring (for example, cyclopentane and cyclohexane)), and examples of such a fused ring include tetrahydronaphthyl and dihydroindenyl.

The aromatic heterocyclic group in the "cyclic group" of the "optionally substituted cyclic group" is preferably a 5- to 14-membered aromatic heterocyclic group, and more preferably a 5- to 6-membered monocyclic aromatic heterocyclic group (for example, pyridyl, thiazolyl, oxazolyl, pyrazolyl, triazolyl and thienyl), or a 8- to 14-membered fused polycyclic (preferably, bicyclic or tricyclic) aromatic heterocyclic group (for example, indazolyl, indolyl, benzimidazolyl, benzotriazolyl, benzothienyl and benzofuryl).

The non-aromatic heterocyclic group in the "cyclic group" of the "optionally substituted cyclic group" is preferably a 3- to 14-membered non-aromatic heterocyclic group, and more preferably a 3- to 8-membered monocyclic nonaromatic heterocyclic group (for example, oxetanyl and tetrahydropyranyl) or a 9- to 14-membered fused polycyclic (preferably, bicyclic or tricyclic) non-aromatic heterocyclic group (for example, dihydrocumenyl, dihydrobenzofuryl, dihydrobenzodioxepinyl, tetrahydroquinolyl, tetrahydroisoquinolyl, indolinyl, dihydrobenzodioxinyl, dihydrobenzoxazinyl and dihydrobenzoxazepinyl).

Furthermore, the non-aromatic heterocyclic group may be a spiro ring, and examples of such a spiro ring include spiro[1-benzofuran-2,1'-cyclopropane]-yl, spiro[1-benzofuran-2,1'-cyclohexane]-yl, tetrahydro-3H-spiro[1-benzofuran-2,4'-pyrane]-yl, spiro[1-benzofuran-2,1'-cyclopentane]-yl, and dihydrospiro[1,4-benzoxazine-2,1'-cyclobutane]-yl.

Examples of the "$C_{3-6}$ cycloalkyl group" as used herein include cyclopropyl, cyclobutyl, cyclopentyl, and cyclohexyl.

Examples of the "$C_{1-6}$ alkoxy group" as used herein include methoxy, ethoxy, propoxy, isopropoxy, butoxy, isobutoxy, sec-butoxy, tert-butoxy, pentyloxy and hexyloxy.

Examples of the "5- or 6-membered aromatic ring which may contain a heteroatom(s) in the ring" as used herein include a 5- or 6-membered aromatic heterocyclic ring containing, other than carbon atoms, 1 to 4 heteroatoms selected from a nitrogen atom, a sulfur atom and an oxygen atom as the constituent atoms of the ring, or a 6-membered aromatic carbocyclic ring not including heteroatoms.

In addition, the "optionally substituted 5- or 6-membered aromatic ring which may contain a heteroatom(s) in the ring" is specifically represented by the following formulas:

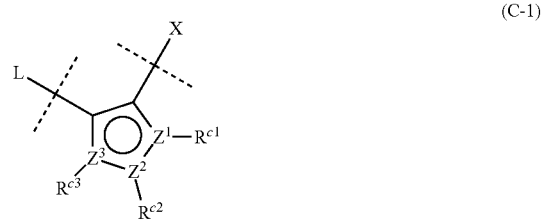

(C-1)

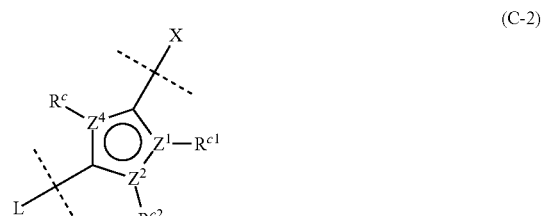

(C-2)

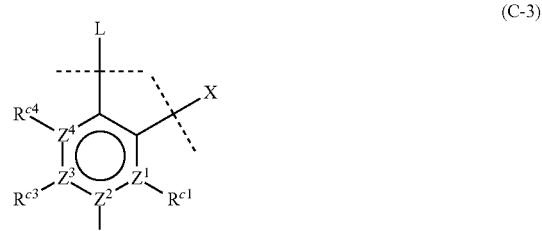

(C-3)

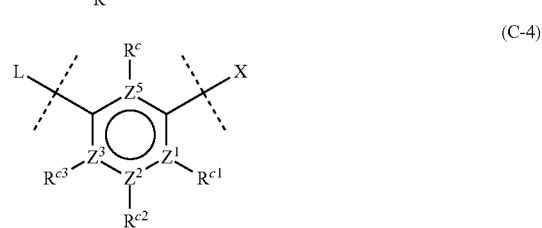

(C-4)

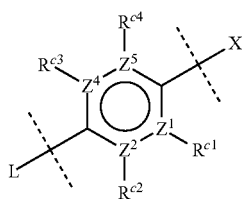

(C-5)

wherein $Z^1$, $Z^2$, $Z^3$, $Z^4$ and $Z^5$, which may be the same or different, are a carbon atom or a nitrogen atom;
$R^c$ represents a hydrogen atom, or a halogen atom, a nitro group, a cyano group, a hydroxy group, an optionally halogenated $C_{1-6}$ alkyl group, an optionally halogenated $C_{1-6}$ alkoxy group, or a $C_{3-10}$ cycloalkyl group; and
$R^{c1}$, $R^{c2}$, $R^{c3}$ and $R^{c4}$, which may be the same or different, are a hydrogen atom, or a halogen atom, a nitro group, a cyano group, a hydroxy group, an optionally halogenated $C_{1-6}$ alkyl group, an optionally halogenated $C_{1-6}$ alkoxy group, or a $C_{3-10}$ cycloalkyl group; or adjacent two of $R^{c1}$, $R^{c2}$, $R^{c3}$ and $R^{c4}$, taken together, may form an optionally substituted ring, provided that when $Z^1$, $Z^2$, $Z^3$, $Z^4$ or $Z^5$ is a nitrogen atom, $R^c$, $R^{c1}$, $R^{c2}$, $R^{c3}$ or $R^{c4}$ is not present.

Note that formulas (C-1) to (C-5) are attached to X and L in formula (I) at certain bonding positions.

"Optionally halogenated" as used herein means, for example, optionally substituted with 1 to 7, preferably 1 to 5 halogen atoms.

Suitable examples of such a 5- or 6-membered aromatic heterocyclic ring include thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, and triazine, and a 6-membered aromatic carbocyclic ring not containing heteroatoms is a benzene ring.

The "saturated or unsaturated linear $C_{4-8}$ alkylene optionally inserted by a heteroatom" as used herein means a saturated or unsaturated linear alkylene group in which one or two heteroatoms selected from a nitrogen atom or $NR^c$ ($R^c$ is a hydrogen atom or a $C_{1-6}$ alkyl group optionally having a substituent), a sulfur atom, SO, $SO_2$, and an oxygen atom are inserted to an arbitrary position of a $C_{4-8}$ alkylene, thereby dividing that alkylene into two or more; a saturated or unsaturated linear alkylene group that is substituted with a heteroatom described above; or a saturated or unsaturated linear C4-8 alkylene group.

Further specifically, it is a group represented by the following formula:
—$(CR^4R^5)n-Y^1$—$(CR^6R^7)m-Y^2$—*
wherein * represents attachment to ring C;
n is an integer of 2 or more and 4 or less;
m is an integer of 1 or more and 4 or less;
$R^4$ and $R^5$, which may be the same as or different from each other, are a hydrogen atom, a halogen atom, OH, an optionally substituted $C_{1-6}$ alkyl group or an optionally substituted $C_{1-6}$ alkoxy group, or $R^4$ and $R^5$ are joined together to form an optionally substituted $C_{3-6}$ cycloalkyl group, and a plurality of $R^4$ or a plurality of $R^5$ may be the same as or different from each other, and the adjacent $R^4$ or $R^5$ may be joined together to form a double bond;
$R^6$ and $R^7$, which may be the same as or different from each other, are each a hydrogen atom, a halogen atom, OH, an optionally substituted $C_{1-6}$ alkyl group or an optionally substituted $C_{1-6}$ alkoxy group, or $R^6$ and $R^7$ are joined together to form an optionally substituted $C_{3-6}$ cycloalkyl group, and when m is 2 or more, a plurality of $R^6$ or a plurality of $R^7$ may be the same as or different from each other, and the adjacent $R^6$ or $R^7$ may be joined together to form a double bond;
$Y^1$ and $Y^2$, which may be the same or different, are a bond, an oxygen atom, $NR^8$, a sulfur atom, SO or $SO_2$, provided that when $Y^1$ is a bond, m is 1 or 4; and
$R^8$ is a hydrogen atom or an optionally substituted $C_{1-6}$ alkyl group, provided that when a plurality of $R^8$ is present, the plurality of $R^8$ may be the same as or different from each other.

"$R^4$ and $R^5$ are joined together to form an optionally substituted $C_{3-6}$ cycloalkyl group" or "$R^6$ and $R^7$ are joined together to form an optionally substituted $C_{3-6}$ cycloalkyl group" means an optionally substituted $C_{3-6}$ cycloalkyl including the carbon atom to which $R^4$ and $R^5$ are attached or the carbon atom to which $R^6$ and $R^7$ are attached as the constituent element of the ring.

"the adjacent $R^6$ or $R^7$ may be joined together to form a double bond" means, for example, in the case of —$CR^6R^7$—$CR^6R^7$—, being —$CR^6=CR^7$—, —$CR^7=CR^6$—, —$CR^7=CR^7$— or —$CR^6=CR^6$—.

Specifically, preferable groups represented by the formula: —$(CR^4R^5)n-Y^1$—$(CR^6R^7)m-Y^2$—* wherein the symbols in the formula are as defined above are the groups shown in Table 1 below.

TABLE 1

| |
|---|
| —CR4R5—CR4R5—CR4R5—CR6R7—* |
| —CR4R5—CR4R5—CR4R5—O—CR6R7—* |
| —CR4R5—CR4R5—CR4R5—NR8—CR6R7—* |
| —CR4R5—CR4R5—CR4R5—CR4R5—CR6R7—* |
| —CR4R5—CR4R5—CR4R5—CR4R5—O—CR6R7—* |
| —CR4R5—CR4R5—CR4R5—CR4R5—NR8—CR6R7—* |
| —CR4R5—CR4R5—O—CR6R7—CR6R7—* |
| —CR4R5—CR4R5—NR8—CR6R7—CR6R7—* |
| —CR4R5—CR4R5—CR4R5—O—CR6R7—CR6R7—* |
| —CR4R5—CR4R5—CR4R5—NR8—CR6R7—CR6R7—* |
| —CR4R5—CR4R5—CR4R5—CR4R5—O—CR6R7—CR6R7—* |
| —CR4R5—CR4R5—CR4R5—CR4R5—NR8—CR6R7—CR6R7—* |
| —CR4R5—CR4R5—O—CR6R7—CR6R7—CR6R7—* |
| —CR4R5—CR4R5—NR8—CR6R7—CR6R7—CR6R7—* |
| —CR4R5—CR4R5—CR4R5—O—CR6R7—CR6R7—CR6R7—* |
| —CR4R5—CR4R5—CR4R5—NR8—CR6R7—CR6R7—CR6R7—* |
| —CR4R5—CR4R5—CR4R5—CR4R5—O—CR6R7—CR6R7—CR6R7—* |
| —CR4R5—CR4R5—CR4R5—CR4R5—NR8—CR6R7—CR6R7—CR6R7—* |
| —CR4R5—CR4R5—CR6R7—CR6R7—CR6R7—CR6R7—* |
| —CR4R5—CR4R5—O—CR6R7—CR6R7—CR6R7—CR6R7—* |

TABLE 1-continued

—CR4R5—CR4R5—NR8—CR6R7—CR6R7—CR6R7—CR6R7—*
—CR4R5—CR4R5—CR4R5—CR6R7—CR6R7—CR6R7—CR6R7—*
—CR4R5—CR4R5—CR4R5—O—CR6R7—CR6R7—CR6R7—CR6R7—*
—CR4R5—CR4R5—CR4R5—NR8—CR6R7—CR6R7—CR6R7—CR6R7—*
—CR4R5—CR4R5—CR4R5—CR4R5—CR6R7—CR6R7—CR6R7—CR6R7—*
—CR4R5—CR4R5—CR4R5—CR4R5—O—CR6R7—CR6R7—CR6R7—CR6R7—*
—CR4R5—CR4R5—CR4R5—CR4R5—NR8—CR6R7—CR6R7—CR6R7—CR6R7—*
—CR4R5—CR4R5—O—CR6R7—CR6R7—O—*
—CR4R5—CR4R5—NR8—CR6R7—CR6R7—O—*
—CR4R5—CR4R5—CR4R5—O—CR6R7—CR6R7—O—*
—CR4R5—CR4R5—CR4R5—NR8—CR6R7—CR6R7—O—*
—CR4R5—CR4R5—CR4R5—CR4R5—O—CR6R7—CR6R7—O—*
—CR4R5—CR4R5—CR4R5—CR4R5—NR8—CR6R7—CR6R7—O—*
—CR4R5—CR4R5—O—CR6R7—CR6R7—CR6R7—O—*
—CR4R5—CR4R5—NR8—CR6R7—CR6R7—CR6R7—O—*
—CR4R5—CR4R5—CR4R5—O—CR6R7—CR6R7—CR6R7—O—*
—CR4R5—CR4R5—CR4R5—NR8—CR6R7—CR6R7—CR6R7—O—*
—CP4R5—CR4R5—CR4R5—CR4R5—O—CR6R7—CR6R7—CR6R7—O—*
—CR4R5—CR4R5—CR4R5—CR4R5—NR8—CR6R7—CR6R7—CR6R7—O—*
—CR4R5—CR4R5—CR6R7—CR6R7—CR6R7—CR6R7—O—*
—CR4R5—CR4R5—O—CR6R7—CR6R7—CR6R7—CR6R7—O—*
—CR4R5—CR4R5—NR8—CR6R7—CR6R7—CR6R7—CR6R7—O—*
—CR4R5—CR4R5—CR4R5—CR6R7—CR6R7—CR6R7—CR6R7—O—*
—CR4R5—CR4R5—CR4R5—O—CR6R7—CR6R7—CR6R7—CR6R7—O—*
—CR4R5—CR4R5—CR4R5—NR8—CR6R7—CR6R7—CR6R7—CR6R7—O—*
—CR4R5—CR4R5—CR4R5—CR4R5—CR6R7—CR6R7—CR6R7—CR6R7—O—*
—CR4R5—CR4R5—CR4R5—CR4R5—O—CR6R7—CR6R7—CR6R7—CR6R7—O—*
—CR4R5—CR4R5—O—CR6R7—CR6R7—NR8—*
—CR4R5—CR4R5—NR8—CR6R7—CR6R7—NR8—*
—CR4R5—CR4R5—CR4R5—O—CR6R7—CR6R7—NR8—*
—CR4R5—CR4R5—CR4R5—NR8—CR6R7—CR6R7—NR8—*
—CR4R5—CR4R5—CR4R5—CR4R5—O—CR6R7—CR6R7—NR8—*
—CR4R5—CR4R5—CR4R5—CR4R5—NR8—CR6R7—CR6R7—NR8—*
—CR4R5—CR4R5—O—CR6R7—CR6R7—CR6R7—NR8—*
—CR4R5—CR4R5—NR8—CR6R7—CR6R7—CR6R7—NR8—*
—CR4R5—CR4R5—CR4R5—O—CR6R7—CR6R7—CR6R7—NR8—*
—CR4R5—CR4R5—CR4R5—NR8—CR6R7—CR6R7—CR6R7—NR8—*
—CR4R5—CR4R5—CR4R5—CR4R5—O—CR6R7—CR6R7—CR6R7—NR8—*
—CR4R5—CR4R5—CR4R5—CR4R5—NR8—CR6R7—CR6R7—CR6R7—NR8—*
—CR4R5—CR4R5—CR6R7—CR6R7—CR6R7—CR6R7—NR8—*
—CR4R5—CR4R5—O—CR6R7—CR6R7—CR6R7—CR6R7—NR8—*
—CR4R5—CR4R5—NR8—CR6R7—CR6R7—CR6R7—CR6R7—NR8—*
—CR4R5—CR4R5—CR4R5—CR6R7—CR6R7—CR6R7—CR6R7NR8—*
—CR4R5—CR4R5—CR4R5—O—CR6R7—CR6R7—CR6R7—CR6R7—NR8—*
—CR4R5—CR4R5—CR4R5—NR8—CR6R7—CR6R7—CR6R7—CR6R7—NR8—*
—CR4R5—CR4R5—CR4R5—CR4R5—CR6R7—CR6R7—CR6R7—CR6R7—NR8—*
—CR4R5—CR4R5—CR4R5—CR4R5—O—CR6R7—CR6R7—CR6R7—CR6R7—NR8—*
—CR4R5—CR4R5—CR4R5—CR4R5—NR8—CR6R7—CR6R7—CR6R7—CR6R7—NR8—*
—CR4R5—CR4R5—CR4R5—CR6R7—O—*
—CR4R5—CR4R5—CR4R5—CR6R7—O—*
—CR4R5—CR4R5—CR4R5—CR6R7—NR8—*
—CR4R5—CR4R5—CR4R5—CR4R5—CR6R7—NR8—*

Preferably, it is any of groups represented by the following formulas: —CR$^4$R$^5$—CR$^4$R$^5$—CR$^4$R$^5$—CR$^4$R$^5$—CR$^6$R$^7$—*;
—CR$^4$R$^5$—CR$^4$R$^5$—CR$^4$R$^5$—CR$^6$R$^7$—O—*;
—CR$^4$R$^5$—CR$^4$R$^5$—CR$^4$R$^5$—O—CR$^6$R$^7$—*; and
—CR$^4$R$^5$—CR$^4$R$^5$—O—CR$^6$R$^7$—CR$^6$R$^7$—*.

More preferably, it is any of groups represented by the following formulas: —CH$_2$—CH$_2$—CH$_2$—CH$_2$—CH$_2$—*; and
—CH$_2$—CH$_2$—CH$_2$—O—CH$_2$—*.

Examples of the substituent in the "optionally substituted $C_{1-6}$ alkyl group", the "optionally substituted cyclic group", the "a benzene ring which may have an additional substituent(s)", the "optionally substituted 5- or 6-membered aromatic ring which may contain a heteroatom(s) in the ring", and the "optionally substituted, saturated or unsaturated linear $C_{4-8}$ alkylene optionally inserted by a heteroatom" as used herein include substituents selected from Substituent Group A described below, and the number of the substituent is, for example, 1 to 5 (preferably 1 to 3). When the number of the substituent is two or more, those substituents may be the same as or different from each other.

[Substituent Group A]
(1) Halogen atom;
(2) Cyano group;
(3) Nitro group;
(4) Optionally substituted hydrocarbon group;
(5) Optionally substituted heterocyclic group;
(6) Acyl group;
(7) Optionally substituted amino group;
(8) Optionally substituted carbamoyl group;
(9) Optionally substituted thiocarbamoyl group;
(10) Optionally substituted sulfamoyl group;
(11) Optionally substituted hydroxy group;
(12) Optionally substituted sulfanyl (SH) group; and (13) Optionally substituted silyl group.

Examples of the "hydrocarbon group" of the "optionally substituted hydrocarbon group" in Substituent Group A include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group, and a $C_{7-16}$ aralkyl group. Examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, and 5-hexenyl.

Examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and 4-methyl-2-pentynyl.

Examples of the "$C_{7-16}$ aralkyl group" include benzyl, phenethyl, naphthylmethyl, and phenylpropyl.

Examples of the "optionally substituted hydrocarbon group" in Substituent Group A include a hydrocarbon group optionally having a substituent selected from Substituent Group B described below.

[Substituent Group B]
(1) Halogen atom;
(2) Nitro group;
(3) Cyano group;
(4) Oxo group;
(5) Hydroxy group;
(6) Optionally halogenated $C_{1-6}$ alkoxy group; (7) $C_{6-14}$ Aryloxy group (for example, phenoxy, naphthoxy);
(8) $C_{7-16}$ Aralkyloxy group (for example, benzyloxy);
(9) 5- to 14-Membered aromatic heterocyclic ring oxy group (for example, pyridyloxy);
(10) 3- to 14-Membered non-aromatic heterocyclic ring oxy group (for example, morpholinyloxy, piperidinyloxy);
(11) $C_{1-6}$ Alkyl-carbonyl oxy group (for example, acetoxy, propanoyloxy);
(12) $C_{6-14}$ Aryl-carbonyloxy group (for example, benzoyloxy, 1-naphthoyloxy, 2-naphthoyloxy);
(13) $C_{1-6}$ Alkoxy-carbonyloxy group (for example, methoxycarbonyloxy, ethoxycarbonyloxy, propoxycarbonyloxy, butoxycarbonyloxy);
(14) Mono- or di-$C_{1-6}$ alkyl-carbamoyloxy group (for example, methylcarbamoyloxy, ethylcarbamoyloxy, dimethylcarbamoyloxy, diethylcarbamoyloxy);
(15) $C_{6-14}$ Aryl-carbamoyloxy group (phenylcarbamoyloxy, naphthylcarbamoyloxy);
(16) 5- to 14-Membered aromatic heterocyclic ring carbonyloxy group (for example, nicotinoyloxy);
(17) 3- to 14-Membered non-aromatic carbonyloxy group (for example, morpholinylcarbonyloxy, piperidinylcarbonyloxy);
(18) Optionally halogenated $C_{1-6}$ alkylsulfonyloxy group (for example, methylsulfonyloxy, trifluoromethylsulfonyloxy);
(19) $C_{6-14}$ Arylsulfonyloxy group optionally substituted with a $C_{1-6}$ alkyl group (for example, phenylsulfonyloxy, toluenesulfonyloxy);
(20) Optionally halogenated $C_{1-6}$ alkylthio group;
(21) 5- to 14-Membered aromatic heterocyclic group;
(22) 3- to 14-Membered non-aromatic heterocyclic group;
(23) Formyl group;
(24) Carboxy group;
(25) Optionally halogenated $C_{1-6}$ alkyl-carbonyl group;
(26) $C_{6-14}$ Aryl-carbonyl group;
(27) 5- to 14-Membered aromatic heterocyclic ring carbonyl group;
(28) 3- to 14-Membered non-aromatic heterocyclic ring carbonyl group;
(29) $C_{1-6}$ Alkoxy-carbonyl group;
(30) $C_{6-14}$ Aryloxy-carbonyl group (for example, phenyloxycarbonyl, 1-naphthyloxycarbonyl, 2-naphthyloxycarbonyl);
(31) $C_{7-16}$ Aralkyloxy-carbonyl group (for example, benzyloxycarbonyl, phenethyloxycarbonyl);
(32) Carbamoyl group;
(33) Thiocarbamoyl group;
(34) Mono- or di-$C_{1-6}$ alkyl-carbamoyl group;
(35) $C_{6-14}$ Aryl-carbamoyl group (for example, phenylcarbamoyl);
(36) 5- to 14-Membered aromatic heterocyclic ring carbamoyl group (for example, pyridylcarbamoyl, thienylcarbamoyl);
(37) 3- to 14-Membered non-aromatic heterocyclic ring carbamoyl group (for example, morpholinylcarbamoyl, piperidinylcarbamoyl);
(38) Optionally halogenated $C_{1-6}$ alkylsulfonyl group;
(39) $C_{6-14}$ Arylsulfonyl group;
(40) 5- to 14-Membered aromatic heterocyclic ring sulfonyl group (for example, pyridylsulfonyl, thienylsulfonyl);
(41) Optionally halogenated $C_{1-6}$ alkylsulfinyl group;
(42) $C_{6-14}$ Arylsulfinyl group (for example, phenylsulfinyl, 1-naphthylsulfinyl, 2-naphthylsulfinyl);
(43) 5- to 14-Membered aromatic heterocyclic ring sulfinyl group (for example, pyridylsulfinyl, thienylsulfinyl);
(44) Amino group; (45) Mono- or di-$C_{1-6}$ alkylamino group (for example, methylamino, ethylamino, propylamino, isopropylamino, butylamino, dimethylamino, diethylamino, dipropylamino, dibutylamino, N-ethyl-N-methylamino);
(46) Mono- or di-$C_{6-14}$ arylamino group (for example, phenylamino);
(47) 5- to 14-Membered aromatic heterocyclic ring amino group (for example, pyridylamino);
(48) $C_{7-16}$ Aralkylamino group (for example, benzylamino);
(49) Formylamino group;
(50) $C_{1-6}$ Alkyl-carbonylamino group (for example, acetylamino, propanoylamino, butanoylamino);
(51) ($C_{1-6}$ Alkyl)($C_{1-6}$ alkyl-carbonyl)amino group (for example, N-acetyl-N-methylamino);
(52) $C_{6-14}$ Aryl-carbonylamino group (for example, phenylcarbonylamino, naphthylcarbonylamino);
(53) $C_{1-6}$ Alkoxy-carbonylamino group (for example, methoxycarbonylamino, ethoxycarbonylamino, propoxycarbonylamino, butoxycarbonylamino, tert-butoxycarbonylamino);
(54) $C_{7-16}$ Aralkyloxy-carbonylamino group (for example, benzyloxycarbonylamino);
(55) $C_{1-6}$ Alkylsulfonylamino group (for example, methylsulfonylamino, ethylsulfonylamino);
(56) $C_{6-14}$ Arylsulfonylamino group optionally substituted with a $C_{1-6}$ alkyl group (for example, phenylsulfonylamino, toluenesulfonylamino);
(57) Optionally halogenated $C_{1-6}$ alkyl group;
(58) $C_{2-6}$ Alkenyl group;
(59) $C_{2-6}$ Alkynyl group;
(60) $C_{3-10}$ Cycloalkyl group;
(61) $C_{3-10}$ Cycloalkenyl group; and
(62) $C_{6-14}$ Aryl group.

The number of the substituent selected from Substituent B described above in the "optionally substituted hydrocarbon group" of Substituent Group A is, for example, 1 to 5, and preferably 1 to 3. When the number of the substituent is two or more, those substituents may be the same as or different from each other.

Examples of the "heterocyclic group" in the "optionally substituted heterocyclic group" of Substituent Group A include (i) an aromatic heterocyclic group, (ii) a non-aromatic heterocyclic group, and (iii) a 7- to 10-membered bridged heterocyclic group, all of which contain, other than carbon atoms, 1 to 4 heteroatoms selected from a nitrogen atom, a sulfur atom and an oxygen atom as the constituent atoms of the ring.

Examples of the "aromatic heterocyclic group" in the "heterocyclic group" of Substituent Group A (including the "5- to 14-membered aromatic heterocyclic group") include a 5- to 14-membered (preferably, 5- to 10-membered) aromatic heterocyclic group containing, other than carbon atoms, 1 to 4 heteroatoms selected from a nitrogen atom, a sulfur atom and an oxygen atom as the constituent atoms of the ring.

Suitable examples of such an "aromatic heterocyclic group" include: a 5- to 6-membered monocyclic aromatic heterocyclic group such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, and triazinyl; and a 8- to 14-membered fused polycyclic (preferably, bicyclic or tricyclic) aromatic heterocyclic group such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolynyl, cinnolinyl, carbazolyl, R-carbolinyl, phenanthridinyl, acridinyl, phenazinyl, phenothiazinyl, and phenoxazinyl.

Examples of the "non-aromatic heterocyclic group" in the "heterocyclic group" of Substituent Group A (including the "3- to 14-membered non-aromatic heterocyclic group") include a 3- to 14-membered (preferably, 4- to 10-membered) non-aromatic heterocyclic group containing, other than carbon atoms, 1 to 4 heteroatoms selected from a nitrogen atom, a sulfur atom and an oxygen atom as the constituent atoms of the ring.

Suitable examples of such a "non-aromatic heterocyclic group" include: a 3- to 8-membered monocyclic non-aromatic heterocyclic group such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisoxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetarhydrothiopyranyl, morpholinyl, thiomorpholinyl, azepanyl, diazepanyl, azepinyl, oxepanyl, azocanyl, and diazocanyl; and a 9- to 14-membered fused polycyclic (preferably, bicyclic or tricyclic) non-aromatic heterocyclic group such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacridinyl], tetrahydrophenazinyl, tetrahydrothioxanthenyl, and octahydroisoquinolyl.

Suitable examples of the "7- to 10-membered bridged heterocyclic group" in the "heterocyclic group" of Substituent Group A include quinuclidinyl and 7-azabicyclo[2.2.1]heptanyl.

Examples of the "optionally substituted heterocyclic group" as used herein include a heterocyclic group optionally having a substituent selected from Substituent Group B described above.

The number of the substituent in the "optionally substituted heterocyclic group" is, for example, 1 to 3. When the number of the substituent is two or more, those substituents may be the same as or different from each other.

Examples of the "optionally substituted amino group" of Substituent Group A include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclic ring carbonyl group, a 3- to 14-membered non-aromatic heterocyclic ring carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group, and a $C_{6-14}$ arylsulfonyl group, all of which optionally have 1 to 3 substituents selected from Substituent Group A".

Suitable examples of the optionally substituted amino group include an amino group, a mono- or di-(optionally halogenated $C_{1-6}$ alkyl)amino group (for example, methylamino, trifluoromethylamino, dimethylamino, ethylamino, diethylamino, propylamino, dibutylamino), a mono- or di-$C_{2-6}$ alkenylamino group (for example, diallylamino), a mono- or di-$C_{3-10}$ cycloalkylamino group (for example, cyclopropylamino, cyclohexylamino), a mono- or di-$C_{6-14}$ arylamino group (for example, phenylamino), a mono- or di-$C_{7-16}$ aralkylamino group (for example, benzylamino, dibenzylamino), a mono- or di-(optionally halogenated $C_{1-6}$ alkyl)-carbonylamino group (for example, acetylamino, propionylamino), a mono- or di-$C_{6-14}$ aryl-carbonylamino group (for example, benzoylamino), a mono- or di-$C_{7-16}$ aralkyl-carbonylamino group (for example, benzylcarbonylamino), a mono- or di-5- to 14-membered aromatic heterocyclic ring carbonylamino group (for example, nicotinoylamino, isonicotinoylamino), a mono- or di-3- to 14-membered nonaromatic heterocyclic ring carbonylamino group (for example, piperidinylcarbonylamino), a mono- or di-$C_{1-6}$ alkoxy-carbonylamino group (for example, tert-butoxycarbonylamino), a 5- to 14-membered aromatic heterocyclic ring amino group (for example, pyridylamino), a carbamoylamino group, a (mono- or di-$C_{1-6}$ alkyl-carbamoyl)amino group (for example, methylcarbamoylamino), a (mono- or di-$C_{7-16}$ aralkyl-carbamoyl)amino group (for example, benzylcarbamoylamino), a $C_{1-6}$ alkylsulfonylamino group (for example, mehtylsulfonylamino, ethylsulfonylamino), a $C_{6-14}$ arylsulfonylamino group (for example, phenylsulfonylamino), a ($C_{1-6}$ alkyl)($C_{1-6}$ alkyl-carbonyl)amino group (for example, N-acetyl-N-methylamino), and a ($C_{1-6}$ alkyl)($C_{6-14}$ aryl-carbonyl)amino group (for example, N-benzoyl-N-methylamino).

Examples of the "optionally substituted carbamoyl group" of Substituent Group A include a carbamoyl group optionally having "1 or 2 substituents selected from a $C_{1-6}$ alkyl group, a $C_{2-6}$ alkenyl group, a $C_3$-10 cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclic ring carbonyl group, a 3- to 14-membered non-aromatic heterocyclic ring carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, and a mono- or di-$C_{7-16}$ aralkyl-carbamoyl group, all of which optionally have 1 to 3 substituents selected from Substituent Group B".

Suitable examples of the optionally substituted carbamoyl group include a carbamoyl group, a mono- or di-$C_{1-6}$ alkyl-carbamoyl group, a mono- or di-$C_{2-6}$ alkenyl-carbamoyl group (for example, diallylcarbamoyl), a mono- or di-$C_{3-10}$ cycloalkyl-carbamoyl group (for example, cyclopropylcarbamoyl, cyclohexylcarbamoyl), a mono- or di-$C_{6-14}$ aryl-carbamoyl group (for example, phenylcarbamoyl), a mono- or di-$C_{7-16}$ aralkyl-carbamoyl group, a mono- or di-$C_{1-6}$ alkyl-carbonyl-carbamoyl group (for example, acetylcarbamoyl, propionylcarbamoyl), a mono- or di-$C_{6-14}$ aryl-carbonyl-carbamoyl group (for example, benzoylcarbamoyl), and a 5- to 14-membered aromatic heterocyclic ring carbamoyl group (for example, pyridylcarbamoyl).

Examples of the "optionally substituted thiocarbamoyl group" of Substituent Group A include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclic ring carbonyl group, a 3- to 14-membered non-aromatic heterocyclic ring carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, and a mono- or di-$C_{7-16}$ aralkyl-carbamoyl group, all of which optionally have 1 to 3 substituents selected from Substituent Group B".

Suitable examples of the optionally substituted thiocarbamoyl group include a thiocarbamoyl group, a mono- or di-$C_{1-6}$ alkyl-thiocarbamoyl group (for example, methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (for example, diallylthiocarbamoyl), a mono- or di-$C_{3-10}$ cycloalkyl-thiocarbamoyl group (for example, cyclopropylthiocarbamoyl, cyclohexylthiocarbamoyl), a mono- or di-$C_{6-14}$ aryl-thiocarbamoyl group (for example, phenylthiocarbamoyl), a mono- or di-$C_{7-16}$ aralkyl-thiocarbamoyl group (for example, benzylthiocarbamoyl, phenethylthiocarbamoyl), a mono- or di-$C_{1-6}$ alkyl-carbonyl-thiocarbamoyl group (for example, acetylthiocarbamoyl, propionylthiocarbamoyl), a mono- or di-$C_{6-14}$ aryl-carbonyl-thiocarbamoyl group (for example, benzoylthiocarbamoyl), and a 5- to 14-membered aromatic heterocyclic ring carbamoyl group (for example, pyridylthiocarbamoyl).

Examples of the "optionally substituted sulfamoyl group" of Substituent Group A include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclic ring carbonyl group, a 3- to 14-membered non-aromatic heterocyclic ring carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, and a mono- or di-$C_{7-16}$ aralkyl-carbamoyl group, all of which optionally have 1 to 3 substituents selected from Substituent Group B".

Suitable examples of the optionally substituted sulfamoyl group include a sulfamoyl group, a mono- or di-$C_{1-6}$ alkyl-sulfamoyl group (for example, methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (for example, diallylsulfamoyl), a mono- or di-$C_{3-10}$ cycloalkyl-sulfamoyl group (for example, cyclopropylsulfamoyl, cyclohexylsulfamoyl), a mono- or di-$C_{6-14}$ aryl-sulfamoyl group (for example, phenylsulfamoyl), a mono- or di-$C_{7-16}$ aralkyl-sulfamoyl group (for example, benzylsulfamoyl, phenethylsulfamoyl), a mono- or di-$C_{1-6}$ alkyl-carbonyl-sulfamoyl group (for example, acetylsulfamoyl, propionylsulfamoyl), a mono- or di-$C_{6-14}$ aryl-carbonyl-sulfamoyl group (for example, benzoylsulfamoyl), and a 5- to 14-membered aromatic heterocyclic ring sulfamoyl group (for example, pyridylsulfamoyl 1).

Examples of the "optionally substituted hydroxy group" of Substituent Group A include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclic ring carbonyl group, a 3- to 14-membered non-aromatic heterocyclic ring carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group, and a $C_{6-14}$ arylsulfonyl group, all of which optionally have 1 to 3 substituents selected from Substituent Group B".

Suitable examples of the optionally substituted hydroxy group include a hydroxy group, a $C_{1-6}$ alkoxy group, a $C_{2-6}$ alkenyloxy group (for example, allyloxy, 2-butenyloxy, 2-pentenyloxy, 3-hexenyloxy), a $C_{3-10}$ cycloalkyloxy group (for example, cyclohexyloxy), a $C_{6-14}$ aryloxy group (for example, phenoxy, naphthyloxy), a $C_{7-16}$ aralkyloxy group (for example, benzyloxy, phenethyloxy), a $C_{1-6}$ alkyl-carbonyloxy group (for example, acetyloxy, propionyloxy, butyryloxy, isobutyryloxy, pivaloyloxy), a $C_{6-14}$ aryl-carbonyloxy group (for example, benzoyloxy), a $C_{7-16}$ aralkyl-carbonyloxy group (for example, benzylcarbonyloxy), a 5- to 14-membered aromatic heterocyclic ring carbonyloxy group (for example, nicotinoyloxy), a 3- to 14-membered non-aromatic heterocyclic ring carbonyloxy group (for example, piperidinylcarbonyloxy), a $C_{1-6}$ alkoxy-carbonyloxy group (for example, tert-butoxycarbonyloxy), a 5- to 14-membered aromatic heterocyclic ring oxy group (for example, pyridyloxy), a carbamoyloxy group, a $C_{1-6}$ alkyl-carbamoyloxy group (for example, methylcarbamoyloxy), a $C_{7-16}$ aralkyl-carbamoyloxy group (for example, benzylcarbamoyloxy), a $C_{1-6}$ alkylsulfonyloxy group (for example, mehtylsulfonyloxy, ethylsulfonyloxy), and a $C_{6-14}$ arylsulfonyloxy group (for example, phenylsulfonyloxy).

Examples of the "optionally substituted sulfanyl group" of Substituent Group A include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, and a 5- to 14-membered aromatic heterocyclic group, all of which optionally have 1 to 3 substituents selected from Substituent Group B", and a halogenated sulfanyl group.

Suitable examples of the optionally substituted sulfanyl group include a sulfanyl (—SH) group, a $C_{1-6}$ alkylthio group, a $C_{2-6}$ alkenylthio group (for example, allylthio, 2-butenylthio, 2-pentenylthio, 3-hexenylthio), a $C_{3-10}$ cycloalkylthio group (for example, cyclohexylthio), a $C_{6-14}$ arylthio group (for example, phenylthio, naphthylthio), a $C_{7-16}$ aralkylthio group (for example, benzylthio, phenethylthio), a $C_{1-6}$ alkyl-carbonylthio group (for example, acetylthio, propionylthio, butyrylthio, isobutyrylthio, pivaloylthio), a $C_{6-14}$ aryl-carbonylthio group (for example, benzoylthio), a 5- to 14-membered aromatic heterocyclic ring thio group (for example, pyridylthio), and a halogenated thio group (for example, pentafluorothio).

Examples of the "$C_{3-10}$ cycloalkyloxy group" as used herein include cyclopropyloxy, cyclobutyloxy, cyclopentyloxy, cyclohexyloxy, cycloheptyloxy, and cyclooctyloxy.

Examples of the "$C_{1-6}$ alkylthio group" as used herein include methylthio, ethylthio, propylthio, isopropylthio, butylthio, sec-butylthio, tert-butylthio, pentylthio, and hexylthio.

Examples of the "optionally substituted silyl group" of Substituent Group A include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group, and a $C_{7-16}$ aralkyl group, all of which optionally have 1 to 3 substituents selected from Substituent Group B".

Suitable examples of the optionally substituted silyl group include a tri-$C_{1-6}$ alkylsilyl group (for example, trimethylsilyl, tert-butyl(dimethyl)silyl).

Hereinafter, the definition of each symbol in formula (I) will be described in detail.

$R^1$ is preferably OH or ORy.

Ry is preferably a $C_{1-6}$ alkyl group.

$R^1$ is more preferably OH.

$R^2$ and $R^3$ are preferably the same or different, and are each a hydrogen atom or an optionally substituted $C_{1-6}$ alkyl group (for example, methyl).

$R^2$ and $R^3$ are more preferably the same or different, and are each a hydrogen atom or a $C_{1-3}$ alkyl group (for example, methyl).

Particularly preferably, $R^2$ and $R^3$ are each a hydrogen atom or a methyl group.

X is preferably C(=O).

The "benzene ring" of the "a benzene ring which may have an additional substituent(s)" indicated as ring A may be further substituted with, for example, a substituent(s) selected from Substituent Group A described above, and the number of the substituent is, for example, 1 to 3. When the number of the substituent is two or more, those substituents may be the same as or different from each other.

Here, when the benzene ring of ring A has an additional substituent(s), that position of substitution preferably includes a position selected from positions a and b indicated by the following arrows:

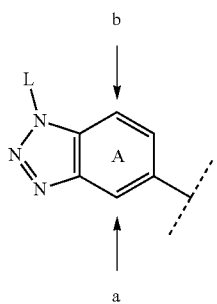

wherein the symbols in the formula are as defined above.

Ring A is preferably a benzene ring which may have an additional substituent(s) of a fluorine atom, a chlorine atom, a $C_{1-3}$ alkyl group optionally substituted with 1 to 3 substituents (selected from a halogen atom and a $C_{1-3}$ alkoxy group), or a $C_{1-3}$ alkoxy group optionally substituted with 1 to 3 substituents (selected from a halogen atom and a $C_{1-3}$ alkoxy group).

Further preferably, ring A is a benzene ring which may have an additional substituent(s) of 1 to 3 substituents selected from:

(a) a $C_{1-6}$ alkyl group (for example, methyl); and (b) a $C_{1-6}$ alkoxy group (for example, methoxy).

More preferably, ring A is a benzene ring which has an additional substituent(s) of one substituent selected from:

(a) a $C_{1-3}$ alkyl group (for example, methyl); and (b) a $C_{1-3}$ alkoxy group (for example, methoxy).

Here, the position of substitution on the benzene ring of ring A is preferably a position a or b indicated by the following arrows:

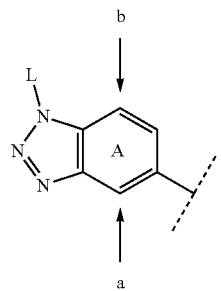

wherein the symbols in the formula are as defined above.

In another embodiment, ring A is more preferably a benzene ring which has an additional substituent(s) of 1 or 2 substituents selected from:

(a) a $C_{1-3}$ alkyl group (for example, methyl); and (b) a $C_{1-3}$ alkoxy group (for example, methoxy).

Here, the position(s) of substitution on the benzene ring of ring A is preferably a position selected from positions a and b indicated by the following arrows:

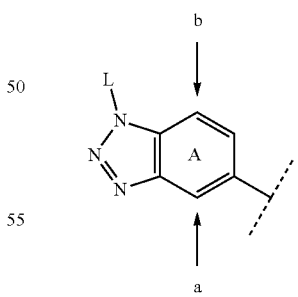

wherein the symbols in the formula are as defined above.

In such an embodiment, ring A is further preferably a benzene ring which has an additional substituent of a $C_{1-3}$ alkyl group (for example, methyl).

Here, the position of substitution on the benzene ring of ring A is preferably position a indicated by the following arrow:

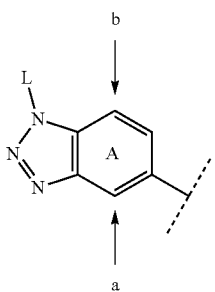

wherein the symbols in the formula are as defined above.

A substructure represented by the following formula:

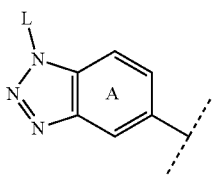

wherein the symbols in the formula are as defined above, is preferably a substructure represented by the following formula:

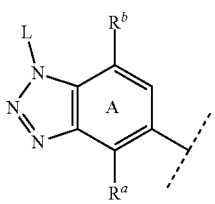

wherein
$R^a$ represents a hydrogen atom or a $C_{1-6}$ alkyl group;
$R^b$ represents a hydrogen atom or a $C_{1-6}$ alkoxy group; and
L has the same meaning as described above.

Here, $R^a$ is preferably a $C_{1-3}$ alkyl group (for example, methyl), and more preferably methyl. $R^b$ is preferably a hydrogen atom or a $C_{1-3}$ alkoxy group (for example, methoxy).

Further preferably, ring A is a substructure represented by the following formula:

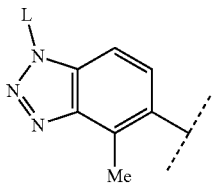

The "benzene ring" of the "a benzene ring which may have an additional substituent(s)" indicated as ring B may have an additional substituent(s), for example, a substituent selected from Substituent Group A described above, and the number of the substituent is, for example, 1 to 3. When the number of the substituent is two or more, those substituents may be the same as or different from each other.

Ring B is preferably a benzene ring which may have an additional substituent(s) of a fluorine atom, a chlorine atom, a cyano group, a $C_{1-3}$ alkyl group optionally substituted with 1 to 3 substituents (selected from a halogen atom and a $C_{1-3}$ alkoxy group), or a $C_{1-3}$ alkoxy group optionally substituted with 1 to 3 substituents (selected from a halogen atom and a $C_{1-3}$ alkoxy group).

Ring B is more preferably a benzene ring which does not have an additional substituent. Here, "which does not have an additional substituent" indicates that ring B is the same as ring B described in formula I and does not have a substituent other than the substituents on ring B described in formula I.

The "optionally substituted 5- or 6-membered aromatic ring which may contain a heteroatom(s) in the ring" indicated as ring C is preferably a ring represented by the following formula:

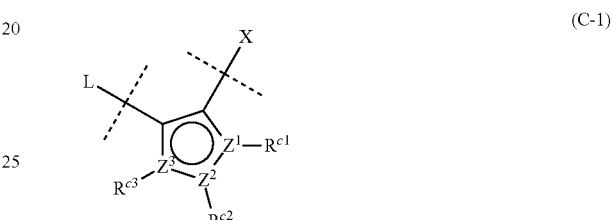
(C-1)

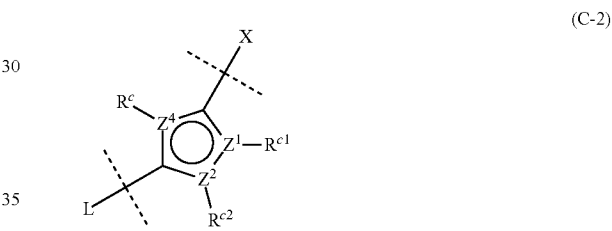
(C-2)

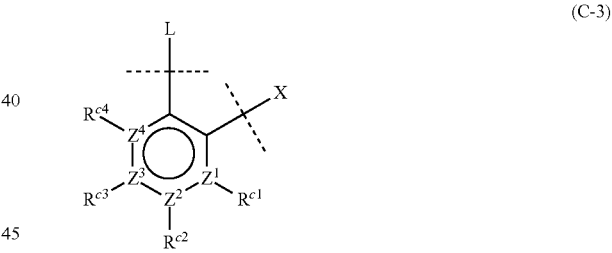
(C-3)

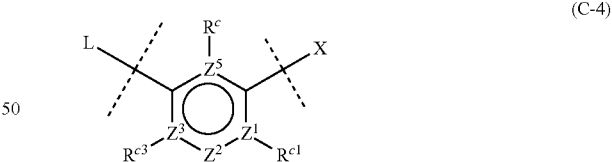
(C-4)

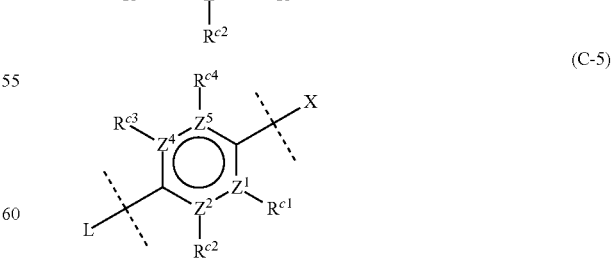
(C-5)

wherein $Z^1$, $Z^2$, $Z^3$, $Z^4$ and $Z^5$, which may be the same or different, are a carbon atom or a nitrogen atom;
$R^c$ represents H, a halogen atom, a nitro group, a cyano group, a hydroxy group, an optionally halogenated $C_{1-6}$ alkyl group, an optionally halogenated $C_{1-6}$ alkoxy group, or a $C_{3-10}$ cycloalkyl group; and $R^{c1}$, $R^{c2}$, $R^{c3}$ and $R^{c4}$, which may be the same or different, are H, a halogen atom, a nitro group, a cyano group, a hydroxy group, an optionally halogenated $C_{1-6}$ alkyl group, an optionally halogenated $C_{1-6}$ alkoxy group, or a $C_{3-10}$ cycloalkyl group; or adjacent two of $R^{c1}$, $R^{c2}$, $R^{c3}$ and $R^{c4}$ may be joined together to form an optionally substituted ring, provided that when $Z^1$, $Z^2$, $Z^3$, $Z^4$ or $Z^5$ is a nitrogen atom, $R^c$, $R^{c1}$, $R^{c2}$, $R^{c3}$ or $R^{c4}$ is not present.

In addition, formulas (C-1) to (C-5) are attached to X and L in formula (I) at certain bonding positions.

Preferably, ring C is any of groups represented by the following formulas:

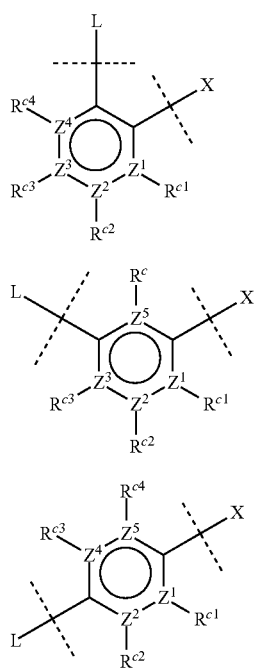

(C-3)

(C-4)

(C-5)

wherein $Z^1$, $Z^2$, $Z^3$, $Z^4$ and $Z^5$, which may be the same or different, are a carbon atom or a nitrogen atom.

Further preferably, ring C is a group wherein $Z^1$, $Z^2$, $Z^3$, $Z^4$ and $Z^5$ are each a carbon atom; and $R^{c1}$, $R^{c2}$, $R^{c3}$ and $R^{c4}$, which may be the same or different, are H, or a halogen atom, a nitro group, a cyano group, a hydroxy group, an optionally halogenated $C_{1-6}$ alkyl group, an optionally halogenated $C_{1-6}$ alkoxy group, or a $C_{3-10}$ cycloalkyl group; or adjacent two of $R^{c1}$, $R^{c2}$, $R^{c3}$ and $R^{c4}$ may be joined together to form an optionally substituted ring, Further preferably, ring C is a ring represented by formula (C-5), and is a group wherein adjacent two of $R^{c1}$, $R^{c2}$, $R^{c3}$ and $R^{c4}$ may be joined together to form an optionally substituted saturated ring.

The "saturated ring" of the "optionally substituted saturated ring" means a $C_{5-8}$ cycloalkyl ring or a saturated heterocyclic ring, and such a saturated heterocyclic ring means a 5- or 8-membered saturated heterocyclic ring containing, other than carbon atoms, 1 to 4 heteroatoms selected from a nitrogen atom, a sulfur atom and an oxygen atom as the constituent atoms of the ring. Preferable examples thereof include a 5- to 6-membered saturated heterocyclic ring (for example, tetrahydrofuran, tetrahydropyran, 1,3-dioxolane, morpholine). More preferably, it is optionally substituted tetrahydropyran or optionally substituted morpholine.

The substituent in the "optionally substituted saturated ring" means 1 to 3 substituents that may be the same or different, and are selected from a halogen atom, a nitro group, a cyano group, a hydroxy group, an oxo group, an optionally halogenated $C_{1-6}$ alkyl group, an optionally halogenated $C_{1-6}$ alkoxy group, a $C_{3-10}$ cycloalkyl group, and a $C_{3-10}$ cycloalkyl-$C_{1-6}$ alkyl group.

More preferably, ring C is a ring represented by formula (C-5), wherein all of $Z^1$, $Z^2$, $Z^4$ and $Z^5$ are carbon atoms; and in one of combinations, $R^{c1}$ and $R^{c2}$ or $R^{c3}$ and $R^{c4}$, the two groups may be the same or different, and are H, or a halogen atom, a nitro group, a cyano group, a hydroxy group, an optionally halogenated $C_{1-6}$ alkyl group, an optionally halogenated $C_{1-6}$ alkoxy group, or a $C_{3-10}$ cycloalkyl group; and in the other combination, adjacent two of $R^{c1}$, $R^{c2}$, $R^{c3}$ and $R^{c4}$ are joined together to form a 5- or 6-membered heterocyclic ring containing, other than carbon atoms, 1 to 4 heteroatoms selected from a nitrogen atom, a sulfur atom and an oxygen atom as the constituent atoms of the ring.

The heterocyclic ring described above may be an aromatic heterocyclic ring or a non-aromatic heterocyclic ring. Examples of the aromatic heterocyclic ring include, among those described as the monocyclic aromatic heterocyclic ring mentioned above, for example, pyridyl, thiazolyl, oxazolyl, pyrazolyl, triazolyl, and thienyl. Examples of the non-aromatic heterocyclic ring include, among the monocyclic non-aromatic heterocyclic ring mentioned above, those that are 5- or 6-membered, such as tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisoxazolyl, piperidinyl, piperazinyl, tetrahydropyridinyl, dihydropyridinyl, dihydrothiopyranyl, tetrahydropyrimidinyl, and tetrahydropyridazinyl. Preferably, it is tetrahydrofuran or morpholine.

When the ring described above is substituted, it may be substituted with 1 to 3 substituents that may be the same or different, and are selected from a halogen atom, a nitro group, a cyano group, a hydroxy group, an oxo group, an optionally halogenated $C_{1-6}$ alkyl group, an optionally halogenated $C_{1-6}$ alkoxy group, a $C_{3-10}$ cycloalkyl group, and a $C_{3-10}$ cycloalkyl-$C_{1-6}$ alkyl group.

More specifically, ring C is preferably a group represented by the following formula:

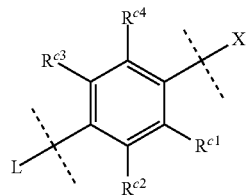

wherein
$R^{c1}$ and $R^{c4}$, which may be the same or different, are a hydrogen atom, an optionally halogenated $C_{1-6}$ alkyl group, a chlorine atom, an optionally halogenated $C_{1-6}$ alkoxy group, or a fluorine atom, and $R^{c2}$ and $R^{c3}$ are each a hydrogen atom.

Further specifically, ring C is preferably a group represented by the following formula:

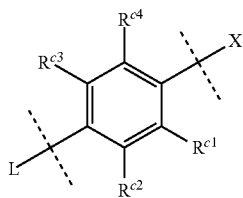

wherein
$R^{c1}$ and $R^{c4}$, which may be the same or different, are a hydrogen atom, a methyl group, or a chlorine atom, and $R^{c2}$ and $R^{c3}$ are each a hydrogen atom.

L is preferably —$(CR^4R^5)$n-$Y^1$—$(CR^6R^7)$m-$Y^2$—*
wherein * represents attachment to ring C;
n is an integer of 2 or more and 4 or less;
m is an integer of 1 or more and 4 or less;
$R^4$ and $R^5$, which may be the same as or different from each other, are each a hydrogen atom, a halogen atom, OH, an optionally substituted $C_{1-6}$ alkyl group or an optionally substituted $C_{1-6}$ alkoxy group, or $R^4$ and $R^5$ are joined together to form an optionally substituted $C_{3-6}$ cycloalkyl group, and a plurality of $R^4$ or a plurality of $R^5$ may be the same as or different from each other, and the adjacent $R^4$ or $R^5$ may be joined together to form a double bond;
$R^6$ and $R^7$, which may be the same as or different from each other, are each a hydrogen atom, a halogen atom, OH, an optionally substituted $C_{1-6}$ alkyl group or an optionally substituted $C_{1-6}$ alkoxy group, or $R^6$ and $R^7$ are joined together to form an optionally substituted $C_{3-6}$ cycloalkyl group, and when m is 2 or more, a plurality of $R^6$ or a plurality of $R^7$ may be the same as or different from each other, and the adjacent $R^6$ or $R^7$ may be joined together to form a double bond;
$Y^1$ and $Y^2$, which may be the same or different, are a bond, an oxygen atom or $NR^8$, provided that when $Y^1$ is a bond, m is 1 or 4; and
$R^8$ is a hydrogen atom or an optionally substituted $C_{1-6}$ alkyl group.

Further preferably, L is any of groups represented by the following formulas:
—$CR^4R^5$—$CR^4R^5$—$CR^4R^5$—$CR^4R^5$—$CR^6R^7$—*;
—$CR^4R^5$—$CR^4R^5$—$CR^4R^5$—$CR^6R^7$—O*;
$CR^4R^5$—$CR^4R^5$—$CR^4R^5$—O—$CR^6R^7$—*; and
—$CR^4R^5$—$CR^4R^5$—O—$CR^6R^7$—$CR^6R^7$—*.

Most preferably, L is
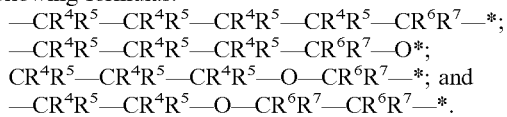
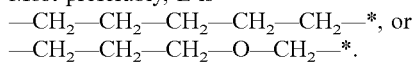

Examples of the compound represented by formula (I) (hereinafter, also referred to as compound (I)) include the following Compounds A to D, or a salt thereof.
[Compound A]
A compound or a salt thereof, in which:
$R^1$ is OH;
$R^2$ and $R^3$, which may be the same or different, are a hydrogen atom or an optionally substituted $C_{1-6}$ alkyl group;
X is C(=O);
ring A is a benzene ring which may have an additional substituent(s);
ring B is a benzene ring which may have an additional substituent(s);
ring C is an optionally substituted benzene ring; and
L is —$CR^4R^5$—$CR^4R^5$—$CR^6R^7$—$CR^6R^7$—$CR^6R^7$—$CR^6R^7$—*—;
—$CR^4R^5$—$CR^4R^5$—$CR^4R^5$—$CR^4R^5$—$CR^6R^7$—*—;
—$CR^4R^5$—$CR^4R^5$—$CR^4R^5$—$CR^6R^7$—O—*;
—$CR^4R^5$—$CR^4R^5$—$CR^4R^5$—O—$CR^6R^7$—*; or
—$CR^4R^5$—$CR^4R^5$—O—$CR^6R^7$—$CR^6R^7$—*.
[Compound B]
A compound or a salt thereof, in which:
$R^1$ is NHRy;
Ry is an optionally substituted cyclic group;
$R^2$ and $R^3$, which may be the same or different, are a hydrogen atom or an optionally substituted $C_{1-6}$ alkyl group;
X is C(=O);
ring A is a benzene ring which may have an additional substituent(s);
ring B is a benzene ring which may have an additional substituent(s);
ring C is an optionally substituted benzene ring; and
L is —$CR^4R^5$—$CR^4R^5$—$CR^6R^7$—$CR^6R^7$—$CR^6R^7$—$CR^6R^7$—*;
—$CR^4R^5$—$CR^4R^5$—$CR^4R^5$—$CR^4R^5$—$CR^6R^7$—*—;
—$CR^4R^5$—$CR^4R^5$—$CR^4R^5$—$CR^6R^7$—O—*
—$CR^4R^5$—$CR^4R^5$—$CR^4R^5$—O—$CR^6R^7$—*; or
—$CR^4R^5$—$CR^4R^5$—O—$CR^6R^7$—$CR^6R^7$—*.
[Compound C]
A compound or a salt thereof, in which:
$R^1$ is OH;
$R^2$ and $R^3$, which may be the same or different, are a hydrogen atom or an optionally substituted $C_{1-6}$ alkyl group;
X is C(=O);
ring A is a benzene ring which may have an additional substituent(s);
ring B is a benzene ring which may have an additional substituent(s);
ring C is a group represented by the following formula:

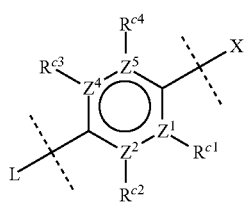

(C-5)

wherein all of $Z^1$, $Z^2$, $Z^4$ and $Z^5$ are carbon atoms; and in one of combinations, $R^{c1}$ and $R^{c2}$ or $R^{c3}$ and $R^{c4}$, the two groups which may be the same or different, are a hydrogen atom, or a halogen atom, a nitro group, a cyano group, a hydroxy group, an optionally halogenated $C_{1-6}$ alkyl group, an optionally halogenated $C_{1-6}$ alkoxy group, or a $C_{3-10}$ cycloalkyl group; and in the other combination, adjacent two of $R^{c1}$, $R^{c2}$, $R^{c3}$ and $R^{c4}$ are joined together to form an optionally substituted ring; and
L is —$CR^4R^5$—$CR^4R^5$—$CR^6R^7$—$CR^6R^7$—$CR^6R^7$—$CR^6R^7$—*—;
—$CR^4R^5$—$CR^4R^5$—$CR^4R^5$—$CR^4R^5$—$CR^6R^7$—*;
—$CR^4R^5$—$CR^4R^5$—$CR^4R^5$—$CR^6R^7$—O—*;
—$CR^4R^5$—$CR^4R^5$—$CR^4R^{1}$—O—$CR^6R^7$—*; or
—$CR^4R^5$—$CR^4R^{1}$—O—$CR^6R^7$—$CR^6R^7$—*.
[Compound D]
A compound or a salt thereof, in which:
$R^1$ is ORy;
Ry is an optionally substituted $C_{1-6}$ alkyl group;

$R^2$ and $R^3$, which may be the same or different, are a hydrogen atom or an optionally substituted $C_{1-6}$ alkyl group;
X is C(=O);
ring A is a benzene ring which may have an additional substituent(s);
ring B is a benzene ring which may have an additional substituent(s);
ring C is an optionally substituted benzene ring; and
L is —$CR^4R^5$—$CR^4R^5$—$CR^6R^7$—$CR^6R^7$—$CR^6R^7$—$CR^6R^7$—*;
—$CR^4R^5$—$CR^4R^5$—$CR^4R^5$—$CR^4R^5$—$CR^6R^7$—*;
—$CR^4R^5$—$CR^4R^5$—$CR^4R^5$—$CR^6R^7$—O—*;
—$CR^4R^5$—$CR^4R^5$—$CR^4R'$—O—$CR^6R^7$—*; or
—$CR^4R^5$—$CR^4R'$—O—$CR^6R^7$—$CR^6R^7$—*.

Preferably, compound (I) is Compound A or a salt thereof.

Specific examples of compound (I) include compounds of Examples 1 to 68 and salts thereof.

When compound (I) is a salt, examples of such a salt include metal salts, ammonium salt, salts with organic bases, salts with inorganic acids, salts with organic acids, and salts with basic or acidic amino acids. Suitable examples of the metal salt include alkali metal salts such as sodium salt and potassium salt; alkaline earth metal salts such as calcium salt, magnesium salt and barium salt; and aluminum salt. Suitable examples of the salt with an organic base include salts with trimethylamine, triethylamine, pyridine, picoline, 2,6-lutidine, ethanolamine, diethanolamine, triethanolamine, cyclohexylamine, dicyclohexylamine, and N,N'-dibenzylethylenediamine. Suitable examples of the metal with an inorganic acid include salts with hydrochloric acid, hydrobromic acid, nitric acid, sulfuric acid, and phosphoric acid. Suitable examples of the salt with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, and p-toluenesulfonic acid. Suitable examples of the salt with a basic amino acid include salts with arginine, lysine and ornithine, and suitable examples of the salt with an acidic amino acid include salts with aspartic acid and glutamic acid. Among them, preferable are pharmaceutically acceptable salts. For example, when an acidic functional group is included in the compound, examples thereof include inorganic salts such as alkali metal salts (for example, sodium salt, potassium salt) and alkaline earth metal salts (for example, calcium salt, magnesium salt, barium salt), ammonium salt and the like, and when a basic functional group is included in the compound, examples thereof include salts with inorganic acids such as hydrochloric acid, hydrobromic acid, nitric acid, sulfuric acid and phosphoric acid, or salts with organic acids such as acetic acid, phthalic acid, fumaric acid, oxalic acid, tartaric acid, maleic acid, citric acid, succinic acid, methanesulfonic acid, and p-toluenesulfonic acid.

When compound (I) has isomers such as tautomers, enantiomers, stereoisomers, regioisomers and rotamers, either one of isomers and a mixture thereof are both encompassed in the inventive compound. Furthermore, when compound (I) has enantiomers, an enantiomer resolved from the racemate is also encompassed in compound (I).

Compound (I) may be a crystal, and whether it has only one crystal form or a mixture of crystal forms, it is encompassed in compound (I).

Compound (I) may be a pharmaceutically acceptable cocrystal or cocrystal salt. Here, the cocrystal or cocrystal salt means a crystalline material composed of two or more unique solids at room temperature, each solid having different physical properties (for example, structure, melting point, heat of fusion, hygroscopicity, solubility and stability). The cocrystal or cocrystal salt can be produced by cocrystallization methods known per se.

Compound (I) may be a solvate (for example, hydrate) or a non-solvate (for example, non-hydrate), and either is encompassed in compound (I).

Further, deuterated products obtained by replacing $^1$H with $^2$H(D) is also encompassed in compound (1).

Compounds labeled or substituted with an isotope (for example, $^3$H, $^{11}$C, $^{14}$C, $^{18}$F, $^{35}$S, $^{125}$I) or the like are also encompassed in compound (I). For example, compounds labeled or substituted with an isotope can be used as a tracer for use in positron emission tomography (PET) (PET tracer), and can be useful in fields such as medical diagnosis.

Hereinafter, a method of producing the inventive compound will be described.

Ingredients and reagents used in each step of the following production method, and obtained compounds may be in their salt forms. Examples of such salts include salts or the like that are the same as salts of the inventive compound mentioned above.

When a compound obtained in each step is a free compound, it can be transformed into a salt of interest by a method known per se. On the other hand, when a compound obtained in each step is a salt, it can be transformed into a free form or another salt of interest by a method known per se.

A compound obtained in each step can remain a reaction solution or be used for next reaction after being obtained as a crude product. Alternatively, a compound obtained in each step can be, in accordance with a normal method, isolated and/or purified from a reaction mixture by separating means such as concentration, crystallization, distillation, solvent extraction, fractional distillation, and chromatography. A racemic compound can be separated into chiral compounds using a chiral column for purification.

When ingredients and reagent compounds for each step are commercially available, commercial products can be used as they are.

In reaction of each step, reaction time may be different depending on reagents and solvents to be used, but it is normally 1 minute to 7 days, and preferably 10 minutes to 8 hours if there is no particular description.

In reaction of each step, reaction temperature may be different depending on reagents and solvents to be used, but it is normally −78° C. to 300° C., and preferably −78° C. to 150° C. if there is no particular description.

In reaction of each step, pressure may be different depending on reagents and solvents to be used, but it is normally 1 atm to 20 atm, and preferably 1 atm to 3 atm if there is no particular description.

In reaction of each step, for example, a microwave synthesis apparatus may be used such as Initiator manufactured by Biotage. Reaction temperature may be different depending on reagents and solvents to be used, but it is normally room temperature to 300° C., and preferably 50° C. to 250° C. if there is no particular description. Reaction time may be different depending on reagents and solvents to be used, but it is normally 1 minute to 48 hours, and preferably 1 minute to 8 hours if there is no particular description.

In reaction of each step, a reagent is used in an amount of 0.5 equivalent to 20 equivalent, and preferably 0.8 equivalent to 5 equivalent relative to a substrate if there is no particular description. When a reagent is used as a catalyst, the reagent is used in an amount of 0.001 equivalent to 1 equivalent, and preferably 0.01 equivalent to 0.2 equivalent relative to a substrate. When a reagent also acts as a reaction solvent, the reagent is used in a solvent amount.

In reaction of each step, that reaction is carried out with no solvent, or in a dissolved or suspended state in an appropriate solvent if there is no particular description. Specific examples of the solvent include solvents described in Examples, or the following: alcohols: methanol, ethanol, tert-butyl alcohol, 2-methoxyethanol and the like;
ethers: diethyl ether, diphenyl ether, tetrahydrofuran, 1,2-dimethoxyethane and the like, cyclopentyl methyl ether;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, dichloroethane, carbon tetrachloride and the like;
nitriles: acetonitrile and the like;
sulfoxides: dimethylsulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; and water.

Two or more of the solvents described above may be mixed in an appropriate proportion for use.

When a base is used in reaction of each step, for example, bases shown below or bases described in Examples are used: inorganic bases: sodium hydroxide, potassium phosphate, sodium phosphate, potassium hydroxide, magnesium hydroxide, sodium carbonate, calcium carbonate, cesium carbonate, sodium bicarbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, potassium trimethylsilanolate and the like;
metal alkoxides; sodium ethoxide, potassium tert-butoxide and the like;
alkali metal hydrides: sodium hydride and the like;
metal amides: sodium amide, lithium diisopropylamide, lithium hexamethyldisilazide and the like; and
organic lithiums: n-butyllithium and the like.

When an acid or an acidic catalyst is used in reaction of each step, for example, acids or acidic catalysts shown below, or acids or acidic catalysts described in Examples are used: inorganic acids: hydrochloric acid, sulfuric acid, nitric acid, hydrobromic acid, phosphoric acid and the like;
organic acids: acetic acid, trifluoroacetic acid, citric acid, 7-toluenesulfonic acid, 10-camphorsulfonic acid and the like; and
Lewis acids: boron trifluoride-diethyl ether complex, zinc iodide, anhydrous aluminum chloride, anhydrous zinc chloride, titanium chloride, anhydrous iron chloride and the like.

Reaction of each step is carried out in accordance with a method known per se, for example, methods described in The Fifth Series of Experimental Chemistry, vol. 13 to 19 (edited by The Chemical Society of Japan); The New Experimental Chemistry, vol. 14 to 15 (edited by The Chemical Society of Japan); Fine Organic Chemistry, Revised 2nd Edition (L. F. Tietze, Th. Eicher, Nankodo); Organic Name Reactions; The Reaction Mechanism and Essence, Revised Edition (Hideo Togo, Kodansha); ORGANIC SYNTHESES Collective Volume I to VII (John Wiley & Sons Inc.); Modern Organic Synthesis in the Laboratory A Collection of Standard Experimental Procedures (written by Jie Jack Li, published by OXFORD UNIVERSITY); Comprehensive Heterocyclic Chemistry III, Vol. 1 to Vol. 14 (Elsevier, Inc.); Strategic Applications of Named Reactions in Organic Synthesis (translated by Kiyoshi Tomioka, issued by Kagakudojin); Comprehensive Organic Transformations (VCH Publishers Inc.), issued in 1989; and the like, or methods described in Examples.

When hydrolysis reaction is carried out in each step, an acid or a base is used as a reagent. In addition, when acid hydrolysis reaction for a tert-butyl ester is carried out, formic acid, triethylsilane or the like may be added in order to reductively trap a secondarily produced tert-butyl cation.

When esterification reaction, amidation reaction, or ureation reaction is carried out in each step, examples of the reagent to be used include acyl halide forms such as acid chlorides and acid bromides; and activated carboxylic acids in the form of acid anhydride, active ester, sulfuric ester or the like. Examples of the activator for a carboxylic acid include carbodiimide-based condensing agents such as 1-ethyl-3-(3-dimethylaminopropyl)carbodiimide hydrochloride (WSCD); triazine-based condensing agents such as 4-(4,6-dimethoxy-1,3,5-triazin-2-yl)-4-methylmorpholinium chloride-n-hydrate (DMT-MM); carbonate ester-based condensing agents such as 1,1-carbonyldiimidazole (CDI); diphenylphosphoryl azide (DPP A); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate; 0-(7-azabenzotriazol-1-yl)-N,N,N',N'-tetramethyluronium hexafluorophosphate (HATU); 1-[bis(dimethylamino)methylene]-1H-benzotriazolium 3-oxide tetrafluoroborate (TBTU); sulfuric acid; and a combination thereof. When a carbodiimide-based condensing agent is used, additives such as 1-hydroxybenzotriazole (HOBt), N-hydroxysuccinimide (HOSu) and dimethylaminopyridine (DMAP) may be further added to the reaction.

When alkylation reaction is carried out in each step, used are an electrophile such as a halogenated alkyl or an optionally substituted sulfonyloxy group (for example, methanesulfonyloxy, ethanesulfonyloxy, trifluoromethanesulfonyloxy, benzenesulfonyloxy, p-toluenesulfonyloxy and the like), and a nucleophile (for example, amine, alcohol, active methylene compound adjacent to an electroattracting group and the like) and a base (for example, organic base, metal alkoxide, inorganic base and the like) as reagents. In addition, the alkylation can also be carried out, after transforming an alcohol into an active ester, in the presence of a silyl enol ether and an acid such as 1,1,1-trifluoro-N-[(trifluoromethyl)sulfonyl]methanesulfonamide. Moreover, the alkylation can also be carried out in the presence of an alcohol, a silyl enol ether and a Lewis acid.

In each step, protection or deprotection reaction of a functional group is carried out in accordance with a method known per se, for example, methods described in "Protective Groups in Organic Synthesis, 4th Ed." (written by Theodora W. Greene, Peter G. M. Wuts), Wiley-Interscience, issued in 2007; "Protecting Groups 3rd Ed." (written by P. J. Kocienski), Thieme, issued in 2004; and the like, or methods described in Examples.

Examples of the protecting group of a hydroxy group of alcohol and the like and a phenolic hydroxy group include ether protecting groups such as methoxymethyl ether, benzyl ether, tert-butyldimethylsilyl ether and tetrahydropyranyl ether; carboxylate ester protecting groups such as acetate ester; sulfonate ester protecting groups such as methanesulfonate ester; and carbonate ester protecting groups such as tert-butylcarbonate.

Examples of the protecting group of a carbonyl group of aldehyde include acetal protecting groups such as dimethyl acetal; and cyclic acetal protecting groups such as 1,3-dioxane.

Examples of the protecting group of a carbonyl group of ketone include ketal protecting groups such as dimethyl ketal; cyclic ketal protecting groups such as 1,3-dioxane; oxime protecting groups such as O-methyloxime; and hydrazone protecting groups such as N,N-dimethylhydrazone.

Examples of the protecting group of a carboxyl group include ester protecting groups such as methyl ester; and amide protecting groups such as N,N-dimethylamide.

Examples of the protecting group of thiol include ether protecting groups such as benzyl thioether; and ester protecting groups such as thioacetate ester, thiocarbonate and thiocarbamate.

Examples of the protecting group of an amino group and an aromatic heterocycle such as imidazole, pyrrole and indole include carbamate protecting groups such as benzyl carbamate and tert-butylcarbamate; amide protecting groups such as acetamide; alkylamine protecting groups such as N-triphenylmethyl amine; and sulfonamide protecting groups such as methanesulfonamide.

The protecting group can be removed by a method known per se, for example, a method using acid, base, ultraviolet light, hydrazine, phenylhydrazine, sodium N-methyldithiocarbamate, tetrabutylammonium fluoride, palladium acetate or trialkylsilyl halide (for example, trimethylsilyl iodide, trimethylsilyl bromide), a reduction method, and the like. Upon transforming an alkyl ester compound into a carboxylic acid compound, the transformation can be carried out using a strong base (potassium trimethylsilanolate), hydrogen-palladium catalyst, or zerovalent palladium catalyst.

When coupling reaction is carried out in each step, examples of the metal catalyst to be used
include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0) and 1,1'-bis(diphenylphosphino)ferrocene palladium(II) chloride; nickel compounds such as tetrakis(triphenylphosphine)nickel(0); rhodium compounds such as chloro(1,5-cyclooctadiene)rhodium(I) (dimer) and tris(triphenylphosphine)rhodium(III) chloride; cobalt compounds; copper compounds such as copper oxide and copper(I) iodide; and platinum compounds. In addition, a phosphine ligand may be added to the reaction, and examples of such a phosphine include triphenylphosphine, 1,1'-bis(diphenylphosphino)ferrocene, and tri-o-tolylphosphine. Further, a base may be added to the reaction, and examples of such a base include organic bases, inorganic bases and the like.

When boration reaction is carried out in each step, examples of the metal catalyst to be used include palladium compounds such as tetrakis(triphenylphosphine)palladium (0), tris(dibenzylideneacetone)dipalladium(0) and 1,1'-bis(diphenylphosphino)ferrocene palladium(II) chloride. Further, a base may be added to the reaction, and examples of such a base include organic bases, inorganic bases and the like. In addition, examples of the boron source include pinacol diborane. Moreover, a borate ester group can be transformed into a boric acid group using ammonium acetate and sodium periodate as reagents.

When cyanation reaction is carried out in each step, examples of the metal catalyst to be used include palladium compounds such as palladium acetate, tetrakis(triphenylphosphine)palladium(0), tris(dibenzylideneacetone)dipalladium(0) and 1,1'-bis(diphenylphosphino)ferrocene palladium(II) chloride; and cyanides such as sodium cyanide, zinc cyanide and copper cyanide. In addition, a phosphine ligand such as 1,1'-bis(diphenylphosphino)ferrocene or zinc powder may be added to the reaction.

Compound (I) can be produced by, for example, the following method.

Production Method 1

Compound (Ia), compound (Ib) and compound (Ic), in which $R^1$ of compound (I) is a hydroxy group, ORy and NHRy, respectively, can be produced by the following method.

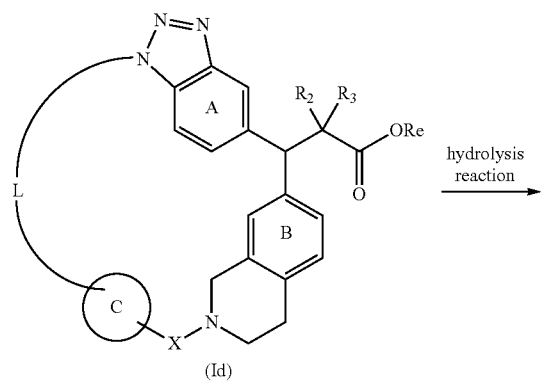

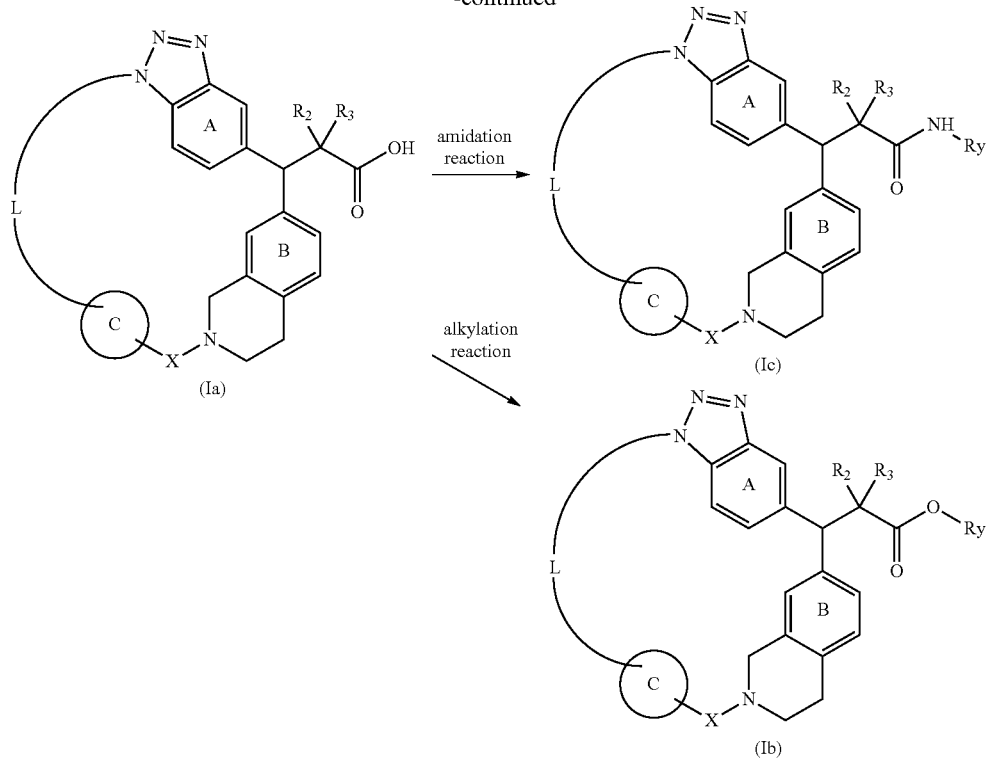

wherein Re represents an optionally substituted $C_{1-6}$ alkyl group (for example, methyl, ethyl, propyl, isopropyl, butyl, tert-butyl), allyl group or benzyl group, and the other symbols are as defined above.

Production Method 2

Compound (Ie), in which X of compound (Id) is C(=O), can be produced by the following method.

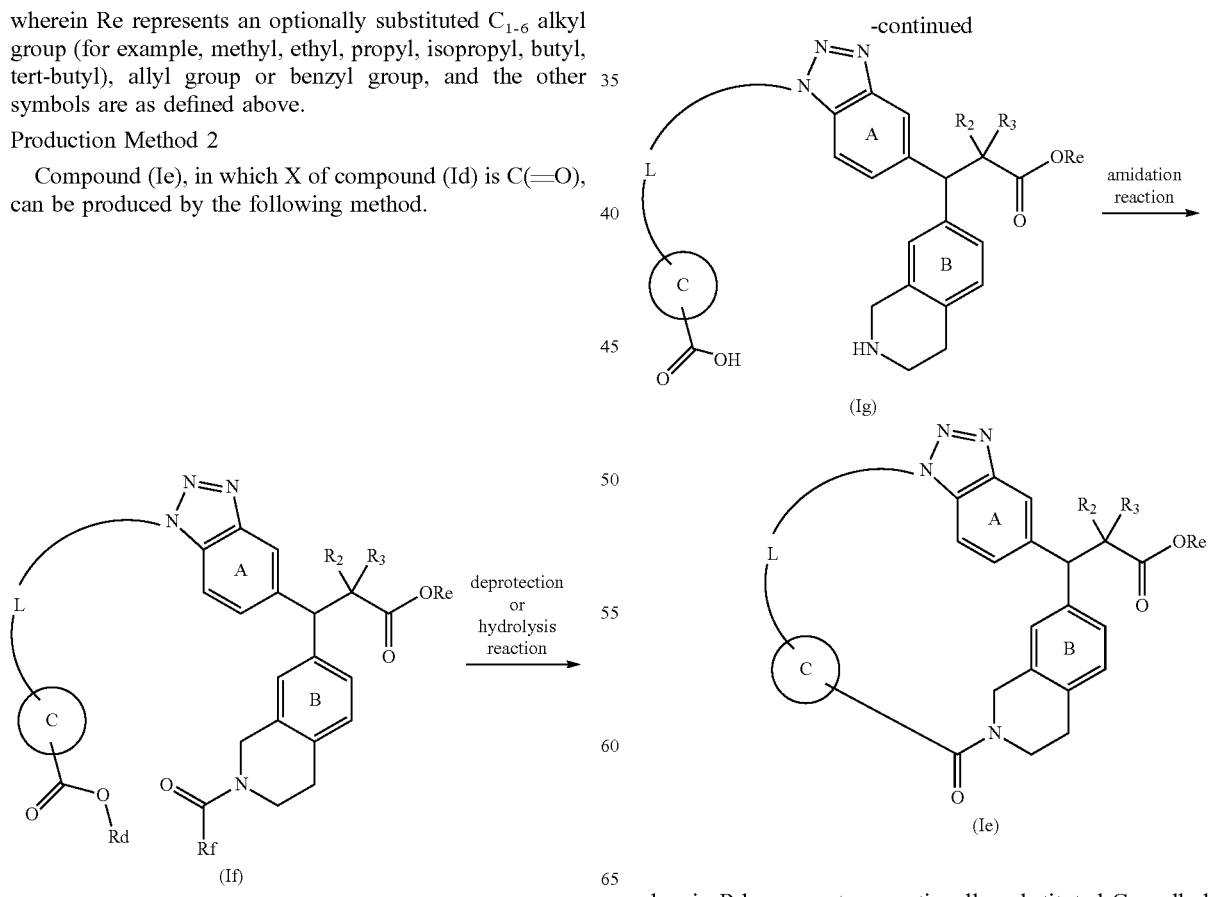

wherein Rd represents an optionally substituted $C_{1-6}$ alkyl group (for example, methyl, ethyl, propyl, isopropyl, butyl, tert-butyl), allyl group or benzyl group; Rf represents a tert-butoxy group or benzyloxy group; and the other symbols are as defined above.
Production Method 3
Compound (Ii), in which $R^2$ and $R^3$ of compound (If) are hydrogen, can be produced by the following method.
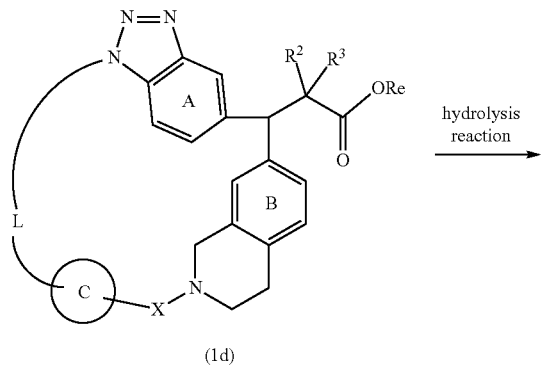
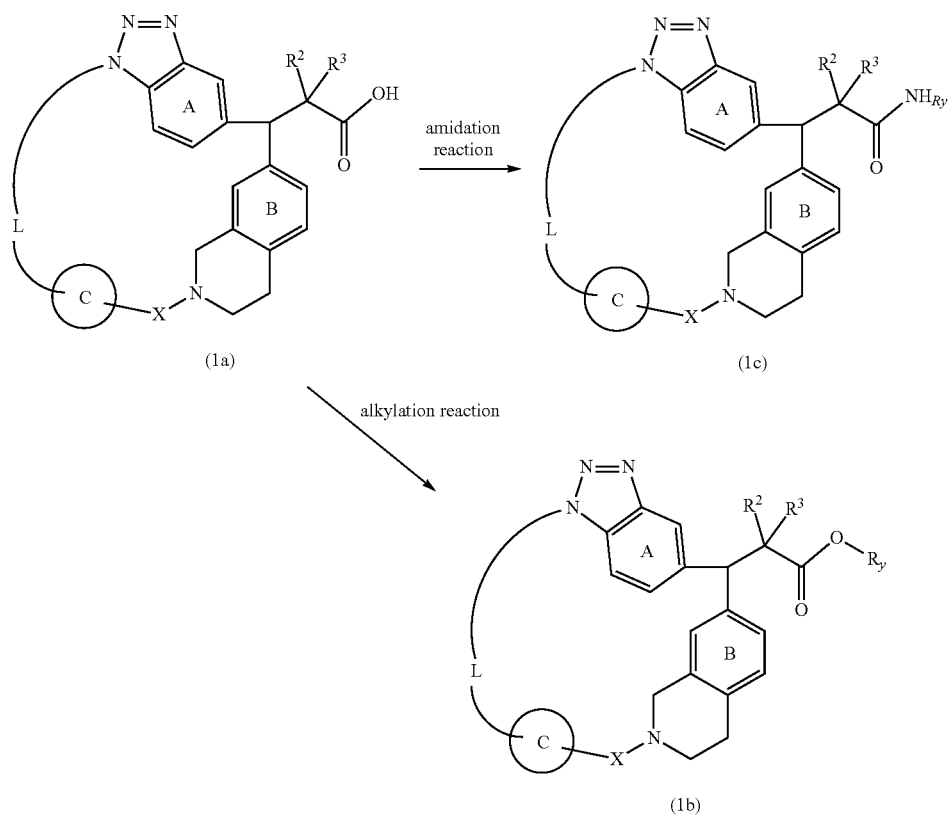

wherein XI represents a chlorine atom, a bromine atom, a iodine atom, an optionally substituted sulfonyloxy group (for example, methanesulfonyloxy, ethanesulfonyloxy, hydrolysis trifluoromethanesulfonyloxy, benzenesulfonyloxy, p-toluenesulfonyloxy and the like); B1 represents a boron group (for example, potassium trifluoroborate (—BF$_3$K), boronic acid group (—B(OH)$_2$), borate ester group (—B(OR')$_2$, wherein R' represents a C$_{1-6}$ alkyl group) or cyclic group thereof (for example, 4,4,5,5-tetramethyl-1,3,2-dioxaborolan-2-yl and the like); and the other symbols are as defined above.

Production Method 4

Compound (II) can be produced by the following method.

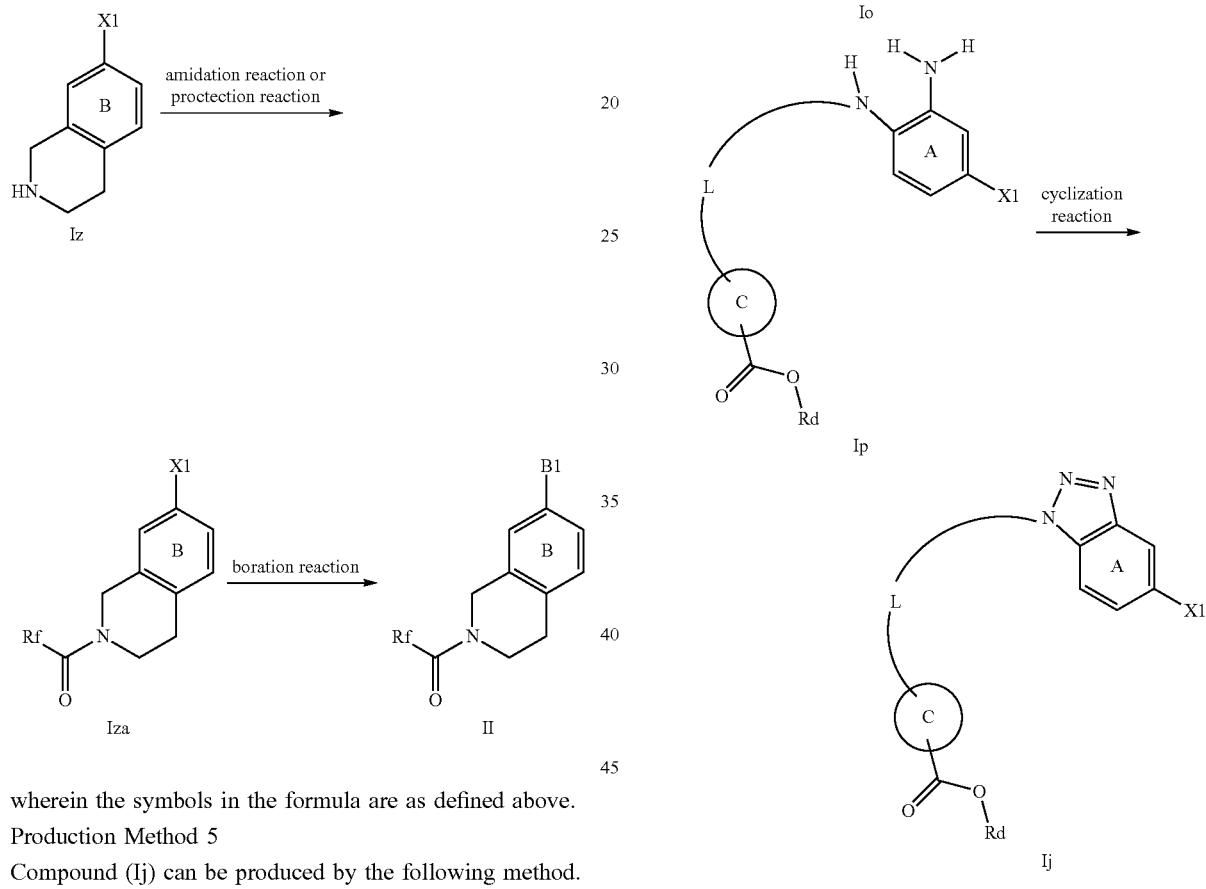

wherein the symbols in the formula are as defined above.

Production Method 5

Compound (Ij) can be produced by the following method.

wherein the symbols in the formula are as defined above.

Production Method 6

Compound (Iq), in L of compound (Ij) is —CR$^4$R$^5$—CR$^4$R$^5$—CR$^4$R$^5$—O—CR$^6$R$^7$—*, can be produced by the following method.

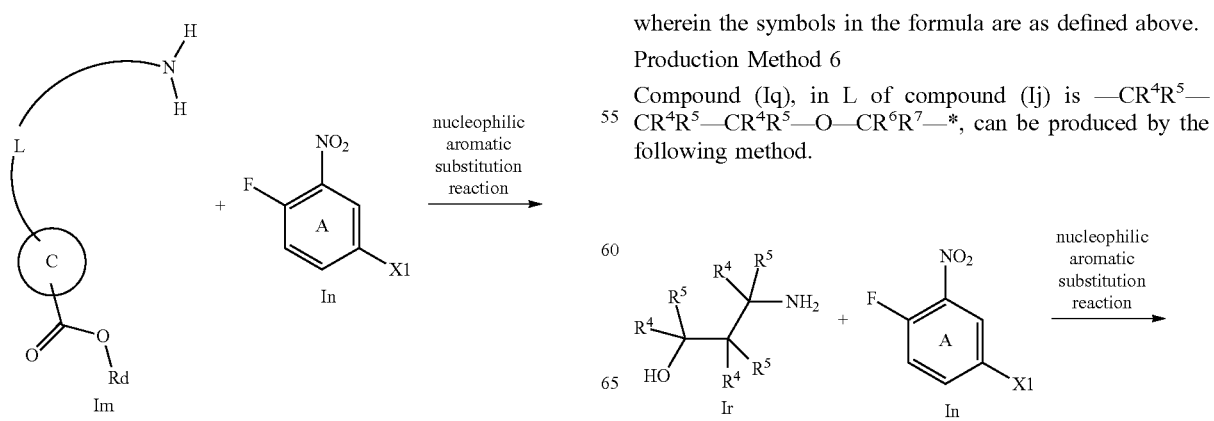

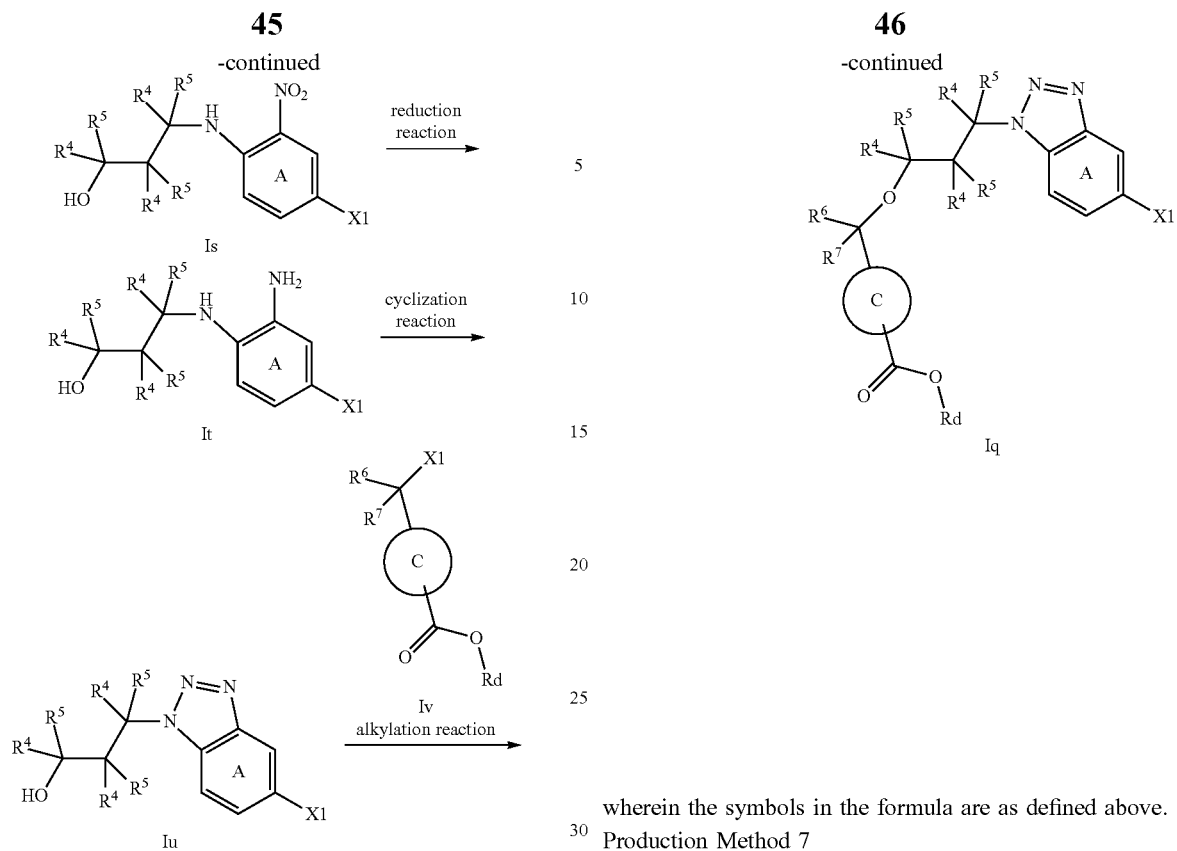
wherein the symbols in the formula are as defined above.
Production Method 7
Compound (If) can be produced by the following method.
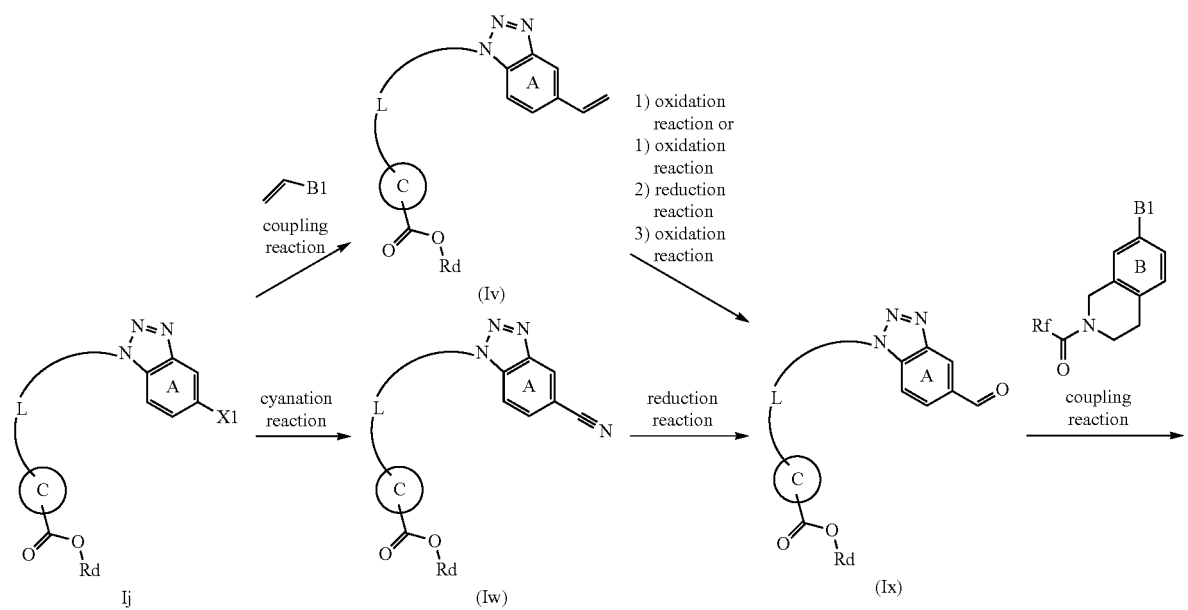

-continued

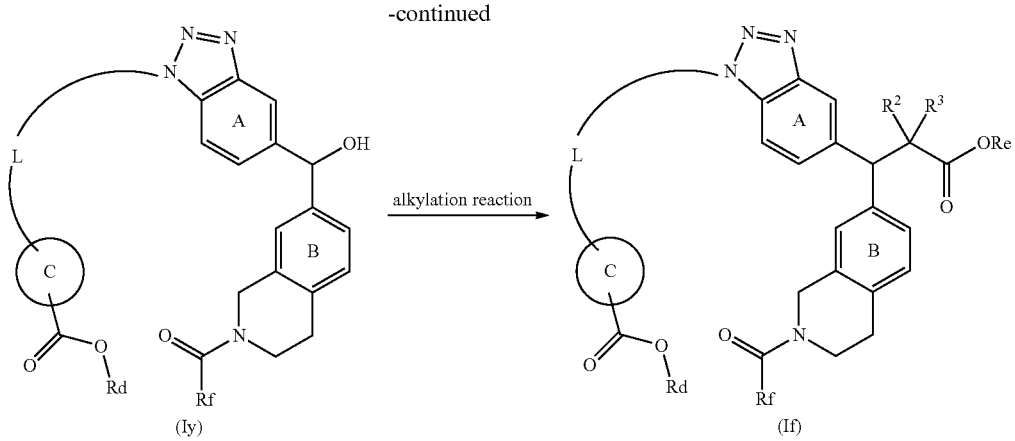

(Iy) alkylation reaction (If)

wherein the symbols in the formula are as defined above.

In addition, in a step of producing compound (I) from ingredient compounds and/or production intermediates of compound (1), compound (1) can be synthesized, if desired, by singly carrying out reduction reaction, oxidation reaction, Wittig reaction, Homer-Emmons reaction, protection reaction, nucleophilic aromatic substitution reaction, nucleophilic addition reaction with carbanion, Grignard reaction, azidation reaction, reductive animation reaction, Claisen rearrangement reaction, Mitsunobu reaction, Wohl-Ziegler reaction, sulfonate esterification reaction, Staudinger reaction, halogenation reaction of hydroxy group, dehydration reaction, cyclization reaction or ring-closing metathesis reaction, or by carrying out two or more of them in combination, depending on various substituents that compound (I) may have.

When reduction reaction is carried out in each step, examples of the reducing agent to be used include iron; metal hydrides such as lithium aluminum hydride, sodium triacetoxyborohydride, sodium cyanoborohydride, diisobutylaluminium hydride (DIBAL-H), sodium borohydride and tetramethylammonium triacetoxyborohydride; boranes such as borane tetrahydrofuran complex; Raney nickel; Raney cobalt; Pd/C; $PtO_2$; zinc; hydrogen; formic acid; and triethylsilane. When a carbon-carbon double bond or triple bond is reduced, the reduction reaction may be carried out by a method using a catalyst such as palladium-carbon, Lindlar catalyst and the like. When a nitro group is reduced, the reduction reaction may also be carried out by using iron and ammonium chloride. When a cyano group is reduced, the reduction reaction may also be carried out by using the reducing agents described above and sodium phosphinate. When a carboxylic acid is reduced, the reduction reaction may also be carried out by, after making a mixed acid anhydride with isobutyl chloroformate or the like, using sodium borohydride. This step can be carried out by using only one of the reagents, or by using two or more of them in combination.

When oxidation reaction is carried out in each step, examples of the oxidizing agent to be used include peracids such as m-chloroperbenzoic acid (mCPBA), hydrogen peroxide and tert-butyl hydroperoxide; perchlorates such as tetrabutylammonium perchlorate; chlorates such as sodium chlorate; chlorites such as sodium chlorite; periodates such as sodium periodate; high valent iodine reagents such as iodosylbenzene; reagents having manganese such as manganese dioxide and potassium permanganate; leads such as lead tetraacetate; reagents having chromium such as pyridinium chlorochromate (PCC), pyridinium dichromate (PDC) and Jones reagent; halogen compounds such as N-bromosuccinimide (NBS); oxygen; ozone; sulfur trioxide-pyridine complex; oxalyl chloride-dimethylsulfoxide; osmium tetroxide; selenium dioxide; and 2,3-dichloro-5,6-dicyano-1,4-benzoquinone (DDQ).

When Wittig reaction is carried out in each step, examples of the Wittig reagent to be used include alkylidene phosphoranes. Alkylidene phosphoranes can be prepared by a method known per se, for example, by allowing a phosphonium salt to react with a strong base.

When Homer-Emmons reaction is carried out in each step, examples of the reagent to be used include phosphonoacetate esters such as methyl dimethylphosphonoacetate and ethyl diethylphosphonoacetate; and bases such as alkali metal hydrides and organic lithiums.

When nucleophilic aromatic substitution reaction is carried out in each step, for the reagent, a nucleophile (for example, an amine) and a base (for example, an inorganic base, an organic base and the like) are used.

When nucleophilic addition reaction with carbanion, nucleophilic 1,4-addition reaction with carbanion (Michael addition reaction) or nucleophilic substitution reaction with carbanion is carried out in each step, examples of the base to be used for generating carbanion include organic lithiums, metal alkoxides, inorganic bases, and organic bases.

When Grignard reaction is carried out in each step, examples of the Grignard reagent include aryl magnesium halides such as phenyl magnesium bromide; and alkyl magnesium halides such as methyl magnesium bromide. The Grignard reagent can be prepared by a method known per se, for example, by allowing an alkyl halide or an aryl halide to react with a metal magnesium in ether or tetrahydrofuran as a solvent.

When azidation reaction of an alcohol, an alkyl halide or a sulfonate ester is carried out in each step, examples of the azidation agent to be used include diphenylphosphoryl azide (DPPA), trimethylsilyl azide and sodium azide. For example, when an alcohol is azidated, the azidation reaction may be carried out by a method using diphenylphosphoryl azide and 1,8-diazabicyclo[5,4,0]undec-7-ene (DBU), a method using trimethylsilyl azide and a Lewis acid, or the like.

When reductive animation reaction is carried out in each step, examples of the reducing agent to be used include sodium triacetoxyborohydride, sodium cyanoborohydride, hydrogen and formic acid. When the substrate is an amine compound, examples of the carbonyl compound to be used include, in addition to paraformaldehyde, aldehydes such as acetaldehyde and ketones such as cyclohexanone. When the substrate is a carbonyl compound, examples of the amine to be used include ammonia; primary amines such as methylamine; and secondary amines such as dimethylamine.

When Mitsunobu reaction is carried out in each step, azodicarboxylate esters (for example, diethyl azodicarboxylate (DEAD), diisopropyl azodicarboxylate (DIAD) and the like) and triphenylphosphine are used as reagents.

When Wohl-Ziegler reaction is carried out in each step, examples of the halogenating agent to be used include N-iodosuccinimide, N-bromosuccinimide (NBS), N-chlorosuccinimide (NCS), bromine and sulfuryl chloride. Further, the reaction can be accelerated by adding heat, light, radical initiators such as benzoyl peroxide and azobisisobutyronitrile to the reaction.

When halogenation reaction of hydroxy group is carried out in each step, examples of the halogenating agent to be used include a hydrohalic acid and an acid halide of an inorganic acid; specifically, hydrochloric acid, thionyl chloride and phosphorus oxychloride for chlorination, and 48% hydrobromic acid for bromination. In addition, a method of obtaining an alkyl halide form from an alcohol through the action between triphenylphosphine and carbon tetrachloride, carbon tetrabromide or the like may be used. Alternatively, a method of synthesizing an alkyl halide form over the course of two-step reaction including converting an alcohol into a sulfonate ester, and allowing it to react with lithium bromide, lithium chloride or sodium iodide may also be used.

When sulfonate esterification reaction is carried out in each step, examples of the sulfonylating agent to be used include methanesulfonyl chloride, p-toluenesulfonyl chloride, methanesulfonic anhydride and p-toluenesulfonic anhydride.

When dehydration reaction is carried out in each step, examples of the dehydrating agent to be used include sulfuric acid, phosphorus pentaoxide, phosphorus oxychloride, N,N'-dicyclohexylcarbodiimide, alumina and polyphosphoric acid.

When cyclization reaction is carried out in each step, sodium nitrite is used as a reagent, and an acidic solvent such as acetic acid and hydrochloric acid is used as a solvent.

When Staudinger reaction is carried out in each step, examples of the reagent include phosphines such as triphenylphosphine and water.

When ring-closing metathesis reaction is carried out in each step, for the metal catalyst to be used, a ruthenium compound such as Grubbs 1st-generation catalyst, Grubbs 2nd-generation catalyst and Grubbs-Hoveyda 2nd-generation catalyst is used.

When Claisen rearrangement reaction is carried out in each step, the reaction can be carried out by heating a reaction solution formed of the ingredients and solvent.

When nucleophilic addition reaction with carbanion, nucleophilic 1,4-addition reaction with carbanion (Michael addition reaction) or nucleophilic substitution reaction with carbanion is carried out in each step, examples of the base to be used for generating carbanion include organic lithiums, metal alkoxides, inorganic bases, and organic bases.

Ingredient compounds and/or production intermediates of compound (I) may be in the salt forms, and although they are not particularly limited as long as the reaction is achieved, for example, salts and the like are used that are the same as salts that compound (I) and the like may form.

In the ingredient compounds and/or production intermediates of compound (I), configurational isomers (E, Z forms) may be generated, and at the time point where configurational isomers (E, Z forms) are generated, they can be isolated and purified by normal separating means such as extraction, recrystallization, distillation and chromatography to produce a pure compound. In addition, isomerization of the double bond can be advanced through heating, an acid catalyst, a transition metal complex, a metal catalyst, a radical species catalyst, photoirradiation, a strong base catalyst or the like to obtain a corresponding pure isomer in accordance with the methods described in The New Experimental Chemistry, vol. 14 (edited by The Chemical Society of Japan), pp. 251 to 253; The Fourth Series of Experimental Chemistry, vol. 19 (edited by The Chemical Society of Japan), pp. 273 to 274, and methods equivalent thereto. When a target compound is obtained in the free form through the reactions described above, it may be transformed into a salt in accordance with a normal method, and when a target compound is obtained in the form of salt, it can be transformed into a free form or another salt in accordance with a normal method. Compound (I) obtained as such can be isolated or purified from the reaction solution by any known means, for example, solvent transition, concentration, solvent extraction, fractional distillation, crystallization, recrystallization, chromatography or the like.

Compound (I) obtained as such, other reaction intermediates and ingredient compounds thereof can be isolated or purified from the reaction mixture in accordance with a method known per se, for example, by using a means such as extraction, concentration, neutralization, filtration, distillation, recrystallization, column chromatography, thin layer chromatography, preparative high performance liquid chromatography (preparative HPLC) and moderate pressure preparative liquid chromatography (moderate pressure preparative LC).

Compound (I) may be in the form of salt, and a salt of compound (I) can be produced according to a method known per se. For example, when compound (I) is a basic compound, it can be produced by adding an inorganic acid or organic acid, or when compound (I) is an acidic compound, it can be produced by adding an organic base or inorganic base.

When compound (I) is a solvate (for example, hydrate), a solvate of the target compound can be isolated from the reaction mixture by various methods such as distillation and crystallization after allowing the ingredient compounds to react in an appropriate solvent. A non-solvate can be produced by desolvation transition of a solvate through temperature rising, drying or the like. When compound (I) may have enantiomers, individual enantiomers and a mixture thereof are of course all encompassed in the scope of the present invention, and these isomers may be subjected to optical resolution or may be produced individually, in accordance with a method known per se, if desired.

When compound (I) is present as configurational isomers, diastereomers, conformers or the like, they can be isolated in accordance with the separation or purification means described above, if desired. In addition, when compound (I) is a racemate, it can be isolated into S-form and R-form in accordance with a normal optical resolution means.

When compound (I) has stereoisomers, the present invention encompasses a single stereoisomer and a mixture thereof.

Compound (I) may be a prodrug. The prodrug refers to a compound that is converted into compound (I) as a result of reaction with an enzyme, gastric acid or the like under physiological conditions in vivo, that is, a compound that undergoes enzymatic oxidation, reduction, hydrolysis or the like to be converted into compound (I) and a compound that undergoes hydrolysis or the like by gastric acid or the like to be converted into compound (I).

Examples of the prodrug for compound (I) include compounds with an amino group in compound (I) acylated, alkylated and phosphorylated (for example, compounds with an amino group in compound (I) eicosanoylated, alanylated, pentylaminocarbonylated, (5-methyl-2-oxo-1,3-dioxolen-4-yl)methoxycarbonylated, tetrahydrofuranylated, pyrrolidyl-methylated, pivaloyloxymethylated, tert-butylated and the like); compounds with a hydroxyl group in compound (I) acylated, alkylated, phosphorylated and borated (for example, compounds with a hydroxy group in compound (I) acetylated, palmitoylated, propanoylated, pivaloylated, succinylated, fumarylated, alanylated, dimethylaminomethyl-carbonylated and the like); and compounds with a carboxyl group in compound (I) esterified and amidated (for example, compounds with a carboxyl group in compound (I) ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified, methylamidated and the like). These compounds can be produced from compound (I) according to a known method. In addition, a prodrug of compound (I) may also be one that is converted into compound (I) under physiological conditions as described in "Pharmaceutical Research and Development", vol. 7, Design of Molecules, pp. 163-198, issued in 1990 by HIROKAWA SHOTEN.

Compound (I) or a prodrug thereof (hereinafter, may be simply abbreviated as the inventive compound) can have an excellent NRF2 activating activity in vivo, and can be useful as a preventive or therapeutic agent for diseases associated with oxidative stress.

The inventive compound is expected to be excellent in pharmacokinetics (for example, oral absorbability, drug half-life in blood, intracerebral transferability, metabolic stability) and have low toxicity (for example, acute toxicity, chronic toxicity, genetic toxicity, reproductive toxicity, cardiotoxicity, drug interaction, carcinogenicity), and can be safely administered orally or parenterally to a mammal (for example, human, monkey, cattle, horse, pig, mouse, rat, hamster, rabbit, cat, dog, sheep, goat) as a medicament with no change or as a pharmaceutical composition formed by mixing the inventive compound with a pharmaceutically acceptable carrier or the like. Examples of the "parenteral" administration include sublingual, intravenous, intramuscular, subcutaneous, intraorgan, intranasal, intradermal, instillation, intracerebral, intrarectal, intravaginal, intraperitoneal and intratumor administrations, administration to the vicinity of tumor and the like, and direct administration to the lesion.

It is believed that the inventive compound has a fixed conformation because it has a macrocyclic structure, and has an excellent NRF2 activating activity, and therefore, it can exhibit effectiveness in prevention or treatment for diseases associated with oxidative stress and caused by oxidative stress, such as hepatic disease (for example, hepatitis (for example, non-alcoholic steatohepatitis, fatty liver, alcoholic hepatitis, hepatitis B, hepatitis C, hepatic veno-occlusive disease), hepatic cirrhosis, bile duct disease (for example, primary sclerosing cholangitis (PSC)), cardiovascular disease (for example, heart failure, pulmonary arterial hypertension, myocardial infarction, arteriosclerosis, angina pectoris, brain infarction, cerebral hemorrhage, aortic aneurysm, aortic dissection, nephrosclerosis (for example, hypertensive nephrosclerosis), peripheral arterial disease (PAD), arteriosclerosis obliterans, dysrhythmia), lung disease (for example, chronic obstructive pulmonary disease (COPD), idiopathic pulmonary fibrosis (IPF), cystic fibrosis, asthma, pneumonia, aspiration pneumonia, interstitial pneumonia, respiratory infection, acute lung injury, acute respiratory distress syndrome (ARDS), al-antitrypsin deficiency), kidney disease (for example, chronic kidney disease (CKD), diabetic kidney disease (DKD), acute kidney injury (AKI), glomerular nephritis, pyelonephritis, interstitial nephritis, glomerulosclerosis, nephrotic syndrome, lupus nephritis, Alport syndrome, IgA nephropathy, polycystic kidney), central nervous system disease (for example, Parkinson's disease, Alzheimer's disease, dementia, cerebral stroke, amyotrophic lateral sclerosis (ALS), spinocerebellar degeneration (SCD), polyglutamine disease, prion disease, Huntington's disease, traumatic brain injury, epilepsy, autism, depression, adrenoleukodystrophy), mitochondrial disease (for example, Friedreich motor ataxia, mitochondrial myopathy), inflammatory disease (for example, multiple sclerosis, chronic rheumatism, systemic lupus erythematosus, Sjoegren syndrome, scleroderma, autoimmune hepatitis, type 1 diabetes mellitus, ulcerous colitis, Crohn disease, inflammatory bowel disease (IBD), spondylarthritis, pollinosis, collagen disease), life style related disease (for example, diabetes mellitus, hyperlipidemia, obesity, high blood pressure, hypercholesterolemia) and complication thereof (for example, diabetic retinopathy, DKD, diabetic neuropathy), sickle cell disease, thalassemia, anemia (for example, aplastic anemia, hemolytic anemia), cancer (for example, liver cancer, lung cancer, renal cancer, colon cancer, melanoma, medulloblastoma, neuroblastoma, leukemia), cachexia, gastrointestinal disease (for example, functional gastrointestinal disorder, gastric ulcer, reflux esophagitis, pancreatitis), endocrine disease (for example, Cushing syndrome, Hashimoto disease), eye disease (for example, age-related macular degeneration, corneal endothelial disorder, Fuchs endothelial corneal dystrophy (FECD), eye inflammation, ophthalmalgia, retinopathy of prematurity, cataract, dry eye), skin disease (for example, psoriasis, dermatitis, radiation dermatitis, epidermolysis bullosa, atopic dermatitis, stomatitis), wound healing failure, bone disease (for example, osteoporosis, systemic bone disease, bone fracture), viral infection (for example, HIV virus, cytomegalovirus, respiratory syncytial virus, influenza vims), heavy metal poisoning (for example, lead poisoning, mercury poisoning), pesticide poisoning (for example, paraquat poisoning, organophosphorus poisoning), drug-induced disorder (for example, drug-induced renal disorder, drug-induced hepatic disorder (for example, hepatic disorder due to acetaminophen), drug-induced lung disorder, orthopedic disease (for example, low back pain, sciatic neuralgia, intervertebral disk displacement, neck ache, stiff shoulder), pain (for example, fibromyalgia, neuropathic pain), ischemia-reperfusion injury and shock upon organ transplantation and surgery, aging, progeria, hyperanakinesia (for example, sarcopenia), urologic disease (for example, urination disorder), dental disease (for example, periodontal disease), otolaryngologic disease (for example, hearing difficulty), altitude sickness, chronic fatigue syndrome, and thinning hair. In addition, the inventive compound can exhibit enhancement of the effect of cancer treatment and the effect of improving survival rate by a combined use with an immunity anticancer agent (for example, immune checkpoint inhibiting antibody). Further, it can exhibit a regeneration promoting activity (for example, hepatic regeneration promoting agent after hepatectomy).

In particular, the inventive compound can be, based on its NRF2 activating activity, useful as a preventive or therapeutic agent for hepatic disease (for example, non-alcoholic steatohepatitis (NASH), alcoholic hepatitis, drug-induced hepatic disorder), bile duct disease (for example, primary sclerosing cholangitis (PSC)), cardiovascular disease (for example, heart failure or pulmonary arterial hypertension), lung disease (for example, chronic obstructive pulmonary disease (COPD)), kidney disease (for example, chronic kidney disease (CKD) or acute kidney injury (AKI)), acetaminophen poisoning, central nervous system disease (for example, Parkinson's disease, Alzheimer's disease, cerebral stroke), mitochondrial disease (for example, Friedreich motor ataxia, mitochondrial myopathy), inflammatory disease (for example, multiple sclerosis, inflammatory bowel disease (IBD)), sickle cell disease, or the like.

The dosage of the inventive compound varies depending on an administration route, symptom and the like. For example, for oral administration to a patient with hepatitis (adult, body weight 40 to 80 kg, for example, 60 kg), the dosage is, for example, 0.001 to 1000 mg/kg body weight/day, preferably 0.01 to 100 mg/kg body weight/day, and further preferably 0.1 to 10 mg/kg body weight/day. This amount can be administered in one to three portions per day.

A medicament containing the inventive compound may be used as the inventive compound solely or as a pharmaceutical composition formed by mixing the inventive compound with a pharmaceutically acceptable carrier in accordance with a method (for example, the methods described in The Pharmacopoeia of Japan) that is known per se as a method of producing a pharmaceutical formulation. The medicament containing the inventive compound can be safely administered orally or parenterally (for example, intravenous, intramuscular, subcutaneous, intraorgan, intranasal, intradermal, instillation, intracerebral, intrarectal, intravaginal and intraperitoneal administrations, and administration to the lesion) in the form of, for example, tablet (including sugar-coated tablet, film-coated tablet, sublingual tablet, orally disintegrating tablet, buccal or the like), pill, powder, granule, capsule (including soft capsule, microcapsule), troche, syrup, liquid, emulsion, suspension, release control formulation (for example, immediate-release formulation, sustained-release formulation, sustained-release microcapsule), aerosol, film (for example, orally disintegrating film, oral mucosa-adhesive film), injection (for example, subcutaneous injection, intravenous injection, intramuscular injection, intraperitoneal injection), drip infusion, transdermal absorption type formulation, ointment, lotion, patch, suppository (for example, rectal suppository, vaginal suppository), pellet, nasal formulation, pulmonary formulation (inhalant), eye drop or the like.

For the "pharmaceutically acceptable carrier" described above, a variety of organic or inorganic carriers that have been conventionally used as formulation materials (starting materials) are used. For example, an excipient, a lubricant, a binder, a disintegrant and the like are used for a solid formulation, and a solvent, a dissolving aid, a suspending agent, an isotonizing agent, a buffering agent, a soothing agent and the like are used for a liquid formulation. In addition, as necessary, formulation additives such as a preservative, an antioxidant, a colorant and a sweetening agent can also be used.

Examples of the excipient include lactose, white sugar, D-mannitol, starch, corn starch, crystalline cellulose and light anhydrous silicic acid.

Examples of the lubricant include magnesium stearate, calcium stearate, talc and colloidal silica.

Examples of the binder include crystalline cellulose, white sugar, D-mannitol, dextrin, hydroxypropyl cellulose, hydroxypropylmethyl cellulose, polyvinylpyrrolidone, starch, sucrose, gelatin, methyl cellulose and sodium carboxymethyl cellulose.

Examples of the disintegrant include starch, carboxymethyl cellulose, calcium carboxymethyl cellulose, sodium carboxymethyl starch and L-hydroxypropyl cellulose.

Examples of the solvent include water for injection, alcohol, propylene glycol, macrogol, sesame oil, corn oil and olive oil.

Examples of the dissolving aid include polyethylene glycol, propylene glycol, D-mannitol, benzyl benzoate, ethanol, tris-aminomethane, cholesterol, triethanolamine, sodium carbonate and sodium citrate.

Examples of the suspending agent include surfactants such as stearyl triethanolamine, sodium lauryl sulfate, lauryl aminopropionic acid, lecithin, benzalkonium chloride, benzetonium chloride and glycerin monostearate; and hydrophilic polymers such as polyvinyl alcohol, polyvinylpyrrolidone, sodium carboxymethyl cellulose, methyl cellulose, hydroxymethyl cellulose, hydroxyethyl cellulose and hydroxypropyl cellulose.

Examples of the isotonizing agent include glucose, D-sorbitol, sodium chloride, glycerin and D-mannitol. Examples of the buffering agent include buffering solutions of phosphate salt, acetate salt, carbonate salt and citrate salt.

Examples of the soothing agent include benzyl alcohol.

Examples of the preservative include para-oxybenzoate esters, chlorobutanol, benzyl alcohol, phenylethyl alcohol, dehydroacetic acid and sorbic acid.

Examples of the antioxidant include sulfite salt, ascorbic acid, V-tocopherol.

The pharmaceutical composition can be produced in accordance with a normal method by adding the inventive compound in a proportion of normally 0.01 to 100% (w/w) and preferably 0.1 to 95% (w/w) relative to the whole amount of the formulation although the proportion varies depending on the dosage from, administration method, carrier and the like.

The inventive compound may be used in combination with another active ingredient (hereinafter, abbreviated as a concomitant drug).

As the concomitant drug, a compound that may have a preventive and/or therapeutic effect against oxidative stress diseases or a salt thereof can be appropriately compounded depending on the disease to be a treatment target. Examples of the compound that may have a preventive and/or therapeutic effect against oxidative stress diseases or a salt thereof include cardiotonic agents such as digoxin, β agonists such as dobutamine, β inhibitors such as carvedilol, vasodilator drugs such as nitroglycerin, prostacyclin and riociguat, angiotensin converting enzyme inhibitors such as ramipril, angiotensin II receptor antagonists such as candesartan, diuretic drugs such as hydrochlorothiazide and furosemide, calcium receptor antagonists such as amlodipine, mineralocorticoid receptor antagonists such as eplerenone, endothelin receptor antagonists such as bosentan, anticoagulant drugs such as rivaroxaban, antiplatelet drugs such as clopidogrel, antidiabetic drugs such as metformin, alogliptin, pioglitazone and ipragliflozin, dyslipidemia improving drugs such as atorvastatin, fenofibrate, ezetimibe and niacin, anti-inflammatory drugs such as roflumilast, adrenergic β-2 receptor agonists such as salbutamol, steroidal formulations, Dopamine precursors such as levodopa, monoamine oxidase B inhibitors such as selegiline, and anticholinergic drugs such as biperiden. Other examples of the concomitant drug include immune checkpoint inhibitors such as anti-PD-1 antibodies, anti-PD-L1 antibodies and anti-CTLA-4 antibodies.

By combining the inventive compound with a concomitant drug, excellent effects can be achieved, such as:
(1) the dosage can be reduced as compared to single administration of the inventive compound or a concomitant drug;
(2) the drug to be combined with the inventive compound can be selected depending on symptoms of the patient (mild symptom, severe symptom and the like);
(3) the treatment duration can be set long by selecting a concomitant drug having an action mechanism different from that of the inventive compound;
(4) a sustained treatment effect can be designed by selecting a concomitant drug having an action mechanism different from the inventive compound; and
(5) a synergistic effect can be afforded by a combined use of the inventive compound and a concomitant drug.

Hereinafter, using the inventive compound with a concomitant drug in combination is referred to as a "combination agent according to the present invention".

Upon using the combination agent according to the present invention, administration time of the inventive compound and the concomitant drug is not limited, and the inventive compound or a pharmaceutical composition thereof and the concomitant drug or a pharmaceutical composition thereof may be administered to an administration subject simultaneously, of may be administered with time difference. The dosage of the concomitant drug may be determined in accordance with a dosage that is clinically used, and can be appropriately selected depending on an administration subject, administration route, disease, combination and the like.

The administration mode of the combination agent according to the present invention is not particularly limited, and it is sufficient that the inventive compound and the concomitant drug are combined upon administration. Examples of such an administration mode include (1) administration of a single formulation obtained by simultaneously formulating the inventive compound and the concomitant drug, (2) simultaneous administration of two kinds of formulations obtained by separately formulating the inventive compound and the concomitant drug through the same administration route, (3) administration of two kinds of formulations obtained by separately formulating the inventive compound and the concomitant drug through the same administration route but with time difference, (4) simultaneous administration of two kinds of formulations obtained by separately formulating the inventive compound and the concomitant drug through different administration routes, (5) administration of two kinds of formulations obtained by separately formulating the inventive compound and the concomitant drug through different administration routes with time difference (for example, administration of the inventive compound and the concomitant drug in the order described, or in the reverse order) and the like.

The combination agent according to the present invention has low toxicity. For example, the inventive compound or(and) the concomitant drug described above can be combined with a pharmacologically acceptable carrier according to a known method to prepare a pharmaceutical composition such as a tablet (including sugar-coated tablet and film-coated tablet), powder, granule, capsule (including soft capsule), liquid, injection, suppository, sustained-release agent and the like. These compositions can be safely administered orally or parenterally (for example, topical, rectal, intravenous administration). The injection can be administered intravenously, intramuscularly, subcutaneously, or by intraorgan administration or direct administration to the lesion.

Examples of the pharmacologically acceptable carrier that may be used for production of the combination agent according to the present invention include a variety of organic or inorganic carrier substances that are conventionally used as formulation materials. For example, an excipient, a lubricant, a binder and a disintegrant can be used for a solid formulation. For a liquid formulation, a solvent, a dissolving aid, a suspending agent, an isotonizing agent, a buffering agent, a soothing agent and the like can be used. Further, as necessary, normal additives such as a preservative, an antioxidant, a colorant, a sweetening agent, an adsorbent, and a wetting agent can be appropriately used in an appropriate amount.

Examples of the excipient include lactose, white sugar, D-mannitol, starch, corn starch, crystalline cellulose and light anhydrous silicic acid.

Examples of the lubricant include magnesium stearate, calcium stearate, talc and colloidal silica.

Examples of the binder include crystalline cellulose, white sugar, D-mannitol, dextrin, hydroxypropyl cellulose, hydroxypropylmethyl cellulose, polyvinylpyrrolidone, starch, sucrose, gelatin, methyl cellulose and sodium carboxymethyl cellulose.

Examples of the disintegrant include starch, carboxymethyl cellulose, calcium carboxymethyl cellulose, sodium carboxymethyl starch and L-hydroxypropyl cellulose.

Examples of the solvent include water for injection, alcohol, propylene glycol, macrogol, sesame oil, corn oil and olive oil.

Examples of the dissolving aid include polyethylene glycol, propylene glycol, D-mannitol, benzyl benzoate, ethanol, tris-aminomethane, cholesterol, triethanolamine, sodium carbonate and sodium citrate.

Examples of the suspending agent include surfactants such as stearyl triethanolamine, sodium lauryl sulfate, lauryl aminopropionic acid, lecithin, benzalkonium chloride, benzetonium chloride and glycerin monostearate; and hydrophilic polymers such as polyvinyl alcohol, polyvinylpyrrolidone, sodium carboxymethyl cellulose, methyl cellulose, hydroxymethyl cellulose, hydroxyethyl cellulose and hydroxypropyl cellulose.

Examples of the isotonizing agent include glucose, D-sorbitol, sodium chloride, glycerin and D-mannitol.

Examples of the buffering agent include buffering solutions of phosphate salt, acetate salt, carbonate salt and citrate salt.

Examples of the soothing agent include benzyl alcohol.

Examples of the preservative include para-oxybenzoate esters, chlorobutanol, benzyl alcohol, phenylethyl alcohol, dehydroacetic acid and sorbic acid.

Examples of the antioxidant include sulfite salt, ascorbic acid, V-tocopherol.

The mixing ratio of the inventive compound and the concomitant drug in the combination agent according to the present invention can be appropriately selected depending on an administration subject, administration route, disease and the like.

For example, the content of the inventive compound in the combination agent according to the present invention varies depending on the form of the formulation, but is normally from about 0.01 to 100% by weight, preferably from about 0.1 to 50% by weight, and further preferably approximately from about 0.5 to 20% by weight relative to the entire formulation.

The content of the concomitant drug in the combination agent according to the present invention varies depending on the form of the formulation, but is normally from about 0.01 to 100% by weight, preferably from about 0.1 to 50% by weight, and further preferably approximately from about 0.5 to 20% by weight relative to the entire formulation.

The content of additives such as a carrier in the combination agent according to the present invention varies depending on the form of the formulation, but is normally from about 1 to 99.99% by weight, and preferably approximately from about 10 to 90% by weight relative to the entire formulation.

In addition, when the inventive compound and the concomitant drug are separately formulated, the contents thereof may be the same as above.

EXAMPLES

The present invention will be further described in detail with reference to the following Examples, Test Examples, and Formulation Examples. However, they do not limit the present invention, and may be varied in the range without departing the scope of the present invention.

In the following Examples, "room temperature" normally indicates about 10° C. to about 35° C. Ratios shown in mixed solvents indicate volume ratios unless otherwise noted. % indicates % by weight unless otherwise noted.

Elution in column chromatography in Examples were carried out under observation by TLC (Thin Layer Chromatography) unless otherwise mentioned. In the TLC observation, 60 F254 manufactured by Merck KGaA was used as a TLD plate, and a solvent that was used as an eluting solvent in column chromatography was used as a developing solvent. In addition, an UV detector was employed for detection. In silica gel column chromatography, when NH is described, aminopropylsilane-binding silica gel was used, and when Diol is described, 3-(2,3-dihydroxypropoxy)propylsilane-binding silica gel was used. In HPLC (High Performance Liquid Chromatography), when C18 is described, octadecyl-binding silica gel was used. Ratios of eluting solvents indicate volume ratios unless otherwise noted.

In the following Examples, abbreviations described below will be used.
mp: melting point
MS: mass spectrum
M: molar concentration
N: normality
CDCl$_3$: deuterated chloroform
DMSO-d$_6$: deuterated dimethylsulfoxide
$^1$H NMR: proton nuclear magnetic resonance
LC/MS: liquid chromatograph mass spectrometer
ESI: electrospray ionization
EtOAc: ethyl acetate
APCI: atmospheric pressure chemical ionization
DMF: N,N-dimethylformamide
DMSO: dimethylsulfoxide
DMAP: N,N-dimethylamino-4-aminopyridine
Et: ethyl
EDCI: 1-ethyl-3-(3-dimethylaminopropyl)carbodiimide hydrochloride
HATU: 2-(7-azabenzotriazol-1-yl)-1,1,3,3-tetramethyluronium hexafluorophosphate
HOBt: 1-hydroxybenzotriazole
PPh$_3$: triphenylphosphine
THF: tetrahydrofuran
CPME: cyclopentyl methyl ether
AcOH: acetic acid
HPLC: high performance liquid chromatogram
Boc: tert-butoxycarbonyl
Ts: p-toluenesulfonyl
TBTU: 1-[bis(dimethylamino)methylene]-1H-benzotriazolium 3-oxide tetrafluoroborate
KHMDS: potassium hexamethyl disilazide
BuLi: butyllithium
COD: 1,5-cyclooctadiene
DCM: dichloromethane
DEAD: diethyl azodicarboxylate
DIPEA: diisopropylethylamine
DMA: N,N-dimethylacetamide
dba: dibenzylideneacetone
dppf: 1,1'-bis(diphenylphosphino)ferrocene
iPr: isopropyl
NBS: N-bromosuccinimide
NMM: N-methylmorpholine
TFA: Trifluoroacetic acid
TLC: thin-layer chromatography
TMS: Trimethylsilyl
Reverse Phase Preparative HPLC: Method A Preparative HPLC was done on Waters auto purification instrument. Column name: YMC Triart C18 (100×30 mm, 5 μm) operating at ambient temperature and flow rate of 30 mL/min. Mobile phase: A=20 mM Ammonium Bicarbonate in water, B=Acetonitrile; Gradient Profile: Mobile phase initial composition of 80% A and 20% B, then 60% A and 40% B in 2 min, then to 20% A and 80% B in 12 min., then to 5% A and 95% B in 13 min., held this composition up to 15 min. for column washing, then returned to initial composition in 16 min. and held till 18 min.

Reverse Phase Chiral Preparative HPLC: Method B

Preparative HPLC was done on Waters auto purification instrument. Column name: REFLECT I CELLULOSE C (250×21.2 mm, 5 μm) operating at ambient temperature and flow rate of 16 mL/min. Mobile phase: A=0.1% TFA in water, B=Acetonitrile; Gradient Profile: Mobile phase initial composition of 80% A and 20% B, then 70% A and 30% B in 2.5 min, then to 55% A and 45% B in 6 min., then to 15% A and 85% B in 25 min., then to 5% A and 95% B in 26 min., held this composition up to 30 min for column washing, then returned to initial composition in 30.5 min and held till 36 min.

Normal Phase Chiral Preparative HPLC: Method C

Preparative HPLC was done on Agilent Prep-HPLC. Column name: Chiralpak IA (21.0×250 mm, 5 μm) operating at ambient temperature and flow rate of 21 mL/min. Mobile phase: Hexane/DCM/EtOH/TFA: 70/15/15/0.1; Gradient Profile: Mobile phase initial composition of 80% A and 20% B, then 70% A and 30% B in 2.5 min, then to 55% A and 45% B in 6 min., then to 15% A and 85% B in 25 min., then to 5% A and 95% B in 26 min., held this composition up to 30 min. for column washing, then returned to initial composition in 30.5 min. and held till 36 min.

Normal Phase Chiral Preparative HPLC: Method D

Chiral HPLC was carried out on Waters Manual purification system with 2545 Quaternary Gradient Pump and 2489 UV Detector. Column name: Chiralpak IA (250×21.2 mm, 5 μm) operating at ambient temperature and flow rate of 26 mL/min. Mobile phase: A=Ethanol, B=0.1% TEA in n-Hexane; Isocratic Profile: A: B=30%: 70%, same composition was held up for the total runtime of 35 min. Detector was programmed at compound's wavelength i.e. 293 nm and sample preparation was done by using Methanol and DCM.

For $^1$H NMR, Fourier transform NMR was used for measurement. For analysis, ACD/SpecManager (product name) or the like was used. Very gentle peaks of protons such as those for hydroxy groups or amino groups are not described.

MS was measured by LC/MS. For ionization method, ESI method or APCI method was used. For data, measured values (found) are described. Normally, molecular ion peaks (such as [M+H]$^+$ and [M−H]$^−$) are observed, but for example, in the case of a compound having a tert-butoxycarbonyl group, a peak for which a tert-butoxycarbonyl group or tert-butyl group is desorbed may be observed as a fragment ion, and in the case of a compound having a hydroxy group, a peak for which H$_2$O is desorbed may be observed as a fragment ion. In the case of a salt, the molecular ion peak of the free form or a fragment ion peak is normally observed.

The unit of sample concentration (c) in optical rotation ([α]$_D$) is g/100 mL.

For the elementary analysis value (Anal.), calculated values (Calcd) and measured values (Found) are described.

The powder X-ray diffraction pattern was measured by using Cu-Kα characteristic X-ray of Rigaku Ultima IV, and characteristic peaks are described.

Example 1

[32-Methyl-20-oxo-8,9,10,21-tetraazahexacyclo[19.5.3.2$^{16,19}$]$^{3,7}$.0$^{6,10}$.0$^{24,28}$]dotriaconta-1(26),3(32),4,6,8,16,18,24,27,30-decaen-2-yl]acetic acid

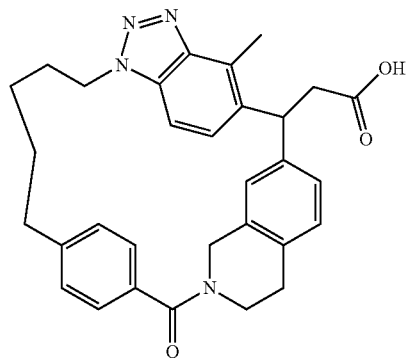

A) tert-Butyl 4-(5-hydroxypent-1-yn-1-yl)benzoate

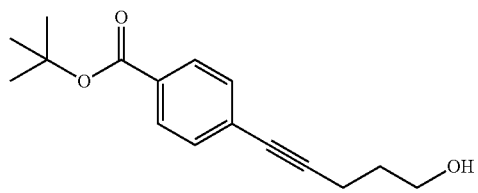 [SMILES: CC(C)(C)OC(=O)c1ccc(C#CCCCO)cc1]

A mixture of tert-butyl 4-iodobenzoate (3.68 g), 4-pentyn-1-ol (1.32 g), PdCl$_2$(PPh$_3$)$_2$ (425 g), copper iodide (46.1 mg), and triethylamine (20 ml) was stirred at room temperature overnight. To the mixture was added ethyl acetate at room temperature, and the reaction mixture was washed with saturated aqueous ammonium chloride solution and saturated brine, followed by drying over anhydrous magnesium sulfate and concentration under reduced pressure. The residue was purified by silica gel column chromatography (ethyl acetate/hexane) to give the title compound (3.15 g).

$^1$H NMR (300 MHz, DMSO-d$_6$) δ 1.54 (9H, s), 1.64-1.76 (2H, m), 2.45-2.49 (2H, m), 3.47-3.56 (2H, m), 4.56 (1H, t, J=5.2 Hz), 7.49 (2H, d, J=8.1 Hz), 7.85 (2H, d, J=8.1 Hz).

B) tert-Butyl 4-(5-hydroxypentyl)benzoate

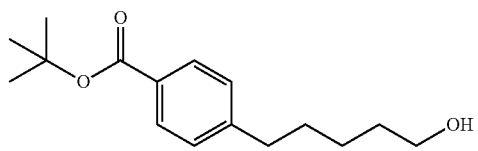 [SMILES: CC(C)(C)OC(=O)c1ccc(CCCCCO)cc1]

tert-Butyl 4-(5-hydroxypent-1-yn-1-yl)benzoate (3.15 g) and a suspension of palladium/carbon (500 mg) in ethanol (50 ml) were stirred under hydrogen atmosphere overnight. Palladium/carbon was removed and the reaction mixture was concentrated under reduced pressure to give the title compound (3.05 g).

$^1$H NMR (300 MHz, DMSO-d$_6$) δ 1.23-1.34 (2H, m), 1.37-1.49 (2H, m), 1.51-1.65 (11H, m), 2.63 (2H, t, J=7.3 Hz), 3.34-3.41 (2H, m), 4.34 (1H, t, J=4.9 Hz), 7.31 (2H, d, J=7.9 Hz), 7.81 (2H, d, J=8.0 Hz).

C) tert-Butyl 4-{5-[(4-methylbenzene-1-sulfonyl)oxy]pentyl}benzoate

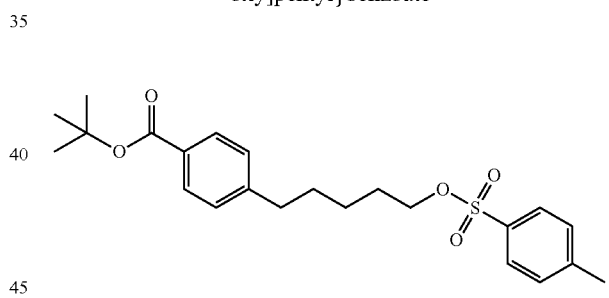

To a solution of tert-butyl 4-(5-hydroxypentyl)benzoate (22.4 g) in tetrahydrofuran (200 ml), triethylamine (17.2 g), p-toluenesulfonyl chloride (19.4 g) and 4-dimethylaminopyridine (1.04 g) were added at room temperature, and the reaction mixture was stirred at room temperature for 2 hours. Then, p-toluenesulfonyl chloride (19.4 g) and triethylamine (8.6 g) were added thereto, and the reaction mixture was further stirred at 60° C. for 3 hours. To the reaction solution, triethylamine (8.6 g) and p-toluenesulfonyl chloride (19.4 g) were further added, and the reaction solution was stirred at 50° C. for 5 hours. To the mixture was added ethyl acetate at room temperature, and the reaction mixture was washed with water and saturated brine, followed by drying over anhydrous magnesium sulfate and concentration under reduced pressure. The residue was purified by silica gel column chromatography (ethyl acetate/hexane) to give the title compound (30.2 g).

$^1$H NMR (300 MHz, DMSO-d$_6$) δ 1.19-1.32 (2H, m), 1.39-1.67 (13H, m), 2.41 (3H, s), 2.56 (2H, br t, J=7.5 Hz), 4.00 (2H, t, J=6.2 Hz), 7.26 (2H, d, J=7.8 Hz), 7.47 (2H, br d, J=7.9 Hz), 7.79 (4H, br t, J=9.0 Hz).

D) tert-Butyl 4-(5-azidopentyl)benzoate

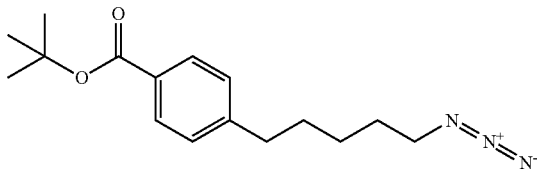 [SMILES: CC(C)(C)OC(=O)c1ccc(CCCCCN=[N+]=[N-])cc1]

To a solution of tert-butyl 4-{5-[(4-methylbenzene-1-sulfonyl)oxy]pentyl}benzoate (30.2 g) in N,N-dimethylformamide (150 ml), sodium iodide (10.8 g) and sodium azide (9.39 g) were added, and the reaction mixture was stirred at 90° C. for 3 hours. To the mixture was added ethyl acetate at room temperature, and the reaction mixture was washed with water and saturated brine, followed by drying over anhydrous magnesium sulfate and concentration under reduced pressure. The residue was purified by silica gel column chromatography (ethyl acetate/hexane) to give the title compound (18.8 g).

$^1$H NMR (300 MHz, DMSO-$d_6$) δ 1.27-1.40 (2H, m), 1.47-1.69 (13H, m), 2.64 (2H, br t, J=7.5 Hz), 3.27-3.33 (2H, m), 7.32 (2H, d, J=7.7 Hz), 7.82 (21H, d, J=7.9 Hz).

E) tert-Butyl 4-[5-(4-bromo-3-methyl-2-nitroanilino)pentyl]benzoate

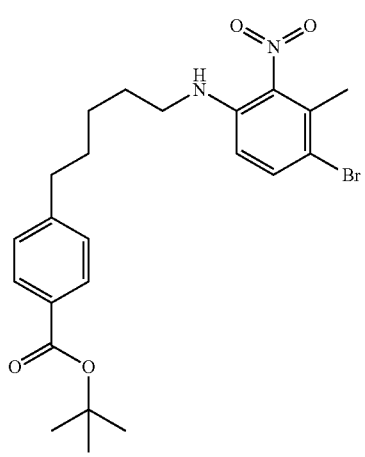 [SMILES: Cc1c(Br)ccc(NCCCCCc2ccc(C(=O)OC(C)(C)C)cc2)c1[N+](=O)[O-]]

To a solution of tert-butyl 4-(5-azidopentyl)benzoate (141 mg) in tetrahydrofuran (1 ml) and water (1 ml), triphenylphosphine (128 mg) was added at room temperature. The mixture was stirred for 4 hours, and then concentrated. To a solution of the residue in N,N-dimethylformamide (3 ml), potassium carbonate (135 mg) and 1-bromo-4-fluoro-2-methyl-3-nitro-benzene (101 mg) were added at room temperature, and the reaction mixture was stirred at 80° C. overnight. To the mixture, water was added at 0° C., and the mixture was extracted with ethyl acetate. The extract solution was washed with saturated brine, followed by drying over anhydrous magnesium sulfate and concentration under reduced pressure. The residue was purified by silica gel column chromatography (ethyl acetate/hexane) to give the title compound (189 mg).

$^1$H NMR (300 MHz, CDCl$_3$) δ 1.35-1.52 (2H, m), 1.59 (9H, s), 1.61-1.78 (4H, m), 2.44 (3H, s), 2.67 (2H, t, J=7.5 Hz), 3.13 (2H, q, J=6.5 Hz), 5.68 (1H, br s), 6.52 (1H, d, J=9.1 Hz), 7.21 (2H, d, J=7.9 Hz), 7.46 (1H, d, J=9.1 Hz), 7.90 (2H, d, J=8.0 Hz).

F) tert-Butyl 4-[5-(2-amino-4-bromo-3-methylanilino)pentyl]benzoate

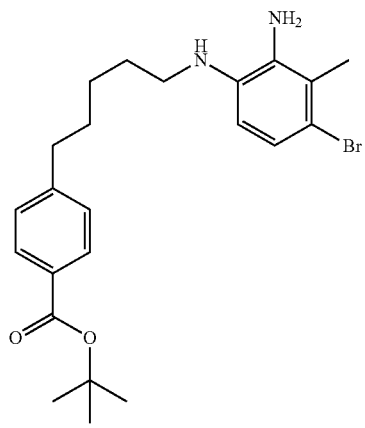 [SMILES: Cc1c(Br)ccc(NCCCCCc2ccc(C(=O)OC(C)(C)C)cc2)c1N]

A mixture of tert-butyl 4-[5-(4-bromo-3-methyl-2-nitroanilino)pentyl] benzoate (9.27 g), ammonium chloride (5.19 g), iron (5.42 g), ethanol (100 ml), ethyl acetate (30 ml), and water (50 ml) was stirred at 85° C. for 4 hours. The mixture was filtered, and the filtrate was concentrated to a half volume. To the mixture thus obtained, water was added, and the mixture was extracted with ethyl acetate. The extract solution was washed with saturated brine, followed by drying over anhydrous magnesium sulfate and concentration under reduced pressure. The residue was purified by silica gel column chromatography (ethyl acetate/hexane) to give the title compound (7.4 g).

$^1$H NMR (300 MHz, DMSO-$d_6$) δ 1.27-1.69 (15H, m), 2.16 (3H, s), 2.65 (2H, br t, J=7.3 Hz), 2.86-3.14 (2H, m), 4.44-4.71 (3H, m), 6.23 (1H, d, J=8.4 Hz), 6.70 (1H, d, J=8.4 Hz), 7.31 (2H, d, J=7.9 Hz), 7.81 (2H, d, J=7.9 Hz).

MS m/z 447.2 [M+H]$^-$.

G) tert-Butyl 4-[5-(5-bromo-4-methyl-1H-benzotriazol-1-yl)pentyl]benzoate

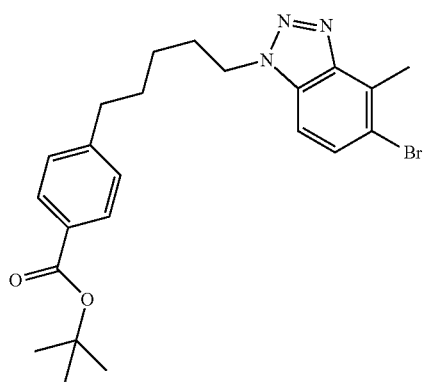 [SMILES: Cc1c(Br)ccc2c1nnn2CCCCCc1ccc(C(=O)OC(C)(C)C)cc1]

To a mixture of tert-butyl 4-[5-(2-amino-4-bromo-3-methylanilino)pentyl]benzoate (7.4 g) in acetic acid (80 ml), aqueous solution (25 ml) of sodium nitrite (2.28 g) was added at room temperature over 1 hour. To the mixture, ice was added, and the mixture was extracted with ethyl acetate. The extract solution was washed with water, saturated aqueous sodium bicarbonate solution, and saturated brine, followed by drying over anhydrous magnesium sulfate and concentration under reduced pressure. The residue was purified by silica gel column chromatography (ethyl acetate/hexane) and silica gel column chromatography (NH, ethyl acetate/hexane) to give the title compound (4.9 g).

$^1$H NMR (300 MHz, DMSO-$d_6$) δ 1.07-1.28 (2H, m), 1.49-1.65 (HH, m), 1.84-1.96 (2H, m), 2.57 (2H, br t, J=7.6 Hz), 2.72 (3H, s), 4.69 (2H, t, J=6.7 Hz), 7.21 (2H, d, J=7.8 Hz), 7.69 (2H, s), 7.75 (2H, d, J=7.9 Hz).

MS m/z 458.2 [M+H]$^-$.

H) tert-Butyl 4-(5-{5-[(1E)-3-ethoxy-3-oxoprop-1-en-1-yl]-4-methyl-1H-benzotriazol-1-yl}pentyl)benzoate

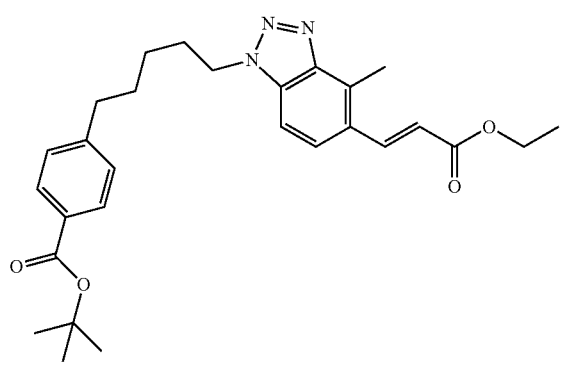 [SMILES: CCOC(=O)/C=C/c1ccc2c(nnn2CCCCCc2ccc(C(=O)OC(C)(C)C)cc2)c1C]

To a solution of tert-butyl 4-[5-(5-bromo-4-methyl-1H-benzotriazol-1-yl)pentyl]benzoate (4.8 g), ethyl acrylate (6.85 ml), and N,N-diisopropylethyl amine (7.72 mL) in N,N-dimethylformamide (50 ml), tri(o-tolyl)phosphine (0.96 g) and palladium acetate (353 mg) were added, and the reaction mixture was stirred at 120° C. for 4 hours under nitrogen atmosphere. Further, to the reaction mixture, ethyl acrylate (6.9 ml), N,N-diisopropylethylamine (7.72 mL), tri(o-tolyl)phosphine (0.96 g) and palladium acetate (353 mg) were added, and the reaction mixture was stirred at 120° C. for 1 hour under nitrogen atmosphere. To the mixture thus obtained, water was added, and the mixture was extracted with ethyl acetate. The extract solution was washed with water and saturated brine, followed by drying over anhydrous magnesium sulfate and concentration under reduced pressure. The residue was purified by silica gel column chromatography (ethyl acetate/hexane) and silica gel column chromatography (NH, ethyl acetate/hexane) to give the title compound (4.84 g).

$^1$H NMR (300 MHz, DMSO-$d_6$) δ 1.10-1.33 (5H, m), 1.44-1.67 (11H, m), 1.85-1.98 (2H, m), 2.58 (2H, br t, J=7.2 Hz), 2.81 (3H, s), 4.22 (2H, q, J=7.2 Hz), 4.69 (2H, br t, J=6.6 Hz), 6.66 (1H, d, J=16.0 Hz), 7.21 (2H, br d, J=7.7 Hz), 7.61-7.78 (3H, m), 7.91-8.14 (2H, m). MS m/z 478.3 [M+H]$^-$.

I) tert-Butyl 7-[1-(1-{5-[4-(tert-butoxycarbonyl)phenyl]pentyl}-4-methyl-1H-benzotriazol-5-yl)-3-ethoxy-3-oxopropyl]-3,4-dihydroisoquinoline-2(1H)-carboxylate

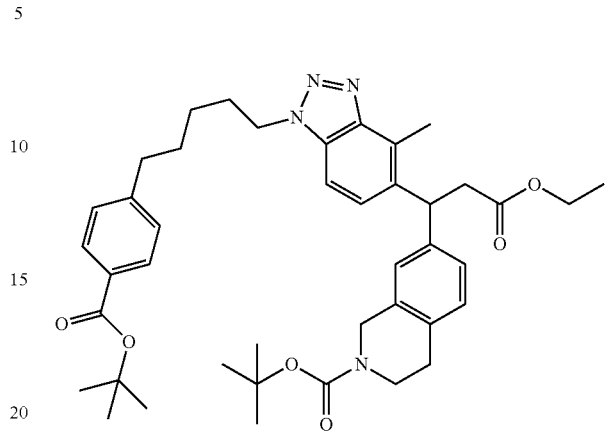

To a mixture of tert-butyl 4-(5-{5-[(1E)-3-ethoxy-3-oxoprop-1-en-1-yl]-4-methyl-1H-benzotriazol-1-yl}pentyl)benzoate (4.8 g), tert-butyl 7-(4,4,5,5-tetramethyl-1,3,2-dioxaborolan-2-yl)-3,4-dihydro-1H-isoquinoline-2-carboxylate (10.8 g), sodium dodecyl sulfate (1.45 g), and triethylamine (4.2 ml) in CPME (100 ml) and water (50 ml), chloro(1,5-cyclooctadiene)rhodium (I) dimer (496 mg) was added. The mixture was stirred at 100° C. for 4 hours under argon atmosphere. To the mixture thus obtained, saturated aqueous ammonium chloride solution was added, and the mixture was extracted with ethyl acetate. The extract solution was washed with saturated brine, followed by drying over anhydrous magnesium sulfate and concentration under reduced pressure. The residue was purified by silica gel column chromatography (ethyl acetate/hexane) to give the title compound (6.55 g).

$^1$H NMR (300 MHz, CDCl$_3$) δ 1.10 (3H, t, J=7.2 Hz), 1.32-1.43 (2H, m), 1.47 (9H, s), 1.54-1.60 (9H, m), 1.62-1.76 (2H, m), 1.93-2.03 (2H, m), 2.62 (2H, br t, J=7.3 Hz), 2.71-2.79 (2H, m), 2.86 (3H, s), 2.95-3.22 (2H, m), 3.49-3.69 (2H, m), 4.02 (2H, q, J=7.0 Hz), 4.45-4.51 (2H, m), 4.56 (2H, br t, J=6.8 Hz), 4.88-5.09 (1H, m), 6.89-6.96 (1H, m), 7.03 (2H, s), 7.17 (2H, br d, J=7.8 Hz), 7.26 (1H, s), 7.31-7.39 (1H, m), 7.88 (2H, d, J=8.0 Hz).

MS m/z 711.5 [M+H]$^-$.

J) Ethyl [32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate

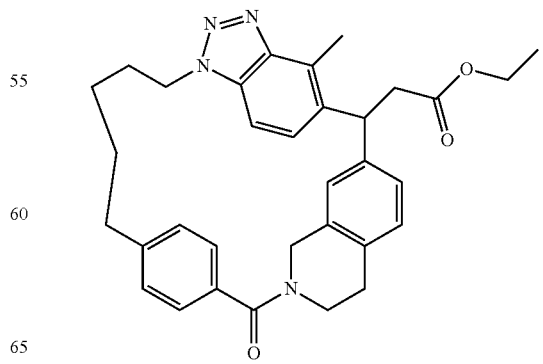

To a solution of tert-butyl 7-[1-(1-{5-[4-(tert-butoxycarbonyl)phenyl]pentyl}-4-methyl-1H-benzotriazol-5-yl)-3-ethoxy-3-oxopropyl]-3,4-dihydroisoquinoline-2(1H)-carboxylate (6.55 g) in CPME (10 ml), 4N HCl/CPME solution (70 ml) was added at room temperature. The mixture was stirred at room temperature for 2 hours, and then concentrated. To the mixture thus obtained, tetrahydrofuran was added, and the mixture was concentrated. A solution of the residue thus obtained and N,N-diisopropylethylamine (9.65 mL) in N,N-dimethylformamide (30 ml) was added dropwise to a solution of HATU (5.25 g) in N,N-dimethylformamide (150 ml) over 1 hour. The mixture was stirred at room temperature for 3 hours. To the mixture, saturated aqueous sodium bicarbonate solution was added, and the mixture was extracted with ethyl acetate. The extract solution was washed with water and saturated brine, followed by drying over anhydrous magnesium sulfate and concentration under reduced pressure. The residue was purified by silica gel column chromatography (ethyl acetate/hexane) to give the title compound (2.59 g).

MS m/z 537.4 [M+H]⁻.

K) [32-Methyl-20-oxo-8,9,10,21-tetraazahexacyclo[19.5.3.2$^{16,19}$.1$^{3,7}$.0$^{6,10}$.0$^{24,28}$] dotriaconta-1(26),3(32),4,6,8,16,18,24,27,30-decaen-2-yl]acetic acid

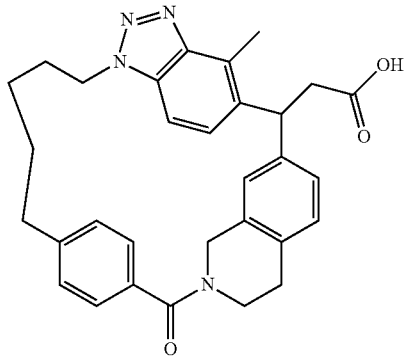

To a solution of ethyl [32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (280 mg) in tetrahydrofuran (4 ml) and ethanol (4 ml), 2N aqueous sodium hydroxide solution (4 mL) was added, and the reaction mixture was stirred at room temperature for 3 hours. Under reduced pressure, organic solvents were removed, and the reaction mixture was then neutralized at 0° C. with 2N hydrochloric acid. The precipitate was filtered and washed with water to give the title compound (265 mg).

¹H NMR (300 MHz, DMSO-d₆) δ 0.76-1.16 (2H, m), 1.35-1.62 (2H, m), 1.79-2.21 (2H, m), 2.37-2.73 (5H, m), 2.75-2.90 (2H, m), 2.91-3.21 (2H, m), 3.58-4.23 (4H, m), 4.48-4.91 (3H, m), 5.89 (1 H, s), 6.77-7.00 (4H, m), 7.08-7.19 (1H, m), 7.27-7.47 (2H, m), 7.60 (1H, br d, J=8.9 Hz), 12.30 (1H, br s).

Example 2

[20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid

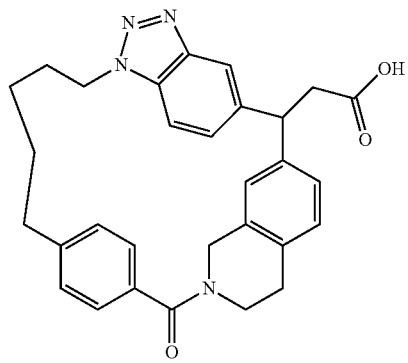 [SMILES: O=C(O)CC1c2ccc3c(c2)CN(CC3)C(=O)c2ccc(cc2)CCCCCn2nnc3cc1ccc32]

Synthesis was carried out in accordance with the methods shown in Example 9 or methods equivalent thereto.

Example 3

[18-Ethyl-32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid

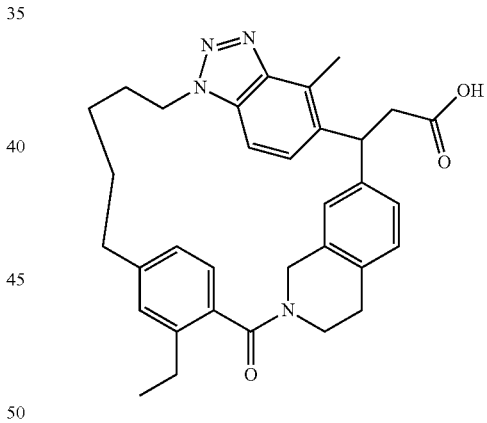

A) Methyl 4-bromo-2-ethylbenzoate

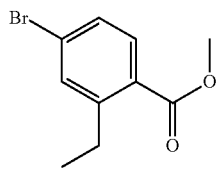

To a mixture of 4-bromo-2-fluorobenzoic acid (10.2 g) and tetrahydrofuran (50 ml), an about 1M solution of ethylmagnesium chloride in tetrahydrofuran (140 ml) was added dropwise at 0° C. After stirring the reaction mixture at 0° C. for 4 hours, 1N hydrochloric acid was added at 0° C. Under reduced pressure, organic solvents were removed, and the residue was then extracted with ethyl acetate. The extract solution was washed with saturated brine, followed by drying over anhydrous magnesium sulfate and concentration under reduced pressure. To a mixture of the residue and methanol (100 ml), concentrated sulfuric acid (5.00 ml) was added at room temperature, and the reaction mixture was stirred overnight under heating reflux. The reaction mixture was concentrated under reduced pressure, and then extracted with ethyl acetate. The extract solution was washed with saturated brine, followed by drying over anhydrous magnesium sulfate and concentration under reduced pressure. The residue was purified by silica gel column chromatography (ethyl acetate/hexane) to give the title compound (3.26 g).

$^1$H NMR (300 MHz, DMSO-$d_6$) δ 1.15 (3H, t, J=7.6 Hz), 2.88 (2H, q, J=7.5 Hz), 3.83 (3H, s), 7.53 (1H, br d, J=8.6 Hz), 7.57-7.60 (1H, s), 7.71 (1H, d, J=8.6 Hz).

B) Methyl 2-ethyl-4-(3-hydroxyprop-1-yn-1-yl)benzoate

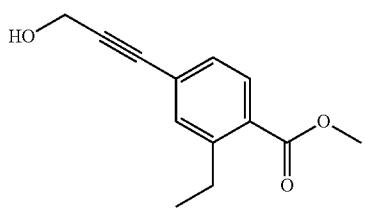 [SMILES: CCc1cc(C#CCO)ccc1C(=O)OC]

To a mixture of methyl 4-bromo-2-ethylbenzoate (3.26 g), 4-pentyn-1-ol (3.74 ml) and triethylamine (35.0 ml), dichlorobis(triphenylphosphine)palladium (II) (0.941 g) and copper (I) iodide (0.255 g) were added at room temperature. Then, the mixture was deaerated by repeatedly reducing the pressure and purging nitrogen gas. The mixture was stirred at 70° C. for 3 hours, and then concentrated under reduced pressure. The residue was purified by silica gel column chromatography (ethyl acetate/hexane) to give the title compound (2.78 g).

$^1$H NMR (300 MHz, DMSO-$d_6$) δ 1.14 (3H, t, J=7.5 Hz), 2.88 (2H, q, J=7.6 Hz), 3.83 (3H, s), 4.32 (2H, d, J=5.7 Hz), 5.36-5.42 (1H, m), 7.35 (1H, br d, J=7.8 Hz), 7.40 (1H, s), 7.76 (1H, d, J=8.0 Hz).

C) Methyl 2-ethyl-4-(3-hydroxypropyl)benzoate

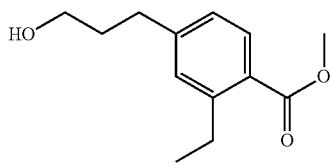 [SMILES: CCc1cc(CCCO)ccc1C(=O)OC]

A mixture of methyl 2-ethyl-4-(3-hydroxyprop-1-yn-1-yl) benzoate (2.78 g), 10% palladium/carbon (wetted with ca. 50% water) (1.50 g) and methanol (50 ml) was stirred under hydrogen atmosphere for 2 hours. Palladium/carbon was removed by filtration, the residue was washed with ethyl acetate, and the filtrate was then concentrated under reduced pressure. The residue was purified by silica gel column chromatography (ethyl acetate/hexane) to give the title compound (1.47 g).

MS m/z 223.2 [M+H]$^-$.

D) Methyl 2-ethyl-4-(3-oxopropyl)benzoate

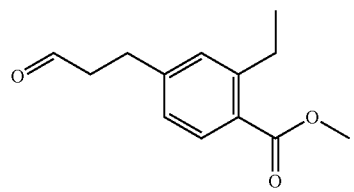 [SMILES: CCc1cc(CCC=O)ccc1C(=O)OC]

To a mixture of methyl 2-ethyl-4-(3-hydroxypropyl)benzoate (1.47 g), triethylamine (4.60 ml) and DMSO (30 ml), sulfur trioxide-pyridine complex (3.15 g) was added, and the reaction mixture was then stirred at room temperature overnight. Water was added to the reaction mixture, and the mixture was then extracted with ethyl acetate. The extract solution was washed with saturated brine, followed by drying over anhydrous magnesium sulfate and concentration under reduced pressure. The residue was purified by silica gel column chromatography (ethyl acetate/hexane) to give the title compound (0.420 g).

MS m/z 221.2 [M+H]$^-$.

E) Methyl 4-(but-3-en-1-yl)-2-ethylbenzoate

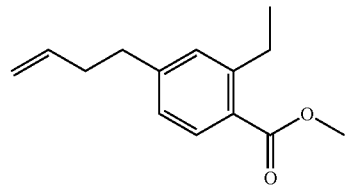 [SMILES: C=CCCc1ccc(C(=O)OC)c(CC)c1]

To a mixture of methyltriphenylphosphonium bromide (1.02 g) and tetrahydrofuran (5.00 ml), a 1.6M solution of n-butyllithium in hexane (1.79 ml) was added at 0° C., and the reaction mixture was stirred at 0° C. for 30 minutes. Then, a solution of methyl 2-ethyl-4-(3-oxopropyl)benzoate (420 mg) in tetrahydrofuran (5.00 ml) was added at 0° C. After stirring the reaction mixture at 0° C. for 1 hour, saturated aqueous ammonium chloride solution was added thereto, and the mixture was extracted with ethyl acetate. The extract solution was washed with saturated brine, followed by drying over anhydrous magnesium sulfate and concentration under reduced pressure. The residue was purified by silica gel column chromatography (ethyl acetate/ hexane) to give the title compound (254 mg).

MS m/z 219.2 [M+H]$^-$.

F) 4-(But-3-en-1-yl)-2-ethylbenzoic acid

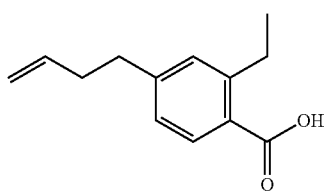

To a mixture of methyl 4-(but-3-en-1-yl)-2-ethylbenzoate (254 mg), ethanol (5.00 ml) and tetrahydrofuran (5.00 ml), 1N aqueous sodium hydroxide solution (5.00 ml) was added at room temperature, and the reaction mixture was stirred at 50° C. overnight. The reaction mixture was concentrated under reduced pressure. The residue was neutralized with 1M hydrochloric acid, and then extracted with ethyl acetate. The extract solution was washed with saturated brine, followed by drying over anhydrous magnesium sulfate and concentration under reduced pressure. The residue was purified by silica gel column chromatography (ethyl acetate/hexane) to give the title compound (187 mg).

MS m/z 205.2 [M+H]$^-$.

G) [18-Ethyl-32-methyl-20-oxo-8,9,10,21-tetraazahexacyclo[19.5.3.2$^{16,19}$.1$^{3,7}$.0$^{6,10}$.0$^{24,28}$]dotriaconta-(26),3(32),4,6,8,16,18,24,27,30-decaen-2-yl]acetic acid

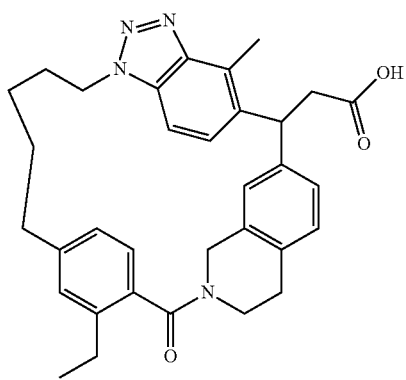 [SMILES: CCc1cc2ccc1C(=O)N1CCc3ccc(cc3C1)C(CC(=O)O)c1ccc3c(nnn3CCCCC2)c1C]

The title compound was obtained using 4-(but-3-en-1-yl)-2-ethylbenzoic acid in accordance with the methods shown in Example 9 or methods equivalent thereto.

Example 4

[33-Methyl-2-oxo-7-oxa-1,15,16,17-tetraazaheptacyclo[22.5.3.2$^{3,9}$.1$^{18,22}$.0$^{4,8}$.0$^{15,19}$.0$^{27,31}$]]pentatriaconta-3,8,16,18(33),19,21,24,26,31,34-decaen-23-yl] acetic acid

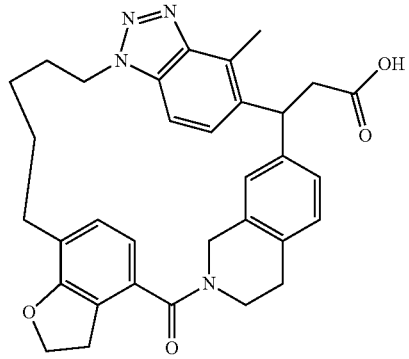 [SMILES: Cc1c2ccc3c1nnn3CCCCCc1ccc(c3c1OCC3)C(=O)N1CCc3ccc(cc3C1)C2CC(=O)O]

A) Methyl 4-bromo-3-[(prop-2-en-1-yl)oxy]benzoate

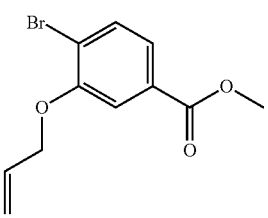

A mixture of methyl 4-bromo-3-hydroxybenzoate (5.07 g), potassium carbonate (4.55 g), 3-bromoprop-1-ene (2.28 ml) and N,N-dimethylformamide (50 ml) was stirred at 60° C. for 3 hours. Water was added to the reaction mixture, and the mixture was extracted with ethyl acetate. The organic layer was separated and washed with water and saturated brine, followed by drying over anhydrous magnesium sulfate and concentration under reduced pressure. The residue was purified by silica gel column chromatography (ethyl acetate/hexane) to give the title compound (5.93 g).

MS m/z 271.0 [M+H]$^-$.

B) Methyl 4-bromo-3-hydroxy-2-(prop-2-en-1-yl)benzoate

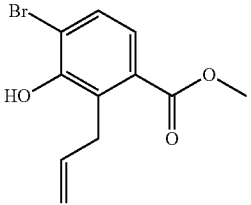

A mixture of methyl 4-bromo-3-[(prop-2-en-1-yl)oxy]benzoate (2.06 g) and N-methyl-2-pyrrolidone (12 ml) was stirred at 200° C. for 3 hours under microwave irradiation. Water was added to the reaction mixture, and the mixture was extracted with ethyl acetate. The organic layer was separated and washed with water and saturated brine, followed by drying over anhydrous magnesium sulfate and concentration under reduced pressure. The residue was purified by silica gel column chromatography (ethyl acetate/hexane) to give the title compound (1.38 g).

MS m/z 271.0 [M+H]⁻.

C) Methyl 7-bromo-2-hydroxy-2,3-dihydro-1-benzofuran-4-carboxylate

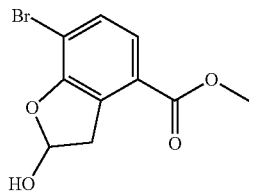

A mixture of methyl 4-bromo-3-hydroxy-2-(prop-2-en-1-yl)benzoate (1.38 g), sodium periodate (2.17 g), microencapsulated osmium tetroxide (7.00%, 923 mg), tetrahydrofuran (25 ml) and water (25 ml) was stirred at room temperature for 6 hours. The reaction mixture was filtered, and the filtrate was concentrated. Water was added to the residue, and the residue was extracted with ethyl acetate. The organic layer was separated and washed with water and saturated brine, followed by drying over anhydrous magnesium sulfate and concentration under reduced pressure. The residue was purified by silica gel column chromatography (ethyl acetate/hexane) to give the title compound (711 mg).

MS m/z 273.0 [M+H]⁻.

D) Methyl 4-bromo-3-hydroxy-2-(2-hydroxyethyl)benzoate

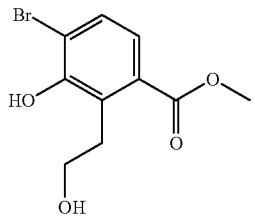

To a mixture of methyl 7-bromo-2-hydroxy-2,3-dihydro-1-benzofuran-4-carboxylate (711 mg), tetrahydrofuran (10 ml) and methanol (10 ml), sodium borohydride (98.5 mg) was added at 0° C., and the reaction mixture was stirred at the same temperature for 1 hour. To the reaction mixture, saturated aqueous ammonium chloride solution was added at 0° C., and the mixture was extracted with ethyl acetate. The organic layer was separated and washed with saturated brine, followed by drying over anhydrous magnesium sulfate and concentration under reduced pressure. The residue was purified by silica gel column chromatography (ethyl acetate/hexane) to give the title compound (640 mg).

MS m/z 275.0 [M+H]⁻.

D) Methyl 7-bromo-2,3-dihydro-1-benzofuran-4-carboxylate

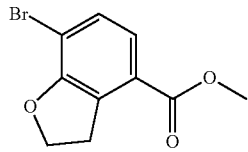

To a mixture of methyl 4-bromo-3-hydroxy-2-(2-hydroxyethyl)benzoate (640 mg), triphenylphosphine (733 mg) and tetrahydrofuran (20 ml), diisopropyl azodicarboxylate (1.9M toluene solution, 1.47 ml) was added at room temperature, and the reaction mixture was stirred at 50° C. for 5 hours. The reaction mixture was concentrated under reduced pressure, and the residue was purified by silica gel column chromatography (ethyl acetate/hexane) to give the title compound (590 mg).

MS m/z 257.0 [M+H]⁻.

F) 7-(But-3-en-1-yl)-2,3-dihydro-1-benzofuran-4-carboxylic acid

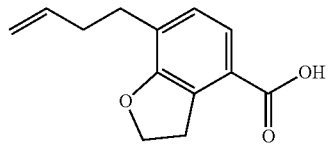 [SMILES: C=CCCc1ccc(C(=O)O)c2c1OCC2]

The title compound was obtained using methyl 7-bromo-2,3-dihydro-1-benzofuran-4-carboxylate in accordance with the methods shown in Example 3 or methods equivalent thereto.

MS m/z 219.2 [M+H]⁻.

G) [33-Methyl-2-oxo-7-oxa-1,15,16,17-tetraazaheptacyclo[22.5.3.2³,⁹.1¹⁸,²².0⁴,⁸.0¹⁵,¹⁹.0²⁷,³¹]pentatriaconta-3,8,16,18(33),19,21,24,26,31,34-decaen-23-yl] acetic acid

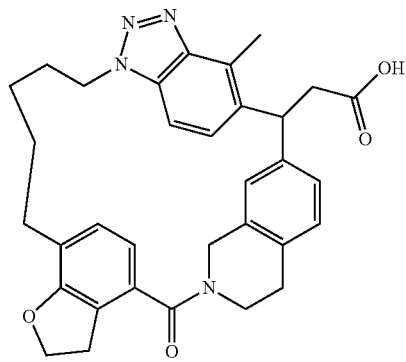 [SMILES: Cc1c2ccc3c1nnn3CCCCCc1ccc(c3c1OCC3)C(=O)N1CCc3ccc(cc3C1)C2CC(=O)O]

The title compound was obtained using 7-(but-3-en-1-yl)-2,3-dihydro-1-benzofuran-4-carboxylic acid in accordance with the methods shown in Example 9 or methods equivalent thereto.

Example 5

[6,6,33-Trimethyl-2-oxo-7-oxa-1,15,16,17-tetraaza-heptacyclo[22.5.3.2$^{3,9}$.1$^{18,22}$.0$^{4,8}$.0$^{15,19}$.0$^{27,31}$]penta-triaconta-3,8,16,18(33),19,21,24,26,31,34-decaen-23-yl]acetic acid

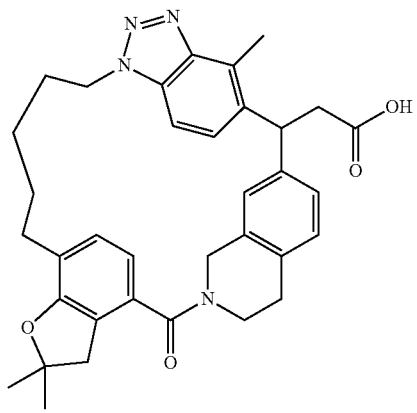 [SMILES: Cc1c2ccc3c1nnn3CCCCCc1ccc(c3c1OC(C)(C)C3)C(=O)N1CCc3ccc(cc3C1)C2CC(=O)O]

A) Ethyl 3-hydroxy-4-iodobenzoate

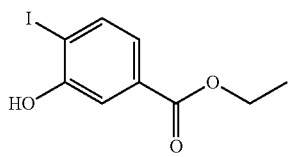

A mixture of 3-hydroxy-4-iodobenzoic acid (5.00 g), concentrated sulfuric acid (1.01 ml) and ethanol (50 ml) was stirred at 80° C. overnight. The reaction mixture was concentrated under reduced pressure. To the residue, water and saturated aqueous sodium bicarbonate solution were added, and the residue was extracted with ethyl acetate. The organic layer was separated and washed with water and saturated brine, followed by drying over anhydrous magnesium sulfate and concentration under reduced pressure. The residue was purified by silica gel column chromatography (ethyl acetate/hexane) to give the title compound (4.67 g).
MS m/z 293.0 [M+H]$^-$.

B) Ethyl 4-iodo-3-[(2-methylprop-2-en-1-yl)oxy]benzoate

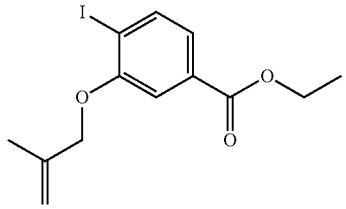 [SMILES: C=C(C)COc1cc(C(=O)OCC)ccc1I]

A mixture of ethyl 3-hydroxy-4-iodobenzoate (4.67 g), potassium carbonate (4.42 g), 3-chloro-2-methylprop-1-ene (2.35 ml) and N,N-dimethylformamide (50 ml) was stirred at 70° C. overnight. Water was added to the reaction mixture, and the mixture was extracted with ethyl acetate. The organic layer was separated and washed with water and saturated brine, followed by drying over anhydrous magnesium sulfate and concentration under reduced pressure. The residue was purified by silica gel column chromatography (ethyl acetate/hexane) to give the title compound (5.48 g).
MS m/z 347.1 [M+H]$^-$.

C) Ethyl 7-iodo-2,2-dimethyl-2,3-dihydro-1-benzofuran-4-carboxylate

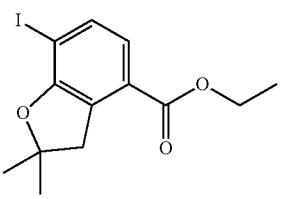 [SMILES: CCOC(=O)c1ccc(I)c2c1CC(C)(C)O2]

A mixture of ethyl 4-iodo-3-[(2-methylprop-2-en-1-yl)oxy]benzoate (5.48 g) and N-methyl-2-pyrrolidone (50 ml) was stirred at 190° C. overnight. Water was added to the reaction mixture, and the mixture was extracted with ethyl acetate. The organic layer was separated and washed with water and saturated brine, followed by drying over anhydrous magnesium sulfate and concentration under reduced pressure. The residue was purified by silica gel column chromatography (ethyl acetate/hexane) to give the title compound (1.69 g).
MS m/z 347.1 [M+H]$^-$.

D) 7-(But-3-en-1-yl)-2,2-dimethyl-2,3-dihydro-1-benzofuran-4-carboxylic acid

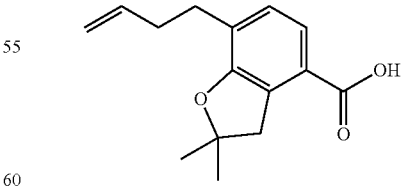

The title compound was obtained using ethyl 7-iodo-2,2-dimethyl-2,3-dihydro-1-benzofuran-4-carboxylate in accordance with the methods shown in Example 3 or methods equivalent thereto.
MS m/z 247.2 [M+H]$^-$.

E) [6,6,33-Trimethyl-2-oxo-7-oxa-1,15,16,17-tetraazaheptacyclo[22.5.3.2$^{3,9}$.1$^{18,22}$.0$^{4,8}$.0$^{15,19}$.0$^{27,31}$]pentatriaconta-3,8,16,18(33),19,21,24,26,31,34-decaen-23-yl]acetic acid

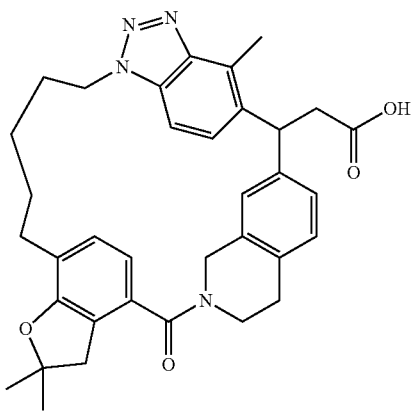 [SMILES: Cc1c2ccc3c1nnn3CCCCCc1ccc(c3c1OC(C)(C)C3)C(=O)N1CCc3ccc(cc3C1)C2CC(=O)O]

The title compound was obtained using 7-(but-3-en-1-yl)-2,2-dimethyl-2,3-dihydro-1-benzofuran-4-carboxylic acid in accordance with the methods shown in Example 9 or methods equivalent thereto.

Example 6

2-[32-Methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]propanoic acid

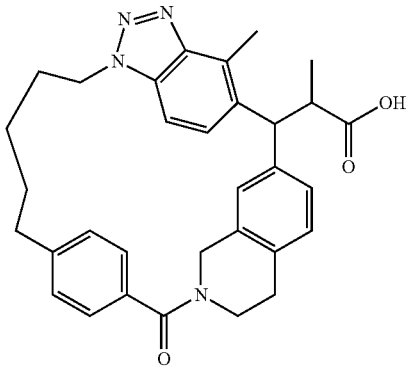 [SMILES: Cc1c2ccc3c1nnn3CCCCCc1ccc(cc1)C(=O)N1CCc3ccc(cc3C1)C2C(C)C(=O)O]

To a solution of ethyl [32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (90 mg) in tetrahydrofuran (2 ml), 1M solution of KHMDS/tetrahydrofuran (0.389 ml) was added dropwise at −78° C. After stirring the mixture at −78° C. for 45 minutes, methyl iodide (0.0242 ml) was added dropwise. While stirring the mixture, the temperature was raised from −78° C. to 0° C. over an hour. To the reaction solution, saturated aqueous ammonium chloride solution was added, and the reaction mixture was extracted with ethyl acetate. The extract solution was washed with saturated brine, followed by drying over anhydrous magnesium sulfate and concentration under reduced pressure. The residue was purified by silica gel column chromatography (ethyl acetate/hexane).

To a solution of the residue thus obtained in tetrahydrofuran (1 ml) and ethanol (1 ml), 2M aqueous sodium hydroxide solution (1 mL) was added, and the reaction mixture was stirred at room temperature overnight. The reaction solution was neutralized at 0° C. with 2N hydrochloric acid and concentrated. The residue was purified by preparative HPLC (YMC-Actus Triart C18, mobile phase: water/acetonitrile (0.1% TFA-containing system) to give the title compound (4 mg).

$^1$H NMR (300 MHz, DMSO-d$_6$) δ 0.76-1.21 (6H, m), 1.37-1.74 (2H, m), 1.79-2.22 (2H, m), 2.43 (3H, s), 2.54-2.68 (1H, m), 2.71-2.96 (2H, m), 3.09-3.33 (2H, m), 3.87-4.05 (1H, m), 4.08-4.49 (3H, m), 4.52-4.94 (2H, m), 6.26 (1H, br s), 6.76-6.96 (4H, m), 7.02-7.38 (2H, m), 7.47-7.76 (2H, m), 12.16 (1H, br s).

Example 7

[33-Methyl-2-oxo-5-oxa-1,15,16,17-tetraazaheptacyclo[22.5.3.2$^{3,9}$.1$^{18,22}$.0$^{4,8}$.0$^{15,19}$.0$^{27,31}$]pentatriaconta-3,8,16,18(33),19,21,24,26,31,34-decaen-23-yl]acetic acid

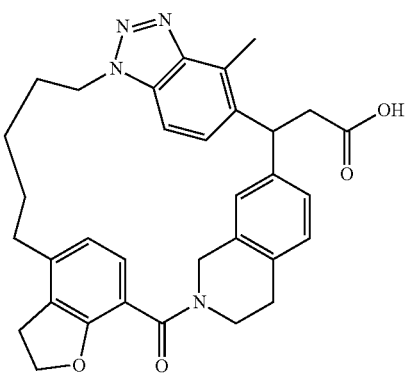 [SMILES: Cc1c2ccc3c1nnn3CCCCCc1ccc(c3c1CCO3)C(=O)N1CCc3ccc(cc3C1)C2CC(=O)O]

A) Methyl 4-bromo-2-hydroxy-3-(prop-2-en-1-yl)benzoate

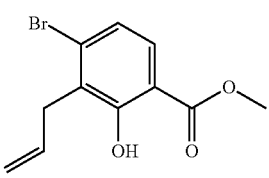

The title compound was obtained using methyl 4-bromo-2-hydroxybenzoate in accordance with the methods shown in Example 4 or methods equivalent thereto.

MS m/z 271.0 [M+H]$^-$.

B) Methyl 4-bromo-3-(2,3-dihydroxypropyl)-2-hydroxybenzoate

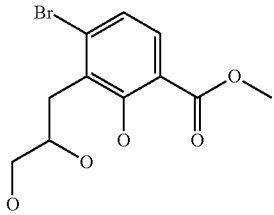 [SMILES: COC(=O)c1ccc(Br)c(CC(O)CO)c1O]

A mixture of methyl 4-bromo-2-hydroxy-3-(prop-2-en-1-yl)benzoate (1.50 g), microencapsulated osmium tetroxide (7.00%, 1.00 g), N-methylmorpholine N-oxide (1.94 g), acetonitrile (10 ml), acetone (10 ml) and water (10 ml) was stirred at room temperature overnight. The reaction mixture was filtered, and the filtrate was concentrated. Water was added to the residue, and the residue was extracted with ethyl acetate. The organic layer was separated and washed with water and saturated brine, followed by drying over anhydrous magnesium sulfate and concentration under reduced pressure. The residue was purified by silica gel column chromatography (ethyl acetate/hexane) to give the title compound (1.18 g).

MS m/z 305.1 [M+H]⁻.

C) Methyl 4-bromo-2-hydroxy-3-(2-hydroxyethyl)benzoate

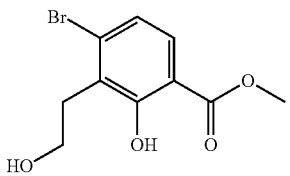

To a mixture of methyl 4-bromo-3-(2,3-dihydroxypropyl)-2-hydroxybenzoate (1.18 g), tetrahydrofuran (15 ml) and water (15 ml), sodium periodate (2.49 g) was added at 0° C., and the reaction mixture was stirred at room temperature for 3 hours. Water was added to the reaction mixture, and the mixture was extracted with ethyl acetate. The organic layer was separated and washed with water and saturated brine, followed by drying over anhydrous magnesium sulfate and concentration under reduced pressure. To a mixture of the residue, tetrahydrofuran (15 ml) and methanol (15 ml), sodium borohydride (147 mg) was added at 0° C., and the reaction mixture was stirred at the same temperature for 1 hour. To the reaction mixture, saturated aqueous ammonium chloride solution was added at 0° C., and the mixture was extracted with ethyl acetate. The organic layer was separated and washed with saturated brine, followed by drying over anhydrous magnesium sulfate and concentration under reduced pressure. The residue was purified by silica gel column chromatography (ethyl acetate/hexane) to give the title compound (870 mg).

MS m/z 275.1 [M+H]⁻.

D) Methyl 4-bromo-2,3-dihydro-1-benzofuran-7-carboxylate

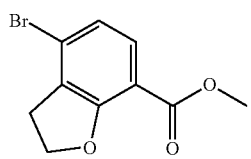

The title compound was obtained using methyl 4-bromo-2-hydroxy-3-(2-hydroxyethyl)benzoate in accordance with the methods shown in Example 4 or methods equivalent thereto.

MS m/z 257.1 [M+H]⁻.

E) 4-(But-3-en-1-yl)-2,3-dihydro-1-benzofuran-7-carboxylic acid

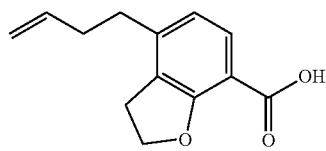 [SMILES: C=CCCc1ccc(C(=O)O)c2c1CCO2]

The title compound was obtained using methyl 4-bromo-2,3-dihydro-1-benzofuran-7-carboxylate in accordance with the methods shown in Example 3 or methods equivalent thereto.

MS m/z 219.2 [M+H]⁻.

F) [33-Methyl-2-oxo-5-oxa-1,15,16,17-tetraazaheptacyclo[22.5.3.2³,⁹1¹⁸,²².0⁴,⁸.0¹⁵,¹⁹.0²⁷,³¹]pentatriaconta-3,8,16,18(33),19,21,24,26,31,34-decaen-23-yl] acetic acid

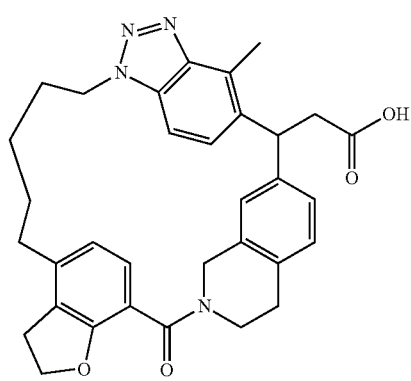 [SMILES: Cc1c2ccc3c1nnn3CCCCCc1ccc(c3c1CCO3)C(=O)N1CCc3ccc(cc3C1)C2CC(=O)O]

The title compound was obtained using 4-(but-3-en-1-yl)-2,3-dihydro-1-benzofuran-7-carboxylic acid in accordance with the methods shown in Example 9 or methods equivalent thereto.

Example 8

[6,6,33-Trimethyl-2-oxo-5-oxa-1,15,16,17-tetraazaheptacyclo[22.5.3.2$^{3,9}$.1$^{18,22}$.0$^{4,8}$.0$^{15,19}$.0$^{27,31}$]pentatriaconta-3,8,16,18(33),19,21,24,26,31,34-decaen-23-yl]acetic acid

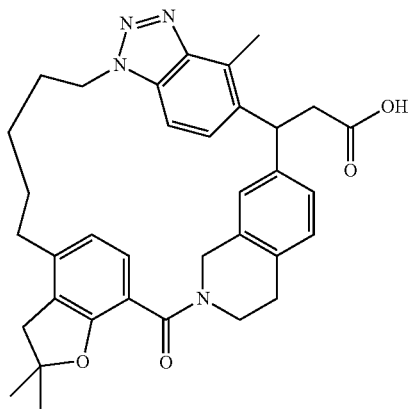 [SMILES: Cc1c2ccc3c1nnn3CCCCCc1ccc(c3c1CC(C)(C)O3)C(=O)N1CCc3ccc(cc3C1)C2CC(=O)O]

A) Methyl 4-iodo-2-[(2-methylprop-2-en-1-yl)oxy]benzoate

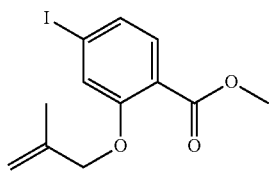 [SMILES: C=C(C)COc1cc(I)ccc1C(=O)OC]

The title compound was obtained using methyl 2-hydroxy-4-iodobenzoate in accordance with the methods shown in Example 5 or methods equivalent thereto.
MS m/z 333.0 [M+H]$^{+}$.

B) Methyl 2-hydroxy-4-iodo-3-(2-methylprop-2-en-1-yl)benzoate

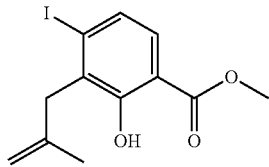 [SMILES: C=C(C)Cc1c(I)ccc(C(=O)OC)c1O]

A mixture of methyl 4-iodo-2-[(2-methylprop-2-en-1-yl)oxy]benzoate (5.93 g) and N-methyl-2-pyrrolidone (50 ml) was stirred at 190° C. overnight. Water was added to the reaction mixture, and the mixture was extracted with ethyl acetate. The organic layer was separated and washed with water and saturated brine, followed by drying over anhydrous magnesium sulfate and concentration under reduced pressure. The residue was purified by silica gel column chromatography (ethyl acetate/hexane) to give the title compound (3.97 g).
MS m/z 333.1 [M+H]$^{-}$.

C) Methyl 4-iodo-2,2-dimethyl-2,3-dihydro-1-benzofuran-7-carboxylate

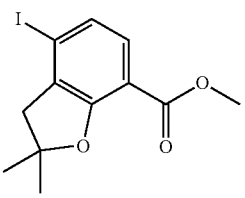

A mixture of methyl 2-hydroxy-4-iodo-3-(2-methylprop-2-en-1-yl)benzoate (310 mg) and formic acid (3 ml) was stirred at 100° C. overnight. The reaction mixture was concentrated under reduced pressure, and the residue was purified by silica gel column chromatography (ethyl acetate/hexane) to give the title compound (212 mg).
MS m/z 333.0 [M+H]$^{-}$.

D) 4-(But-3-en-1-yl)-2,2-dimethyl-2,3-dihydro-1-benzofuran-7-carboxylic acid

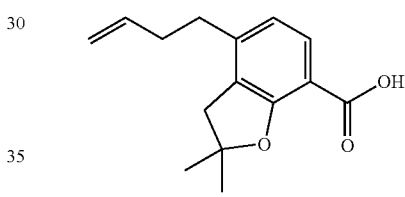

The title compound was obtained using methyl 4-iodo-2,2-dimethyl-2,3-dihydro-1-benzofuran-7-carboxylate in accordance with the methods shown in Example 3 or methods equivalent thereto.
MS m/z 247.2 [M+H]$^{-}$.

E) [6,6,33-Trimethyl-2-oxo-5-oxa-1,15,16,17-tetraazaheptacyclo[22.5.3.2$^{3,9}$.1$^{18,22}$.0$^{4,8}$.0$^{15,19}$.0$^{27,31}$]pentatriaconta-3,8,16,18(33),19,21,24,26,31,34-decaen-23-yl]acetic acid

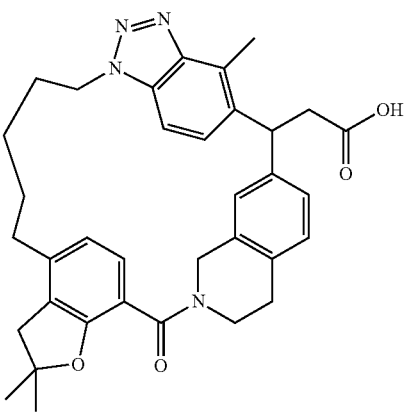 [SMILES: Cc1c2ccc3c1nnn3CCCCCc1ccc(c3c1CC(C)(C)O3)C(=O)N1CCc3ccc(cc3C1)C2CC(=O)O]

The title compound was obtained using 4-(but-3-en-1-yl)-2,2-dimethyl-2,3-dihydro-1-benzofuran-7-carboxylic acid in accordance with the methods shown in Example 9 or methods equivalent thereto.

Example 9

[18-Chloro-32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid

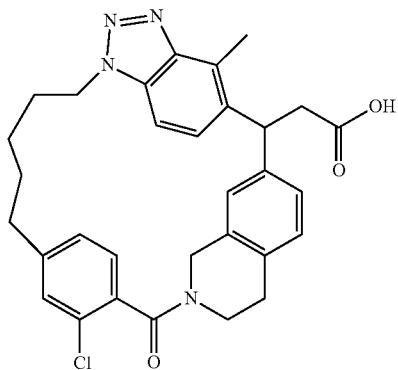 [SMILES: Cc1c2ccc3c1nnn3CCCCCc1ccc(c(Cl)c1)C(=O)N1CCc3ccc(cc3C1)C2CC(=O)O]

A) tert-Butyl (4-bromo-3-methyl-2-nitrophenyl)carbamate

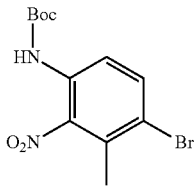 [SMILES: Cc1c(Br)ccc(NC(=O)OC(C)(C)C)c1[N+](=O)[O-]]

To a mixture of 4-bromo-3-methyl-2-nitro-aniline (2 g) and di-tert-butyl dicarbonate (3.97 g) in tetrahydrofuran (20 ml), N,N-dimethyl-4-aminopyridine (106 mg) was added, and the reaction mixture was stirred at room temperature for 3 days. After concentrating the reaction solution, tetrahydrofuran (20 ml) was added, 2M aqueous sodium hydroxide solution (5.2 ml) was added, and the reaction mixture was stirred at 70° C. overnight. Water was added to the mixture thus obtained, and the mixture was extracted with diisopropyl ether. The extract solution was washed with saturated brine, followed by drying over anhydrous magnesium sulfate and concentration under reduced pressure. The residue was purified by silica gel column chromatography (ethyl acetate/hexane) to give the title compound (2.13 g).

$^1$H NMR (300 MHz, DMSO-d$_6$) δ 1.42 (9H, s), 2.30 (3H, s), 7.32 (1H, d, J=8.9 Hz), 7.82 (1H, d, J=8.8 Hz), 9.35 (1H, s).

B) tert-Butyl (4-bromo-3-methyl-2-nitrophenyl)(2E)-but-2-en-1-ylcarbamate

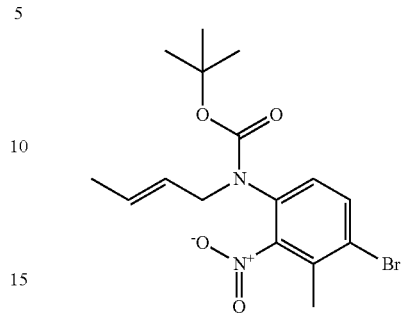

To a solution of 4-bromo-3-methyl-2-nitro-aniline (8.5 g) and di-tert-butyl dicarbonate (17.7 ml) in tetrahydrofuran (80 ml), N,N-dimethyl-4-aminopyridine (900 mg) was added, and the reaction mixture was stirred at room temperature overnight. To the reaction solution, 2M aqueous sodium hydroxide solution (37 ml) was added, and the reaction mixture was stirred at 70° C. overnight. Water was added to the mixture thus obtained, and the mixture was extracted with diethyl ether. The extract solution was washed with saturated brine, followed by drying over anhydrous magnesium sulfate and concentration under reduced pressure. The residue was purified by silica gel column chromatography (ethyl acetate/hexane) to give Boc-form (11.4 g). To a solution of the Boc-form (10 g) in N,N-dimethylformamide (70 ml), sodium hydride (50%, 1.59 g) was added at 0° C. After stirring the reaction mixture at 0° C. for 30 minutes, crotyl bromide (4.48 g) was added at 0° C. After stirring the mixture at room temperature for 4 hours, further crotyl bromide (4.48 g) was added at 0° C. The reaction mixture was stirred at room temperature overnight. To the mixture, saturated aqueous ammonium chloride solution was added at 0° C., and the mixture was extracted with ethyl acetate. The organic layer was separated and washed with water and saturated brine, followed by drying over anhydrous magnesium sulfate and concentration under reduced pressure. The residue was purified by silica gel column chromatography (ethyl acetate/hexane) to give the title compound (7 g).

$^1$H NMR (300 MHz, CDCl$_3$) δ 1.37 (9H, br s), 1.66 (3H, br s), 2.37 (3H, s), 3.43-4.00 (1H, m), 4.15-4.61 (1H, m), 5.41-5.71 (2H, m), 6.97 (1H, br d, J=7.7 Hz), 7.64 (1H, d, J=8.5 Hz).

C) 4-Bromo-N-[(2E)-but-2-en-1-yl]-3-methyl-2-nitroaniline

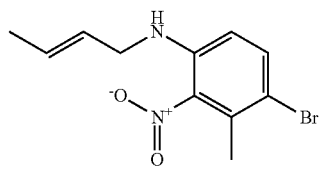

To a mixture of tert-butyl (4-bromo-3-methyl-2-nitrophenyl)(2E)-but-2-en-1-ylcarbamate (7 g) in ethyl acetate (10 ml), 4N HCl/ethyl acetate solution (30 ml) was added at room temperature. The mixture was stirred at room temperature overnight, and concentrated. To the residue thus obtained, saturated aqueous sodium bicarbonate solution was added, and the mixture was extracted with ethyl acetate. The organic layer was separated and washed with saturated brine, followed by drying over anhydrous magnesium sulfate and concentration under reduced pressure, to give the title compound (4.9 g).

$^1$H NMR (300 MHz, DMSO-d$_6$) δ 1.58-1.74 (3H, m), 2.24 (3H, s), 3.61-3.87 (2H, m), 5.24-5.72 (2H, m), 6.24-6.43 (1H, m), 6.55-6.74 (1H, m), 7.45-7.65 (1H, m).

D) 4-Bromo-N-1-[(2E)-but-2-en-1-yl]-3-methylbenzene-1,2-diamine

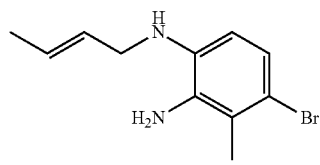

A mixture of 4-bromo-N-[(2E)-but-2-en-1-yl]-3-methyl-2-nitroaniline (4.9 g), ammonium chloride (9.19 g) and iron (4.8 g) in ethanol (50 ml) and water (10 ml) was stirred at 85° C. for 6 hours. The mixture was filtered, saturated aqueous sodium bicarbonate solution was added to the filtrate, and the mixture was extracted with ethyl acetate. The extract solution was washed with saturated brine, followed by drying over anhydrous magnesium sulfate and concentration under reduced pressure. The residue was purified by silica gel column chromatography (ethyl acetate/hexane) to give the title compound (3.8 g).

$^1$H NMR (300 MHz, CDCl$_3$) δ 1.72 (3H, br d, J=5.9 Hz), 2.31 (3H, s), 3.02-3.31 (1H, m), 3.35-3.58 (2H, m), 3.59-3.78 (2H, m), 5.53-5.89 (2H, m), 6.45 (1H, d, J=8.5 Hz), 7.00 (1H, d, J=8.5 Hz).

E) Ethyl (2E)-3-[1-(but-2-en-1-yl)-4-methyl-1H-benzotriazol-5-yl]prop-2-enoate (E/Z Isomer Mixture)

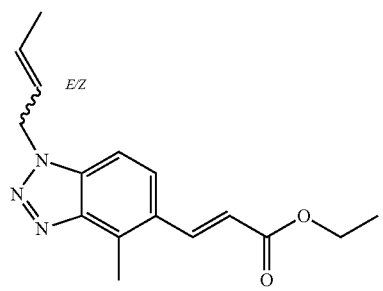 [SMILES: CC=CCn1nnc2c(C)c(/C=C/C(=O)OCC)ccc21]

To a mixture of 4-bromo-N-1-[(2E)-but-2-en-1-yl]-3-methylbenzene-1,2-diamine (3.6 g) in 6M hydrochloric acid (38 ml), a solution of sodium nitrite (2.06 g) in water (4 ml) was slowly added at 0° C. The mixture was stirred at room temperature for 2 hours. To the reaction solution, 2M aqueous sodium hydroxide solution was added at 0° C., and the mixture was extracted with ethyl acetate. The extract solution was washed with saturated brine, followed by drying over anhydrous magnesium sulfate and concentration under reduced pressure. The residue was purified by silica gel column chromatography (ethyl acetate/hexane) to give cyclized form (3.2 g).

To a solution of the cyclized form (3.13 g), ethyl acrylate (7.7 ml) and N,N-diisopropylethylamine (8.11 mL) in N,N-dimethyl form amide (14 ml), tri(o-tolyl)phosphine (1.07 g) and palladium acetate (396 mg) were added, and the reaction mixture was stirred at 120° C. for 6 hours. Further, after cooling the reaction mixture to room temperature, water was added thereto, and the mixture was extracted with ethyl acetate. The extract solution was washed with water and saturated brine, followed by drying over anhydrous magnesium sulfate and concentration under reduced pressure. The residue was purified by silica gel column chromatography (ethyl acetate/hexane) to give the title compound (3.2 g).

$^1$H NMR (300 MHz, DMSO-d$_6$) δ 1.28 (3H, t, J=7.1 Hz), 1.62-1.98 (3H, m), 2.81 (3H, s), 4.22 (2H, q, J=7.1 Hz), 5.22-5.44 (2H, m), 5.56-5.94 (2H, m), 6.65 (1H, d, J=15.9 Hz), 7.58-7.72 (1H, m), 7.87-8.19 (2H, m).

MS m/z 286.2 [M+H]$^-$.

F) tert-Butyl 7-{1-[1-(but-2-en-1-yl)-4-methyl-1H-benzotriazol-5-yl]]-3-ethoxy-3-oxopropyl}-3,4-dihydroisoquinoline-2(1H)-carboxylate (E/Z Isomer Mixture)

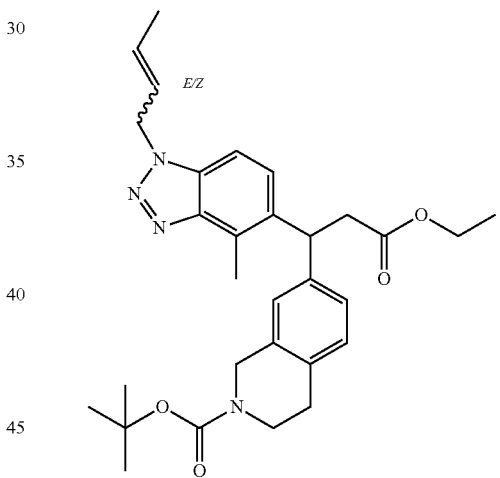

To a mixture of ethyl (2E)-3-[1-(but-2-en-1-yl)-4-methyl-1H-benzotriazol-5-yl]prop-2-enoate (E/Z isomer mixture) (3.1 g), tert-butyl 7-(4,4,5,5-tetramethyl-1,3,2-dioxaborolan-2-yl)-3,4-dihydro-1H-isoquinoline-2-carboxylate (5.85 g), sodium dodecyl sulfate (1.57 g), and triethylamine (4.54 ml) in CPME (50 ml) and water (25 ml), chloro(1,5-cyclooctadiene)rhodium (I) dimer (536 mg) was added at room temperature. The mixture was stirred at 90° C. for 4 hours under nitrogen atmosphere. Water was added to the mixture thus obtained, and the mixture was extracted with ethyl acetate. The extract solution was washed with saturated brine, followed by drying over anhydrous magnesium sulfate and concentration under reduced pressure. The residue was purified by silica gel column chromatography (ethyl acetate/hexane) to give the title compound (4.27 g).

$^1$H NMR (300 MHZ, DMSO-d$_6$) δ 1.01 (3H, br t, J=7.0 Hz), 1.41 (9H, s), 1.59-1.88 (3H, m), 2.68 (2H, br t, J=5.7 Hz), 2.77 (3H, s), 3.16 (2H, br d, J=7.6 Hz), 3.49 (2H, br t, J=5.4 Hz), 3.93 (21H, q, J=7.0 Hz), 4.43 (2H, br s), 4.82

(1H, br t, J=7.8 Hz), 5.14-5.41 (2H, m), 5.50-5.93 (2H, m), 6.96-7.24 (3H, m), 7.53 (2H, q, J=8.5 Hz).

MS m/z 519.4 [M+H]⁻.

G) Ethyl 3-[1-(but-2-en-1-yl)-4-methyl-1H-benzotriazol-5-yl]-3-(1,2,3,4-tetrahydroisoquinolin-7-yl)propanoate (E/Z Isomer Mixture)

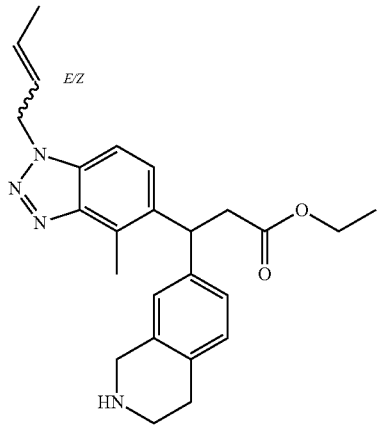 [SMILES: CC=CCn1nnc2c(C)c(C(CC(=O)OCC)c3ccc4c(c3)CNCC4)ccc21]

To a mixture of tert-butyl 7-{1-[1-(but-2-en-1-yl)-4-methyl-1H-benzotriazol-5-yl]-3-ethoxy-3-oxopropyl}-3,4-dihydroisoquinoline-2(1H)-carboxylate (E/Z isomer mixture) (4.2 g) in ethyl acetate (5 ml), 4N HCl/ethyl acetate solution (40 ml) was added, and the reaction mixture was stirred at room temperature for 5 hours. The mixture was concentrated, and to the residue thus obtained, saturated aqueous sodium bicarbonate solution was added, and the mixture was extracted with ethyl acetate. The organic layer was separated and washed with saturated brine, followed by drying over anhydrous magnesium sulfate and concentration under reduced pressure. The residue was purified by silica gel column chromatography (ethyl acetate/hexane) to give the title compound (2.4 g).

¹H NMR (300 MHz, DMSO-d₆) δ 1.01 (3H, t, J=6.8 Hz), 1.53-1.87 (3H, m), 2.22-2.43 (1H, m), 2.54-2.61 (2H, m), 2.75 (3H, s), 2.87 (2H, br t, J=5.3 Hz), 3.12 (2H, br d, J=7.6 Hz), 3.74 (2H, s), 3.93 (2H, q, J=7.1 Hz), 4.79 (1H, br t, J=7.7 Hz), 5.13-5.40 (2H, m), 5.54-5.90 (2H, m), 6.81-7.11 (3H, m), 7.35-7.67 (2H, m).

H) tert-Butyl 2-chloro-4-(3-hydroxyprop-1-yn-1-yl)benzoate

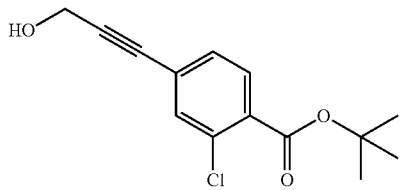 [SMILES: CC(C)(C)OC(=O)c1ccc(C#CCO)cc1Cl]

tert-Butyl 4-bromo-2-chlorobenzoate (3.67 g), 2-propyn-1-ol (2.117 g), copper (I) iodide (120 mg), triethylamine (3.54 ml), and bis(triphenylphosphine)palladium (II) dichloride (442 mg) were suspended in DMF (30 ml), and the reaction mixture was stirred at 80° C. for 8 hours under nitrogen atmosphere. The reaction solution was diluted with ethyl acetate and washed with saturated brine, followed by drying over anhydrous sodium sulfate and concentration under reduced pressure. The residue was purified by silica gel chromatography (ethyl acetate/hexane) to give the title compound (1.85 g).

¹H NMR (300 MHz, CDCl₃) δ 1.60 (9H, s), 4.51 (2H, d, J=6.1 Hz), 7.30-7.36 (1H, m), 7.45-7.50 (1H, m), 7.68 (1H, d, J=8.0 Hz).

I) tert-Butyl 2-chloro-4-(3-hydroxypropyl)benzoate

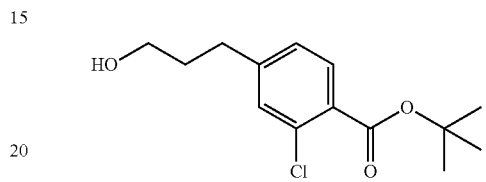

tert-Butyl 2-chloro-4-(3-hydroxyprop-1-yn-1-yl)benzoate (1.2 g) and tris(triphenylphosphine)rhodium (I) chloride (208 mg) were dissolved in toluene (100 mL), and the reaction mixture was stirred at 60° C. for 20 hours under hydrogen atmosphere. The reaction solution was cooled and then concentrated under reduced pressure, and the residue product thus obtained was purified by silica gel column chromatography (ethyl acetate/hexane) to give the title compound (1.047 g).

¹H NMR (300 MHz, DMSO-d6) δ 1.54 (9H, s), 1.64-1.78 (2H, m), 2.65 (2H, br t, J=7.7 Hz), 3.39 (2H, q, J=5.9 Hz), 4.51 (1H, t, J=5.0 Hz), 7.26 (1H, d, J=8.0 Hz), 7.38 (1H, s), 7.60-7.67 (1H, m).

J) tert-Butyl 2-chloro-4-(3-oxopropyl)benzoate

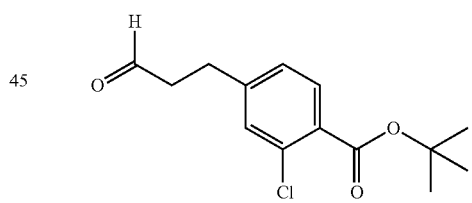

A solution of tert-butyl 2-chloro-4-(3-hydroxypropyl)benzoate (600 mg) and triethylamine (2.49 ml) in DMSO (30 ml) was cooled to 0° C., sulfur trioxide-pyridine complex (1.764 g) was added in several portions, and the reaction mixture was stirred at room temperature for 15 hours. The reaction solution was diluted with ethyl acetate, and then washed with water. The organic layer was dried over anhydrous sodium sulfate and concentrated under reduced pressure, and the residue product thus obtained was purified by silica gel chromatography (ethyl acetate/hexane) to give the title compound (476 mg).

¹H NMR (300 MHz, CDCl₃) δ 1.60 (9H, s), 2.75-2.84 (2H, m), 2.90-3.01 (2H, m), 7.12 (1H, d, J=8.0 Hz), 7.26 (11H, s), 7.68 (1H, d, J=8.0 Hz), 9.81 (1H, s).

K) tert-Butyl 4-(but-3-en-1-yl)-2-chlorobenzoate

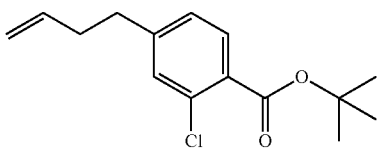 [SMILES: C=CCCc1ccc(C(=O)OC(C)(C)C)c(Cl)c1]

A suspension of methyltriphenylphosphonium bromide (2924 mg) in THF (30 ml) was cooled to 0° C., and potassium tert-butoxide (835 mg) was added in several portions. After raising the temperature of the reaction solution to room temperature, the solution was stirred for further 1 hour. The reaction solution was cooled to 0° C. again, and a solution of tert-butyl 2-chloro-4-(3-oxopropyl)benzoate (400 mg) in THF (1 ml) was added dropwise thereto. The temperature of the reaction mixture was raised to room temperature, and the mixture was then stirred for 15 hours. The reaction solution was poured into saturated aqueous ammonium chloride solution, and the reaction mixture was extracted with ethyl acetate. The organic layer was washed with saturated brine, dried over anhydrous sodium sulfate, and then concentrated under reduced pressure. The residue product thus obtained was purified by silica gel chromatography (ethyl acetate/hexane) to give the title compound (270 mg).

$^1$H NMR (300 MHz, CDCl$_3$) δ 1.55-1.66 (9H, m), 2.25-2.45 (2H, m), 2.61-2.77 (2H, m), 4.90-5.11 (2H, m), 5.68-5.90 (1H, m), 7.10 (1H, d, J=7.9 Hz), 7.33 (1H, s), 7.68 (1H, d, J=7.9 Hz).

L) 4-(But-3-en-1-yl)-2-chlorobenzoic acid

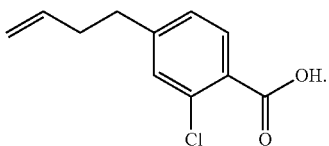

To a solution of tert-butyl 4-(but-3-en-1-yl)-2-chlorobenzoate (200 mg) in toluene (2.0 ml), trifluoroacetic acid (2.0 ml) was added dropwise at room temperature. The reaction solution was stirred at the same temperature for 2 hours, and then concentrated under reduced pressure to give the title compound (150 mg).

$^1$H NMR (300 MHz, DMSO-d$_6$) δ 2.27-2.41 (2H, m), 2.72 (2H, t, J=7.6 Hz), 4.93-5.08 (2H, m), 5.70-5.91 (1H, m), 7.27 (1H, d, J=7.9 Hz), 7.41 (1H, s), 7.72 (1H, d, J=7.9 Hz), 13.02-13.34 (1H, m).

M) Ethyl 3-{2-[4-(but-3-en-1-yl)-2-chlorobenzoyl]-1,2,3,4-tetrahydroisoquinolin-7-yl}-3-{1-[(2E)-but-2-en-1-yl]-4-methyl-1H-benzotriazol-5-yl}propanoate

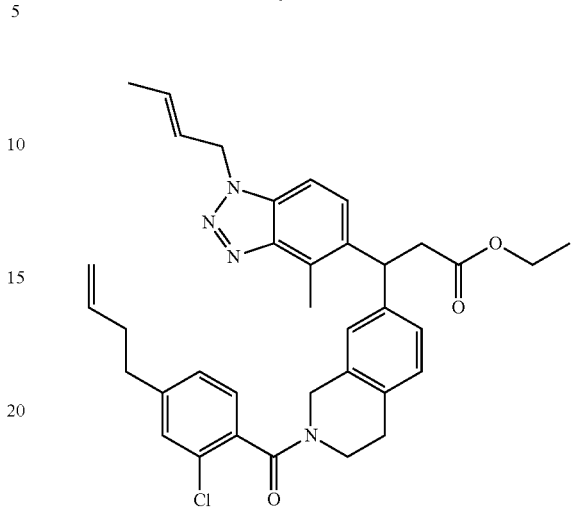

To a solution of ethyl 3-[1-(but-2-en-1-yl)-4-methyl-1H-benzotriazol-5-yl]-3-(1,2,3,4-tetrahydroisoquinolin-7-yl)propanoate (E/Z isomer mixture) (25 mg), 4-(but-3-en-1-yl)-2-chlorobenzoic acid (18.5 mg), anhydrous 1-hydroxybenzotriazole (16.1 mg) and triethylamine (0.025 ml) in DMF (1 ml), 1-[3-(dimethylamino)propyl]-3-ethylcarbodiimide (18.5 mg) was added, and the reaction mixture was stirred at room temperature for 15 hours. The reaction solution was diluted with ethyl acetate, and then washed with saturated brine. The organic layer was dried over anhydrous sodium sulfate and concentrated under reduced pressure, and the crude product thus obtained was purified by silica gel chromatography (ethyl acetate/hexane) to give the title compound (30 mg).

MS m/z 61 1.3 [M+H]$^+$.

N) Ethyl [(12Z)-18-chloro-32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,12,16,18,24,27,30-undecaen-2-yl]acetate

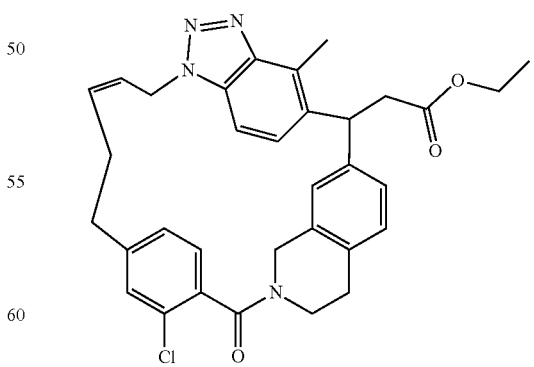

Ethyl 3-{2-[4-(but-3-en-1-yl)-2-chlorobenzoyl]-1,2,3,4-tetrahydroisoquinolin-7-yl}-3-{1-[(2E)-but-2-en-1-yl]-4-methyl-1H-benzotriazol-5-yl}propanoate (30 mg) was dissolved in 1,2-dichloroethane (35 ml), (1,3-bis-(2,4,6- trimethylphenyl)-2-imidazolidinylidene)dichloro(o-isopropoxyphenylmethylene)ruthenium (6.15 mg) was added, and the reaction mixture was stirred at 50° C. for 15 hours. The reaction solution was concentrated under reduced pressure, and the crude product thus obtained was purified by silica gel chromatography (ethyl acetate/hexane) to give the title compound (15 mg).

MS m/z 569.3 [M+H]⁻.

O) [18-Chloro-32-methyl-20-oxo-8,9,10,21-tetraaza-hexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid

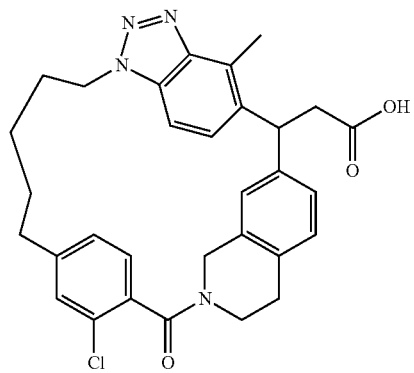 [SMILES: Cc1c2ccc3c1nnn3CCCCCc1ccc(c(Cl)c1)C(=O)N1CCc3ccc(cc3C1)C2CC(=O)O]

Ethyl [(12Z)-18-chloro-32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,12,16,18,24,27,30-undecaen-2-yl]acetate (33 mg) and tris(triphenylphosphine)rhodium (I) chloride (3.0 mg) were dissolved in toluene (10 ml), and the reaction mixture was stirred at 60° C. for 20 hours under hydrogen atmosphere, and then concentrated under reduced pressure. The residue was purified by silica gel chromatography (ethyl acetate/hexane). The crude product thus obtained was dissolved in a mixture of ethanol (1 ml) and THF (1 ml), 2M aqueous sodium hydroxide solution (1 ml) was added, and the reaction mixture was stirred at room temperature for 1 hour. To the reaction solution, 1M HCl (2.1 ml) was added to acidify the solution, and the mixture was then extracted with ethyl acetate. The extract solution was dried over anhydrous magnesium sulfate and then concentrated under reduced pressure to give the title compound (12.0 mg).

¹H NMR (300 MHz, DMSO-d₆) δ 1.29-1.68 (2H, m), 1.88-2.14 (2H, m), 2.45 (3H, m), 2.85 (2H, m), 2.90-3.17 (3H, m), 3.57-3.77 (3H, m), 3.80-4.07 (3H, m), 4.60-4.89 (4H, m), 5.68-5.90 (1H, m), 6.56 (2H, m), 6.91-7.07 (1H, m), 7.11-7.23 (1H, m), 7.25-7.44 (2H, m), 7.55-7.66 (1H, m), 12.12-12.34 (1H, m).

Example 10

[18-Fluoro-32-methyl-20-oxo-8,9,10,21-tetraaza-hexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid

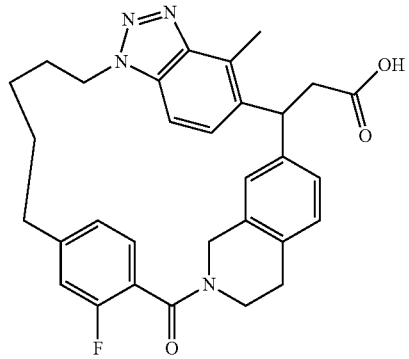 [SMILES: Cc1c2ccc3c1nnn3CCCCCc1ccc(c(F)c1)C(=O)N1CCc3ccc(cc3C1)C2CC(=O)O]

A) 4-(But-3-en-1-yl)-2-fluorobenzoic acid

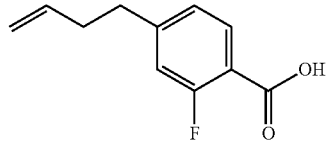

The title compound was obtained by subjecting tert-butyl 4-bromo-2-fluoro-benzoate to the same operation as Example 9.

¹H NMR (300 MHz, DMSO-d₆) δ 2.24-2.43 (2H, m), 2.67-2.81 (2H, m), 4.87-5.13 (2H, m), 5.82 (1H, ddt, J=16.7, 10.1, 6.5 Hz), 7.06-7.25 (2H, m), 7.78 (1H, br t, J=8.0 Hz), 13.08 (1H, br s).

B) [18-Fluoro-32-methyl-20-oxo-8,9,10,21-tetraaza-hexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid

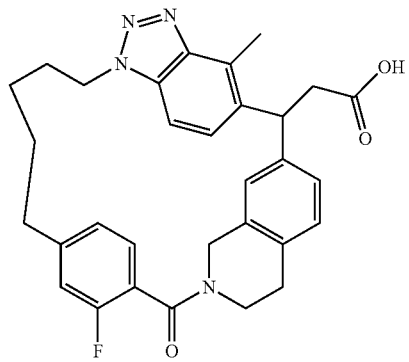

The title compound was obtained by subjecting 4-(but-3-en-1-yl)-2-fluorobenzoic acid to the same operation as Example 9.

Example 11

[32-Methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid Chiral, Synthesis from chiral ethyl [32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Retention Time Short)

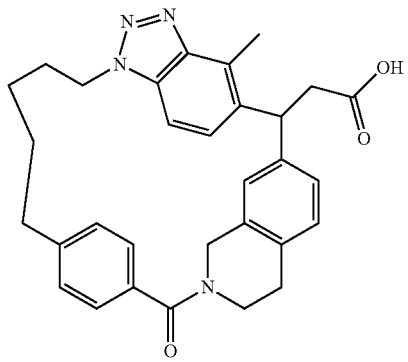 [SMILES: Cc1c2ccc3c1nnn3CCCCCc1ccc(cc1)C(=O)N1CCc3ccc(cc3C1)C2CC(=O)O]

A) Ethyl [32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Chiral, Retention Time Long)

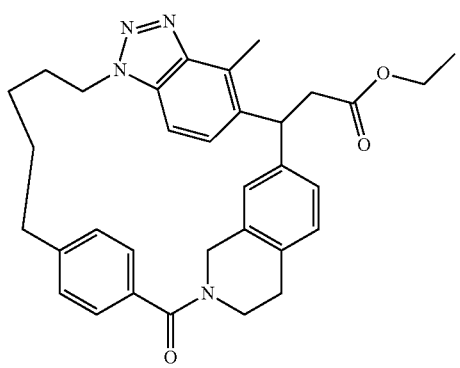 [SMILES: CCOC(=O)CC1c2ccc3c(c2)CN(CC3)C(=O)c2ccc(cc2)CCCCCn2nnc3c(C)c1ccc32]

Racemate of ethyl 2-(32-methyl-20-oxo-8,9,10,21-tetraazahexacyclo[19.5.3.216,19.13,7.06,10.024,28]dotriaconta-1(26),3,5,7(32),8,16(31),17,19(30),24,27-decaen-2-yl]acetate (2.59 g) was fractionated by preparative supercritical CO$_2$ chromatography system (column: Cellulose-C (5 µm) 250×30 mm I.D., mobile phase: carbon dioxide/methanol=65/35). The fraction thus obtained was concentrated under reduced pressure to give the title compound (1.22 g) (chiral, retention time long).

Analysis conditions retention time: 4.997 minutes (column: Alcyon SFC CSP Cellulose-C (5 µm), 250×4.6 mm I.D., mobile phase: carbon dioxide/methanol=65/35, flow rate: 3.0 mL/min, temperature: 35° C., detection: UV 210 nm, sample concentration: 1 mg/mL, injection volume: 0.005 mL).

B) Ethyl [32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Chiral, Retention Time Short)

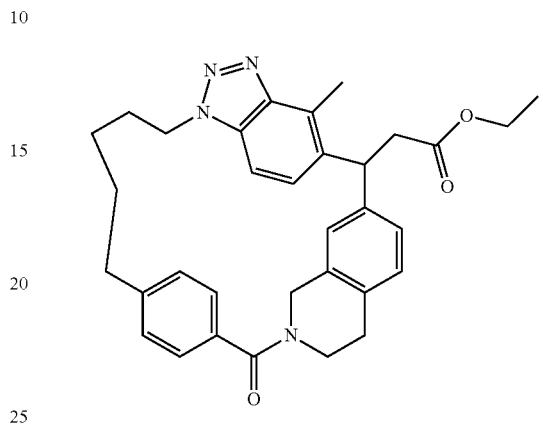

Racemate of ethyl [32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (2.59 g) was fractionated by preparative supercritical CO$_2$ chromatography system (column: Cellulose-C (5 µm) 250×30 m I.D., mobile phase: carbon dioxide/methanol=65/35). The fraction thus obtained was concentrated under reduced pressure to give the title compound (1.23 g) (chiral, retention time short).

Analysis conditions retention time: 3.795 minutes (column: Alcyon SFC CSP Cellulose-C (5 µm), 250×4.6 mm I.D., mobile phase: carbon dioxide/methanol=65/35, flow rate: 3.0 mL/min, temperature: 35° C., detection: UV 210 nm, sample concentration: 1 mg/mL, injection volume: 0.005 mL).

C) [32-Methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid Chiral, Synthesis from Chiral ethyl [32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Retention Time Short)

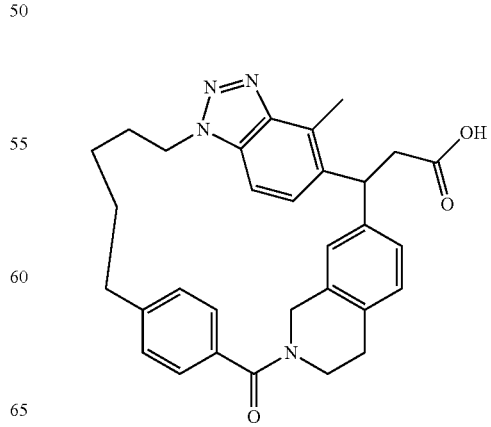

To a solution of ethyl [32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (chiral, retention time short) (1.23 g) in tetrahydrofuran (12 ml) and ethanol (6 ml), 1N aqueous sodium hydroxide solution (11.5 mL) was added, and the reaction mixture was stirred at room temperature for 6 hours. The reaction solution was concentrated to remove organic solvents. Subsequently, the solution was diluted with water, and then made slightly acidic (pH4-7) with 1N hydrochloric acid at 0° C. The precipitate was filtered and washed with water to give the title compound (1 g).

$^1$H NMR (300 MHz, DMSO-d$_6$) δ 0.70-1.12 (2H, m), 1.30-1.66 (2H, m), 1.80-2.21 (2H, m), 2.50 (5H, br s), 2.75-2.88 (2H, m), 2.91-3.18 (2H, m), 3.57-4.20 (4H, m), 4.55-4.89 (3H, m), 5.89 (1H, s), 6.80-6.94 (4H, m), 7.14 (1H, br d, J=7.0 Hz), 7.27-7.45 (2H, m), 7.60 (1H, d, J=9.1 Hz), 12.25 (1H, s).

Analysis conditions retention time: 19.0 minutes (column: DAICEL CHIRALPAK IB N-5 (5 μm), 250×4.6 mm I.D., mobile phase: A/B=82.5/17.5, A=hexane (0.1% trifluoroacetic acid), B=ethanol (0.1% trifluoroacetic acid), measurement temperature: room temperature, flow rate: 2.0 mL/min, detection: UV 220 nm and 254 nm, sample concentration: 0.5 mg/mL, injection volume: 0.01 mL).

Example 12

[32-Methyl-20-oxo-8,9,10,21-tetraazahexacyclo[19.5.3.2$^{16,19}$.0$^{3,7}$.0$^{6,10}$.0$^{24,28}$]dotriaconta-1(26),3(32),4,6,8,16,18,24,27,30-decaen-2-yl]acetic acid Chiral, Synthesis from chiral ethyl [32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Retention Time Long)

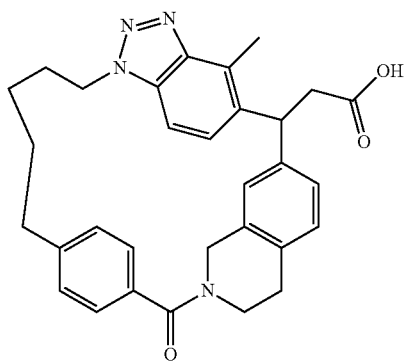 [SMILES: Cc1c2ccc3c1nnn3CCCCCc1ccc(cc1)C(=O)N1CCc3ccc(cc3C1)C2CC(=O)O]

To a solution of ethyl [32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (chiral, retention time long) (1.22 g) in tetrahydrofuran (12 ml) and ethanol (6 ml), 1M aqueous sodium hydroxide solution (11 mL) was added, and the reaction mixture was stirred at room temperature for 6 hours. The reaction solution was concentrated to remove organic solvents. Subsequently, the solution was diluted with water, and made slightly acidic (pH4-7) with 1N hydrochloric acid at 0° C. The precipitate was filtered and washed with water to give the title compound (1.12 g).

$^1$H NMR (300 MHz, DMSO-d$_6$) δ 0.72-1.09 (2H, m), 1.38-1.64 (2H, m), 1.71-2.25 (2H, m), 2.42-2.63 (5H, m), 2.83 (2H, br t, J=6.1 Hz), 2.92-3.20 (2H, m), 3.67 (1H, dt, J=13.0, 6.4 Hz), 3.81-4.24 (3H, m), 4.42-5.07 (3H, m), 5.89 (1H, s), 6.77-6.98 (4H, m), 7.14 (1H, d, J=7.9 Hz), 7.28-7.47 (2H, m), 7.61 (1H, d, J=8.6 Hz), 12.21 (1H, br s).

Analysis conditions retention time: 29.9 minutes (column: DAICEL CHIRALPAK 1B N-5 (5 μm), 250×4.6 mm I.D., mobile phase: A/B=82.5/17.5, A=hexane (0.1% trifluoroacetic acid), B=ethanol (0.1% trifluoroacetic acid), measurement temperature: room temperature, flow rate: 2.0 mL/min, detection: UV 220 nm and 254 nm, sample concentration: 0.5 mg/mL, injection volume: 0.01 mL).

Example 13

[31-Methyl-19-oxo-8,9,10,20-tetraazahexacyclo[18.5.3.2$^{15,18}$.1$^{3,7}$.0$^{6,10}$.0$^{23,27}$]hentriaconta-1(25),3(31),4,6,8,15,17,23,26,29-decaen-2-yl]acetic acid

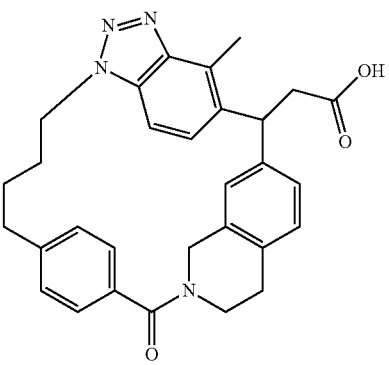 [SMILES: Cc1c2ccc3c1nnn3CCCCc1ccc(cc1)C(=O)N1CCc3ccc(cc3C1)C2CC(=O)O]

Synthesis was carried out in accordance with the methods shown in Example 9 or methods equivalent thereto.

Example 14

[(13Z)-33-Methyl-21-oxo-8,9,10,22-tetraazahexacyclo[20.5.3.2$^{17,20}$.1$^{3,7}$.0$^{6,10}$.0$^{25,29}$]tritriaconta-1(27),3(33),4,6,8,13,17,19,25,28,31-undecaen-2-yl]acetic acid

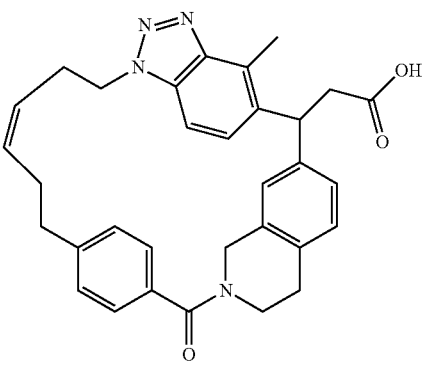 [SMILES: Cc1c2ccc3c1nnn3CC/C=C\CCc1ccc(cc1)C(=O)N1CCc3ccc(cc3C1)C2CC(=O)O]

A) tert-Butyl but-3-en-1-yl(3-methyl-2-nitrophenyl) carbamate

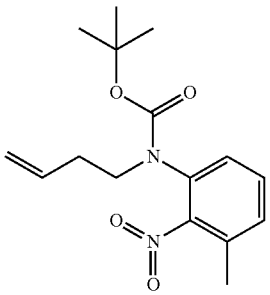 [SMILES: C=CCCN(C(=O)OC(C)(C)C)c1cccc(C)c1[N+](=O)[O-]]

To a solution of tert-butyl N-(3-methyl-2-nitro-phenyl)carbamate (7 g) in N,N-dimethylformamide (70 ml), sodium hydride (50%, 1.33 g) was added at 0° C. After stirring the reaction mixture at 0° C. for 20 minutes, 4-bromo-1-butene (3.75 g) was added at 0° C. After stirring the mixture at room temperature for 4 hours, further 4-bromo-1-butene (3.75 g) was added at 0° C. The reaction mixture was stirred at 60° C. overnight. To the mixture, saturated aqueous ammonium chloride solution was added at 0° C., and the mixture was extracted with ethyl acetate. The organic layer was separated and washed with water and saturated brine, followed by drying over anhydrous magnesium sulfate and concentration under reduced pressure. The residue was purified by silica gel column chromatography (ethyl acetate/hexane) to give the title compound (4.33 g).

$^1$H NMR (300 MHz, DMSO-$d_6$) δ 1.27 (9H, br s), 2.14-2.38 (5H, s), 3.25-3.85 (2H, m), 4.92-5.19 (2H, m), 5.65-5.87 (1H, m), 7.29-7.48 (2H, m), 7.49-7.60 (1H, m).

B) 4-Bromo-N-(but-3-en-1-yl)-3-methyl-2-nitroaniline

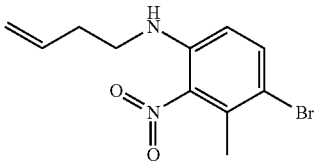 [SMILES: C=CCCNc1ccc(Br)c(C)c1[N+](=O)[O-]]

To a mixture of tert-butyl but-3-en-1-yl(3-methyl-2-nitrophenyl)carbamate (4.33 g) in ethyl acetate (10 ml), 4N HCl/ethyl acetate solution (40 ml) was added at 0° C. The mixture was stirred at 0° C. for 20 minutes, stirred at room temperature overnight, and then concentrated. To the residue thus obtained, saturated aqueous sodium bicarbonate solution was added, and the mixture was extracted with ethyl acetate. The organic layer was separated and washed with saturated brine, followed by drying over anhydrous magnesium sulfate and concentration under reduced pressure.

To a solution of the residue thus obtained in N,N-dimethylformamide (25 ml), N-bromosuccinimide (2.5 g) was added at 0° C. After stirring the reaction solution at room temperature overnight, water was added thereto at 0° C., and the mixture was extracted with ethyl acetate. The organic layer was separated and washed with water and saturated brine, followed by drying over anhydrous magnesium sulfate and concentration under reduced pressure. The residue was purified by silica gel column chromatography (ethyl acetate/hexane) to give the title compound (3.38 g).

$^1$H NMR (300 MHz, DMSO-$d_6$) δ 2.18-2.36 (5H, m), 3.20 (2H, q, J=6.6 Hz), 4.92-5.16 (2H, m), 5.81 (1H, ddt, J=17.1, 10.3, 6.6 Hz), 6.09 (1H, br t, J=5.3 Hz), 6.76 (1H, d, J=9.1 Hz), 7.55 (1H, d, J=9.1 Hz). MS m/z 285.0 [M+H]$^+$.

C) Ethyl (2E)-3-[1-(but-3-en-1-yl)-4-methyl-1H-benzotriazol-5-yl]prop-2-enoate

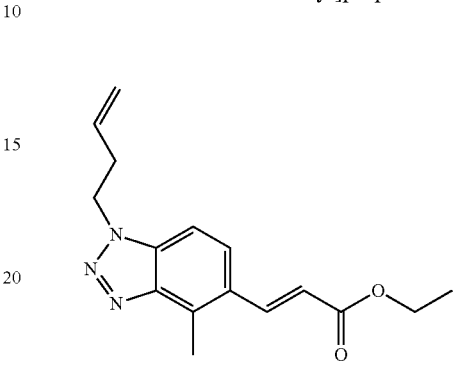

To a mixture of 4-bromo-N-(but-3-en-1-yl)-3-methyl-2-nitroaniline (3.18 g) in ethanol (40 ml), tin chloride dihydrate (2.53 g) was added. After stirring the mixture at 90° C. for 3 hours, further tin chloride dihydrate (2.53 g) was added. The reaction mixture was stirred at 90° C. for 3 hours, and then concentrated. To the residue thus obtained, ice was added. Further, 1M sodium hydroxide was added to the mixture for neutralization, and the mixture was then extracted with ethyl acetate. The organic layer was separated and washed with saturated brine, followed by drying over anhydrous magnesium sulfate and concentration under reduced pressure. The residue thus obtained was purified by silica gel column chromatography (ethyl acetate/hexane).

To a mixture of the residue thus obtained (1.6 g) in 6M hydrochloric acid (16 ml), a solution of sodium nitrite (865 mg) in water (2 ml) was slowly added at 0° C. The mixture was stirred at room temperature overnight. To the reaction solution, 2M aqueous sodium hydroxide solution was added, and the mixture was extracted with ethyl acetate. The extract solution was washed with saturated brine, followed by drying over anhydrous magnesium sulfate and concentration under reduced pressure. The residue was purified by silica gel column chromatography (ethyl acetate/hexane) to give benzotriazole derivative (1.23 g). To a solution of the benzotriazole derivative (1.23 g), ethyl acrylate (2.78 g), N,N-diisopropylethylamine (2.39 g) and tri(o-tolyl)phosphine (422 mg) in N,N-dimethylformamide (20 ml), palladium acetate (156 mg) was added, and the reaction mixture was stirred at 120° C. for 4 hours under microwave irradiation. After cooling the reaction mixture to room temperature, water and ethyl acetate were added thereto, and the insoluble material was filtered. Water was added to the filtrate, and the mixture was extracted with ethyl acetate. The extract solution was washed with water and saturated brine, followed by drying over anhydrous magnesium sulfate and concentration under reduced pressure. The residue was purified by silica gel column chromatography (ethyl acetate/hexane) to give the title compound (490 mg).

$^1$H NMR (300 MHz, DMSO-$d_6$) δ 1.28 (3H, t, J=7.1 Hz), 2.68 (2H, q, J=6.7 Hz), 2.80 (3H, s), 4.22 (2H, q, J=7.1 Hz), 4.78 (2H, t, J=6.8 Hz), 4.89-5.09 (2H, m), 5.79 (1H, ddt, J=17.1, 10.1, 6.8 Hz), 6.65 (1H, d, J=15.9 Hz), 7.74 (1H, d, J=8.7 Hz), 7.90-8.09 (2H, m). MS m/z 286.2 [M+H]+.

D) Ethyl [(13Z)-33-methyl-21-oxo-8,9,10,22-tetraazahexacyclo[20.5.3.2$^{17,20}$.1$^{3,7}$.0$^{6,10}$.0$^{25,29}$]tritriaconta-1(27),3(33),4,6,8,13,17,19,25,28,31-undecaen-2-yl] acetate

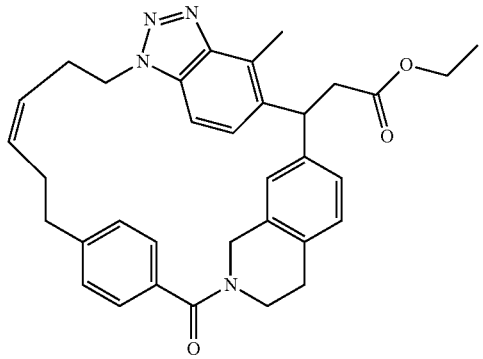 [SMILES: CCOC(=O)CC1c2ccc3c(c2)CN(CC3)C(=O)c2ccc(cc2)CC/C=C\CCn2nnc3c(C)c1ccc32]

Synthesis was carried out using ethyl (2E)-3-[1-(but-3-en-1-yl)-4-methyl-1H-benzotriazol-5-yl]prop-2-enoate in accordance with the methods shown in Example 9 or methods equivalent thereto.

E) [(13Z)-33-Methyl-21-oxo-8,9,10,22-tetraazahexacyclo[20.5.3.2$^{17,20}$.1$^{3,7}$.0$^{6-10}$.0$^{25-29}$]tritriaconta-1(27),3(33),4,6,8,13,17,19,25,28,31-undecaen-2-yl] acetic acid

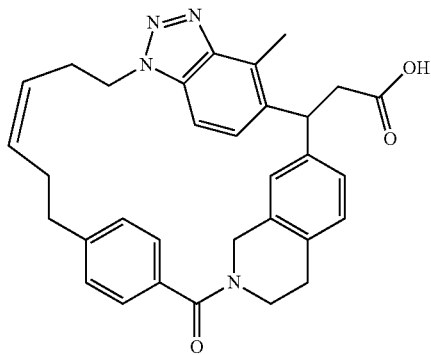 [SMILES: Cc1c2ccc3c1nnn3CC/C=C\CCc1ccc(cc1)C(=O)N1CCc3ccc(cc3C1)C2CC(=O)O]

To a solution of ethyl [(13Z)-33-methyl-21-oxo-8,9,10, 22-tetraazahexacyclo[20.5.3.2$^{17,20}$.1$^{3,7}$.0$^{6,10}$.0$^{25,29}$]tritriaconta-1(27),3(33),4,6,8,13,17,19,25,28,31-undecaen-2-yl] acetate (40 mg) in tetrahydrofuran (1 ml) and ethanol (1 ml), 2M aqueous sodium hydroxide solution (2 mL) was added, and the reaction mixture was stirred at room temperature overnight. The reaction solution was concentrated to remove organic solvents, and then neutralized with 1N hydrochloric acid at 0° C. The precipitate was filtered and washed with water to give the title compound (30 mg).

Example 15

[33-Methyl-21-oxo-8,9,10,22-tetraazahexacyclo [20.5.3.2$^{17,20}$.1$^{3,7}$.0$^{6,10}$.0$^{25,29}$]tritriaconta-1(27),3 (33),4,6,8,17,19,25,28,31-decaen-2-yl]acetic acid

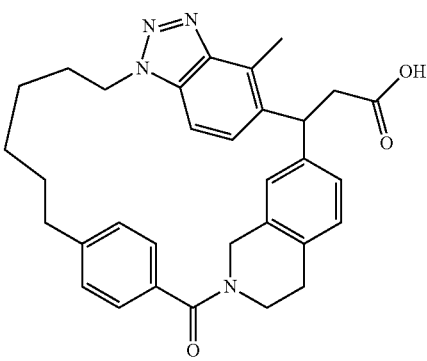 [SMILES: Cc1c2ccc3c1nnn3CCCCCCc1ccc(cc1)C(=O)N1CCc3ccc(cc3C1)C2CC(=O)O]

Synthesis was carried out in accordance with the methods shown in Example 9 or 14, or methods equivalent thereto.

Example 16

[32-Methyl-20-oxo-14-oxa-8,9,10,21-tetraazahexacyclo[19.5.3.2$^{16,19}$.1$^{3,7}$.0$^{6,10}$.0$^{24,28}$]dotriaconta-1 (26),3(32),4,6,8,16,18,24,27,30-decaen-2-yl]acetic acid

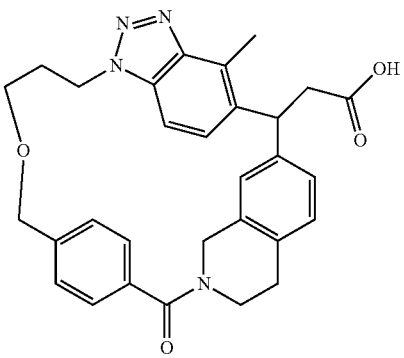 [SMILES: Cc1c2ccc3c1nnn3CCCOCc1ccc(cc1)C(=O)N1CCc3ccc(cc3C1)C2CC(=O)O]

A) 3-(4-Bromo-3-methyl-2-nitroanilino)propan-1-ol

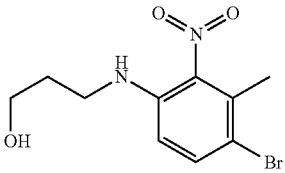 [SMILES: Cc1c(Br)ccc(NCCCO)c1[N+](=O)[O-]]

To a solution of 1-bromo-4-fluoro-2-methyl-3-nitro-benzene (2 g) in N,N-dimethylformamide (15 ml), potassium carbonate (2.36 g) and 3-amino-1-propanol (0.83 g) were added at room temperature, and the reaction mixture was stirred at 80° C. overnight. Water (80 ml) was added to the mixture at 0° C. The precipitate was separated by filtration, and then washed with water to give the title compound (2-4 g).

¹H NMR (300 MHz, DMSO-d₆) δ 1.67 (2H, quin, J=6.3 Hz), 2.25 (3H, s), 3.19 (2H, q, J=6.1 Hz), 3.47 (2H, q, J=5.5 Hz), 4.59 (1H, t, J=4.9 Hz), 6.08-6.35 (1H, m), 6.74 (1H, d, J=9.2 Hz), 7.54 (1H, d, J=9.1 Hz).

B) 3-(2-Amino-4-bromo-3-methylanilino)propan-1-ol

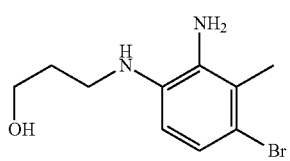

A mixture of 3-(4-bromo-3-methyl-2-nitroanilino)propan-1-ol (7.53 g), ammonium chloride (13.9 g), iron (7.27 g), ethanol (54 ml) and water (20 ml) was stirred at 85° C. overnight. The mixture was filtered, and the filtrate was concentrated. To the mixture thus obtained, saturated aqueous sodium bicarbonate solution was added, and the mixture was extracted with ethyl acetate. The extract solution was washed with saturated brine, followed by drying over anhydrous magnesium sulfate and concentration under reduced pressure. The residue was washed with ethyl acetate to give the title compound. The washing liquid was concentrated, and the residue thus obtained was purified by silica gel column chromatography (ethyl acetate/hexane) to further give the title compound. In total, 4.8 g of the title compound was obtained.

¹H NMR (300 MHz, DMSO-d₆) δ 1.73 (2H, quin, J=6.6 Hz), 2.16 (3H, s), 3.04 (2H, q, J=6.5 Hz), 3.51 (2H, q, J=5.6 Hz), 4.40-4.67 (4H, m), 6.25 (1H, d, J=8.6 Hz), 6.71 (1H, d, J=8.5 Hz).

C) 3-(5-Bromo-4-methyl-1H-benzotriazol-1-yl)propan-1-ol

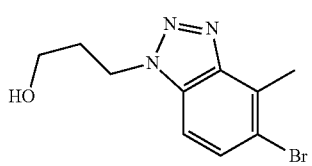

To a mixture of 3-(2-amino-4-bromo-3-methylanilino)propan-1-ol (4.8 g) in 6N hydrochloric acid (45 ml), a solution of sodium nitrite (2.56 g) in water (10 ml) was slowly added at 0° C. The mixture was stirred at room temperature for 2 hours. To the reaction solution, 4N aqueous sodium hydroxide solution was added at 0° C. for neutralization, and the mixture was extracted with ethyl acetate. The extract solution was washed with saturated brine, followed by drying over anhydrous magnesium sulfate and concentration under reduced pressure. The residue was purified by silica gel column chromatography (ethyl acetate/hexane) to give the title compound (4 g).

¹H NMR (300 MHz, DMSO-d₆) δ 2.04 (2H, quin, J=6.4 Hz), 2.72 (3H, s), 3.39 (2H, q, J=5.5 Hz), 4.67 (1H, br t, J=4.7 Hz), 4.74 (2H, t, J=6.9 Hz), 7.69 (2H, s).

MS m/z 270.1 [M+H]⁻.

D) tert-Butyl 4-{[3-(5-bromo-4-methyl-1H-benzotriazol-1-yl)propoxy]methyl} benzoate

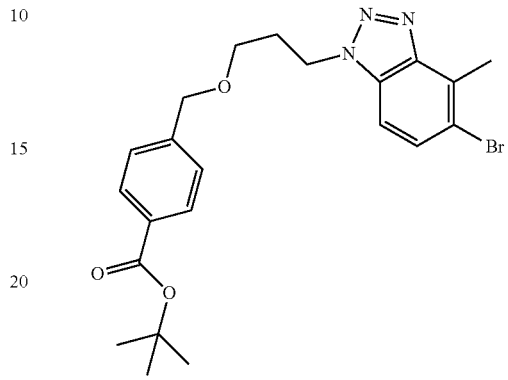

To a solution of 3-(5-bromo-4-methyl-1H-benzotriazol-1-yl)propan-1-ol (6.55 g) in N,N-dimethylformamide (100 ml), sodium hydride (oily, 50%, 1.51 g) was added at 0° C. under nitrogen atmosphere. After stirring the reaction mixture at 0° C. for 30 minutes, tert-butyl 4-(bromomethyl) benzoate (7.23 g) was added at 0° C. After stirring the mixture at room temperature for 2 hours, saturated aqueous ammonium chloride solution was added thereto, and the mixture was extracted with ethyl acetate. The organic layer was separated and washed with saturated brine, followed by drying over anhydrous magnesium sulfate and concentration under reduced pressure. The residue was purified by silica gel column chromatography (ethyl acetate/hexane) to give the title compound (8.61 g).

¹H NMR (300 MHz, DMSO-d₆) δ 1.55 (9H, s), 2.21 (2H, quin, J=6.1 Hz), 2.69 (3H, s), 3.43 (2H, br t, J=5.6 Hz), 4.43 (2H, s), 4.79 (2H, t, J=6.5 Hz), 7.26 (2H, br d, J=7.8 Hz), 7.66 (2H, s), 7.81 (2H, d, J=7.8 Hz).

MS m/z 460.2 [M+H]⁻.

E) tert-Butyl 4-[(3-{5-[(1E)-3-ethoxy-3-oxoprop-1-en-1-yl]-4-methyl-1H-benzotriazol-1-yl}propoxy)methyl] benzoate

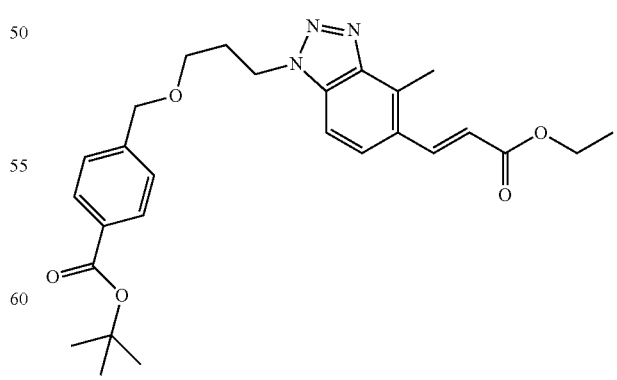

To a solution of tert-butyl 4-{[3-(5-bromo-4-methyl-1H-benzotriazol-1-yl)propoxy]methyl} benzoate (9 g), ethyl acrylate (11.7 g) and N,N-diisopropylethylamine (13.5 ml)

in N,N-dimethylformamide (200 ml), tri(o-tolyl)phosphine (1.79 g) and palladium acetate (658 mg) were added, and the reaction mixture was stirred at 120° C. for 4 hours under argon atmosphere. The reaction mixture was concentrated, water was added thereto, and the mixture was extracted with ethyl acetate. The extract solution was washed with water and saturated brine, followed by drying over anhydrous magnesium sulfate and concentration under reduced pressure. The residue was purified by silica gel column chromatography (ethyl acetate/hexane) to give the title compound (7.9 g).

$^1$H NMR (300 MHz, DMSO-$d_6$) δ 1.28 (3H, t, J=7.2 Hz), 1.54 (9H, s), 2.10-2.32 (2H, m), 2.79 (3H, s), 3.43 (2H, br t, J=5.5 Hz), 4.22 (2H, q, J=7.0 Hz), 4.44 (2H, s), 4.79 (2H, br t, J=6.4 Hz), 6.64 (1H, d, J=15.8 Hz), 7.28 (2H, d, J=7.9 Hz), 7.59-7.84 (3H, m), 7.87-8.14 (2H, m).

F) tert-Butyl 7-{1-[1-(3-{[4-(tert-butoxycarbonyl)phenyl]methoxy}propyl)-4-methyl-1H-benzotriazol-5-yl]-3-ethoxy-3-oxopropyl}-3,4-dihydroisoquinoline-2(1H)-carboxylate

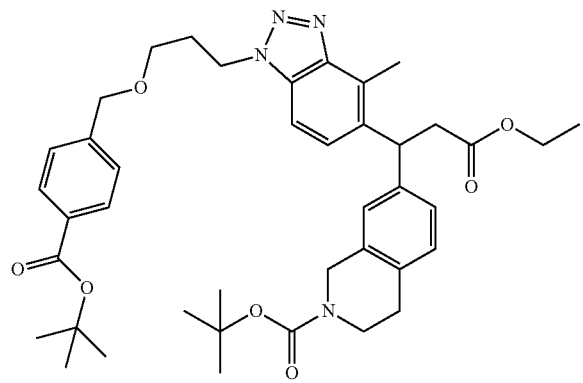

To a mixture of tert-butyl 4-[(3-{5-[(1E)-3-ethoxy-3-oxoprop-1-en-1-yl]-4-methyl-1H-benzotriazol-1-yl}propoxy)methyl]benzoate (6.88 g), tert-butyl 7-(4,4,5,5-tetramethyl-1,3,2-dioxaborolan-2-yl)-3,4-dihydro-1H-isoquinoline-2-carboxylate (15.5 g), sodium dodecyl sulfate (2.07 g), triethylamine (6 ml), CPME (200 ml) and water (100 ml), chloro(1,5-cyclooctadiene)rhodium (I) dimer (707 mg) was added at room temperature. The mixture was stirred at 100° C. for 3 hours under argon atmosphere. To the mixture thus obtained, saturated aqueous ammonium chloride solution was added, and the mixture was extracted with ethyl acetate. The extract solution was washed with saturated brine, followed by drying over anhydrous magnesium sulfate and concentration under reduced pressure. The residue was purified by silica gel column chromatography (ethyl acetate/hexane) to give the title compound (10.2 g).

$^1$H NMR (300 MHz, DMSO-$d_6$) δ 1.00 (3H, t, J=7.0 Hz), 1.40 (9H, s), 1.54 (9H, s), 2.06-2.32 (2H, m), 2.63-2.72 (2H, m), 2.77 (3H, s), 3.06-3.20 (2H, m), 3.37-3.55 (4H, m), 3.92 (2H, q, J=7.0 Hz), 4.36-4.50 (4H, m), 4.73 (2H, br t, J=6.3 Hz), 4.76-5.00 (1H, m), 6.99-7.20 (3H, m), 7.33 (2H, br d, J=7.7 Hz), 7.42-7.65 (2H, m), 7.83 (2H, d, J=7.7 Hz).

MS m/z 713.4 [M+H]$^-$.

G) Ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate

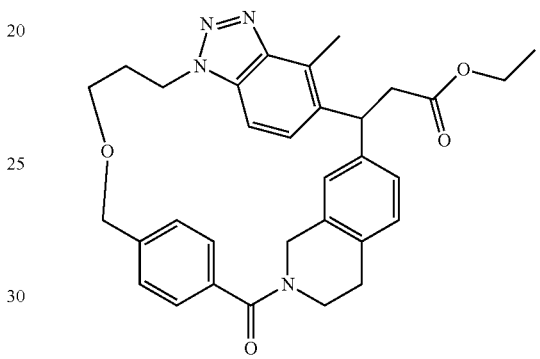

To a solution of tert-butyl 7-{1-[1-(3-{[4-(tert-butoxycarbonyl)phenyl]methoxy}propyl)-4-methyl-1H-benzotriazol-5-yl]-3-ethoxy-3-oxopropyl}-3,4-dihydroisoquinoline-2(1H)-carboxylate (6.55 g) in CPME (10 ml), 4N HCl/CPME solution (69 ml) was added at room temperature. The mixture was stirred at room temperature for 2 hours, and then concentrated. To the mixture thus obtained, tetrahydrofuran was added, and the mixture was concentrated. To a solution of the residue thus obtained in N,N-dimethylformamide (50 ml), N,N-diisopropylethylamine (8.35 ml) was added at 0° C. The solution thus obtained was slowly added dropwise to a solution of HATU (4.55 g) in N,N-dimethylformamide (350 ml) at room temperature. The mixture was stirred at room temperature for 3 hours. To the mixture, saturated aqueous sodium bicarbonate solution was added, and the mixture was extracted with ethyl acetate. The extract solution was washed with water and saturated brine, followed by drying over anhydrous magnesium sulfate and concentration under reduced pressure. The residue was purified by silica gel column chromatography (ethyl acetate/hexane) to give the title compound (3.35 g).

$^1$H NMR (300 MHz, DMSO-$d_6$) δ 1.05 (3H, t, J=7.1 Hz), 2.35 (2H, br s), 2.55 (3H, s), 2.90 (2H, br t, J=6.4 Hz), 3.02-3.48 (4H, m), 3.79 (2H, br t, J=6.6 Hz), 3.85-4.09 (4H, m), 4.18-4.50 (2H, m), 4.67-5.06 (3H, m), 6.08 (1H, s), 6.59-6.87 (4H, m), 7.20 (1H, d, J=7.7 Hz), 7.38 (2H, br d, J=8.1 Hz), 7.66 (1H, d, J=8.7 Hz).

MS m/z 539.3 [M+H]$^-$.

H) [32-Methyl-20-oxo-14-oxa-8,9,10,21-tetraaza-hexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid

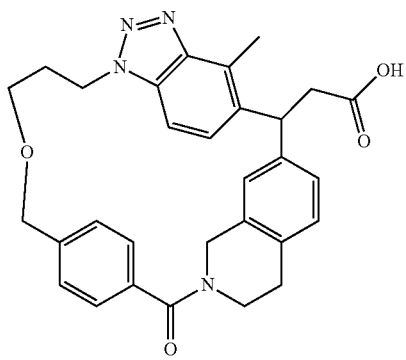 [SMILES: Cc1c2ccc3c1nnn3CCCOCc1ccc(cc1)C(=O)N1CCc3ccc(cc3C1)C2CC(=O)O]

To a solution of ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (19 mg) in tetrahydrofuran (0.5 ml) and ethanol (0.5 ml), 2N aqueous sodium hydroxide solution (0.5 mL) was added, and the reaction mixture was stirred at room temperature for 5 hours. The reaction solution was neutralized with 2N hydrochloric acid, and then concentrated. The residue was purified by preparative HPLC (YMC-Actus Triart C18, mobile phase: 10 mM aqueous ammonium bicarbonate solution/acetonitrile) to give the title compound (11 mg).

$^1$H NMR (300 MHz, CDCl$_3$) δ 2.34-2.60 (2H, m), 2.68 (3H, s), 2.88-3.08 (3H, m), 3.12-3.27 (1H, m), 3.30-3.53 (2H, m), 3.69-3.88 (1H, m), 3.97-4.15 (3H, m), 4.25 (1H, d, J=13.2 Hz), 4.52 (1H, d, J=12.7 Hz), 4.61-4.83 (2H, m), 4.85-4.98 (1H, m), 6.04 (1H, s), 6.70-6.80 (2H, m), 6.88 (2H, d, J=8.2 Hz), 7.10-7.25 (2H, m), 7.35 (2H, br t, J=9.2 Hz).

Example 17

[18,32-Dimethyl-20-oxo-14-oxa-8,9,10,21-tetraaza-hexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid

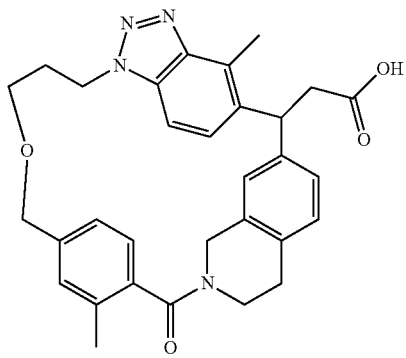 [SMILES: Cc1cc2ccc1C(=O)N1CCc3ccc(cc3C1)C(CC(=O)O)c1ccc3c(nnn3CCCOC2)c1C]

Synthesis was carried out in accordance with the methods shown in Example 16 or methods equivalent thereto.

Example 18

[18-Ethyl-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl] acetic acid

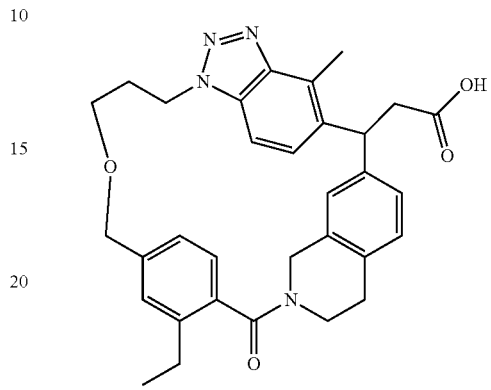

A) 3-Ethyl-4-hydroxybenzaldehyde

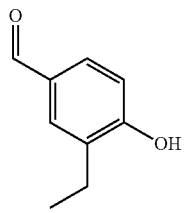

To a mixture of 3-bromo-4-hydroxybenzaldehyde (10.0 g), [1,1'-bis(diphenylphosphino)ferrocene]dichloropalladium (II) (3.64 g), cesium carbonate (48.6 g) and tetrahydrofuran (150 ml), 1M solution of triethylboran in hexane (100 ml) was added. The reaction mixture was deaerated by repeatedly reducing the pressure and purging nitrogen, and then stirred at 70° C. overnight. The reaction mixture was concentrated under reduced pressure, and water and ethyl acetate were then added to the residue. After removing the insoluble material by filtration and washing the residue with ethyl acetate, the filtrate was extracted with ethyl acetate. The extract solution was washed with saturated brine, followed by drying over anhydrous magnesium sulfate and concentration under reduced pressure. The residue was purified by silica gel column chromatography (ethyl acetate/hexane) to give the title compound (3.71 g).

MS m/z 151.1 [M+H]$^-$.

B) 2-Ethyl-4-formylphenyl trifluoromethanesulfonate

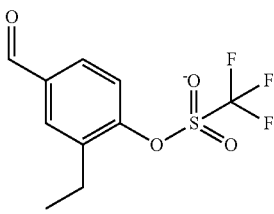

To a mixture of 3-ethyl-4-hydroxybenzaldehyde (2.10 g), N,N-diisopropylethylamine (4.89 ml), 4-dimethylaminopyridine (0.171 g) and tetrahydrofuran (25 ml), N-phenylbis(trifluoromethanesulfonimide) (5.00 g) was added, and the reaction mixture was stirred at room temperature overnight. Water and ethyl acetate were added to the reaction mixture, and the mixture was then extracted with ethyl acetate. The extract solution was washed with saturated brine, followed by drying over anhydrous magnesium sulfate and concentration under reduced pressure. The residue was purified by silica gel column chromatography (ethyl acetate/hexane) to give the title compound (3.22 g).

$^1$H NMR (300 MHz, DMSO-$d_6$) δ 1.25 (3H, t, J=7.6 Hz), 2.78 (2H, q, J=7.6 Hz), 7.64 (1H, d, J=8.5 Hz), 7.95 (1H, br d, J=8.6 Hz), 8.07 (1H, s), 10.05 (1H, s).

C) Ethyl 2-ethyl-4-formylbenzoate

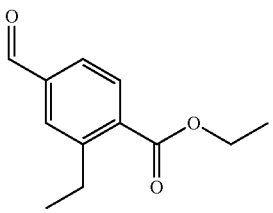

A mixture of 2-ethyl-4-formylphenyl trifluoromethanesulfonate (3.22 g), [1,1'-bis(diphenylphosphino)ferrocene]dichloropalladium (II) (0.835 g), triethylamine (1.59 ml), ethanol (30 ml) and DMF (30 ml) was stirred overnight under heating reflux and under carbon monoxide atmosphere. Then, water and ethyl acetate were added to the reaction mixture. After removing the insoluble material by filtration and washing the residue with ethyl acetate, the filtrate was extracted with ethyl acetate. The extract solution was washed with saturated brine, followed by drying over anhydrous magnesium sulfate and concentration under reduced pressure. The residue was purified by silica gel column chromatography (ethyl acetate/hexane) to give the title compound (0.577 g).

$^1$H NMR (300 MHz, DMSO-$d_6$) δ 1.20 (3H, t, J=7.4 Hz), 1.33 (3H, t, J=7.1 Hz), 2.94 (2H, q, J=7.4 Hz), 4.34 (2H, q, J=7.0 Hz), 7.80-7.86 (1H, m), 7.87-7.93 (2H, m), 10.06 (1H, s).

D) tert-Butyl 2-ethyl-4-formylbenzoate

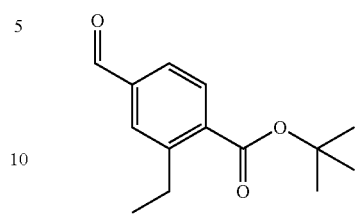

To a mixture of ethyl 2-ethyl-4-formylbenzoate (577 mg), ethanol (10.0 ml) and tetrahydrofuran (10.0 ml), 2M aqueous sodium hydroxide solution (5.00 ml) was added at room temperature, and the reaction mixture was stirred at 50° C. overnight. Under reduced pressure, organic solvents were removed, and the residue was then neutralized with 1M hydrochloric acid. The precipitate thus produced was collected by filtration, and washed with water to obtain a solid. To a mixture of the solid thus obtained and toluene (10 ml), N,N-dimethylformamide di-tert-butyl acetal (2.22 ml) was added at 100° C., and the reaction mixture was then stirred at 100° C. for 1 hour. Additionally, N,N-dimethylformamide di-tert-butylacetal (2.22 ml) was added, the reaction mixture was stirred at 100° C. for 2 hours, and then, N,N-dimethylformamide di-tert-butylacetal (2.22 ml) was further added at 100° C. The reaction mixture was stirred at 100° C. for 30 minutes, and then concentrated under reduced pressure. The residue was purified by silica gel column chromatography (ethyl acetate/hexane) to give the title compound (420 mg).

$^1$H NMR (300 MHz, DMSO-$d_6$) δ 1.13-1.24 (3H, m), 1.56 (13H, d, J=2.0 Hz), 2.83-2.97 (2H, m), 7.69-7.88 (3H, m), 10.05 (1H, s).

E) tert-Butyl 2-ethyl-4-(hydroxymethyl)benzoate

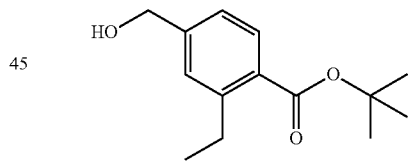

To a mixture of tert-butyl 2-ethyl-4-formylbenzoate (420 mg) and methanol (10 ml), sodium borohydride (102 mg) was added, and the reaction mixture was stirred at room temperature for 1 hour. Additionally, sodium borohydride (33.9 mg) was added, and the reaction mixture was stirred at room temperature for 1 hour and then concentrated under reduced pressure. The residue was purified by silica gel column chromatography (ethyl acetate/hexane) to give the title compound (191 mg).

$^1$H NMR (300 MHz, DMSO-$d_6$) δ 1.10-1.20 (3H, m), 1.54 (9H, s), 2.86 (2H, q, J=7.4 Hz), 4.51 (2H, d, J=5.6 Hz), 5.28 (1H, t, J=5.7 Hz), 7.17-7.26 (2H, m), 7.63 (1H, d, J=7.9 Hz).

F) tert-Butyl 4-(bromomethyl)-2-ethylbenzoate

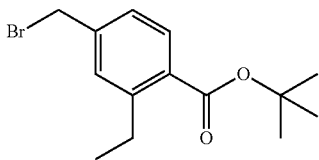 [SMILES: CCc1cc(CBr)ccc1C(=O)OC(C)(C)C]

To a mixture of tert-butyl 2-ethyl-4-(hydroxymethyl)benzoate (191 mg), triphenylphosphine (318 mg) and tetrahydrofuran (5 ml), carbon tetrabromide (402 mg) was added, and the reaction mixture was stirred at room temperature overnight. Water was added to the reaction mixture, and the mixture was extracted with ethyl acetate. The extract solution was washed with saturated brine, followed by drying over anhydrous magnesium sulfate and concentration under reduced pressure. The residue was purified by silica gel column chromatography (ethyl acetate/hexane) twice to give the title compound (178 mg).

$^1$H NMR (300 MHz, DMSO-$d_6$) δ 1.15 (3H, t, J=7.4 Hz), 1.54 (9H, s), 2.84 (2H, q, J=7.3 Hz), 4.70 (2H, s), 7.31-7.41 (2H, m), 7.64 (1H, d, J=7.7 Hz). G) [18-Ethyl-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid Example 19

[18-Cyclopropyl-32-methyl-20-oxo-14-oxa-8,9,10,21-tetraazahexacyclo[19.5.3.2$^{16,19}$.1$^{3,8}$.0$^{6,10}$.0$^{24,28}$]dotriaconta-1(26),3(32),4,6,8,16,18,24,27,30-decaen-2-yl]acetic acid

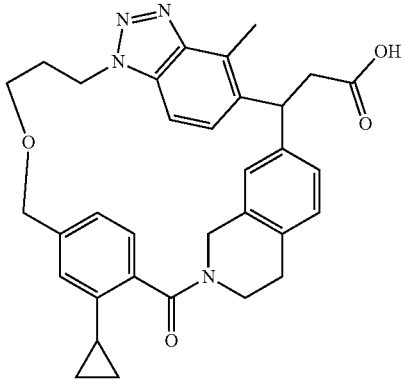

Synthesis was carried out using 3-cyclopropyl-4-hydroxybenzaldehyde in accordance with the methods shown in Example 18 or methods equivalent thereto.

Example 20

[32-Methyl-20-oxo-18-(trifluoromethoxy)-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl] acetic acid

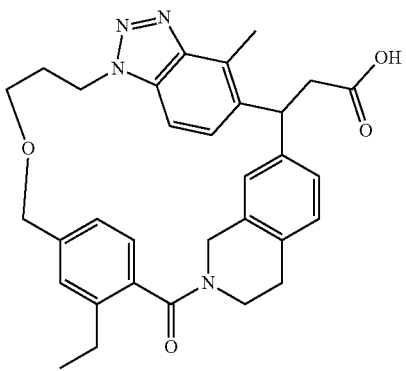 [SMILES: CCc1cc2ccc1C(=O)N1CCc3ccc(cc3C1)C(CC(=O)O)c1ccc3c(nnn3CCCOC2)c1C]

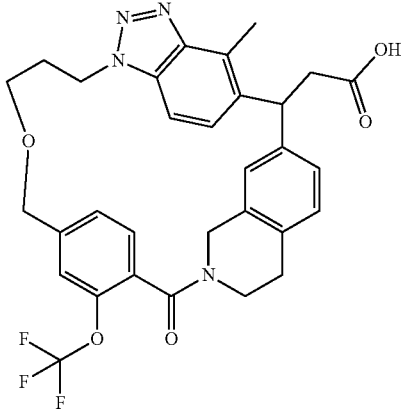 [SMILES: Cc1c2ccc3c1nnn3CCCOCc1ccc(c(OC(F)(F)F)c1)C(=O)N1CCc3ccc(cc3C1)C2CC(=O)O]

Synthesis was carried out using tert-butyl 4-(bromomethyl)-2-ethylbenzoate in accordance with the methods shown in Example 16 or methods equivalent thereto.

Synthesis was carried out in accordance with the methods shown in Example 16 or methods equivalent thereto.

Example 21

[18-Fluoro-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid

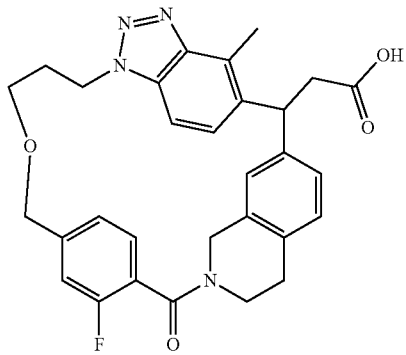 [SMILES: Cc1c2ccc3c1nnn3CCCOCc1ccc(c(F)c1)C(=O)N1CCc3ccc(cc3C1)C2CC(=O)O]

Synthesis was carried out in accordance with the methods shown in Example 16 or methods equivalent thereto.

Example 22

[18-Methoxy-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid

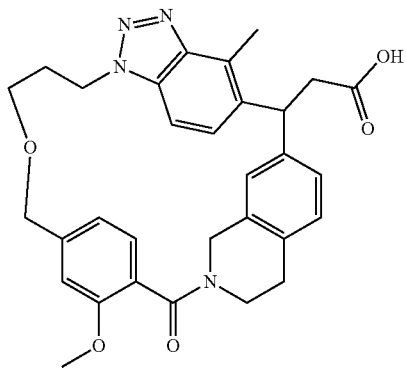 [SMILES: COc1cc2ccc1C(=O)N1CCc3ccc(cc3C1)C(CC(=O)O)c1ccc3c(nnn3CCCOC2)c1C]

Synthesis was carried out in accordance with the methods shown in Example 16 or methods equivalent thereto.

Example 23

[32-Methyl-20-oxo-18-(trifluoromethyl)-14-oxa-8,9,10,21-tetraazahexacyclo[19.5.3.2$^{16-19}$.1$^{3,7}$.0$^{6,10}$.0$^{24,28}$]dotriaconta-1(26),3(32),4,6,8,16,18,24,27,30-decaen-2-yl]acetic acid

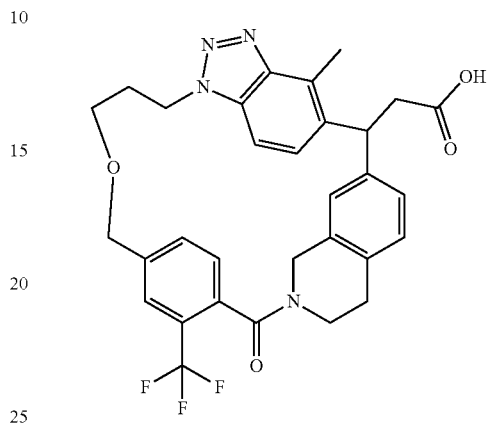

Synthesis was carried out in accordance with the methods shown in Example 16 or methods equivalent thereto.

Example 24

[18-Chloro-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid

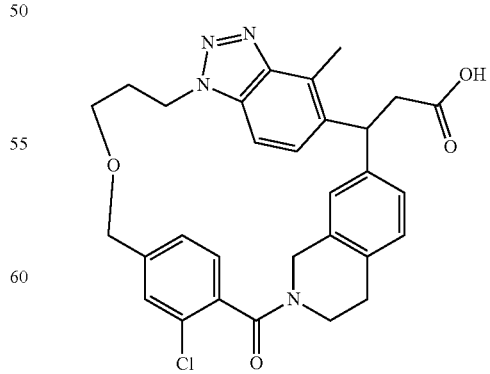

Synthesis was carried out in accordance with the methods shown in Example 16 or methods equivalent thereto.

Example 25

[32-Methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid Synthesis from Chiral ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-(26),3(32),4,6,8,16,18,24,27,30-decaen-2-yl]acetate (Retention Time Short)

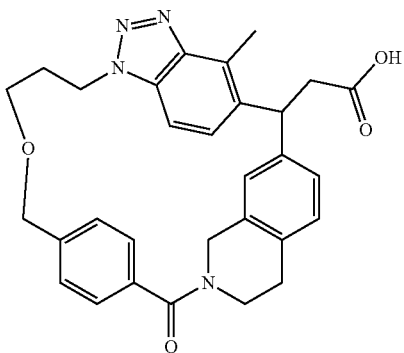 [SMILES: Cc1c2ccc3c1nnn3CCCOCc1ccc(cc1)C(=O)N1CCc3ccc(cc3C1)C2CC(=O)O]

A) Ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Chiral, Retention Time Long)

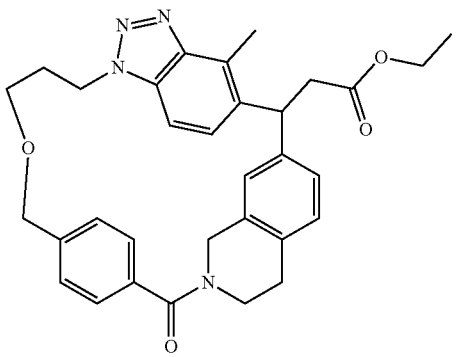 [SMILES: CCOC(=O)CC1c2ccc3c(c2)CN(CC3)C(=O)c2ccc(cc2)COCCCn2nnc3c(C)c1ccc32]

Racemate of ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (3.2 g) was fractionated by preparative supercritical $CO_2$ chromatography system (column: Cellulose-C (5 μm) 250×30 mm I.D., mobile phase: carbon dioxide/methanol=70/30). The fraction thus obtained was concentrated under reduced pressure to give ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (1.5 g) (chiral, retention time long).

Analysis conditions retention time: 5.706 minutes (column: Alcyon SFC CSP Cellulose-C (5 μm), 250×4.6 mm I.D., mobile phase: carbon dioxide/methanol=70/30, flow rate: 3.0 mL/min, temperature: 35° C., detection: UV 210 nm, sample concentration: 1 mg/mL, injection volume: 0.005 mL).

B) Ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Chiral, Retention Time Short)

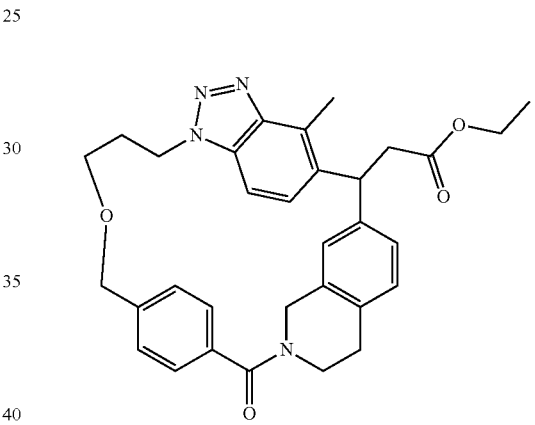

Racemate of ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-(26),3(32),4,6,8,16,18,24,27,30-decaen-2-yl]acetate (3.2 g) was fractionated by preparative supercritical $CO_2$ chromatography system (column: Cellulose-C (5 μm) 250×30 mm I.D., mobile phase: carbon dioxide/methanol=70/30). The fraction thus obtained was concentrated under reduced pressure to give ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (1.5 g) (chiral, retention time short).

Analysis conditions retention time: 4.465 minutes (column: Alcyon SFC CSP Cellulose-C (5 μm), 250×4.6 mm I D., mobile phase: carbon dioxide/methanol=70/30, flow rate: 3.0 mL/min, temperature: 35° C., detection: UV 210 nm, sample concentration: 1 mg/mL, injection volume: 0.005 mL).

C) [32-Methyl-20-oxo-14-oxa-8,9,10,21-tetraaza-hexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid Chiral, Synthesis from Chiral ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Retention Time Short)

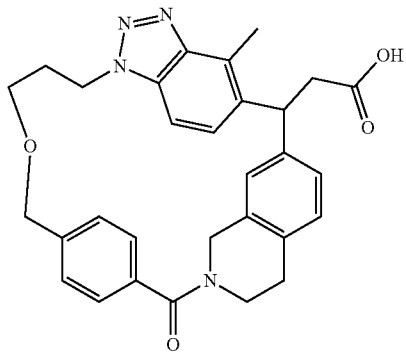 [SMILES: Cc1c2ccc3c1nnn3CCCOCc1ccc(cc1)C(=O)N1CCc3ccc(cc3C1)C2CC(=O)O]

To a solution of ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (chiral, retention time short) (1.5 g) in tetrahydrofuran (15 ml) and ethanol (7.5 ml), 1N aqueous sodium hydroxide solution (14 mL) was added, and the reaction mixture was stirred at room temperature for 6 hours. Under reduced pressure, organic solvents were removed. Subsequently, the reaction solution was diluted with water, and then made acidic with 1N hydrochloric acid at 0° C. The precipitate was separated by filtration, washed with water, and then recrystallized from a mixture of ethanol (50 ml) and water (45 ml) to give the title compound (1.37 g).

$^1$H NMR (300 MHz, DMSO-d$_6$) δ 2.35 (2H, br s), 2.54 (3H, s), 2.90 (2H, br t, J=6.5 Hz), 2.96-3.20 (2H, m), 3.35-3.47 (2H, m), 3.72-3.83 (2H, m), 3.84-4.09 (2H, m), 4.19-4.32 (1H, m), 4.36-4.46 (1H, m), 4.66-4.90 (3H, m), 6.07 (1H, s), 6.66-6.85 (4H, m), 7.20 (1H, d, J=8.1 Hz), 7.33-7.45 (2H, m), 7.65 (1H, d, J=8.5 Hz), 11.86-12.62 (1H, m).

Analysis conditions retention time: 22.3 minutes, column: DAICEL CHIRALPAK IB N-5 (5 μm, 250×4.6 mm ID.), mobile phase: A/B=82.5/17.5, A=hexane (0.1% trifluoroacetic acid), B=ethanol (0.1% trifluoroacetic acid), flow rate: 2.0 mL/min, detection: UV 220 nm and 254 nm, measurement temperature: room temperature, sample concentration: 0.5 mg/mL, injection volume: 0.01 mL.

Example 26

[32-Methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid Chiral, Synthesis from Chiral ethyl [32-methyl-20-oxo-14-oxa-8,9,10,21-tetraazahexacyclo[19.5.3.2$^{16,19}$.1$^{3,7}$.0$^{6,10}$.0$^{24,28}$] dotriaconta-1(26),3(32),4,6,8,16,18,24,27,30-decaen-2-yl]acetate (Retention Time Long)

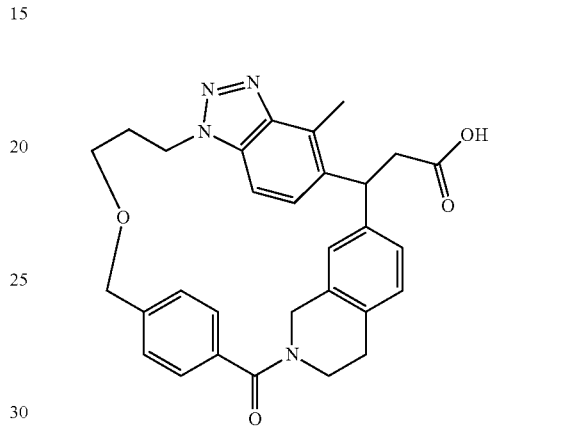

To a solution of ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (chiral, retention time long) (1.5 g) in tetrahydrofuran (15 ml) and ethanol (7.5 ml), 1M aqueous sodium hydroxide solution (13.9 mL) was added, and the reaction mixture was stirred at room temperature overnight. Under reduced pressure, organic solvents were removed. Subsequently, the reaction solution was diluted with water, and then made acidic with 1N hydrochloric acid at 0° C. The precipitate was separated by filtration, and recrystallized using ethanol (38 ml) and water (38 ml) to give the title compound (1.38 g).

$^1$H NMR (300 MHz, DMSO-d$_6$) δ 2.35-2.36 (2H, m), 2.54 (3H, s), 2.87-3.18 (4H, m), 3.25-3.51 (2H, m), 3.79 (2H, br t, J=6.3 Hz), 3.85-4.09 (2H, m), 4.20-4.52 (2H, m), 4.71-4.91 (3H, m), 6.07 (1H, s), 6.66-6.82 (4H, m), 7.20 (1H, d, J=7.8 Hz), 7.34-7.44 (2H, m), 7.65 (1H, d, J=8.3 Hz), 12.27 (1H, s).

Analysis conditions retention time: 32.4 minutes, column: DAICEL CHIRALPAK IB N-5 (5 μm, 250×4.6 mm I.D.), mobile phase: A/B=82.5/17.5, A=hexane (0.1% trifluoroacetic acid), B=ethanol (0.1% trifluoroacetic acid), flow rate: 2.0 mL/min, detection: UV 220 nm and 254 nm, measurement temperature: room temperature, sample concentration: 0.5 mg/mL, injection volume: 0.01 mL.

Example 27

Ethyl [32-methyl-20-oxo-14-oxa-8,9,10,21-tetraaza-hexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate

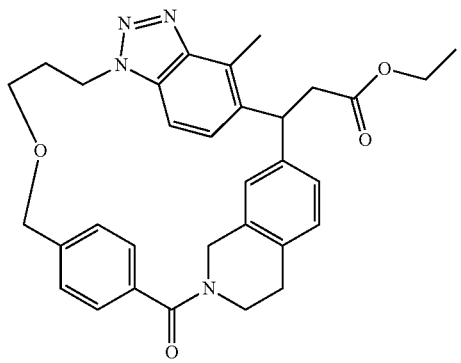 [SMILES: CCOC(=O)CC1c2ccc3c(c2)CN(CC3)C(=O)c2ccc(cc2)COCCCn2nnc3c(C)c1ccc32]

Synthesis was carried out in accordance with the methods shown in Example 16 or methods equivalent thereto.

Example 28

2-Methyl-2-[32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-(26),3(32),4,6,8,16,18,24,27,30-decaen-2-yl]propanoic acid

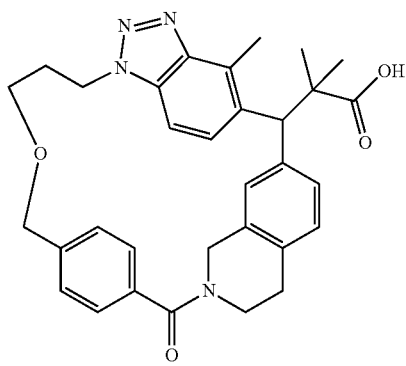 [SMILES: Cc1c2ccc3c1nnn3CCCOCc1ccc(cc1)C(=O)N1CCc3ccc(cc3C1)C2C(C)(C)C(=O)O]

A) ter-Butyl 4-{[3-(5-cyano-4-methyl-1H-benzotriazol-1-yl)propoxy]methyl}benzoate

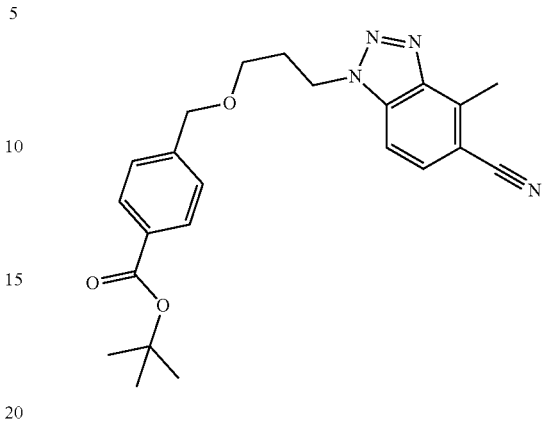

To a solution of tert-butyl 4-{[3-(5-bromo-4-methyl-1H-benzotriazol-1-yl)propoxy]methyl} benzoate (1.4 g) in A,/V-dimethylformamide (20 ml), tetrakis(triphenylphosphine)palladium (0) (351 mg) and zinc cyanide (1.07 g) were added, and the reaction mixture was stirred at 120° C. overnight. To the reaction solution, saturated aqueous ammonium chloride solution was added, and the reaction mixture was extracted with ethyl acetate. The extract solution was separated and washed with water and saturated brine, followed by drying over anhydrous magnesium sulfate and concentration under reduced pressure. The residue was purified by silica gel column chromatography (NH, ethyl acetate/hexane) to give the title compound (1.16 g).

$^1$H NMR (300 MHz, CDCb) δ 1.61 (9H, s), 2.32 (2H, quin, J=6.2 Hz), 3.01 (3H, s), 3.43 (2H, t, J=5.6 Hz), 4.48 (2H, s), 4.79 (2H, t, J=6.7 Hz), 7.32 (2H, d, J=8.3 Hz), 7.40 (1H, d, J=8.6 Hz), 7.58 (1H, d, J=8.6 Hz), 7.89-8.05 (2H, m).

B) tert-Butyl 4-{[3-(5-formyl-4-methyl-1H-benzotriazol-1-yl)propoxy]methyl}benzoate

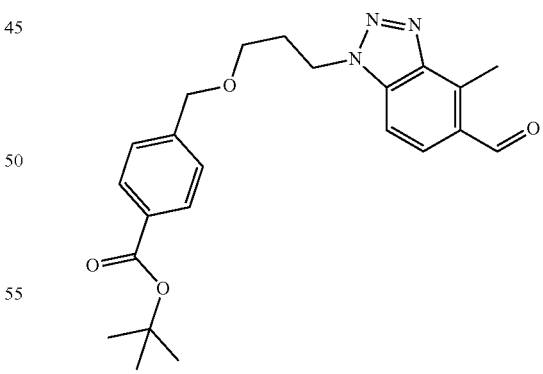

To a mixture of tert-butyl 4-{[3-(5-cyano-4-methyl-1H-benzotriazol-1-yl)propoxy]methyl}benzoate (1 g), acetic acid (7 ml), pyridine (7 ml) and water (7 ml), aqueous suspension of Raney nickel (1.5 ml) was added, and the reaction mixture was stirred overnight under hydrogen atmosphere. After filtering off Raney nickel, water was added to the reaction solution, and the solution was extracted with ethyl acetate. The extract solution was washed with saturated aqueous sodium bicarbonate solution and brine, followed by drying over anhydrous magnesium sulfate and concentration under reduced pressure. The residue was purified by silica gel column chromatography (ethyl acetate/hexane) to give the title compound (450 mg).

$^1$H NMR (300 MHz, CDCl$_3$) δ 1.60 (9H, s), 2.23-2.41 (2H, m), 3.17 (3H, s), 3.44 (2H, t, J=5.6 Hz), 4.48 (2H, s), 4.79 (2H, t, J=6.7 Hz), 7.30-7.43 (3H, m), 7.96 (3H, dd, J=8.5, 2.0 Hz), 10.52 (1H, s). MS m/z 410.3 [M+H]$^+$.

C) tert-Butyl 7-{[1-(3-{[4-(/er/-butoxycarbonyl)phenyl]methoxy}propyl)-4-methyl-1H-benzotriazol-5-yl](hydroxy)methyl}-3,4-dihydroisoquinoline-2(1H)-carboxylate

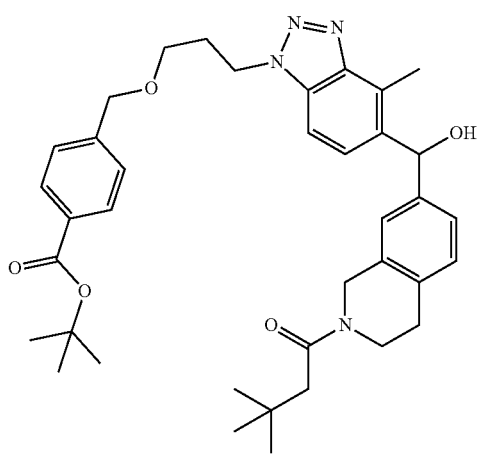 [SMILES: Cc1c(C(O)c2ccc3c(c2)CN(C(=O)CC(C)(C)C)CC3)ccc2c1nnn2CCCOCc1ccc(C(=O)OC(C)(C)C)cc1]

To a mixture of tert-butyl 4-{[3-(5-formyl-4-methyl-1H-benzotriazol-1-yl)propoxy]methyl}benzoate (330 mg), potassium phosphate (513 mg), tert-butyl 7-(4,4,5,5-tetramethyl-1,3,2-dioxaborolan-2-yl)-3,4-dihydro-1H-isoquinoline-2-carboxylate (2 g), CPME (20 ml) and water (4 ml), chloro(1,5-cyclooctadiene)rhodium (I) dimer (80 mg) was added at room temperature. The mixture was stirred at 110° C. for 1 hour under argon atmosphere. To the mixture thus obtained, saturated aqueous ammonium chloride solution was added, and the mixture was extracted with ethyl acetate. The extract solution was washed with saturated brine, followed by drying over anhydrous magnesium sulfate and concentration under reduced pressure. The residue was purified by silica gel column chromatography (ethyl acetate/hexane) and silica gel column chromatography (NH, ethyl acetate/hexane) to give the title compound (260 mg).

$^1$H NMR (300 MHz, CDCl$_3$) δ 1.47 (9H, s), 1.57-1.63 (9H, m), 2.20-2.41 (2H, m), 2.60 (1H, br d, J=2.0 Hz), 2.70-2.89 (5H, m), 3.29-3.51 (2H, m), 3.62 (2H, br t, J=5.7 Hz), 4.40-4.57 (4H, m), 4.73 (2H, t, J=6.6 Hz), 6.23 (1H, d, J=3.2 Hz), 7.04-7.18 (3H, m), 7.27-7.37 (3H, m), 7.64 (1H, d, J=8.7 Hz), 7.89 (2H, d, J=8.3 Hz).

D) 4-[(3-{5-[3-Methoxy-2,2-dimethyl-3-oxo-1-(1,2,3,4-tetrahydroisoquinolin-7-yl)propyl]-4-methyl-1H-benzotriazol-1-yl}propoxy)methyl]benzoic acid

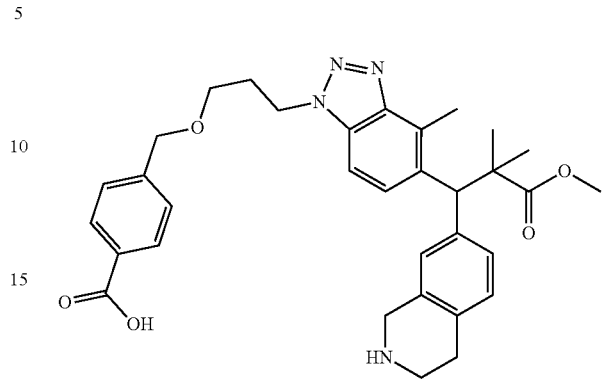

To a solution of tert-butyl 7-{[1-(3-{[4-(tert-butoxycarbonyl)phenyl]methoxy}propyl)-4-methyl-1H-benzotriazol-5-yl](hydroxy)methyl}-3,4-dihydroisoquinoline-2(1H)-carboxylate (50 mg) in acetonitrile (0.5 ml), 2,2,2-trichloroacetonitrile (22.5 mg) was added at room temperature. After stirring the reaction mixture for 5 minutes, 1,8-diazabicyclo[5.4.0]-7-undecene (2.4 mg) was added thereto. The reaction solution was stirred at room temperature for 30 minutes, and (1-methoxy-2-methyl-prop-1-enoxy)-trimethyl-silane (79 ul) and 1,1,1-trifluoro-N-[(trifluoromethyl)sulfonyl]methanesulfonamide (5 mg) were added thereto. After stirring the reaction solution at room temperature for 2 hours, saturated aqueous sodium bicarbonate solution was added thereto, and the mixture was extracted with ethyl acetate. The extract solution was washed with water and saturated brine, followed by drying over anhydrous magnesium sulfate and concentration under reduced pressure. The residue was purified by silica gel column chromatography (NH, ethyl acetate/hexane, ethyl acetate/methanol) to give a mixture. To the mixture, 4M HCl/CPME solution (2 ml) was added to give the title compound. The residue thus obtained was used for next reaction without purification.

E) Methyl 2-methyl-2-[32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]propanoate

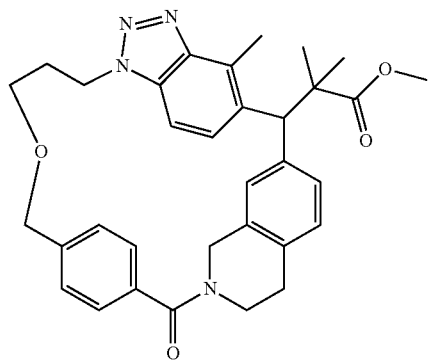 [SMILES: COC(=O)C(C)(C)C1c2ccc3c(c2)CN(CC3)C(=O)c2ccc(cc2)COCCCn2nnc3c(C)c1ccc32]

To a solution of the residue obtained in the previous step in N,N-dimethylformamide (1.5 ml), N,N-diisopropylethylamine (0.062 mL) was added at 0° C. The solution thus obtained was added dropwise to a solution of HATU (40 mg) in N,N-dimethylformamide (2 ml) at room temperature over 1 hour. The mixture was stirred at room temperature for 3 hours. To the mixture, saturated aqueous sodium bicarbonate solution was added, and the mixture was extracted with ethyl acetate. The extract solution was washed with water and saturated brine, followed by drying over anhydrous magnesium sulfate and concentration under reduced pressure. The residue was purified by silica gel column chromatography (ethyl acetate/hexane) to give the title compound. The residue thus obtained was used for next reaction without further purification.

F) 2-Methyl-2-[32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]propanoic acid

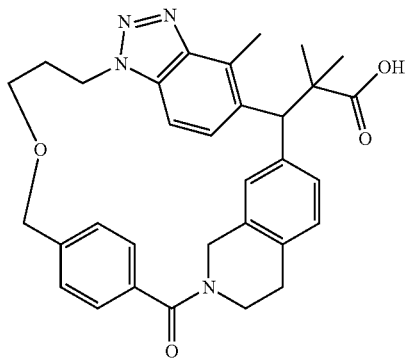 [SMILES: Cc1c2ccc3c1nnn3CCCOCc1ccc(cc1)C(=O)N1CCc3ccc(cc3C1)C2C(C)(C)C(=O)O]

To a solution of the residue obtained in the previous step in dimethylsulfoxide (0.25 ml), potassium trimethylsilanolate (16.2 mg) was added at room temperature. After stirring the mixture at 50° C. for 8 hours, further potassium trimethylsilanolate (8 mg) was added at room temperature. After stirring the mixture at 50° C. overnight, water was added to the mixture, and the mixture was extracted with ethyl acetate. The extract solution was washed with water and saturated brine, followed by drying over anhydrous magnesium sulfate and concentration under reduced pressure. The residue was purified by silica gel column chromatography (ethyl acetate/methanol). To the residue thus obtained, water was added, and the precipitate was separated by filtration to give the title compound (7 mg).

$^1$H NMR (300 MHz, DMSO-d$_6$) δ 1.18 (3H, s), 1.32 (3H, s), 2.31-2.42 (3H, m), 2.85-2.95 (2H, m), 3.36-3.44 (3H, m), 3.57-3.76 (1H, m), 3.83-4.15 (3H, m), 4.23-4.45 (2H, m), 4.73-4.82 (3H, m), 6.13 (1H, s), 6.63-6.80 (4H, m), 7.17 (1H, d, J=8.0 Hz), 7.33-7.42 (1H, m), 7.44-7.53 (1H, m), 7.61 (1H, d, J=9.0 Hz), 12.36 (1H, s).

Example 29

[32-Methyl-20-oxo-13-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid

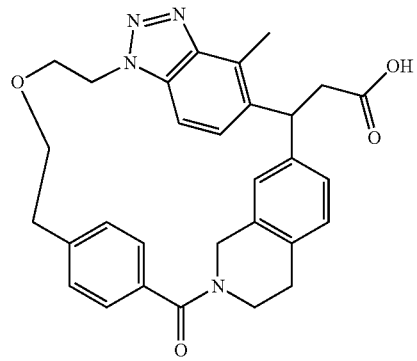 [SMILES: Cc1c2ccc3c1nnn3CCOCCc1ccc(cc1)C(=O)N1CCc3ccc(cc3C1)C2CC(=O)O]

A) 2-{2-[2-(4-Bromophenyl)ethoxy]ethoxy}oxane

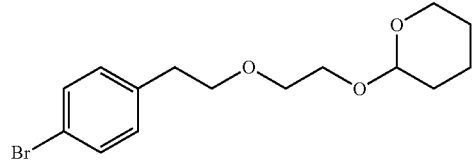 [SMILES: Brc1ccc(CCOCCOC2CCCCO2)cc1]

To a solution of 2-(4-bromophenyl)ethanol (1 g) in N,N-dimethylformamide (20 ml), sodium hydride (50%, 597 mg) was added at 0° C. After stirring the reaction mixture at 0° C. for 1 hour, 2-(2-bromoethoxy)tetrahydropyran (2.08 g) was added at 0° C. The mixture was stirred at room temperature for 2 hours. To the mixture, saturated aqueous ammonium chloride solution was added, and the mixture was extracted with ethyl acetate. The organic layer was separated and washed with saturated brine, followed by drying over anhydrous magnesium sulfate and concentration under reduced pressure. The residue was purified by silica gel column chromatography (ethyl acetate/hexane) to give the title compound (907 mg). MS m/z 353.2 [M+Na]$^-$.

B) 4-(2-{2-[(Oxan-2-yl)oxy]ethoxy}ethyl)benzoic acid

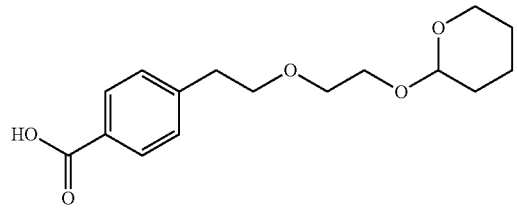 [SMILES: O=C(O)c1ccc(CCOCCOC2CCCCO2)cc1]

To a solution of 2-{2-[2-(4-bromophenyl)ethoxy]ethoxy}oxane (2.81 g) in tetrahydrofuran (30 ml), n-butyllithium (1.6M solution in hexane, 8.01 ml) was added at −78° C., and the reaction mixture was stirred at the same temperature for 1 hour. Carbon dioxide generated from dry ice was passed through the reaction solution at −78° C., and the solution was stirred at the same temperature for 1 hour, and stirred at room temperature overnight. To the mixture, 1M hydrochloric acid was added for neutralization, and the mixture was then extracted with ethyl acetate. The organic layer was separated and washed with saturated brine, followed by drying over anhydrous magnesium sulfate and concentration under reduced pressure. The residue was purified by silica gel column chromatography (ethyl acetate/hexane) to give the title compound (1.76 g).

$^1$H NMR (300 MHz, DMSO-d$_6$) δ 1.30-1.78 (6H, m), 2.88 (2H, br t, J=6.6 Hz), 3.24-3.60 (4H, m), 3.61-3.76 (4H, m), 4.53 (1H, br s), 7.37 (2H, d, J=7.9 Hz), 7.85 (2H, d, J=8.0 Hz), 12.59-12.88 (1H, m).

C) tert-Butyl 4-[2-(2-hydroxyethoxy)ethyl]benzoate

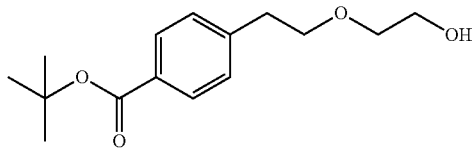 [SMILES: CC(C)(C)OC(=O)c1ccc(CCOCCO)cc1]

To a solution of 4-(2-{2-[(oxan-2-yl)oxy]ethoxy}ethyl) benzoic acid (1.76 g) in toluene (20 ml), 1,1-di-tert-butoxy-N,N-dimethyl-methanamine (6.08 g) was added at 100° C., and the reaction mixture was stirred at the same temperature for 1 hour. Further, 1,1-di-tert-butoxy-N,N-dimethyl-methanamine (6.08 g) was added at 100° C., and the reaction mixture was stirred at the same temperature for 2 hours. The reaction solution was concentrated, and the residue was purified by silica gel column chromatography (ethyl acetate/hexane) to give the title compound (1.47 g). The residue thus obtained was used for next reaction without further purification. To a mixture of the residue thus obtained (1.47 g) in ethanol (15 ml), pyridinium p-toluenesulfonate (105 mg) was added at 50° C., and the reaction mixture was stirred at the same temperature for 2 hours. To the reaction solution, triethylamine was added at room temperature, and the solution was concentrated. The residue was purified by silica gel column chromatography (ethyl acetate/hexane) to give the title compound (1.1 g).

$^1$H NMR (300 MHz, DMSO-de) δ 1.54 (9H, s), 2.88 (2H, t, J=6.8 Hz), 3.37-3.52 (4H, m), 3.62 (2H, t, J=6.6 Hz), 4.57 (1H, t, J=5.1 Hz), 7.37 (2H, br d, J=7.9 Hz), 7.81 (2H, d, J=8.0 Hz).

D) tert-Butyl 4-(2-{2-[(4-methylbenzene-1-sulfonyl) oxy]ethoxy}ethyl)benzoate

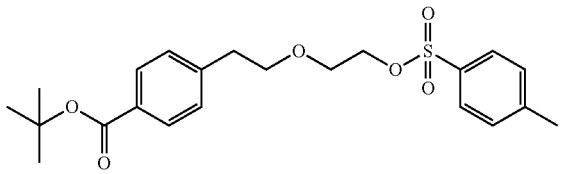 [SMILES: Cc1ccc(S(=O)(=O)OCCOCCc2ccc(C(=O)OC(C)(C)C)cc2)cc1]

To a mixture of tert-butyl 4-[2-(2-hydroxyethoxy)ethyl] benzoate (1.14 g), p-toluenesulfonyl chloride (1.63 g), 4-dimethylaminopyridine (52.3 mg), triethylamine (2.39 ml) and tetrahydrofuran (10 ml), the reaction mixture was stirred at room temperature for 5 hours. To the reaction solution, triethylamine (1.2 ml) and p-toluenesulfonyl chloride (815 mg) were added, and the reaction solution was stirred at room temperature for 3 days. Water was added to the reaction solution, and the mixture was extracted with ethyl acetate. The organic layer was separated and washed with saturated brine, followed by drying over anhydrous magnesium sulfate and concentration under reduced pressure. The residue was purified by silica gel column chromatography (ethyl acetate/hexane) to give the title compound (1.62 g).

$^1$H NMR (300 MHz, DMSO-d$_6$) δ 1.54 (9H, s), 2.42 (3H, s), 2.80 (2H, br t, J=6.5 Hz), 3.50-3.59 (4H, m), 4.05-4.13 (2H, m), 7.30 (2H, d, J=8.0 Hz), 7.47 (2H, br d, J=8.1 Hz), 7.72-7.83 (4H, m). MS m/z 443.2 [M+Na]$^+$.

E) tert-Butyl 4-{2-[2-(4-bromo-3-methyl-2-nitroanilino)ethoxy]ethyl}benzoate

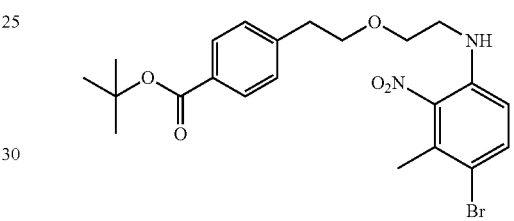

A solution of tert-butyl 4-(2-{2-[(4-methylbenzene-1-sulfonyl)oxy]ethoxy}ethyl)benzoate (1.32 g), 4-bromo-3-methyl-2-nitro-aniline (869 mg) and cesium carbonate (2.04 g) in N,N-dimethylformamide (15 ml) was stirred at 80° C. overnight. Water was added to the mixture, and the mixture was extracted with ethyl acetate. The organic layer was separated and washed with saturated brine, followed by drying over anhydrous magnesium sulfate and concentration under reduced pressure. The residue was purified by silica gel column chromatography (ethyl acetate/hexane) to give the title compound (761 g).

MS m/z 501.2 [M+Na]$^+$.

F) tert-Butyl 4-{2-[2-(5-bromo-4-methyl-1H-benzotriazol-1-yl)ethoxy]ethyl}benzoate

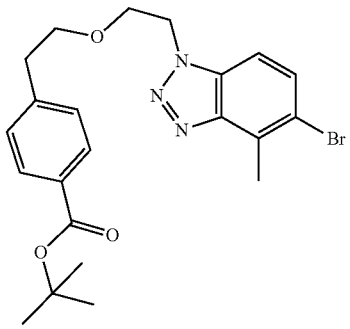 [SMILES: Cc1c(Br)ccc2c1nnn2CCOCCc1ccc(C(=O)OC(C)(C)C)cc1]

A mixture of tert-butyl 4-{2-[2-(4-bromo-3-methyl-2-nitroanilino)ethoxy]ethyl}benzoate (761 mg), ammonium chloride (849 mg), iron (443 mg), ethanol (10 ml) and water (2 ml) was stirred at 80° C. for 3 hours. To the mixture thus obtained, water was added, and the mixture was extracted with ethyl acetate. The extract solution was washed with saturated brine, followed by drying over anhydrous magnesium sulfate and concentration under reduced pressure. The residue was purified by silica gel column chromatography (ethyl acetate/hexane) to give the title compound (299 mg). The residue thus obtained was used for next reaction without further purification.

To a mixture of the residue thus obtained in acetic acid (3 ml) and water (0.5 ml), a solution of sodium nitrite (91.8 mg) in water (1 ml) was added at 0° C. After stirring the mixture at 0° C. for 30 minutes, water was added to the mixture, and the mixture was extracted with ethyl acetate. The extract solution was washed with water, saturated aqueous sodium bicarbonate solution, and saturated brine, followed by drying over anhydrous magnesium sulfate and concentration under reduced pressure. The residue was purified by silica gel column chromatography (ethyl acetate/hexane) and silica gel column chromatography (NH, ethyl acetate/hexane) to give the title compound (223 mg).

$^1$H NMR (300 MHz, CDCl$_3$) δ 1.60 (9H, s), 2.74-2.82 (2H, m), 2.84 (3H, s), 3.59 (2H, t, J=6.5 Hz), 3.89 (2H, t, J=5.0 Hz), 4.74 (2H, t, J=5.0 Hz), 7.07 (2H, br d, J=7.9 Hz), 7.21 (1H, br d, J=8.5 Hz), 7.51 (1H, d, J=8.6 Hz), 7.82 (2H, br d, J=7.8 Hz); MS m/z 460.1 [M+H]$^+$;

G) tert-Butyl 4-[2-(2-{5-[(1E)-3-ethoxy-3-oxoprop-1-en-1-yl]-4-methyl-1H-benzotriazol-1-yl}ethoxy)ethyl]benzoate

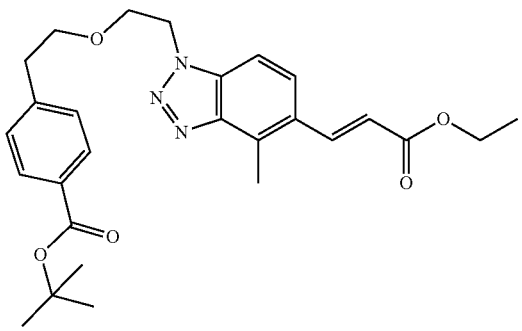 [SMILES: CCOC(=O)/C=C/c1ccc2c(nnn2CCOCCc2ccc(C(=O)OC(C)(C)C)cc2)c1C]

To a solution of tert-butyl 4-{2-[2-(5-bromo-4-methyl-1H-benzotriazol-1-yl)ethoxy]ethyl}benzoate (148 mg), ethyl acrylate (0.211 ml) and N,N-diisopropylethylamine (0.225 ml) in N,N-dimethylformamide (2.5 ml), tri(o-tolyl)phosphine (29.4 mg) and palladium acetate (11 mg) were added, and the reaction mixture was stirred at 120° C. for 4 hours under microwave irradiation. To the mixture thus obtained, water was added, and the mixture was extracted with ethyl acetate. The extract solution was washed with saturated brine, followed by drying over anhydrous magnesium sulfate and concentration under reduced pressure. The residue was purified by silica gel column chromatography (ethyl acetate/hexane) to give the title compound (163 mg).

$^1$H NMR (300 MHz, CDCb) δ 1.36 (3H, t, J=7.1 Hz), 1.58 (9H, s), 2.74-2.83 (2H, m), 2.92 (3H, s), 3.60 (2H, t, J=6.5 Hz), 3.90 (2H, br t, J=4.9 Hz), 4.30 (2H, q, J=7.2 Hz), 4.75 (2H, t, J=4.8 Hz), 6.42 (1H, d, J=16.0 Hz), 7.07 (2H, br d, J=8.0 Hz), 7.34 (1H, d, J=8.8 Hz), 7.64 (1H, d, J=8.7 Hz), 7.81 (2H, br d, J=8.0 Hz), 8.15 (1H, d, J=16.0 Hz).
MS m/z 480.3 [M+H]$^-$.

H) tert-Butyl 7-{1-[1-(2-{2-[4-(tert-butoxycarbonyl)phenyl]ethoxy}ethyl)-4-methyl-1H-benzotriazol-5-yl]-3-ethoxy-3-oxopropyl}-3,4-dihydroisoquinoline-2(1H)-carboxylate

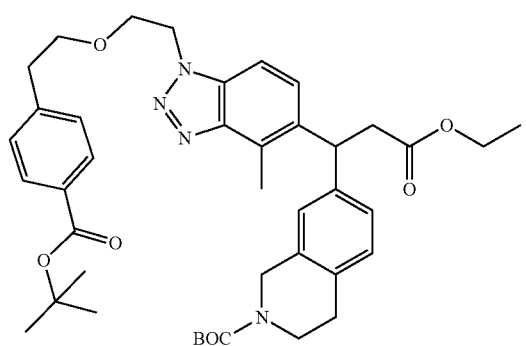 [SMILES: CCOC(=O)CC(c1ccc2c(c1)CN(C(=O)OC(C)(C)C)CC2)c1ccc2c(nnn2CCOCCc2ccc(C(=O)OC(C)(C)C)cc2)c1C]

To a mixture of tert-butyl 4-[2-(2-{5-[(1E)-3-ethoxy-3-oxoprop-1-en-1-yl]-4-methyl-1H-benzotriazol-1-yl}ethoxy)ethyl]benzoate (163 mg), tert-butyl 7-(4,4,5,5-tetramethyl-1,3,2-dioxaborolan-2-yl)-3,4-dihydro-1H-isoquinoline-2-carboxylate (147 mg), sodium dodecyl sulfate (49.1 mg), triethylamine (0.14 ml), CPME (2 ml) and water (1 ml), chloro(1,5-cyclooctadiene)rhodium (I) dimer (16.8 mg) was added at room temperature. The mixture was stirred at 100° C. overnight. Water was added to the mixture thus obtained, and the mixture was extracted with ethyl acetate. The extract solution was washed with saturated brine, followed by drying over anhydrous magnesium sulfate and concentration under reduced pressure. The residue was purified by silica gel column chromatography (NH, ethyl acetate/hexane) to give the title compound (126 mg).

$^1$H NMR (300 MHz, CDCb) δ 1.10 (3H, t, J=7.1 Hz), 1.46 (9H, s), 1.59 (9H, s), 2.70-2.83 (4H, m), 2.86 (3H, s), 2.98-3.19 (2H, m), 3.59 (4H, br t, J=6.2 Hz), 3.89 (2H, br t, J=5.0 Hz), 4.02 (2H, q, J=7.1 Hz), 4.42-4.52 (2H, m), 4.72 (2H, t, J=5.0 Hz), 4.96 (1H, br t, J=7.8 Hz), 6.91-6.97 (1H, m), 7.00-7.06 (2H, m), 7.11 (2H, br d, J=8.0 Hz), 7.30-7.36 (2H, m), 7.84 (2H, d, J=8.1 Hz).
MS m/z 713.4 [M+H]$^-$.

I) Ethyl [32-methyl-20-oxo-13-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl] acetate

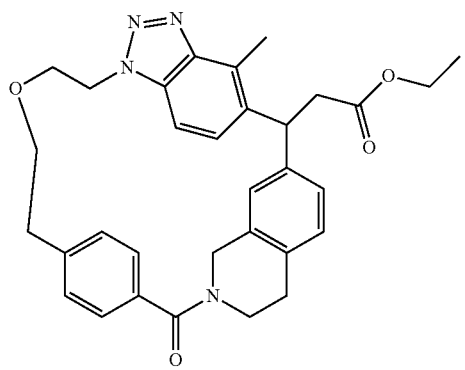 [SMILES: CCOC(=O)CC1c2ccc3c(c2)CN(CC3)C(=O)c2ccc(cc2)CCOCCn2nnc3c(C)c1ccc32]

To a solution of tert-butyl 7-{1-[1-(2-{2-[4-(tert-butoxy-carbonyl)phenyl]ethoxy}ethyl)-4-methyl-1H-benzotriazol-5-yl]-3-ethoxy-3-oxopropyl}-3,4-dihydroisoquinoline-2(1H)-carboxylate (139 mg) in CPME (1.5 ml), 4N HCl/CPME solution (1.27 ml) was added at room temperature. The mixture was stirred at room temperature for 2 hours, and then concentrated. The residue thus obtained was used for next reaction without purification.

A solution of the residue thus obtained and N,N-diisopropylethylamine (0.17 ml) in N,N-dimethylformamide (10 ml) was added dropwise to a solution of HATU (111 mg) in N,N-dimethylformamide (10 ml) at room temperature over 30 minutes. The mixture was stirred at room temperature for 3.5 hours. Water was added to the mixture, and the mixture was extracted with ethyl acetate. The extract solution was washed with saturated brine, followed by drying over anhydrous magnesium sulfate and concentration under reduced pressure. The residue was purified by silica gel column chromatography (ethyl acetate/hexane, methanol/ethyl acetate) and silica gel column chromatography (NH, ethyl acetate/hexane) to give the title compound (80 mg).

$^1$H NMR (300 MHz, CDCl$_3$) δ 1.13 (3H, t, J=7.1 Hz), 2.68-2.91 (5H, m), 2.94-3.11 (3H, m), 3.17-3.29 (1H, m), 3.52-3.63 (1H, m), 3.66-3.76 (1H, m), 3.77-3.90 (1H, m), 3.91-4.19 (7H, m), 4.63-4.78 (1H, m), 4.91-5.05 (2H, m), 6.29 (1H, s), 6.76-6.85 (4H, m), 7.19 (1H, d, J=8.0 Hz), 7.30-7.40 (2H, m), 7.49 (1H, d, J=8.7 Hz).

MS m/z 539.3 [M+H]$^-$.

J) [32-Methyl-20-oxo-13-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid

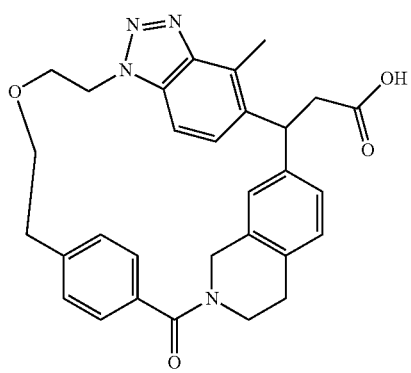 [SMILES: Cc1c2ccc3c1nnn3CCOCCc1ccc(cc1)C(=O)N1CCc3ccc(cc3C1)C2CC(=O)O]

To a solution of ethyl [32-methyl-20-oxo-13-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (105 mg) in tetrahydrofuran (1.5 ml) and ethanol (1.5 ml), 4M aqueous lithium hydroxide solution (0.5 ml) was added, and the reaction mixture was stirred at room temperature for 2 hours. To the reaction solution, 4M aqueous lithium hydroxide solution (0.5 ml) was further added, and the reaction solution was stirred at room temperature for 1 hour. The reaction solution was concentrated, water (3 ml) was added to the residue, and the solution was neutralized at 0° C. with 2N hydrochloric acid. The precipitate was filtered to give the title compound (72.5 mg).

$^1$H NMR (300 MHz, DMSO-d$_6$) δ 2.58 (3H, s), 2.68-2.79 (2H, m), 2.87-2.96 (2H, m), 2.96-3.08 (1H, m), 3.08-3.20 (1H, m), 3.50-3.68 (2H, m), 3.69-3.81 (2H, m), 3.94-4.10 (4H, m), 4.74-4.84 (1H, m), 4.87-4.96 (2H, m), 6.30 (1H, s), 6.59-6.66 (2H, m), 6.69-6.77 (2H, m), 7.21 (1H, d, J=7.5 Hz), 7.38-7.50 (21-, m), 7.70 (1H, d, J=8.5 Hz), 12.19-12.34 (1H, m).

Example 30

[32-Methyl-20-oxo-15-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid

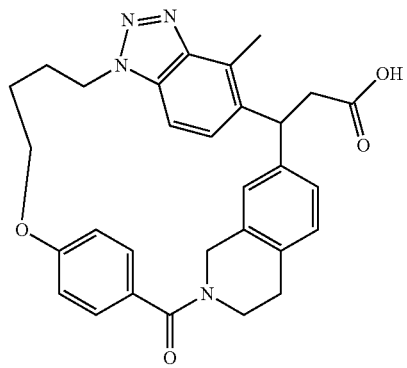 [SMILES: Cc1c2ccc3c1nnn3CCCCOc1ccc(cc1)C(=O)N1CCc3ccc(cc3C1)C2CC(=O)O]

Synthesis was carried out in accordance with the methods shown in Example 9 or methods equivalent thereto.

Example 31

[18-Fluoro-32-methyl-20-oxo-15-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid

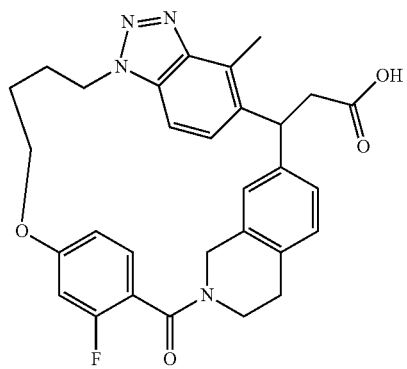 [SMILES: Cc1c2ccc3c1nnn3CCCCOc1ccc(c(F)c1)C(=O)N1CCc3ccc(cc3C1)C2CC(=O)O]

Synthesis was carried out in accordance with the methods shown in Example 9 or methods equivalent thereto.

Example 32

[18,30-Difluoro-32-methyl-20-oxo-15-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid

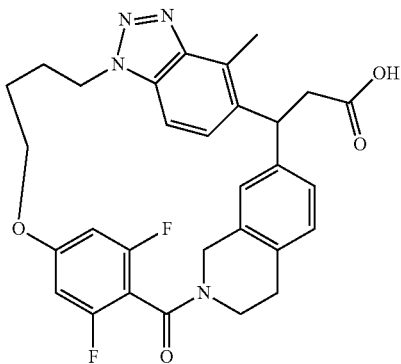 [SMILES: Cc1c2ccc3c1nnn3CCCCOc1cc(F)c(c(F)c1)C(=O)N1CCc3ccc(cc3C1)C2CC(=O)O]

Synthesis was carried out in accordance with the methods shown in Example 9 or methods equivalent thereto.

Example 33

[6,6,33-Trimethyl-2-oxo-7,10-dioxa-1,15,16,17-tetraazaheptacyclo[22.5.3.2$^{3,9}$.1$^{18,22}$.0$^{4,8}$.0$^{15,19}$.0$^{27,31}$]pentatriaconta-3,8,16,18(33),19,21,24,26,31,34-decaen-23-yl]acetic acid

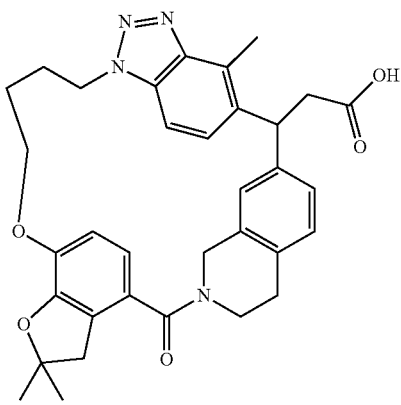 [SMILES: Cc1c2ccc3c1nnn3CCCCOc1ccc(c3c1OC(C)(C)C3)C(=O)N1CCc3ccc(cc3C1)C2CC(=O)O]

A) Methyl 4-(benzyloxy)-3-hydroxy-2-(2-methylprop-2-en-1-yl)benzoate

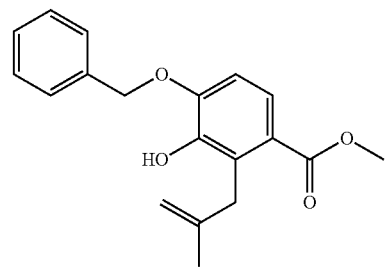 [SMILES: C=C(C)Cc1c(C(=O)OC)ccc(OCc2ccccc2)c1O]

The title compound was obtained using methyl 3-hydroxy-4-phenylmethoxybenzoate in accordance with the methods shown in Example 8A) to Example 8B) or methods equivalent thereto. MS m/z 313.2 [M+H]$^+$.

B) Methyl 7-hydroxy-2,2-dimethyl-2,3-dihydro-1-benzofuran-4-carboxylate

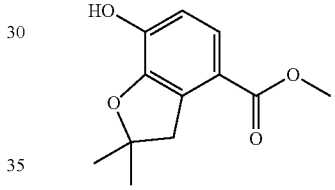

A mixture of methyl 4-(benzyloxy)-3-hydroxy-2-(2-methylprop-2-en-1-yl)benzoate (390 mg), formic acid (5 ml) and water (0.5 ml) was stirred at 100° C. overnight. The reaction mixture was concentrated under reduced pressure, and the residue was purified by silica gel column chromatography (ethyl acetate/hexane) to give the title compound (125 mg).

MS m/z 223.2 [M+H]$^-$.

C) 2,2-Dimethyl-7-[(prop-2-en-1-yl)oxy]-2,3-dihydro-1-benzofuran-4-carboxylic acid

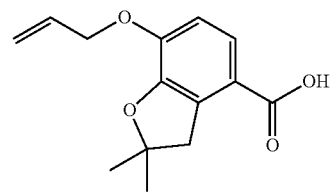 [SMILES: C=CCOc1ccc(C(=O)O)c2c1OC(C)(C)C2]

The title compound was obtained using methyl 7-hydroxy-2,2-dimethyl-2,3-dihydro-1-benzofuran-4-carboxylate in accordance with the methods shown in Example 30 A) to Example 30 B) or methods equivalent thereto.

MS m/z 249.1 [M+H]$^-$.

D) [6,6,33-Trimethyl-2-oxo-7,10-dioxa-1,15,16,17-tetraazaheptacyclo[22.5.3.2$^{3,9}$.1$^{18,22}$.0$^{4,8}$.0$^{15,19}$.0$^{27,31}$]pentatriaconta-3,8,16,18(33),19,21,24,26,31,34-decaen-23-yl]acetic acid

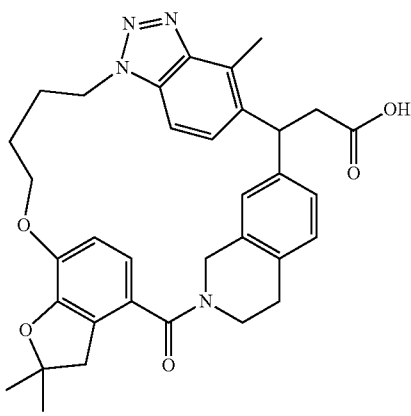 [SMILES: Cc1c2ccc3c1nnn3CCCCOc1ccc(c3c1OC(C)(C)C3)C(=O)N1CCc3ccc(cc3C1)C2CC(=O)O]

The title compound was obtained using 2,2-dimethyl-7-[(prop-2-en-1-yl)oxy]-2,3-dihydro-1-benzofuran-4-carboxylic acid in accordance with the methods shown in Example 9 L) to Example 9 N) or methods equivalent thereto.

Example 34

(5-Methyl-2-oxo-2H-1,3-dioxol-4-yl)methyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate Chiral, Synthesis from chiral ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Retention Time Short)

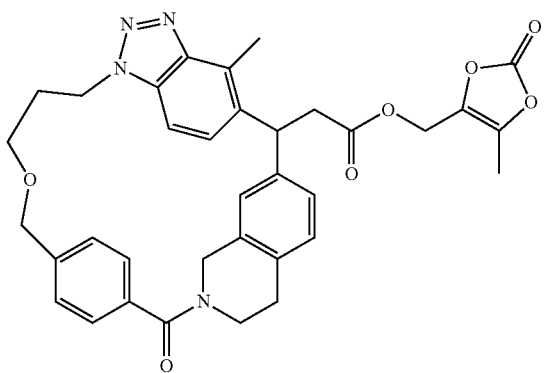 [SMILES: Cc1oc(=O)oc1COC(=O)CC1c2ccc3c(c2)CN(CC3)C(=O)c2ccc(cc2)COCCCn2nnc3c(C)c1ccc32]

To a solution of [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid<52.6 mg, chiral, synthesis from chiral ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (retention time short)> in N,N-dimethylformamide (0.5 ml), potassium carbonate (28.5 mg) and 4-(chloromethyl)-5-methyl-1,3-dioxol-2-one (0.011 ml) were added, and the reaction mixture was stirred at room temperature overnight. The mixture was diluted with ethyl acetate, and washed with water and saturated brine. The mixture was then dried over anhydrous magnesium sulfate and concentrated under reduced pressure. The residue was purified by silica gel column chromatography (ethyl acetate/hexane) to give the title compound (25 mg).

Example 35

(5-Methyl-2-oxo-2H-1,3-dioxol-4-yl)methyl [32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate Synthesis from Chiral ethyl [32-methyl-20-oxo-8,9,10,21-tetraazahexacyclo[19.5.3.2$^{16,19}$.1$^{3,7}$.0$^{6,10}$.0$^{24,28}$]dotriaconta-(26),3(32),4,6,8,16,18,24,27,30-decaen-2-yl]acetate (Retention Time Long)

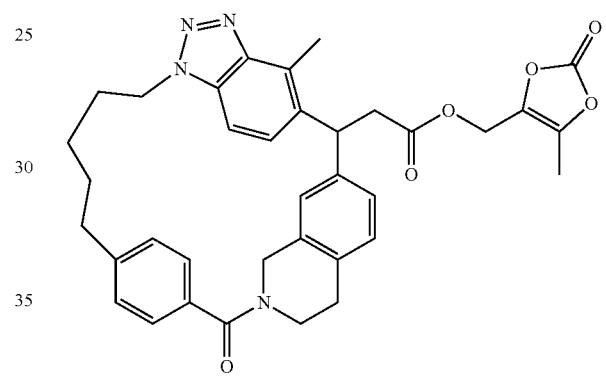

Synthesis was carried out in accordance with the methods shown in Example 34 or methods equivalent thereto.

Example 36

Ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Chiral, Retention Time Short)

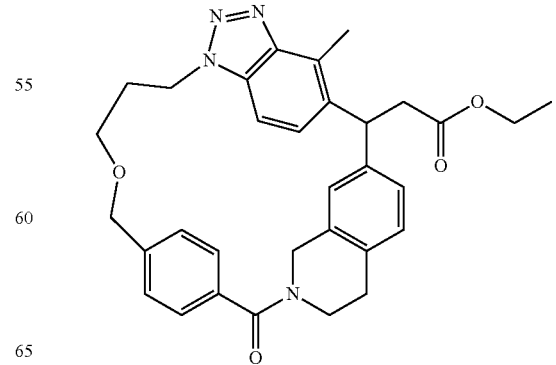

Synthesis was carried out using iodoethane in accordance with the methods shown in Example 34 or methods equivalent thereto.

Example 37

Ethyl [32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Chiral, Retention Time Short)

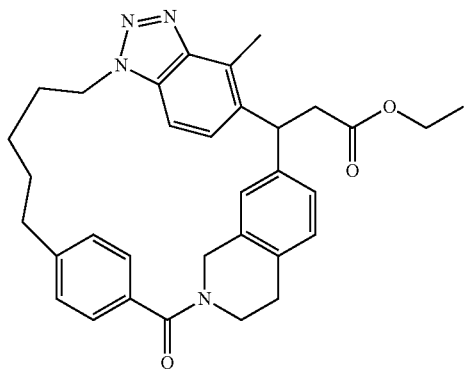 [SMILES: CCOC(=O)CC1c2ccc3c(c2)CN(CC3)C(=O)c2ccc(cc2)CCCCCn2nnc3c(C)c1ccc32]

Synthesis was carried out using iodoethane in accordance with the methods shown in Example 34 or methods equivalent thereto.

Example 38

2-[32-Methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]-N-(6-methylpyridin-3-yl)acetamide<Chiral, synthesis from chiral ethyl [32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (retention time short)>

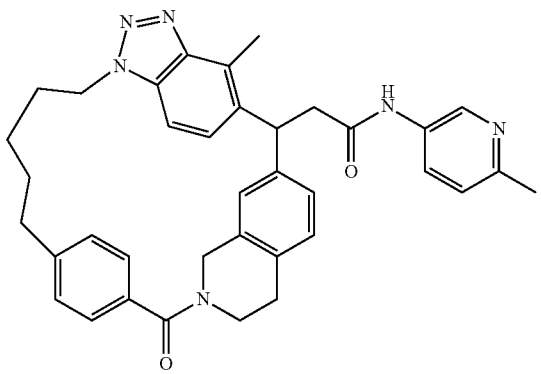 [SMILES: Cc1ccc(NC(=O)CC2c3ccc4c(c3)CN(CC4)C(=O)c3ccc(cc3)CCCCCn3nnc4c(C)c2ccc43)cn1]

To a mixture of [32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid<25 mg, chiral, synthesis from chiral ethyl [32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (retention time short)> and N,N-dimethylformamide (0.25 ml), triethylamine (0.0138 ml), HOBt (8 mg), 1-ethyl-3-(3-dimethylaminopropyl)carbodiimide hydrochloride (11.3 mg) and 6-methylpyridine-3-amine (6 mg) were added, and the reaction mixture was stirred at room temperature overnight. To the mixture, saturated aqueous sodium bicarbonate solution was added, and the precipitate was separated by filtration. The solid was washed with ethyl acetate to give the title compound (20 mg).

Example 39

2-[32-Methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]-]V-(pyridin-3-yl)acetamide Chiral, Synthesis from Chiral ethyl [32-methyl-20-oxo-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Retention Time Short)

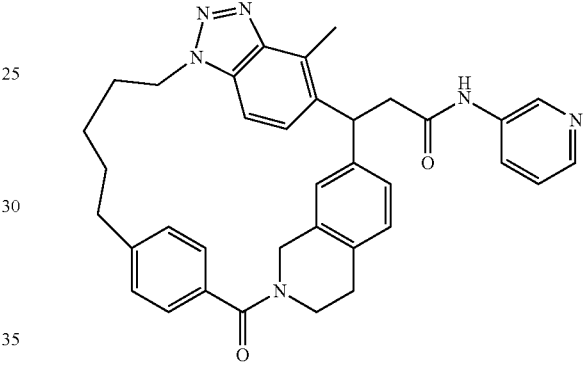

Synthesis was carried out in accordance with the methods shown in Example 38 or methods equivalent thereto.

Example 40

1-{[(Cyclohexyloxy)carbonyl]oxy}ethyl[32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate Synthesis from Chiral ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Retention Time Short)

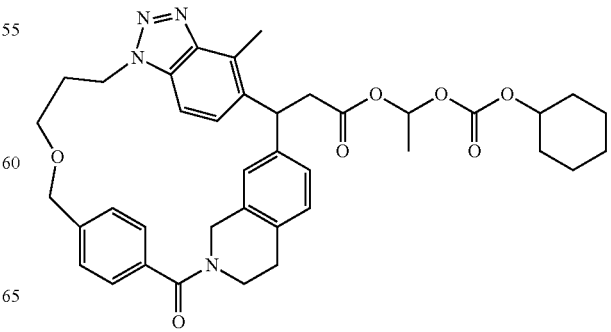

To a solution of [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid<53.3 mg, chiral, synthesis from chiral ethyl [32-methyl-20-oxo-14-oxa-8,9,10,21-tetraazahexacyclo [19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (retention time short)> in N,N-dimethylformamide (0.5 ml), cesium carbonate (51 mg) and 1-chloroethyl cyclohexyl carbonate (34.5 mg) were added, and the reaction mixture was stirred at room temperature overnight. The mixture was diluted with ethyl acetate, and washed with water and saturated brine. The mixture was then dried over anhydrous magnesium sulfate and concentrated under reduced pressure. The residue was purified by silica gel column chromatography (ethyl acetate/hexane). After suspending the residue thus obtained with water, the suspension was concentrated to give the title compound (49 mg).

Example 41

Sodium [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl] acetate Synthesis from Chiral ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Retention Time Short)

To a mixture of [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid<synthesis from chiral ethyl [32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (retention time short)>(42.7 mg) in methanol (0.5 ml), 2N sodium hydroxide (0.0418 ml) was added at room temperature. The reaction solution was concentrated to give the title compound (40 mg).

$^1$H NMR (300 MHz, DMSO-d$_6$) δ 2.25-2.41 (2H, m), 2.53-2.68 (2H, m), 2.88 (2H, t, J=6.7 Hz), 3.35-3.47 (2H, m), 3.77 (2H, t, J=6.7 Hz), 3.82-4.08 (2H, m), 4.20-4.30 (1H, m), 4.34-4.46 (1H, m), 4.67-4.91 (3H, m), 5.96 (1H, s), 6.67-6.74 (2H, m), 6.74-6.87 (2H, m), 7.14 (1H, d, J=7.9 Hz), 7.35 (1H, d, J=8.6 Hz), 7.43 (1H, d, J=7.9 Hz), 7.57 (1H, d, J=8.6 Hz).

Example 42

2-[32-Methyl-20-oxo-8,9,10,21-tetraazahexacyclo [19.5.3.2$^{16,19}$.1$^{3,7}$.0$^{6,10}$.0$^{24,28}$]dotriaconta-1(26),3 (32),4,6,8,16,18,24,27,30-decaen-2-yl]-N-(6-methylpyridin-3-yl)acetamide

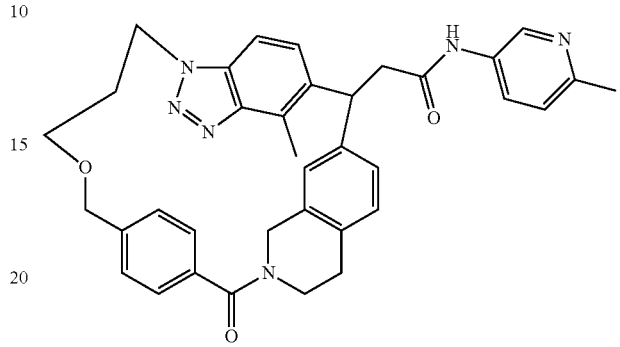

Synthesis was carried out in accordance with the methods shown in Example 38 or methods equivalent thereto.

Compounds of Examples 43 to 54 can be produced in accordance with the methods shown in Example 28 described above or methods equivalent thereto.

Example 43

2-[18,30-Dichloro-32-methyl-20-oxo-14-oxa-8,9,10, 21-tetraazahexacyclo[19.5.3.2$^{16,19}$.1$^{3,7}$.0$^{6,10}$.0$^{24,28}$] dotriaconta-1(26),3(32),4,6,8,16,18,24,27,30-decaen-2-yl]-2-methylpropanoic acid

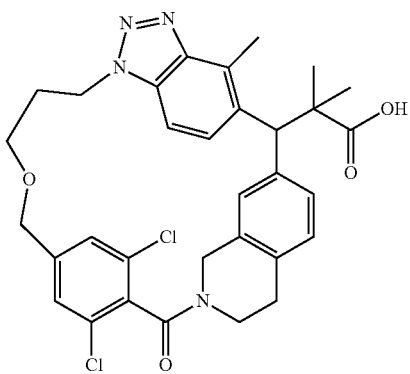 [SMILES: Cc1c2ccc3c1nnn3CCCOCc1cc(Cl)c(c(Cl)c1)C(=O)N1CCc3ccc(cc3C1)C2C(C)(C)C(=O)O]

Example 44

2-Methyl-2-[32-methyl-20-oxo-8,9,10,21-tetraaza-hexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]propanoic acid

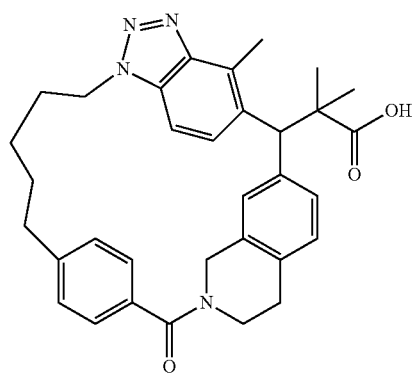 [SMILES: Cc1c2ccc3c1nnn3CCCCCc1ccc(cc1)C(=O)N1CCc3ccc(cc3C1)C2C(C)(C)C(=O)O]

Example 45

2-Methyl-2-[18,30,32-trimethyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]propanoic acid

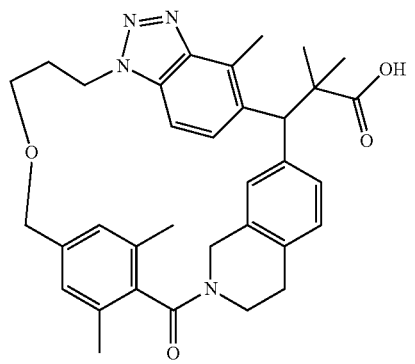 [SMILES: Cc1cc2cc(C)c1C(=O)N1CCc3ccc(cc3C1)C(C(C)(C)C(=O)O)c1ccc3c(nnn3CCCOC2)c1C]

Example 46

2-[18,30-Dichloro-32-methyl-20-oxo-15-oxa-8,9,10,21-tetraazahexacyclo[19.5.3.2$^{16,19}$.1$^{3,7}$.0$^{6,10}$.0$^{24,28}$]dotriaconta-(26),3(32),4,6,8,16,18,24,27,30-decaen-2-yl]-2-methylpropanoic acid

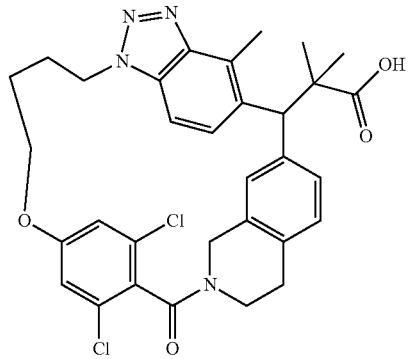 [SMILES: Cc1c2ccc3c1nnn3CCCCOc1cc(Cl)c(c(Cl)c1)C(=O)N1CCc3ccc(cc3C1)C2C(C)(C)C(=O)O]

Example 47

2-Methyl-2-[18,30,32-trimethyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]propanoic acid

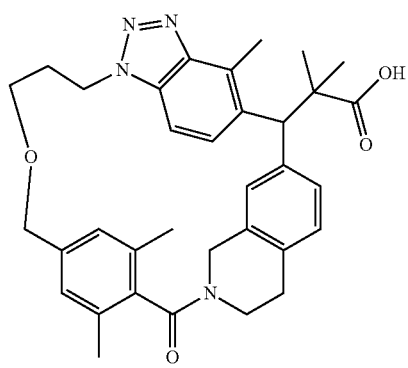 [SMILES: Cc1cc2cc(C)c1C(=O)N1CCc3ccc(cc3C1)C(C(C)(C)C(=O)O)c1ccc3c(nnn3CCCOC2)c1C]

Example 48

2-[18,30-Dichloro-25,32-dimethyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]-2-methylpropanoic acid

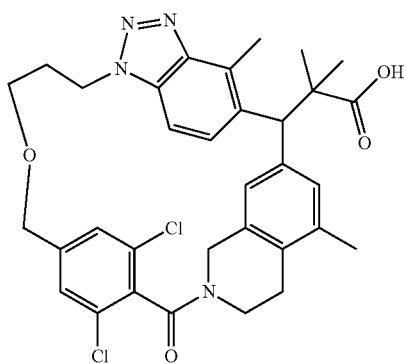 [SMILES: Cc1cc2cc3c1CCN(C3)C(=O)c1c(Cl)cc(cc1Cl)COCCCn1nnc3c(C)c(ccc31)C2C(C)(C)C(=O)O]

Example 50

2-[18,30-Dichloro-32-methyl-20-oxo-25-(trifluoromethyl)-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]-2-methylpropanoic acid

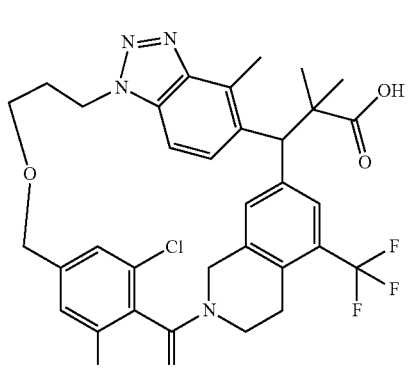

Example 49

2-Methyl-2-[18,25,30-trichloro-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]propanoic acid

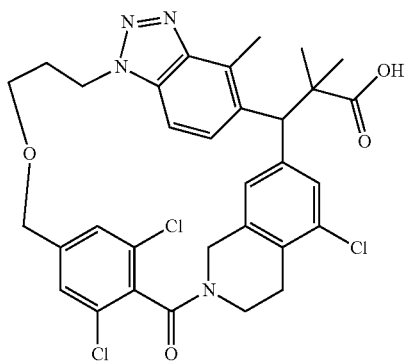 [SMILES: Cc1c2ccc3c1nnn3CCCOCc1cc(Cl)c(c(Cl)c1)C(=O)N1CCc3c(Cl)cc(cc3C1)C2C(C)(C)C(=O)O]

Example 51

2-[8-(Cyclopropylmethyl)-34-methyl-2,7-dioxo-5-oxa-1,8,16,17,18-pentaazaheptacyclo[23.5.3.2$^{3,10}$.1$^{19,23}$.0$^{4,9}$.1$^{16,20}$.0$^{28,32}$]hexatriaconta-3,9,17,19(34),20,22,25,27,32,35-decaen-24-yl]-2-methylpropanoic acid

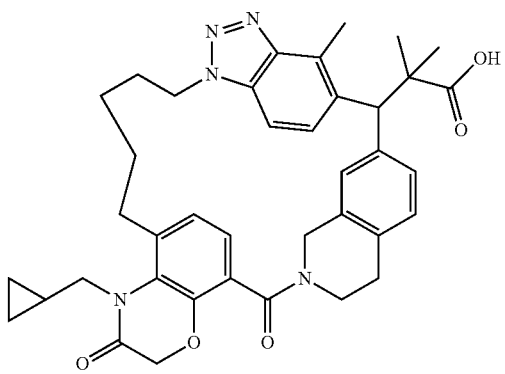 [SMILES: Cc1c2ccc3c1nnn3CCCCCc1ccc(c3c1N(CC1CC1)C(=O)CO3)C(=O)N1CCc3ccc(cc3C1)C2C(C)(C)C(=O)O]

Example 52

2-[18,30-Dichloro-32-methyl-20-oxo-8,9,10,21-tetraazahexacyclo[19.5.3.2$^{16,19}$.1$^{3,7}$.0$^{6,10}$.0$^{24,28}$]dotriaconta-(26),3(32),4,6,8,16,18,24,27,30-decaen-2-yl]-2-methylpropanoic acid

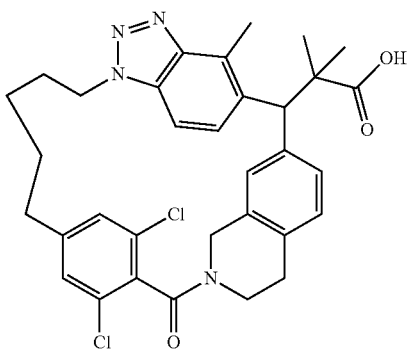 [SMILES: Cc1c2ccc3c1nnn3CCCCCc1cc(Cl)c(c(Cl)c1)C(=O)N1CCc3ccc(cc3C1)C2C(C)(C)C(=O)O]

Example 53

2-[18,30-Dichloro-5-methoxy-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]-2-methylpropanoic acid

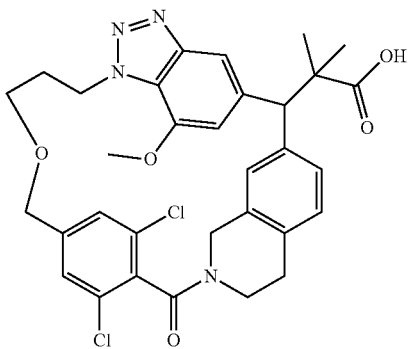 [SMILES: COc1cc2cc3nnn(c13)CCCOCc1cc(Cl)c(c(Cl)c1)C(=O)N1CCc3ccc(cc3C1)C2C(C)(C)C(=O)O]

Example 54

2-[18,30-Dichloro-5-methoxy-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]-2-methylpropanoic acid

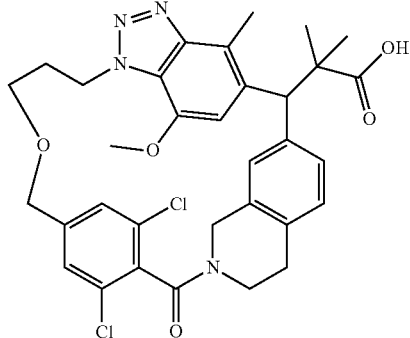 [SMILES: COc1cc2c(C)c3nnn(c13)CCCOCc1cc(Cl)c(c(Cl)c1)C(=O)N1CCc3ccc(cc3C1)C2C(C)(C)C(=O)O]

Example 55

2-methyl-2-[32-methyl-20-oxo-14-oxa-8,9,10,21-tetrazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propanoic acid Chiral, synthesis from chiral methyl 2-methyl-2-[32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propanoate (Retention Time Short)

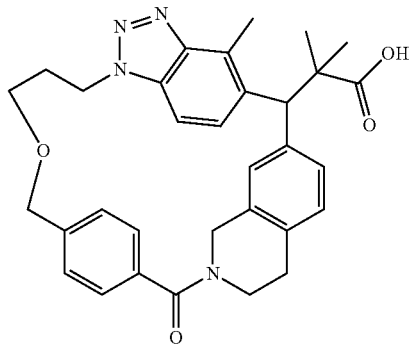 [SMILES: Cc1c2ccc3c1nnn3CCCOCc1ccc(cc1)C(=O)N1CCc3ccc(cc3C1)C2C(C)(C)C(=O)O]

A) 1-bromo-4-fluoro-2-methyl-3-nitro-benzene

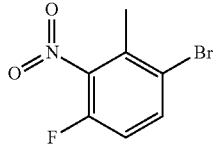

To a solution of 1-fluoro-3-methyl-2-nitro-benzene (10 g) in TFA (23 mL) and H2SO4 (10 mL) was added NBS (14 g)

at 0° C. The mixture was stirred at room temperature overnight. The mixture was poured into ice. The precipitate was filtrated and washed with water to get title compound (14 g) as white solid.

$^1$H NMR (400 MHz, DMSO-d$_6$): δ 2.34 (3H, s), 7.46 (1H, t, J=9.3 Hz), 7.93-7.97 (1H, m)

B) 3-[(4-Bromo-3-methyl-2-nitrophenyl)amino]propan-1-ol

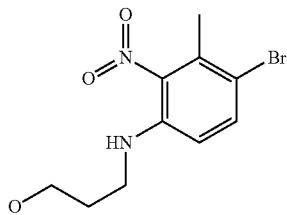 [SMILES: Cc1c(Br)ccc(NCCCO)c1[N+](=O)[O-]]

To a solution of 1-bromo-4-fluoro-2-methyl-3-nitro-benzene (14 g) in DMF (150 mL) was added K2CO3 (16.655 g) and 3-amino propanol (6 mL) at room temperature. The mixture was stirred at 80° C. overnight. After completion of reaction, ice-cold water was added to reaction mass at 0° C. The precipitate was filtrated and washed with water. Residue was evaporated and washed with n-pentane to afford title compound (14 g) as orange solid.

$^1$H NMR (400 MHz, DMSO-d$_6$): δ 1.68 (2H, q, J=5.9 Hz), 2.24 (3H, s), 3.17 (2H, q, J=6.0 Hz), 3.44 (21H, q, J=5.1 Hz), 4.58-4.60 (1H, m), 6.22 (1H, brs), 6.73 (1H, d, J=9.1 Hz), 7.54 (1H, d, J=9.0 Hz). MS m/z 289.2 [M+H]$^+$.

C) 3-[(2-Amino-4-bromo-3-methylphenyl)amino]propan-1-ol

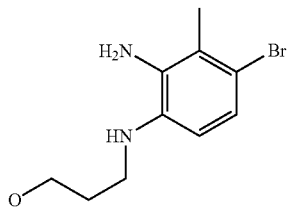

To a stirred solution of 3-[(4-bromo-3-methyl-2-nitrophenyl)amino]propan-1-ol (14.6 g) in ethanol (150 mL) and water (80 mL) were added iron (14.1 g) and NH$_4$Cl (27 g) at 25° C. and reaction mixture was refluxed for 4 h. The reaction mixture was filtered through celite bed and solvent was evaporated. Residue was quenched with sat NaHCO$_3$ aq. The aqueous layer was extracted with ethyl acetate (50 ml×3). The total organic layer was washed with brine, dried over anhydrous Na$_2$O$_4$ and evaporated under reduced pressure to afford title compound (11.8 g) as brown solid.

$^1$H NMR (400 MHz, DMSO-d6): δ 1.69-1.76 (2H, quin, J=6.6 Hz), 2.15 (3H, s), 3.18 (2H, q, J=6.5 Hz), 3.49 (2H, q, J=5.7 Hz), 4.45-4.48 (1H, m), 4.53-4.64 (3H, m), 6.25 (1H, d, J=8.5 Hz), 6.70 (1H, d, J=8.4 Hz). MS m/z 258.9 [M+H]$^+$.

D) 3-(5-Bromo-4-methyl-1H-1,2,3-benzotriazol-1-yl)propan-1-ol

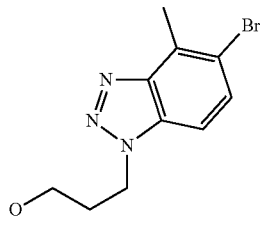

To a solution of 3-[(2-Amino-4-bromo-3-methylphenyl)amino]propan-1-ol (12 g) in 6N HCl (122 mL) was slowly added a solution of NaNO$_2$ (6.4 g) of water (36 mL) at 0° C. The mixture was stirred at room temperature for 2 h. The reaction mixture was neutralized with 4N NaOH at 0° C. The aqueous layer was extracted with EtOAc, combined organics were washed with brine, dried over anhydrous Na2SO$_4$ and concentrated under reduced pressure. Crude was purified by silica gel column (120 g, 60% EtOAc/Hexane) to afford title compound (11 g) as brown solid.

$^1$H NMR (400 MHz, DMSO-d$_6$): δ 2.03 (2H, quin, J=6.4 Hz), 2.71 (3H, s), 3.39 (2H, q, J=5.5 Hz), 4.66 (1H, br t, J=4.7 Hz), 4.74 (2H, t, J=6.7 Hz), 7.68 (2H, s). MS m/z 270.1 [M+H]$^+$.

E) 4-{[3-(5-Bromo-4-methyl-1H-1,2,3-benzotriazol-1-yl)propoxy]methyl}benzoate

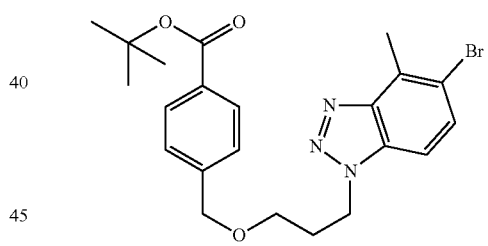

To a stirred solution of 3-(5-bromo-4-methyl-1H-1,2,3-benzotriazol-1-yl)propan-1-ol (11.4 g) in THF (250 ml), NaH (60% in oil, 10.12 g) was added at 0° C. and stirred at 25° C. for 1 h. To this was added TBAI (31 g) and tert-butyl 4-(bromomethyl)benzoate (22.8 g) at 0° C. and stirred at 25° C. for 4 h. The reaction mixture was quenched with ice. The aqueous layer was extracted with EtOAc, combined organics were washed with brine; dried over anhydrous Na$_2$SO$_4$ and concentrated under reduced pressure. The crude thus obtained was purified by silica gel column chromatography (SiO$_2$; 10% EtOAc/Hexanes) to afford title compound (16 g) as light yellow liquid.

$^1$H NMR (400 MHz, DMSO-d$_6$): δ 1.54 (9H, s), 2.17-2.23 (2H, m), 2.67 (3H, s), 3.42 (2H, t, J=5.7 Hz), 4.43 (2H, s), 4.78 (2H, t, J=6.5 Hz), 7.25 (2H, d, J=8.1 Hz), 7.65 (2H, m), 7.80 (2H, d, J=8.1 Hz). MS m/z 460.1 [M+H]$^+$.

F) tert-Butyl 4-{[3-(5-cyano-4-methyl-1H-1,2,3-benzotriazol-1-yl)propoxy]methyl}benzoate

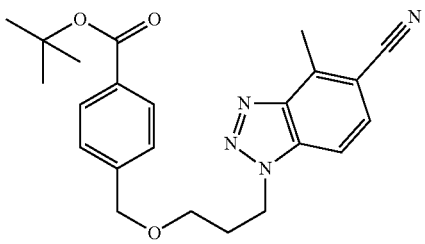 [SMILES: Cc1c(C#N)ccc2c1nnn2CCCOCc1ccc(C(=O)OC(C)(C)C)cc1]

In oven dried sealed tube, to a stirred solution of tert-butyl 4-{[3-(5-bromo-4-methyl-1H-1,2,3-benzotriazol-1-yl)propoxy]methyl}benzoate (15 g) in DMA (125 mL) were added Zn(CN)$_2$ (2.3 g), Zn-dust (0.637 g) at 25° C. and the reaction mixture was de gassed with argon atmosphere for 10 min. To this was added Pd2(dba)3 (1.495 g) followed by dppf (1.8 g) at 25° C. and the reaction mixture was heated at 150° C. for 6 h. The reaction mixture was cooled to 25° C., filtered through celite and washed with EtOAc. The filtrate was diluted with water (10 times) and stirred it for 30 min. The aqueous layer was extracted with EtOAc, combined organics were washed with water, brine, dried over anhydrous Na$_2$SO$_4$, filtered and filtrate was concentrated under reduced pressure. The crude thus obtained was purified by silica gel column chromatography (S1O2, 20-25% EtOAc/Hexane) to give title compound (10 g) as colorless sticky oil.

$^1$H NMR (400 MHz, DMSO-d$_6$): δ 1.54 (9H, s), 2.22 (2H, t, J=6.1 Hz), 2.83-2.85 (3H, m), 3.44 (2H, t, J=5.7 Hz), 4.40 (2H, s), 4.84 (2H, t, J=6.5 Hz), 7.21 (2H, d, J=8.1 Hz), 7.77-7.80 (4H, m). MS m/z 407.0 [M+H]$^+$.

G) tert-butyl 4-{[3-(5-formyl-4-methyl-1H-1,2,3-benzotriazol-1-yl)propoxy]methyl}benzoate

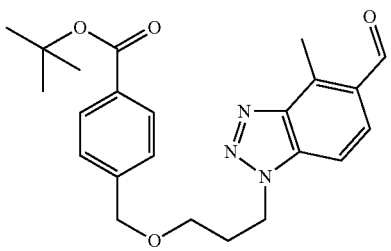 [SMILES: Cc1c(C=O)ccc2c1nnn2CCCOCc1ccc(C(=O)OC(C)(C)C)cc1]

To a stirred solution of 4-{[3-(5-cyano-4-methyl-1H-1,2,3-benzotriazol-1-yl)propoxy]methyl}benzoate (4.7 g) in pyridine (85 mL) were added AcOH (85 mL), water (85 mL) followed by Raney Ni (in water, 47 mL) at 25° C. The reaction mixture was stirred under positive pressure of hydrogen balloon for 24 h at 25° C. The progress of reaction was judged by LC/MS only. After completion of reaction (as judged by LC/MS), the reaction mixture was filtered through celite and washed with EtOAc. Filtrate was diluted with ethyl acetate, washed with 0.5M citric acid, saturated aqueous NaHCO$_3$, combined organics were washed with water, brine, dried over anhydrous Na$_2$SO$_4$, filtered and filtrate was concentrated under reduced pressure. The crude thus obtained was purified by silica gel column chromatography (SiO$_2$, 30-35% EtOAc/Hexane) to give title compound (2.3 g) as brown oil.

$^1$H NMR (400 MHz, DMSO-d$_6$): δ 1.54 (9H, s), 2.21-2.26 (2H, m), 3.04 (3H, s), 3.43 (2H, t, J=5.8 Hz), 4.43 (2H, s), 4.82 (2H, t, J=6.6 Hz), 7.28 (2H, d, J=8.0 Hz), 7.77-7.80 (3H, m), 7.92 (1H, d, J=8.6 Hz), 10.43 (1H, s). MS m/z 410.4 [M+H]$^+$.

H) tert-Butyl 7-({1-[3-({4-[(tert-butoxy)carbonyl]phenyl}methoxy)propyl]-4-methyl-1H-1,2,3-benzotriazol-5-yl}(hydroxy)methyl)-1,2,3,4-tetrahydroisoquinoline-2-carboxylate

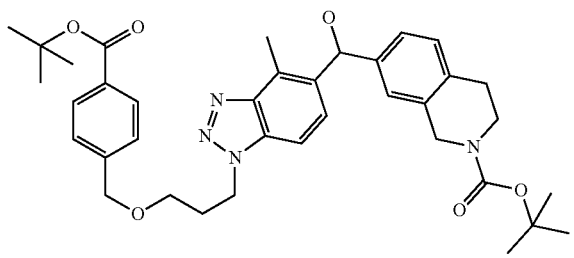 [SMILES: Cc1c(C(O)c2ccc3c(c2)CN(C(=O)OC(C)(C)C)CC3)ccc2c1nnn2CCCOCc1ccc(C(=O)OC(C)(C)C)cc1]

To a degassed solution of tert-butyl 4-{[3-(5-formyl-4-methyl-1H-1,2,3-benzotriazol-1-yl)propoxy]methyl}benzoate (2.6 g) in mixture of CPME (60 ml) and water (12 ml) were added tert-butyl 7-(tetramethyl-1,3,2-dioxaborolan-2-yl)-1,2,3,4-tetrahydroisoquinoline-2-carboxylate (6.8 g), K$_3$PO$_4$ (4.04 g) at 25° C. To this was added [RhCl(COD)]$_2$ (627 mg) and the reaction mixture was heated at 50° C. for 2 h. The reaction mixture was cooled to 25° C. and quenched with sat NH$_4$Cl aq. The aqueous layer was extracted with EtOAc, combined organics were washed with water, brine, dried over anhydrous Na$_2$SO$_4$, filtered and filtrate was concentrated under reduced pressure. The crude thus obtained was purified by silica gel column chromatography (SiO$_2$, 25% EtOAc/Hexane) to give title compound (2 g) as light yellow sticky solid.

$^1$H NMR (400 MHz, DMSO-d$_6$): δ 1.39 (9H, s), 1.53 (9H, s), 2.19-2.16 (2H, m), 2.68-2.72 (5H, m), 3.41 (2H, t, J=5.88 Hz), 3.48-3.51 (2H, m), 4.42-4.46 (4H, m), 4.74 (2H, t, J=6.68 Hz), 5.87-5.88 (1H, m), 6.03-6.04 (1H, m), 7.04-7.12 (3H, m), 7.34 (2H, d, J=8.04 Hz), 7.58 (2H, s), 7.83 (21-, d, J=8.12 Hz). MS m/z 643.1 [M+H]$^+$.

I) 4-[(3-{5-[3-Methoxy-2,2-dimethyl-3-oxo-1-(1,2,3,4-tetrahydroisoquinolin-7-yl)propyl]-4-methyl-1H-1,2,3-benzotriazol-1-yl}propoxy)methyl]benzoic acid

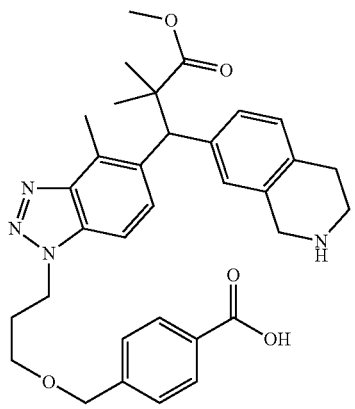 [SMILES: COC(=O)C(C)(C)C(c1ccc2c(c1)CNCC2)c1ccc2c(nnn2CCCOCc2ccc(C(=O)O)cc2)c1C]

To a stirred solution of tert-Butyl 7-({1-[3-({4-[(tert-butoxy)carbonyl]phenyl}methoxy)propyl]-4-methyl-1H-1,2,3-benzotriazol-5-yl}(hydroxy)methyl)-1,2,3,4-tetrahydroisoquinoline-2-carboxylate (700 mg) in DCM (30 ml.) were added [(1-methoxy-2-methylprop-1-en-1-yl)oxy]trimethylsilane (1.2 mL) and TiCl$_4$ (1M in DCM, 2.4 mL) at 0° C. and the reaction mixture was stirred at 0° C. for 5 min. After completion of reaction (as jugged by LCMS and TLC), the reaction mixture was quenched with water. Aqueous layer was basified with saturated NaHCO$_3$ solution (pH ~8) and filtered through celite bed. After filtration, aqueous layer was extracted with 10% MeOH/DCM (3×50 mL), the combined organic layer was washed with brine, dried over anhydrous Na$_2$SO$_4$ and evaporated to give a mixture, which was used to next step without further purification.

To a mixture in dioxane (6 mL) was added 4M HCl/dioxane solution (6 mL) dropwise at 25° C. and the reaction mixture was stirred at that temperature for 2 h. After completion of reaction (as judged by LC/MS), the volatiles were removed under reduced pressure and crude thus obtained was purified by reverse phase prep-HPLC to give title compound (250 mg) as off white solid.

$^1$H NMR (400 MHz, DMSO-d$_6$): δ 1.24-1.29 (6H, m), 2.18 (2H, t, J=5.8 Hz), 2.67-2.71 (5H, m), 3.07-3.08 (2H, m), 3.33-3.42 (2H, m), 3.42 (3H, s), 3.95 (2H, s), 4.28-4.38 (2H, m), 4.70-4.73 (3H, m), 6.95 (1H, d, J=7.7 Hz), 7.01-7.09 (4H, m), 7.47-7.54 (2H, m), 7.61 (2H, d, J=7.9 Hz). MS m/z 571.2 [M+H]$^-$.

J) methyl 2-methyl-2-[32-methyl-20-oxo-14-oxa-8,9,10,21-tetraazahexacyclo[19.5.3.2$^{16-19}$.1$^{3,7}$.0$^{6,10}$.0$^{24,28}$]dotriaconta-1(27),3(32),4,6,8,16,18,24(28),25,30-decaen-2-yl]propanoate (retention time short) and methyl 2-methyl-2-[32-methyl-20-oxo-14-oxa-8,9,10,21-tetraazahexacyclo[19.5.3.2$^{16,19}$.1$^{3,7}$.0$^{6-10}$.0$^{24,28}$]dotriaconta-1(27),3(32),4,6,8,16,18,24(28),25,30-decaen-2-yl]propanoate (Retention Time Long)

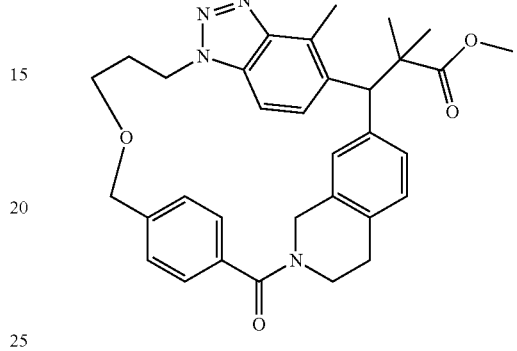

To a solution of HATU (406 mg) in DMF (15 ml) was added a mixture of 4-[[3-[5-[3-methoxy-2,2-dimethyl-3-oxo-1-[1,2,3,4-tetrahydroisoquinolin-7-yl]propyl]-4-methyl-1H-1,2,3-benzotriazol-1-yl]propoxy]methyl]benzoic acid (500 mg) and N,N-diisopropylethylamine (0.74 mL) in DMF (32 ml) at 25° C. by syringe pump for 1 h and the reaction mixture was stirred at that temperature for 3 h. After completion of reaction (as judged by LC/MS), reaction mixture was diluted with saturated NAHCO$_3$ solution. The aqueous layer was extracted with EtOAc. The combined organic layer was washed with brine, dried over anhydrous Na$_2$SO$_4$ and evaporated under reduced pressure. The crude thus obtained was purified by normal phase chiral HPLC (method C) to afford methyl 2-methyl-2-[32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propanoate (retention time short) (55 mg) and methyl 2-methyl-2-[32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27), 3(32),4,6,8,16,18,24(28),25,30-decaen-2-yl]propanoate (retention time long) (45 mg) as white solid.

methyl 2-methyl-2-[32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propanoate (Retention Time Short)

$^1$H NMR (400 MHz, DMSO-d$_6$): δ 1.22-1.34 (6H, m), 2.32-2.36 (21H, m), 2.90 (2H, brs), 3.35-3.38 (4H, m), 3.48 (3H, s), 3.50-3.65 (1H, m), 3.86-3.90 (1H, m), 4.00-4.03 (2H, m), 4.10-4.14 (1H, m), 4.25-4.29 (1H, m), 4.37-4.40 (1H, m), 4.76-4.78 (3H, m), 6.17 (1H, s), 6.66 (2H, d, J=7.8 Hz), 6.76 (2H, d, J=8.1 Hz), 7.18 (1H, d, J=8.0 Hz), 7.31 (1H, d, J=6.5 Hz), 7.41 (1H, d, J=8.9 Hz), 7.61 (1H, d, J=8.9 Hz). MS m/z 553.0 [M+H]$^+$.

methyl 2-methyl-2-[32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propanoate (Retention Time Long)

$^1$H NMR (400 MHz, DMSO-d$_6$): δ 1.22-1.34 (6H, m), 2.32-2.36 (1H, m), 2.90-2.95 (2H, m), 3.35-3.38 (4H, m), 3.48 (3H, s), 3.62-3.63 (1H, m), 3.86-3.90 (11H, m), 4.00-4.03 (2H, m), 4.10-4.14 (1H, m), 4.26-4.29 (1H, m), 4.37-4.40 (1H, m), 4.78 (3H, s), 6.17 (1H, s), 6.66 (2H, d, J=7.5 Hz), 6.76 (2H, d, J=7.8 Hz), 7.18 (1H, d, J=8.0 Hz), 7.31 (1H, d, J=8.0 Hz), 7.41 (1H, d, J=8.1 Hz), 7.61 (1H, d, J=8.8 Hz). MS m/z 553.2 [M+H]$^+$.

K) 2-methyl-2-[32-methyl-20-oxo-14-oxa-8,9,10,21-tetrazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propanoic acid Chiral, Synthesis from Chiral methyl 2-methyl-2-[32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl] propanoate (Retention Time Short)

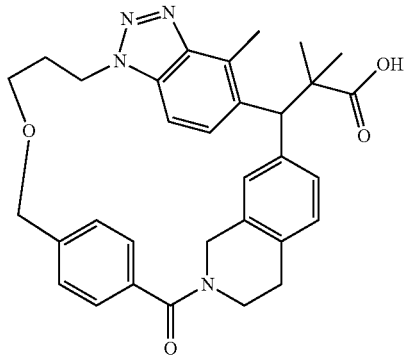 [SMILES: Cc1c2ccc3c1nnn3CCCOCc1ccc(cc1)C(=O)N1CCc3ccc(cc3C1)C2C(C)(C)C(=O)O]

To a stirred solution of chiral methyl 2-methyl-2-[32-methyl-20-oxo-14-oxa-8,9,10,21-tetraazahexacyclo [19.5.3.2$^{16,19}$.1$^{3,7}$.0$^{6,10}$.0$^{24,28}$]dotriaconta-1(27),3(32),4,6,8, 16,18,24(28),25,30-decaen-2-yl]propanoate (retention time short) (80 mg) in DMSO (1.5 ml) was added TMSOK (92 mg) at 25° C. and the reaction mixture was heated at 50° C. for 3 h. After completion of reaction (as jugged by TLC & LC/MS), the reaction mixture was cooled to 25° C. The reaction mixture was diluted with EtOAc and neutralized with 1N HCl. The aqueous layer was extracted with EtOAc. The combined organic layer was washed with brine, dried over anhydrous Na$_2$SO$_4$ and evaporated under reduced pressure The crude thus obtained was purified by reverse phase prep-HPLC (method A) to give title compound (21.15 mg) as white solid.

$^1$H NMR (400 MHz, DMSO-d$_6$): δ 1.22-1.32 (6H, m), 2.36 (2H, brs), 2.90 (2H, brs), 3.35-3.38 (4H, m), 3.65-3.67 (1H, m), 3.86-3.96 (3H, m), 4.08-4.12 (1H, m), 4.25-4.28 (1H, m), 4.37-4.40 (1H, m), 4.76-4.79 (3H, m), 6.13 (1H, s), 6.67 (2H, d, J=7.4 Hz), 6.76 (2H, d, J=7.7 Hz), 7.18 (1H, d, J=7.7 Hz), 7.37 (1H, d, J=7.5 Hz), 7.47 (1H, d, J=8.6 Hz), 7.61 (1H, d, J=8.5 Hz), 12.35 (1H, bs). MS m/z 539.4 [M+H]$^+$.

Example 56

2-methyl-2-[32-methyl-20-oxo-14-oxa-8,9,10,21-tetrazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propanoic acid Chiral, Synthesis from Chiral methyl 2-methyl-2-[32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1 (27),3(32),4,6,8,16,18,24(28),25,30-decaen-2-yl] propanoate (Retention Time Long)

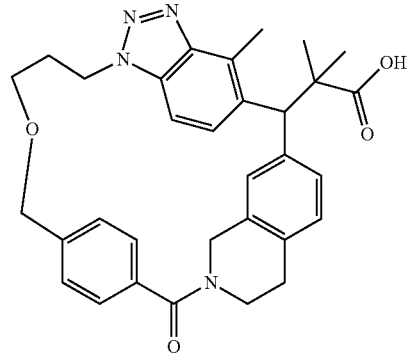 [SMILES: Cc1c2ccc3c1nnn3CCCOCc1ccc(cc1)C(=O)N1CCc3ccc(cc3C1)C2C(C)(C)C(=O)O]

To a stirred solution of chiral methyl 2-methyl-2-[32-methyl-20-oxo-14-oxa-8,9,10,21-tetraazahexacyclo [19.5.3.2$^{16,19}$.1$^{3,7}$.0$^{6,10}$.0$^{24,28}$]dotriaconta-1(27),3(32),4,6,8, 16,18,24(28),25,30-decaen-2-yl]propanoate (retention time long) (73 mg) in DMSO (1.5 ml) was added TMSOK (84 mg) at 25° C., and the reaction mixture was heated at 50° C. for 3 h. After completion of reaction (as jugged by TLC and LC/MS), the reaction mixture was cooled to 25° C. The reaction mixture was diluted with EtOAc and neutralized with 1N HCl. The aqueous layer was extracted with EtOAc. The combined organic layer was washed with brine, dried over anhydrous Na$_2$SC>$_4$ and evaporated under reduced pressure. The crude thus obtained was purified by reverse phase prep-HPLC (method A) to give title compound (16.42 mg) as white solid.

$^1$H NMR (400 MHz, DMSO-d$_6$): δ 1.18-1.32 (6H, m), 2.36 (2H, brs), 2.90 (2H, brs), 3.35-3.38 (4H, m), 3.64 (1H, brs), 3.86-3.99 (3H, m), 4.09-4.12 (1H, m), 4.25-4.28 (1H, m), 4.37-4.40 (1H, m), 4.76-4.79 (3H, m), 6.13 (1H, s), 6.67 (2H, d, J=7.6 Hz), 6.76 (2H, d, J=7.7 Hz), 7.18 (1H, d, J=7.6 Hz), 7.37 (1H, d, J=8.0 Hz), 7.47 (1H, d, J=8.6 Hz), 7.61 (1H, d, J=8.7 Hz), 12.35 (1H, bs). MS m/z 539.4 [M+H]$^+$.

Example 57

2-[18,30-dichloro-32-methyl-20-oxo-8,9,10,21-tetrazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]-2-methylpropanoic acid

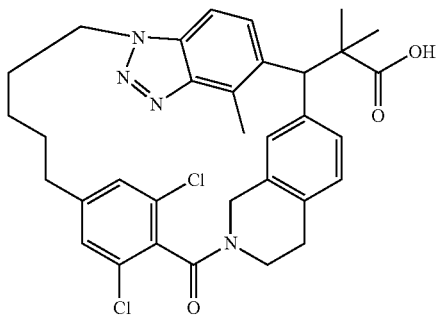 [SMILES: Cc1c2ccc3c1nnn3CCCCCc1cc(Cl)c(c(Cl)c1)C(=O)N1CCc3ccc(cc3C1)C2C(C)(C)C(=O)O]

The compounds of Examples 57 could be produced according to the production methods described in the present specification, a method shown in the Examples, or a method analogous thereto.

Example 58

2-methyl-2-[18,30,32-trimethyl-20-oxo-14-oxa-8,9,10,21-tetrazahexacyclo[19.5.3.2$^{16,19}$.1$^{3,7}$.0$^{6,10}$.0$^{24,28}$]dotriaconta-1(27),3(32),4,6,8,16(31),17,19(30),24(28),25-decaen-2-yl]propanoic acid Chiral, Synthesis from Chiral methyl 2-methyl-2-[18,30,32-trimethyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propanoate (Retention Time Short)

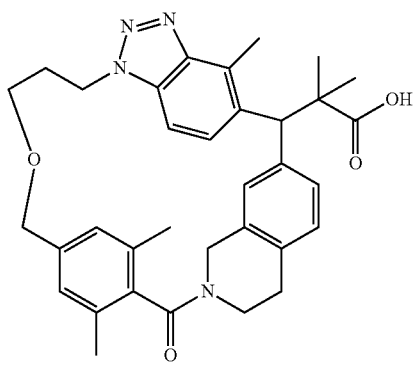 [SMILES: Cc1cc2cc(C)c1C(=O)N1CCc3ccc(cc3C1)C(C(C)(C)C(=O)O)c1ccc3c(nnn3CCCOC2)c1C]

A) tert-butyl 4-bromo-2,6-dimethylbenzoate

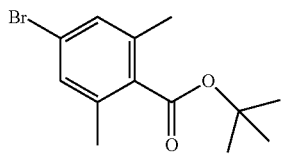 [SMILES: Cc1cc(Br)cc(C)c1C(=O)OC(C)(C)C]

A solution of 4-bromo-2,6-dimethyl-benzoic acid (1 g) in toluene (10 ml) was heated to 100° C. for 1 h. To this was added N,N-dimethylformamide di-tert-butyl acetal (6.2 ml) in toluene (5 ml) dropwise at heating condition, and the reaction mixture was stirred for another 1 h at that temperature. After completion of reaction (as jugged by TLC), the volatiles were evaporated under reduced pressure. The crude thus obtained was purified by silica gel column chromatography (SiO$_2$, 40 g, 12% EtOAc/Hexane) to give title compound (840 mg) as colorless oil.

$^1$H NMR (400 MHz, DMSO-d$_6$): δ 1.53 (9H, s), 2.24 (6H, s), 7.32 (2H, s).

B) tert-butyl 4-formyl-2,6-dimethylbenzoate

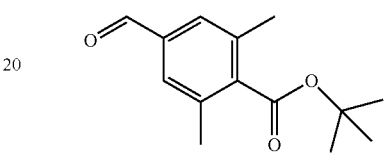

To a stirred solution of tert-butyl 4-bromo-2,6-dimethylbenzoate (2 g) in THF (20 ml) was added n-BuLi (1.6M in hexane) (4.4 ml) at −78° C. and the reaction mixture was stirred at that temperature for 15 min. To this was added DMF (1.1 ml) at −78° C. and the reaction mixture was stirred at that temperature for 15 min. The reaction mixture was quenched by sat. NH$_4$Cl aq. and extracted with ethyl acetate. The combined organic layer was washed with brine, dried over anhydrous Na$_2$SO$_4$ and concentrated under reduced pressure to give title compound (1.5 g) as brown solid which was used into the next step without purification.

$^1$H NMR (400 MHz, DMSO-d$_6$): δ 1.56 (9H, s), 2.33 (6H, s), 7.62 (2H, s), 9.95 (1H, s).

C) tert-butyl 4-[hydroxymethyl]-2,6-dimethylbenzoate

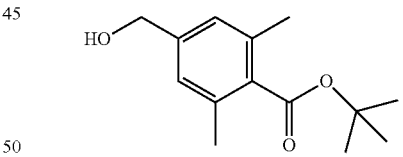

To a stirred solution of tert-butyl 4-formyl-2,6-dimethylbenzoate (3.8 g) in methanol (35 ml) was added NaBH$_4$ (676 mg) slowly portionwise at 0° C., and the reaction mixture was stirred at that temperature for 20 min. After completion of reaction (as judged by TLC), the volatiles were removed under reduce pressure. The residue was dissolved in ice cold water. The aqueous layer was extracted with EtOAc. The organic layer was washed with brine, dried over anhydrous Na$_2$SO$_4$, and concentrated under reduced pressure. The crude thus obtained was purified by silica gel column chromatography (SiO$_2$, 40 g, 15% EtOAc/Hexane) to give title compound (2.7 g) as colorless oil.

1H NMR (400 MHz, DMSO-d$_6$): δ 1.54 (9H, s), 2.23 (6H, s), 4.42 (2H, d, J=5.6 Hz), 5.16 (1H, t, J=5.6 Hz), 6.90 (2H, s).

D) tert-butyl 4-[bromomethyl]-2,6-dimethylbenzoate

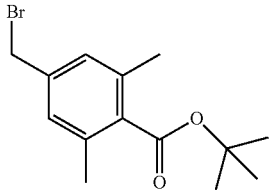 [SMILES: Cc1cc(CBr)cc(C)c1C(=O)OC(C)(C)C]

To a stirred solution of tert-butyl 4-[hydroxymethyl]-2,6-dimethylbenzoate (2.8 g) in THF (60 ml) were added PPh$_3$ (3.734 g) followed by CBr$_4$ (5.9 g) at 0° C. and the reaction mixture was stirred at 0° C. for 30 min. After completion of reaction (as judged by TLC), the volatiles were removed under reduced pressure. The crude thus obtained was purified by silica gel column chromatography (SiO$_2$, 40 g, 12% EtOAc/Hexane) to give title compound (3 g) as white solid.

$^1$H NMR (400 MHz, DMSO-d$_6$): δ 1.54 (9H, s), 2.23 (6H, s), 4.62 (2H, s), 7.15 (2H, s).

E) tert-butyl 4-[[3-[5-bromo-4-methyl-1H-1,2,3-benzotriazol-1-yl]propoxy]methyl]-2,6-dimethylbenzoate

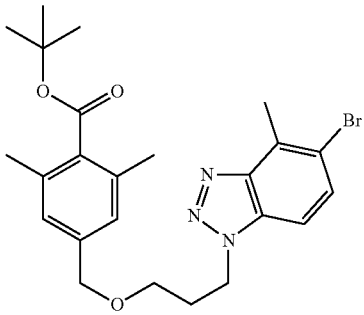 [SMILES: Cc1cc(COCCCn2nnc3c(C)c(Br)ccc32)cc(C)c1C(=O)OC(C)(C)C]

To a stirred solution of 3-(5-bromo-4-methyl-1H-1,2,3-benzotriazol-1-yl)propan-1-ol (7.2 g) in DMF (50 ml) was added NaH (1.28 g) at 0° C. and the reaction mixture was stirred for 30 min at that temperature. To this was added tert-butyl 4-(bromomethyl)-2,6-dimethylbenzoate (8 g) and the reaction mixture was stirred for another 2.5 h at the same temperature. After completion of reaction (as judged by TLC and LC/MS), the reaction mixture was quenched with ice-water. The aqueous layer was extracted with EtOAc. The organic layer was washed with brine, dried over anhydrous Na$_2$SO$_4$ and concentrated under reduced pressure. The crude thus obtained was purified by silica gel column chromatography (SiO$_2$; 120 g; 30% EtOAc/Hexane) to afford title compound (11 g) as brown oil.

$^1$H NMR (400 MHz, DMSO-d$_6$): δ 1.54 (9H, s), 2.16-2.21 (8H, m), 2.70 (3H, s), 3.38 (2H, t, J=5.8 Hz), 4.31 (2H, s), 4.77 (2H, t, J=6.6 Hz), 6.89 (2H, s), 7.79-7.87 (2H, m). MS m/z 489.3 [M+H]$^+$.

F) tert-butyl 4-[[3-[5-cyano-4-methyl-1H-1,2,3-benzotriazol-1-yl]propoxy]methyl]-2,6-dimethylbenzoate

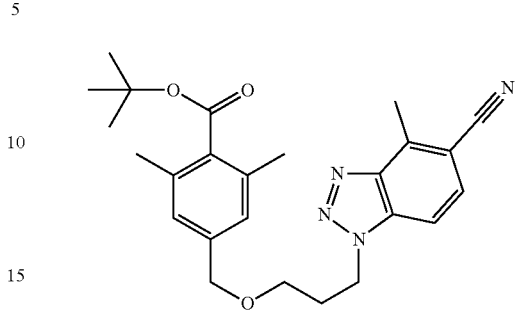

To a stirred solution of tert-butyl 4-[[3-[5-bromo-4-methyl-1H-1,2,3-benzotriazol-1-yl]propoxy]methyl]-2,6-dimethylbenzoate (6 g) in DMA (30 mL) were added Zn(CN)$_2$ (866 mg) and Zn-dust (240 mg) at 25° C., and the reaction mixture was degassed with argon atmosphere for 10 min. To this was added Pd$_2$(dba)$_3$ (563 mg) followed by dppf (681 mg) at 25° C. and the reaction mixture was heated at 150° C. for 6 h. After completion of reaction (as judged by TLC and LC/MS), the reaction mixture was cooled to 25° C., filtered through celite and washed with EtOAc. The filtrate was diluted with water (10 times) and stirred for 30 min. The aqueous layer was extracted with EtOAc. The organic layer was washed with water and brine, dried over anhydrous Na$_2$SO$_4$, filtered and concentrated under reduced pressure. The crude thus obtained was purified by silica gel column chromatography (SiO$_2$, 40 g, 20-25% EtOAc/Hexane) to give title compound (3 g) as colorless sticky oil.

$^1$H NMR (400 MHz, DMSO-d$_6$): δ 1.54 (9H, s), 2.16-2.21 (8H, m), 2.85 (3H, s), 3.41 (2H, t, J=5.8 Hz), 4.26 (2H, s), 4.83 (2H, t, J=6.6 Hz), 6.84 (2H, s), 7.78 (1H, d, J=8.7 Hz), 7.93 (1H, d, J=8.7 Hz). MS m/z 435.0 [M+H]$^+$.

G) tert-butyl 4-[[3-[5-formyl-4-methyl-1H-1,2,3-benzotriazol-1-yl]propoxy]methyl]-2,6-dimethylbenzoate

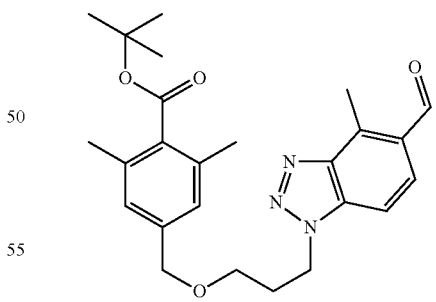

To a stirred solution of tert-butyl 4-[[3-[5-cyano-4-methyl-1H-1,2,3-benzotriazol-1-yl]propoxy]methyl]-2,6-dimethylbenzoate (3 g) in mixture of pyridine (120 ml), AcOH (60 ml) and water (60 ml) was added NaPO$_2$H$_2$(6 g) followed by Raney Ni (in water) (15 ml), and the reaction mixture was stirred at 50° C. for 1 h. After completion of reaction (as judged by TLC and LC/MS), the reaction mixture was filtered through celite and washed with EtOAc. Filtrate was diluted with ethyl acetate, washed with 0.5M aqueous citric acid, saturated aqueous NAHCO₃, water, and brine. The organic layer was dried over anhydrous Na₂SO₄, filtered and concentrated under reduced pressure. The crude thus obtained was purified by silica gel column chromatography (SiO₂, 40 g, 30-35% EtOAc/Hexane) to give title compound (2.1 g) as brown oil.

¹H NMR (400 MHz, DMSO-d₆): δ 1.54 (9H, s), 2.17-2.20 (8H, m), 3.05 (3H, s), 3.40 (2H, t, J=5.8 Hz), 4.30 (2H, s), 4.81 (2H, t, J=6.6 Hz), 6.88 (2H, s), 7.78 (1H, d, J=8.6 Hz), 7.93 (1H, d, J=8.6 Hz), 10.44 (1H, s). MS m/z 438.1 [M+H]⁺.

H) tert-butyl 7-[[1-[3-[[4-[[tert-butoxy]carbonyl]-3,5-dimethylphenyl]methoxy]propyl]-4-methyl-1H-1,2,3-benzotriazol-5-yl][hydroxy]methyl]-1,2,3,4-tetrahydroisoquinoline-2-carboxylate

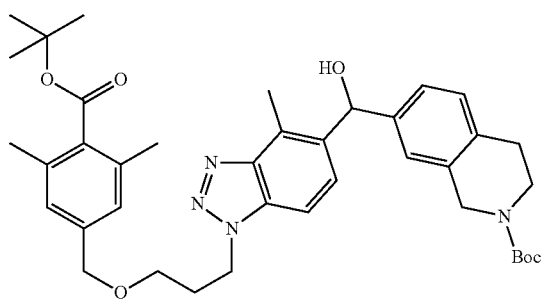 [SMILES: Cc1cc(COCCCn2nnc3c(C)c(C(O)c4ccc5c(c4)CN(C(=O)OC(C)(C)C)CC5)ccc32)cc(C)c1C(=O)OC(C)(C)C]

To a degassed solution of tert-butyl 4-[[3-[5-formyl-4-methyl-1H-1,2,3-benzotriazol-1-yl]propoxy]methyl]-2,6-dimethylbenzoate (700 mg) in mixture of CPME (45 ml) and water (9 ml) was added tert-butyl 7-[tetramethyl-1,3,2-dioxaborolan-2-yl]-1,2,3,4-tetrahydroisoquinoline-2-carboxylate (1.725 g), followed by K₃PO₄ (1.02 g) and [RhCl(COD)]₂ (158 mg) at 25° C. The reaction mixture was heated at 50° C. for 2 h. The reaction mixture was cooled to 25° C. and quenched with sat NH₄Cl. The aqueous layer was extracted with ethyl acetate. The organic layer was washed with brine, dried over anhydrous Na₂SO₄ and concentrated under reduced pressure. The crude thus obtained was purified by silica gel column chromatography (SiO₂, 12 g, 25% EtOAc/Hexane) to give title compound (500 mg) as light yellow sticky solid.

MS m/z 671.1 [M+H]⁺.

I) tert-butyl 7-[1-[1-[3-[[4-[(tert-butoxy]carbonyl]-3,5-dimethylphenyl]methoxy]propyl]-4-methyl-1H-1,2,3-benzotriazol-5-yl]-3-methoxy-2,2-dimethyl-3-oxopropyl]-1,2,3,4-tetrahydroisoquinoline-2-carboxylate

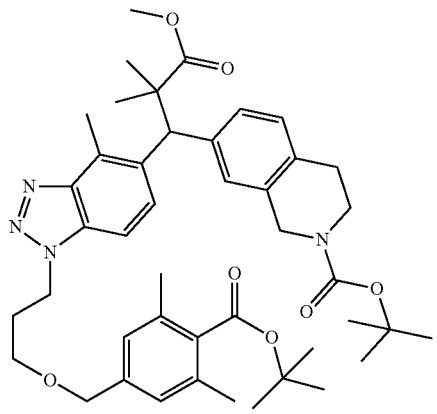 [SMILES: COC(=O)C(C)(C)C(c1ccc2c(c1)CN(C(=O)OC(C)(C)C)CC2)c1ccc2c(nnn2CCCOCc2cc(C)c(C(=O)OC(C)(C)C)c(C)c2)c1C]

To a stirred solution of tert-butyl 7-[[1-[3-[[4-[[tert-butoxy]carbonyl]-3,5-dimethylphenyl]methoxy]propyl]-4-methyl-1H-1,2,3-benzotriazol-5-yl][hydroxy]methyl]-1,2,3,4-tetrahydroisoquinoline-2-carboxylate (550 mg) in DCM (30 ml) was added [[1-methoxy-2-methylprop-1-en-1-yl]oxy]trimethylsilane (0.9 ml) followed by TiCl₄ (1M in DCM, 1.8 ml) at −10° C. and the reaction mixture was stirred at −10° C. for 5 min. After completion of reaction (as jugged by LC/MS and TLC), the reaction mixture was quenched with water. Aqueous layer was basified with saturated aqueous NAHCO₃ solution (pH ~8) and filtered through celite bed. The aqueous layer was extracted with 10% MeO/DCM (3×10 ml), the combined organic layer was washed with brine, dried over anhydrous Na₂SO₄ and concentrated in vacuo to give title compound (600 mg) as light grey solid, which was used to next step without further purification.

MS m/z 755.6 [M+H]⁻.

J) 4-[[3-[5-[3-methoxy-2,2-dimethyl-3-oxo-1-[1,2,3,4-tetrahydroisoquinolin-7-yl]propyl]-4-methyl-1H-1,2,3-benzotriazol-1-yl]propoxy]methyl]-2,6-dimethylbenzoic acid

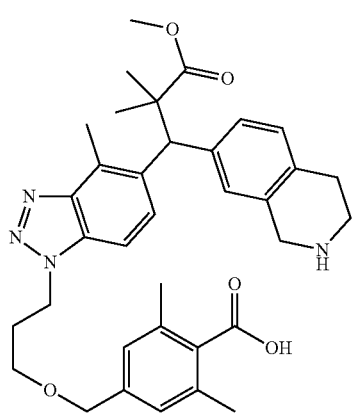 [SMILES: COC(=O)C(C)(C)C(c1ccc2c(c1)CNCC2)c1ccc2c(nnn2CCCOCc2cc(C)c(C(=O)O)c(C)c2)c1C]

To a stirred solution of tert-butyl 7-[1-[1-[3-[[4-[[tert-butoxy]carbonyl]-3,5-dimethylphenyl]methoxy]propyl]-4-methyl]-1H-1,2,3-benzotriazol-5-yl]-3-methoxy-2,2-dimethyl-3-oxopropyl]-1,2,3,4-tetrahydroisoquinoline-2-carboxylate (1.4 g) in dioxane (14 ml) was added HCl (4M in dioxane, 14 ml) dropwise at 25° C. and the reaction mixture was stirred at that temperature for 2 h. After completion of reaction (as judged by LC/MS), the volatiles were removed under reduced pressure and crude thus obtained was purified by reverse phase prep-HPLC (method A) to give title compound (600 mg) as off white solid.

$^1$H NMR (400 MHz, DMSO-$d_6$): δ 1.24-1.30 (6H, m), 1.61 (6H, s), 2.23-2.25 (2H, m), 2.74 (3H, s), 2.90 (2H, brs), 3.13-3.33 (5H, m), 3.42 (5H, s), 3.82-3.86 (1H, m), 4.02-4.05 (1H, m), 4.31-4.34 (1H, m), 4.69-4.73 (3H, m), 6.18 (2H, s), 6.73 (1H, s), 7.07 (1H, d, J=7.9 Hz), 7.34 (1H, d, J=7.0 Hz), 7.54 (1H, d, J=8.9 Hz), 7.62 (1H, d, J=8.7 Hz). MS m/z 599.1 [M+H]$^-$.

K) methyl 2-methyl-2-[18,30,32-trimethyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propanoate (Retention Time Short)

L) methyl 2-methyl-2-[18,30,32-trimethyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propanoate (Retention Time Long)

20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propanoate (retention time long) (60 mg).

methyl 2-methyl-2-[18,30,32-trimethyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propanoate (Retention Time Short)

MS m/z 581.0 [M+H]$^-$.

methyl 2-methyl-2-[18,30,32-trimethyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propanoate (Retention Time Long)

MS m/z 580.9 [M+H]$^+$.

M) 2-methyl-2-[18,30,32-trimethyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16(31),17,19(30),24(28),25-decaen-2-yl]propanoic acid Chiral, Synthesis from chiral methyl 2-methyl-2-[18,30,32-trimethyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propanoate (Retention Time Short)

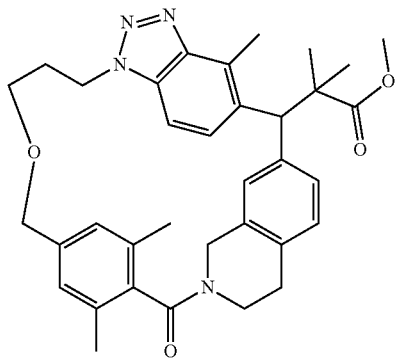 [SMILES: COC(=O)C(C)(C)C1c2ccc3c(c2)CN(CC3)C(=O)c2c(C)cc(cc2C)COCCCn2nnc3c(C)c1ccc32]

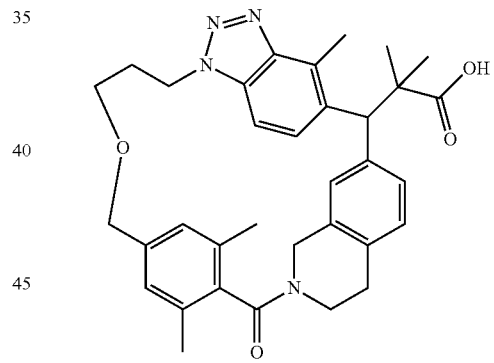

To a stirred solution of HATU (330.643 mg) in DMF (10 ml) was added a mixture of 4-[[3-[5-[3-methoxy-2,2-dimethyl-3-oxo-1-[1,2,3,4-tetrahydro isoquinolin-7-yl]propyl]-4-methyl-1H-1,2,3-benzotriazol-1-yl]propoxy]methyl]benzoic acid (400 mg, 0.669 mmol) and N,N-diisopropylethylamine (0.437 mL, 2.508 mmol) in DMF (12 ml) by syringe pump for 1 h at 25° C. and the reaction mixture was stirred at room temperature for 3 h. After completion of reaction (as judged by LC/MS); reaction mixture was diluted with saturated NaHCO$_3$ solution. The aqueous layer was extracted with EtOAc, the combined organic layer was washed with brine, dried over anhydrous Na$_2$SO$_4$ and evaporated under reduced pressure. The crude thus obtained was purified by normal phase chiral preparative HPLC (method C) to afford methyl 2-methyl-2-[18,30,32-trimethyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propanoate (retention time short) (55 mg) and methyl 2-methyl-2-[18,30,32-trimethyl- To a stirred solution of methyl 2-methyl-2-[18,30,32-trimethyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propanoate (retention time short) (121 mg) in DMSO (2.3 ml) was added TMSOK (133.82 mg) at 25° C. and the reaction mixture was heated at 50° C. for 3 h. After completion of reaction (as jugged by TLC and LC/MS), the reaction mixture was cooled to 25° C. The reaction mixture was diluted with EtOAc and neutralized with 1N HCl. The organic layer was separated and the aqueous layer was extracted with EtOAc. The combined organic layer was washed with brine, dried over anhydrous Na$_2$SO$_4$ and concentrated under reduced pressure. This crude thus obtained was purified by reverse phase prep-HPLC (method A) to give title compound (40 mg) as white solid.

$^1$H NMR (400 MHz, DMSO-$d_6$): δ 1.15 (3H, s), 1.31 (3H, s), 1.34 (3H, s), 1.92 (3H, s), 2.39 (5H, brs), 2.90 (2H, t, J=6.4 Hz), 3.34-3.35 (2H, m), 3.52-3.63 (2H, m), 3.98-4.25 (4H, m), 4.68-4.73 (2H, m), 4.80-4.85 (1H, m), 5.84 (1H, s), 5.94 (1H, s), 6.78 (1H, s), 7.15 (1H, d, J=7.9 Hz), 7.32-7.38 (2H, m), 7.55 (1H, d, J=8.7 Hz), 12.30 (1H, brs). MS m/z 567.5 [M+H]$^-$.

Example 59

2-methyl-2-[18,30,32-trimethyl-20-oxo-14-oxa-8,9,10,21-tetrazahexacyclo[19.5.3.2$^{16,19}$.1$^{3,7}$.0$^{6,10}$.0$^{24,28}$]dotriaconta-1(27),3(32),4,6,8,16(31),17,19(30),24(28),25-decaen-2-yl]propanoic acid Chiral, Synthesis from Chiral methyl 2-methyl-2-[18,30,32-trimethyl-20-oxo-14-oxa-8,9,10, 21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]propanoate (Retention Time Long)

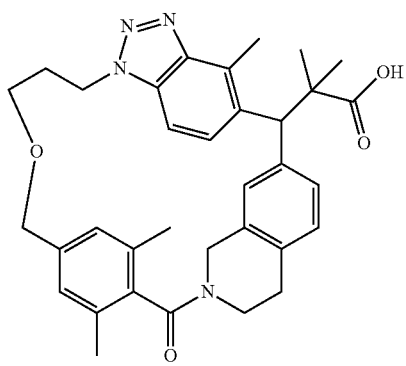

To a stirred solution of methyl 2-methyl-2-[18,30,32-trimethyl-20-oxo-14-oxa-8,9,10,21-tetraazahexacyclo[19.5.3.2$^{16,19}$.1$^{3,7}$.00$^{6,10}$.0$^{24,28}$]dotriaconta-1(27),3(32),4,6,8,16,18,24(28), 25,30-decaen-2-yl]propanoate (retention time long) (100 mg) in DMSO (1.8 ml) was added TMSOK (110.59 mg) at 25° C. and the reaction mixture was heated at 50° C. for 3 h. After completion of reaction (as jugged by TLC and LC/MS), the reaction mixture was cooled to 25° C. The reaction mixture was diluted with EtOAc and neutralized with 1N HCl. The aqueous layer was extracted with EtOAc. The organic layer was washed with brine, dried over anhydrous Na$_2$SO$_4$ and concentrated under reduced pressure. The crude thus obtained was purified by reverse phase prep-HPLC (method A) to give title compound (40 mg) as white solid.

$^1$H NMR (400 MHz, DMSO-d$_6$): δ 1.15 (3H, s), 1.31 (3H, s), 1.34 (3H, s), 1.92 (3H, s), 2.39 (5H, brs), 2.90 (2H, t, J=6.3 Hz), 3.33-3.34 (2H, m), 3.52-3.65 (2H, m), 3.98-4.02 (1H, m), 4.09-4.25 (3H, m), 4.66-4.71 (2H, m) 4.80-4.85 (1H, m), 5.83 (1H, s), 5.94 (1H, s), 6.78 (1H, s), 7.15 (1H, d, J=7.8 Hz), 7.33 (1H, d, J=8.0 Hz), 7.37 (1H, d, J=8.8 Hz), 7.55 (1H, d, J=8.8 Hz), 12.22 (1H, brs). MS m/z 567.5 [M+H]$^+$.

Example 60

2-[18,30-dichloro-32-methyl-20-oxo-14-oxa-8,9,10,21-tetrazahexacyclo[19.5.3.2$^{16-19}$.1$^{3,7}$.0$^{6,10}$.0$^{24,28}$]dotriaconta-1(27),3(32),4,6,8,16,18,24(28),25,30-decaen-2-yl]-2-methylpropanoic acid Chiral, Synthesis from Chiral methyl 2-[18,30-dichloro-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]-2-methylpropanoate (Retention Time Short)>6-dichlorobenzoate

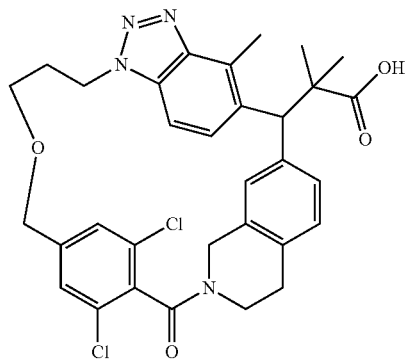 [SMILES: Cc1c2ccc3c1nnn3CCCOCc1cc(Cl)c(c(Cl)c1)C(=O)N1CCc3ccc(cc3C1)C2C(C)(C)C(=O)O]

A) tert-butyl 4-bromo-2,6-dichlorobenzoate

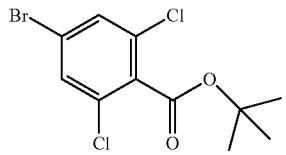 [SMILES: CC(C)(C)OC(=O)c1c(Cl)cc(Br)cc1Cl]

A solution of 4-bromo-2,6-dichlorobenzoic acid (5 g) in toluene (50 mL) was heated to 100° C. for 1 h. To this was added N,N-dimethylformamide di-tert-butyl acetal (27 mL) in toluene (20 mL) dropwise at heating condition and stirred the reaction mixture for another 1 h. After completion of reaction (as jugged by TLC), the volatiles were evaporated under reduced pressure and the crude thus obtained was purified by silica gel column chromatography (SiO$_2$, 40 g, 10% EtOAc/Hexane) to give title compound (5.6 g) as white solid.

$^1$H NMR (400 MHz, DMSO-d$_6$): δ 1.54 (9H, s), 7.90 (2H, s).

B) tert-butyl 2,6-dichloro-4-formylbenzoate

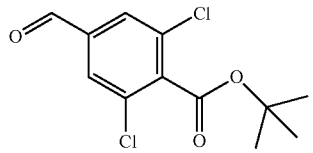 [SMILES: CC(C)(C)OC(=O)c1c(Cl)cc(C=O)cc1Cl]

To a stirred solution of tert-butyl 4-bromo-2,6-dichlorobenzoate (5.6 g) in THF (100 ml) was added iPrMgBr (2M in THF) (17 ml) at 0° C. and the reaction mixture was stirred at that temperature for another 15 min. To this was added DMF (0.6 ml) at 0° C. and stirred the reaction mixture at that temperature for another 15 min. After completion of reaction (as jugged by TLC), the reaction mixture was quenched with sat. aq. NH$_4$Cl. The aqueous was extracted with EtOAc, combined organics were washed with brine; dried over anhydrous Na$_2$SO$_4$ and concentrated under reduced pressure to give title compound (4.6 g) as colorless oil, which was used to next step without further purification.

$^1$H NMR (400 MHz, DMSO-d$_6$): δ 1.55 (9H, s), 8.04 (2H, s), 9.97 (1H, s).

C) tert-butyl 2,6-dichloro-4-[hydroxymethyl]benzoate

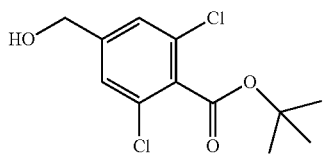 [SMILES: CC(C)(C)OC(=O)c1c(Cl)cc(CO)cc1Cl]

To a stirred solution of tert-butyl 2,6-dichloro-4-formylbenzoate (4.6 g) in methanol (35 ml) was added NaBH$_4$ (700 mg) slowly portionwise at 0° C., and the reaction mixture was stirred at that temperature for 20 min. After completion of reaction (as judged by TLC), the volatiles were removed under reduce pressure. The residue was poured in ice cold water. The aqueous was extracted with EtOAc, combined organics were washed with brine; dried over anhydrous Na$_2$SO$_4$ and concentrated under reduced pressure. The crude thus obtained was purified by silica gel column chromatography (SiO$_2$, 40 g, 10% EtOAc/Hexane) to give title compound (3.3 g) as colorless liquid.

$^1$H NMR (400 MHz, DMSO-d$_6$): δ 1.54 (9H, s), 4.51 (2H, d, J=5.8 Hz), 5.51 (1H, t, J=5.8 Hz), 7.44 (2H, s).

D) tert-butyl 4-(bromomethyl)-2,6-dichlorobenzoate

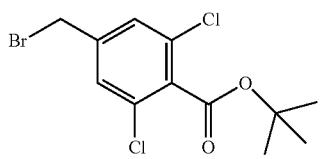 [SMILES: CC(C)(C)OC(=O)c1c(Cl)cc(CBr)cc1Cl]

To a stirred solution of tert-butyl 2,6-dichloro-4-[hydroxymethyl]benzoate (3.7 g) in THF (45 ml) were added PPh$_3$ (8.7 g) followed by NBS (5.24 g) at 0° C. and the reaction mixture was stirred at 0° C. for 2 h. After completion of reaction (as judged by TLC), the volatiles were removed under reduced pressure. The crude thus obtained was purified by silica gel column chromatography (SiO$_2$, 40 g, 10% EtOAc/Hexane) to give title compound (3.8 g) as white solid.

$^1$H NMR (400 MHz, DMSO-d$_6$): δ 1.55 (9H, s), 4.69 (2H, s), 7.67 (2H, s).

E) 3-[5-ethenyl-4-methyl-1H-1,2,3-benzotriazol-1-yl]propan-1-ol

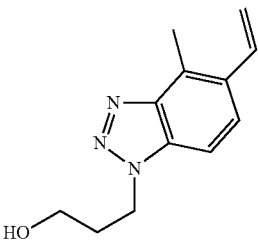 [SMILES: C=Cc1ccc2c(nnn2CCCO)c1C]

To a degassed solution of 3-[5-bromo-4-methyl-1H-1,2,3-benzotriazol-1-yl]propan-1-ol (5 g) in mixture of THF (50 ml) and n-propanol (100 ml) were added potassium vinyltrifluoroborate (10 g) followed by TEA (10 ml) at 25° C. and the reaction mixture was degassed with argon for 15 min. To this was added PdCl$_2$(dppf), DCM (1.5 g) at 25° C. and the reaction mixture was heated at 100° C. for 2 h. After completion of reaction (as jugged by TLC and LC/MS), the reaction mixture was cooled to 25° C. The volatiles were removed under reduced pressure and crude thus obtained was dissolved with water. The aqueous layer was extracted with EtOAc, combined organics were washed with brine; dried over anhydrous Na$_2$SO$_4$ and concentrated under reduced pressure. The crude thus obtained was purified by silica gel column chromatography (SiO$_2$, 40 g, 60% EtOAc/Hexane) to give title compound (3.5 g) as brown liquid.

$^1$H NMR (400 MHz, DMSO-d$_6$): δ 2.04 (2H, t, J=6.4 Hz), 2.70 (3H, s), 3.38 (2H, q, J=5.6 Hz), 4.71 (3H, t, J=7.0 Hz), 5.38 (1H, d, J=11.0 Hz), 5.75-5.83 (1H, m), 7.08-7.15 (1H, m), 7.60-7.69 (1H, m), 7.75 (1H, d, J=8.7 Hz). MS m/z 218.0 [M+H]$^+$.

F) tert-butyl 2,6-dichloro-4-[[3-[5-ethenyl-4-methyl-1H-1,2,3-benzotriazol-1-yl]propoxy]methyl]benzoate

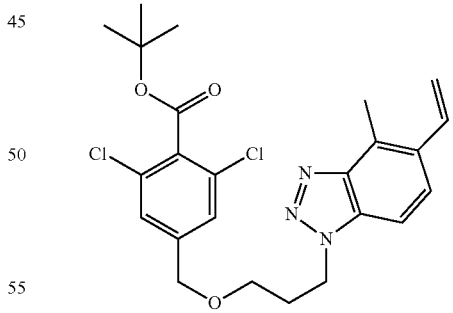

To a stirred solution of 3-[5-ethenyl-4-methyl-1H-1,2,3-benzotriazol-1-yl]propan-1-ol (4.5 g) in THF (100 ml) was added NaH (60% in oil, 2.5 g) at 0° C. and the reaction mixture was stirred at 25° C. for 30 min. To this was added tert-butyl 4-[bromomethyl]-2,6-dichlorobenzoate (7 g) at 0° C. and stirred the reaction mixture at 25° C. for 4 h. After completion of reaction (as judged by TLC and LC/MS), the reaction mixture was quenched with ice-water. The aqueous layer was extracted with EtOAc, combined organics were washed with brine; dried over anhydrous Na$_2$SO$_4$ and concentrated under reduced pressure. The crude thus obtained was purified by silica gel column chromatography (SiO$_2$; 120 g; 10% EtOAc/Hexane) to afford title compound (6 g) as brown liquid.

$^1$H NMR (400 MHz, DMSO-d$_6$): δ 1.55 (9H, s), 2.15-2.21 (2H, m), 2.68 (3H, s), 3.42 (2H, t, J=5.7 Hz), 4.39 (2H, s), 4.77 (2H, t, J=6.6 Hz), 5.36-5.39 (1H, m), 5.77-5.80 (1H, m), 7.07-7.11 (1H, m), 7.34 (2H, s), 7.62 (1H, d, J=8.8 Hz), 7.73 (1H, d, J=8.7 Hz). MS m/z 475.8 [M+H]$^+$.

G) tert-butyl 2,6-dichloro-4-[[3-[5-(hydroxymethyl)-4-methyl-1H-1,2,3-benzotriazol-1-yl]propoxy]methyl]benzoate

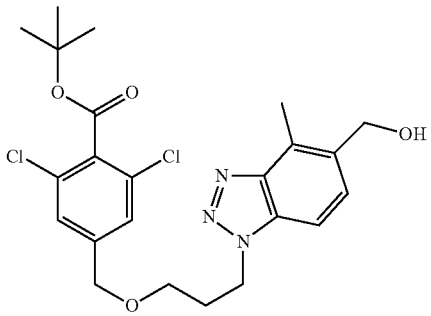 [SMILES: Cc1c(CO)ccc2c1nnn2CCCOCc1cc(Cl)c(C(=O)OC(C)(C)C)c(Cl)c1]

To a stirred solution of tert-butyl 2,6-dichloro-4-[[3-[5-ethenyl-4-methyl-1H-1,2,3-benzotriazol-1-yl]propoxy]methyl]benzoate (4.1 g) in DCM (80 ml) was added pyridine (2.08 ml) and cooled to −78° C. To this ozone gas was passed for 10 min at −78° C. After completion of reaction (as jugged by TLC), the reaction mixture was warmed to 25° C. Reaction mixture was diluted with DCM and quenched with 0.5 N citric acid. The aqueous layer was extracted with DCM, combined organics were washed with brine; dried over anhydrous Na$_2$SO$_4$ and concentrated under reduced pressure to afford in separable mixture of 1-[3-[{4-[[tert-butoxy) carbonyl]-3,5-dichlorophenyl} methoxy) propyl]-4-methyl-1H-1,2,3-benzotriazole-5-carboxylic acid and tert-butyl 2,6-dichloro-4-[[3-[5-formyl-4-methyl-1H-1,2,3-benzotriazol-1-yl] propoxy] methyl]benzoate (4 g, crude) as colorless liquid, which was used to next step without further purification.

To a solution of 1-[3-[[4-[[tert-butoxy] carbonyl]-3,5-dichlorophenyl] methoxy] propyl]-4-methyl-1H-1,2,3-benzotriazole-5-carboxylic acid and tert-butyl 2,6-dichloro-4-[[3-[5-formyl-4-methyl-1H-1,2,3-benzotriazol-1-yl] propoxy] methyl] benzoate (4.6 g) in THF (50 ml) were successively added NMM (1.5 ml) followed by isobutyl chloroformate (2.4 ml) at −15° C. and the reaction mixture was stirred for 10 min at that temperature. After completion of reaction (as jugged by TLC), the reaction mixture was filtered and the precipitate was washed with THF (2×50 ml). To this was added NaBH$_4$ (1.4 g) in water (10 ml) at −15° C. in one portion and the reaction mixture was stirred at that temperature for 5 min. After completion of starting (as judged by TLC), water (125 ml) was added. The aqueous layer was extracted with DCM, combined organics were washed with brine; dried over anhydrous Na$_2$SO$_4$ and concentrated under reduced pressure. The crude thus obtained was purified by silica gel column chromatography (SiO$_2$; 40 g; 40% EtOAc/Hexane) to afford title compound (1.9 g) as colorless liquid.

MS m/z 479.7 [M+H]$^-$.

H) tert-butyl 2,6-dichloro-4-[[3-[5-formyl-4-methyl-1H-1,2,3-benzotriazol-1-yl]propoxy]methyl]benzoate

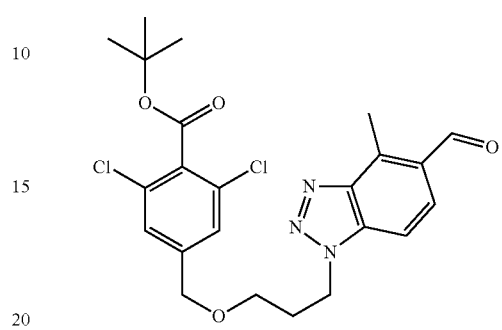

To a stirred solution of tert-butyl 2,6-dichloro-4-[[3-[5-[hydroxymethyl]-4-methyl-1H-1,2,3-benzotriazol-1-yl] propoxy]methyl]benzoate (1.9 g) in DCM (50 ml) was added active MnO$_2$ (6 g) at 25° C. and the reaction mixture was stirred at 25° C. for 4 h. After completion of reaction (as jugged by TLC), the insoluble material was filtered through celite bed. Filtrate was evaporated under reduced pressure to give title compound (1.7 g) as brown liquid, which was used to next step without further purification.

$^1$H NMR (400 MHz, DMSO-d$_6$): δ 1.55 (9H, s), 2.19-2.25 (2H, m), 3.02 (3H, s), 3.47 (2H, t, J=5.7 Hz), 4.33 (2H, s), 4.83 (2H, t, J=6.4 Hz), 7.24 (2H, s), 7.80 (1H, d, J=8.6 Hz), 7.92 (1H, d, J=8.6 Hz), 10.42 (1H, s). MS m/z 477.9 [M+H]$^+$.

I) tert-butyl 7-[[1-(3-[[3,5-dichloro-4-[methoxycarbonyl] phenyl] methoxy]propyl]-4-methyl-1H-1,2,3-benzotriazol-5-yl] [hydroxy]methyl]-1,2,3,4-tetrahydroisoquinoline-2-carboxylate

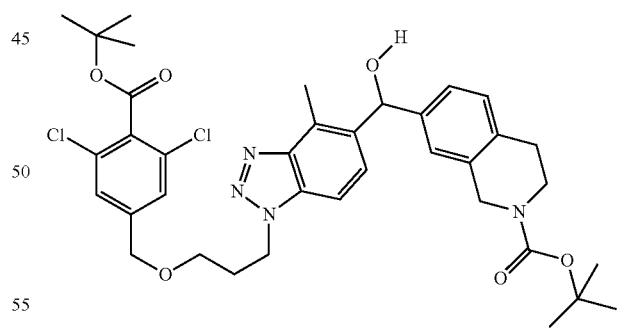

To a degassed solution of tert-butyl 2,6-dichloro-4-[[3-[5-formyl-4-methyl-1H-1,2,3-benzotriazol-1-yl]propoxy] methyl]benzoate (1.2 g) in mixture of CPME (50 ml) and water (10 ml) were added tert-butyl 7-[tetramethyl-1,3,2-dioxaborolan-2-yl]-1,2,3,4-tetrahydroisoquinoline-2-carboxylate (2.7 g) followed by K$_3$PO$_4$ (1.6 g) at 25° C. To this was added [RhCl(COD)]$_2$ (627 mg) at 25° C. and reaction mixture was heated at 50° C. for 2 h. TLC and LC/MS of reaction mixture showed formation of desired product along with un-reacted starting material. The reaction mixture was cooled to 25° C. and quenched with sat. aq. NH₄Cl. The aqueous layer was extracted with EtOAc, combined organics were washed with water, brine, dried over anhydrous Na₂SO₄, filtered and filtrate was concentrated under reduced pressure. The crude thus obtained was purified by silica gel column chromatography (SiO₂, 12 g, 25% EtOAc/Hexane) to give title compound (800 mg) as yellow solid.

¹H NMR (400 MHz, DMSO-d₆): δ 1.40 (9H, s), 1.55 (9H, s), 2.18 (2H, t, J=5.8 Hz), 2.69-2.74 (5H, m), 3.42-3.50 (4H, m), 4.36-4.42 (4H, m), 4.74 (2H, t, J=6.1 Hz), 5.86 (1H, d, J=3.4 Hz), 6.03 (1H, d, J=3.7 Hz), 7.04-7.13 (3H, m), 7.41 (2H, s), 7.59 (2H, s). MS m/z 711.2 [M+H]⁺.

J) tert-butyl 2,6-dichloro-4-[[3-[5-[3-methoxy-2,2-dimethyl-3-oxo-1-[1,2,3,4-tetrahydroisoquinolin-7-yl]propyl]-4-methyl-1H-1,2,3-benzotriazol-1-yl]propoxy]methyl]benzoate

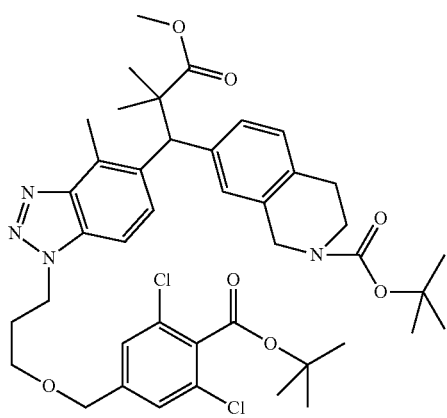 [SMILES: COC(=O)C(C)(C)C(c1ccc2c(c1)CN(C(=O)OC(C)(C)C)CC2)c1ccc2c(nnn2CCCOCc2cc(Cl)c(C(=O)OC(C)(C)C)c(Cl)c2)c1C]

To a stirred solution of tert-butyl 7-[[1-(3-[[3,5-dichloro-4-[methoxy carbonyl] phenyl]methoxy]propyl]-4-methyl-1H-1,2,3-benzotriazol-5-yl][hydroxy]methyl]-1,2,3,4-tetrahydroisoquinoline-2-carboxylate (970 mg)) in DCM (30 mL) were added [(1-methoxy-2-methylprop-1-en-1-yl)oxy] trimethylsilane (1.5 ml) followed by TiCl₄ (1M in DCM, 3 ml) at 0° C. and the reaction mixture was stirred at that temperature for 5 min. After completion of reaction (as jugged by LC/MS and TLC), the reaction mixture was quenched with water. Aqueous layer was basified with saturated NaHCO₃ solution (pH ~8) and filtered through celite bed. After filtration, aqueous layer was extracted with 10% MeOH/DCM (3×50 mL), the combined organic layer was washed with brine, dried over anhydrous Na₂SO₄ and evaporated to give title compound (1 g, crude) as colorless liquid, which was used to next step without further purification.

MS m/z 795.3 [M+H]⁻.

K) 2,6-dichloro-4-[[3-[5-[3-methoxy-2,2-dimethyl-3-oxo-1-[1,2,3,4-tetrahydroisoquinolin-7-yl]propyl]-4-methyl-1H-1,2,3-benzotriazol-1-yl]propoxy] methyl]benzoic acid

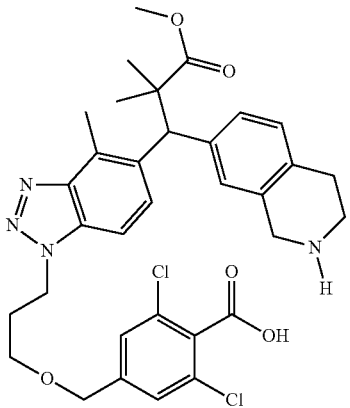 [SMILES: COC(=O)C(C)(C)C(c1ccc2c(c1)CNCC2)c1ccc2c(nnn2CCCOCc2cc(Cl)c(C(=O)O)c(Cl)c2)c1C]

To a stirred solution of tert-butyl 2,6-dichloro-4-[[3-[5-[3-methoxy-2,2-dimethyl-3-oxo-1-[1,2,3,4-tetrahydroisoquinolin-7-yl]propyl]-4-methyl-1H-1,2,3-benzotriazol-1-yl] propoxy]methyl] benzoate (970 mg) in dioxane (10 mL) was added HCl (4M in dioxane, 10 mL) dropwise at 25° C. and the reaction mixture was stirred at that temperature for 2 h. After completion of reaction (as judged by LC/MS), the volatiles were removed under reduced pressure and crude thus obtained was purified by reverse phase prep-HPLC (method A) to give title compound (250 mg) as white solid.

¹H NMR (400 MHz, DMSO-d₆): δ 1.26-1.30 (6H, m), 2.25-2.29 (2H, m), 2.78 (3H, s), 2.90-2.92 (2H, m), 3.13-3.28 (4H, m), 3.39-3.41 (1H, m), 3.43 (3H, s), 3.82-3.87 (1H, m), 4.04-4.13 (2H, m), 4.34-4.38 (1H, m), 4.63-4.68 (1H, m), 4.74-4.79 (2H, m), 6.71 (2H, s), 6.98 (1H, s), 7.03 (1H, d, J=8.0 Hz), 7.32 (1H, d, J=7.5 Hz), 7.54 (1H, d, J=8.8 Hz), 7.59 (1H, d, J=8.6 Hz), 10.10 (1H, brs). MS m/z 638.6 [M+H]⁺.

L) methyl 2-[18,30-dichloro-32-methyl-20-oxo-14-oxa-8,9,10,21-tetraazahexacyclo[19.5.3. 2¹⁶,¹⁹.1³,⁷.0⁶,¹⁰.0²⁴,²⁸]dotriaconta-1(27),3(32),4,6,8, 16,18,24(28),25,30-decaen-2-yl]-2-methylpropanoate (Retention Time Short)

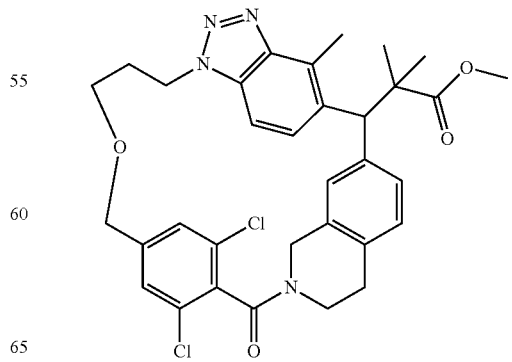

M) methyl 2-[18,30-dichloro-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]-2-methylpropanoate (Retention Time Long)

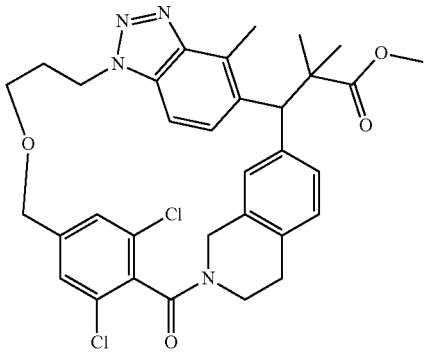 [SMILES: COC(=O)C(C)(C)C1c2ccc3c(c2)CN(CC3)C(=O)c2c(Cl)cc(cc2Cl)COCCCn2nnc3c(C)c1ccc32]

To a solution of HATU (293 mg) in DMF (15 ml) was added a mixture of 2,6-dichloro-4-[[3-[5-[3-methoxy-2,2-dimethyl-3-oxo-1-[1,2,3,4-tetrahydroisoquinolin-7-yl]propyl]-4-methyl-1H-1,2,3-benzotriazol-1-yl]propoxy]methyl] benzoic acid (380 mg) and N,N-diisopropylethylamine (0.5 ml) in DMF (20 ml) at 25° C. by syringe pump for 1 h and the reaction mixture was stirred at that temperature for 3 h. After completion of reaction (as judged by LC/MS); reaction mixture was diluted with saturated NaHCO$_3$ solution. The aqueous layer was extracted with EtOAc, the combined organic layer was washed with brine, dried over anhydrous Na$_2$SO$_4$ and evaporated under reduced pressure to give methyl 2-[18,30-dichloro-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]-2-methylpropanoate (racemate, 250 mg, crude) as white solid. The crude thus obtained was purified by normal phase chiral HPLC (method C) to afford methyl 2-[18,30-dichloro-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]-2-methylpropanoate (retention time short) (55 mg) and methyl 2-[18,30-dichloro-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]-2-methylpropanoate (retention time long) (45 mg) as white solid.

methyl 2-[18,30-dichloro-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]-2-methylpropanoate (Retention Time Short)

$^1$H NMR (400 MHz, DMSO-d$_6$): δ 1.23-1.27 (6H, m), 1.32 (3H, s), 2.19-2.52 (5H, m), 2.89-2.92 (2H, m), 3.39-3.40 (2H, m), 3.61-3.70 (2H, m), 4.01-4.09 (2H, m), 4.22-4.34 (2H, m), 4.72-4.80 (3H, m), 5.98 (1H, s), 6.31 (1H, s), 7.12 (1H, d, J=7.6 Hz), 7.24-7.29 (3H, m), 7.55 (1H, d, J=8.7 Hz). MS m/z 621.0 [M+H]$^+$.

methyl 2-[18,30-dichloro-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]-2-methylpropanoate (Retention Time Long)

$^1$H NMR (400 MHz, DMSO-d$_6$): δ 1.17-1.30 (6H, m), 1.32 (3H, s), 2.19-2.52 (5H, m), 2.90-2.92 (2H, m), 3.39-3.40 (2H, m), 3.57-3.68 (2H, m), 4.01-4.09 (2H, m), 4.22-4.34 (2H, m), 4.72-4.80 (3H, m), 5.98 (1H, s), 6.31 (1H, s), 7.12 (1H, d, J=8.1 Hz), 7.24-7.29 (3H, m), 7.55 (1H, d, J=9.0 Hz). MS m/z 621.0 [M+H]$^+$.

N) 2-[18,30-dichloro-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]-2-methylpropanoic acid Chiral, Synthesis from Chiral methyl 2-[18,30-dichloro-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]-2-methylpropanoate (Retention Time Short)

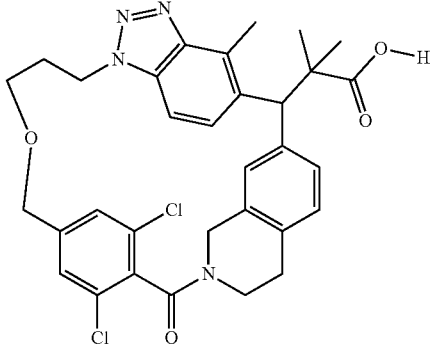 [SMILES: Cc1c2ccc3c1nnn3CCCOCc1cc(Cl)c(c(Cl)c1)C(=O)N1CCc3ccc(cc3C1)C2C(C)(C)C(=O)O]

To a stirred solution of methyl 2-[18,30-dichloro-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]-2-methylpropanoate (retention time short) (100 mg) in mixture of DMSO (2 ml) and MeOH (2 ml) was added aqueous KOH (8N, 1 ml) at 25° C. and the reaction mixture was heated at 100° C. for 3 h. After completion of reaction (as jugged by LC/MS), the reaction mixture was cooled to 25° C. The reaction mixture was diluted with EtOAc and neutralized with 1N HCl. The aqueous layer was extracted with EtOAc, the combined organic layer was washed with brine, dried over anhydrous Na$_2$SO$_4$ and evaporated under reduced pressure. The crude thus obtained was purified by reverse phase prep-HPLC (method A) to give title compound (32.65 mg) as off white sticky solid.

$^1$H NMR (400 MHz, DMSO-d$_6$): δ 1.15-1.30 (6H, m), 2.38-2.50 (5H, m), 2.91 (2H, t, J=6.5 Hz), 3.29-3.42 (2H, m), 3.58-3.62 (1H, m), 3.69-3.72 (1H, m), 3.99-4.07 (2H, m), 4.22-4.35 (2H, m), 4.71-4.82 (3H, m), 5.95 (1H, s), 6.34 (1H, s), 7.12 (1H, d, J=7.9 Hz), 7.28-7.36 (3H, m), 7.55 (1H, d, J=8.7 Hz), 12.30 (1H, brs). MS m/z 607.5 [M+H]$^+$.

Example 61

2-[18,30-dichloro-32-methyl-20-oxo-14-oxa-8,9,10,21-tetrazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]-2-methylpropanoic acid Chiral, Synthesis from Chiral methyl 2-[18,30-dichloro-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]-2-methylpropanoate (Retention Time Long)

Example 62

2-methyl-2-[32-methyl-20-oxo-8,9,10,21-tetrazahexacyclo[19.5.3.2$^{16,19}$.1$^{3,7}$.0$^{6,10}$.0$^{24,28}$]dotriaconta-1(27),3(32),4,6,8,16(31),17,19(30),24(28),25-decaen-2-yl]propanoic acid Chiral, Synthesis from Chiral methyl 2-methyl-2-[32-methyl-20-oxo-8,9,10,21-tetrazahexacyclo[19.5.3.2$^{16,19}$.1$^{3,7}$.0$^{6,10}$.0$^{24,28}$] dotriaconta-1(27),3(32),4,6,8,16(31),17,19(30),24(28),25-decaen-2-yl]propanoate (Retention Time Short)

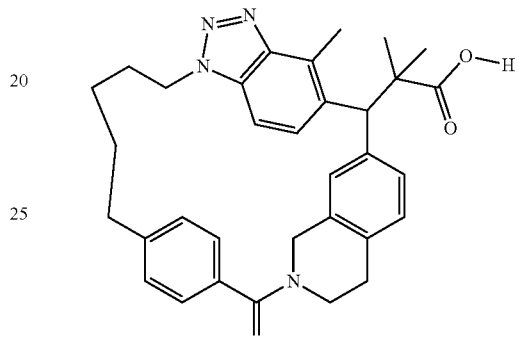

A) tert-butyl 4-[5-[4-methyl-5-vinyl-1H-benzo[d][1,2,3]triazol-1-yl]pentyl]benzoate

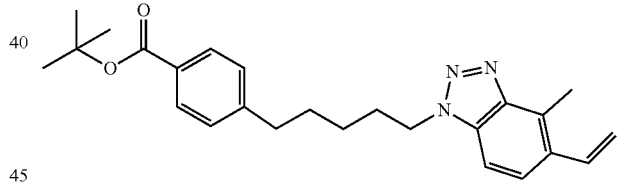

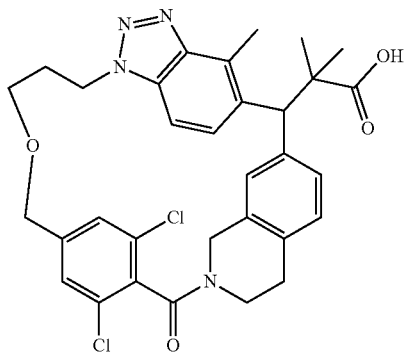 [SMILES: Cc1c2ccc3c1nnn3CCCOCc1cc(Cl)c(c(Cl)c1)C(=O)N1CCc3ccc(cc3C1)C2C(C)(C)C(=O)O]

To a stirred solution of methyl 2-[18,30-dichloro-32-methyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]-2-methylpropanoate (retention time long) (100 mg) in mixture of DMSO (2 ml) and MeOH (2 ml) was added KOH (8N, 1 ml) at 25° C. and the reaction mixture was heated at 100° C. for 3 h. After completion of reaction (as jugged by LC/MS), the reaction mixture was cooled to 25° C. The reaction mixture was diluted with EtOAc and neutralized with 1N HCl. The aqueous layer was extracted with EtOAc, the combined organic layer was washed with brine, dried over anhydrous Na$_2$SO$_4$ and evaporated under reduced pressure. The crude thus obtained was purified by reverse phase prep-HPLC (method A) to give title compound (22.16 mg) as off white sticky solid.

$^1$H NMR (400 MHz, DMSO-d$_6$): δ 1.14-1.33 (6H, m), 2.32-2.42 (5H, m), 2.90 (2H, t, J=6.2 Hz), 3.31-3.41 (2H, m), 3.58-3.62 (1H, m), 3.67-3.63 (1H, m), 3.98-4.06 (2H, m), 4.22-4.34 (2H, m), 4.70-4.81 (3H, m), 5.95 (1H, s), 6.34 (1H, s), 7.12 (1H, d, J=7.8 Hz), 7.28-7.36 (3H, m), 7.55 (1H, d, J=8.7 Hz), 12.27 (1H, brs). MS m/z 607.5 [M+H]$^+$.

A solution of potassium vinyltrifluoroborate (1.50 g), PdCl$_2$(dppf)-CH$_2$Cl$_2$ (0.28 g), tert-Butyl 4-[5-(5-bromo-4-methyl-1H-benzotriazol-1-yl)pentyl]benzoate (3.50 g) and K$_2$CO$_3$ (3.10 g) in DMSO (35 mL) was heated to 80° C. for 16 h. After the reaction was completed, the reaction mixture was cooled to room temperature, diluted with ethyl acetate, filtrated through a celite pad. The filtrate was washed with water followed by brine and dried over anhydrous Na$_2$SO$_4$. Na$_2$SO$_4$ was filtered off and the filtrate was concentrated in vacuo. The crude obtained was purified by flash chromatography, using 40 g Redisep silica gel cartridge, on a silica gel chromatography instrument, eluted with 20-50% gradient of ethyl acetate in hexanes, to obtain title compound (2.50 g) as brown oil. $^1$H NMR (400 MHz, DMSO-d$_6$) δ1.34-1.42 (2H, m), 1.58 (9H, m), 1.62-1.70 (2H, m), 1.86-2.04 (2H, m), 2.61 (2H, t, J=7.2 Hz), 2.82 (3H, s), 4.59 (2H, t, J=6.8 Hz), 5.40 (1H, t, J=11.2 Hz), 5.71 (1H, t, J=17.6 Hz), 7.07-7.11 (1H, m), 7.16 (2H, t, J=8.0 Hz), 7.26-7.29 (1H, m), 7.66 (1H, t, J=8.8 Hz), 7.87 (2H, t, J=8.0 Hz). MS m/z 406.15 [M+H]$^+$.

B) tert-butyl 4-[5-[5-formyl-4-methyl-1H-benzo[d][1,2,3]triazol-1-yl)pentyl)benzoate

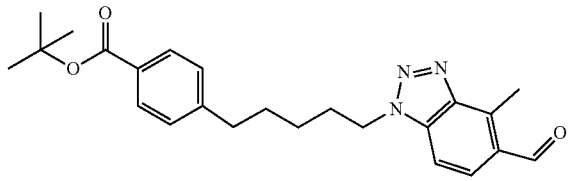 [SMILES: Cc1c(C=O)ccc2c1nnn2CCCCCc1ccc(C(=O)OC(C)(C)C)cc1]

To a solution of tert-butyl 4-[5-[4-methyl-5-vinyl-1H-benzo[d][1,2,3]triazol-1-yl]pentyl]benzoate (3.40 g) in 1,4-dioxane (100 mL) were added 2,6-lutidine (1.50 g, 14.70 mmol) and OsO$_4$ (0.21 g, 0.84 mmol), and the mixture was stirred at room temperature for 20 min. To that mixture, a solution of NaIO$_4$ (6.30 g, 29.40 mmol) in water (25 mL) was added and stirring continued at room temperature for 2 h. After the reaction was completed, reaction mixture was filtrated through celite, and the filtrate was extracted with ethyl acetate. The organic extract was dried over Na$_2$SO$_4$, filtered and solvent evaporated from the filtrate under reduced pressure. The crude obtained was purified by flash chromatography, using 40 g Redisep silica gel cartridge, on a silica gel chromatography instrument, eluted with 20-50% gradient of ethyl acetate in hexanes, to obtain title compound (3.00 g) as off white solid. $^1$H NMR (400 MHz, DMSO-d$_6$) δ1.17-1.23 (2H, m), 1.52 (9H, s), 1.56-1.61 (2H, m), 1.90-1.97 (2H, m), 2.57 (2H, t, J=7.5 Hz), 3.06 (3H, s), 4.72 (2H, t, J=6.8 Hz), 7.20 (2H, d, J=8.0 Hz), 7.73 (2H, d, J=8.0 Hz), 7.81 (1H, d, J=8.7 Hz), 7.94 (1H, d, J=8.7 Hz), 10.44 (1H, s). MS: purity m/z 408.24 [M+H]$^+$.

C) tert-butyl 7-[[1-[5-[4-[tert-butoxycarbonyl]phenyl]pentyl]-4-methyl-1H-benzo[d][1,2,3]triazol-5-yl][hydroxy]methyl]-3,4-dihydroisoquinoline-2(1H)-carboxylate

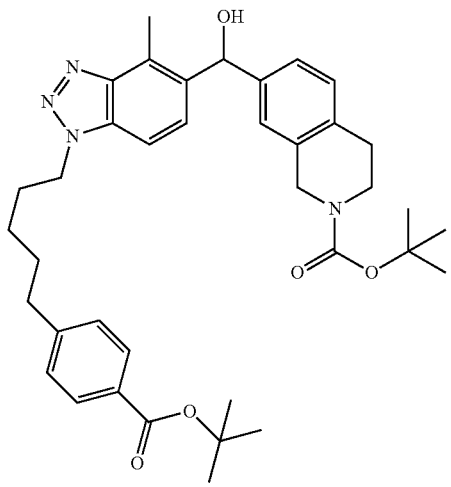 [SMILES: Cc1c(C(O)c2ccc3c(c2)CN(C(=O)OC(C)(C)C)CC3)ccc2c1nnn2CCCCCc1ccc(C(=O)OC(C)(C)C)cc1]

To a solution of tert-butyl 4-[5-[5-formyl-4-methyl-1H-benzo[d][1,2,3]triazol-1-yl]pentyl]benzoate (0.50 g) and tripotassium phosphate (0.78 g) in CPME (30 mL) and water (6 mL), 7-[4,4,5,5-tetramethyl-1,3,2-dioxaborolan-2-yl]-3,4-dihydroisoquinoline-2(1H)-carboxylate (1.30 g) and chloro [1,5-cyclooctadiene]rhodium(I) dimer (0.21 g) were added, under argon atmosphere and the mixture was stirred at room temperature for 16 h. After completion of the reaction, the mixture was diluted with sat. NH$_4$Cl aq. and extracted with ethyl acetate. The organic extract was washed with brine, dried over anhydrous Na$_2$SO$_4$, filtered and solvents evaporated from the filtrate under reduced pressure. The crude obtained was purified by flash chromatography, using 12 g Redisep silica gel cartridge, on a silica gel chromatography instrument, eluted with 20-70% gradient of ethyl acetate in hexanes, to obtain title compound (0.25 g) as an off white solid. $^1$H NMR (400 MHz, DMSO-d$_6$) δ1.04-1.13 (2H, m), 1.47 (9H, s), 1.58-1.74 (11H, m), 1.74-1.84 (2H, m), 2.00-2.04 (2H, m), 2.59-2.62 (2H, m), 2.80 (3H, s), 2.46-2.53 (2H, m), 2.80 (2H, brs), 3.62-3.66 (2H, m), 4.52 (1H, s), 4.59-4.61 (1H, m), 6.25 (1H, s), 7.04-7.12 (4H, m), 7.26 (1H, s), 7.65 (1H, d, J=8.2 Hz), 7.81 (2H, d, J=7.9 Hz). MS m/z 641.46 [M+H$^+$].

D) 4-[5-[5-[3-methoxy-2,2-dimethyl-3-oxo-1-[1,2,3,4-tetrahydroisoquinolin-7-yl)propyl]-4-methyl-1H-benzo[d][1,2,3]triazol-1-yl]pentyl]benzoic acid hydrochloride

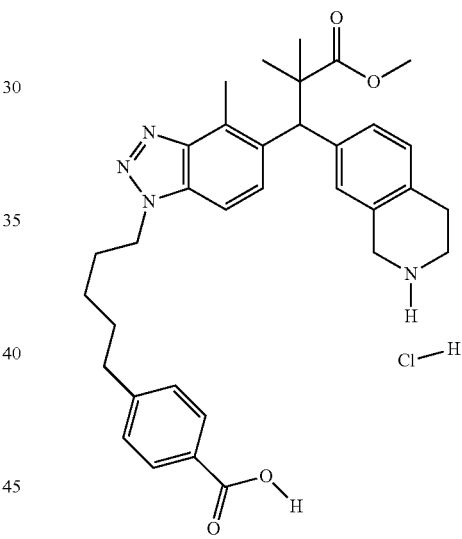

To a stirred solution of tert-butyl 7-[[1-[5-[4-tert-butoxycarbonyl]phenyl]pentyl]-4-methyl-1H-benzo[d][1,2,3]triazol-5-yl][hydroxy]methyl]-3,4-dihydroisoquinoline-2(1H)-carboxylate (0.35 g) in DCM (14 mL), [[1-methoxy-2-methylprop-1-en-1-yl]oxy]trimethylsilane (0.57 g) and TiCl$_4$ (1M in DCM, 0.54 mL) were added at 0° C. and the reaction mixture was stirred for 5 min. After completion of reaction (as jugged by LCMS and TLC), the reaction mixture was quenched with water. Aqueous layer was basified with saturated NaHCO$_3$ solution (pH ~8) and filtered through celite pad. After filtration aqueous layer was extracted with 10% methanol in dichloromethane. The combined organic extract was washed with brine, dried over anhydrous Na$_2$SO$_4$, filtered and solvent evaporated from the filtrate to obtain a mixture (0.43 g) as light grey solid, which was used as such in the next step.

To a mixture in 1,4-dioxane (5 mL) was added 4M HCl in 1,4-dioxane (6 mL) dropwise at 25° C. and the reaction mixture was stirred for 6 h. After completion of reaction (as judged by LCMS), the volatiles were removed under reduced pressure to obtain title compound (0.40 g, crude) as a grey solid, which was used as such in the next step.

MS m/z 569.43 [M+H$^+$].

E) methyl 2-methyl-2-[32-methyl-20-oxo-8,9,10,21-tetrazahexacyclo[19.5.3.2$^{16,19}$.1$^{3,7}$.0$^{6,10}$.0$^{24,28}$]dotriaconta-1(27),3(32),4,6,8,16(31),17,19(30),24(28),25-decaen-2-yl]propanoate

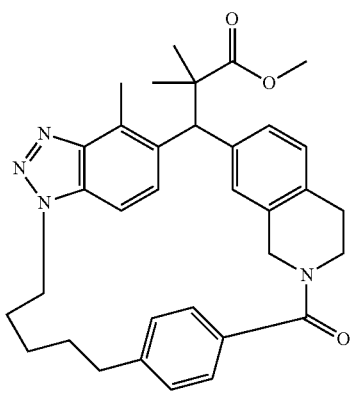 [SMILES: COC(=O)C(C)(C)C1c2ccc3c(c2)CN(CC3)C(=O)c2ccc(cc2)CCCCCn2nnc3c(C)c1ccc32]

To a solution of HATU (0.66 g, 1.75 mmol) in DMF (10 ml) was added a mixture of 4-[5-[5-[3-methoxy-2,2-dimethyl-3-oxo-1-[1,2,3,4-tetrahydroisoquinolin-7-yl]propyl]-4-methyl-1H-benzo[d][1,2,3]triazol-1-yl]pentyl]benzoic acid (0.4 g, crude) and N,N-diisopropylethylamine (2.3 g, 17.6 mmol) in DMF (30 ml) by syringe pump for 3 h at 30° C. and the reaction mixture was stirred at room temperature for 16 h. After completion of reaction (as judged by LCMS); reaction mixture was diluted with saturated NaHCO$_3$ solution. The aqueous layer was extracted with ethyl acetate. The combined organic extract was washed with brine, dried over anhydrous Na$_2$SO$_4$, filtered and solvents evaporated from the filtrate under reduced pressure. The crude obtained was purified by flash chromatography, using 12 g Redisep silica gel cartridge, on a silica gel chromatography instrument, eluted with 20-60% gradient of ethyl acetate in hexane, to obtain title compound (0.048 g) as a white solid. $^1$H NMR (400 MHz, CDCl$_3$) δ1.03-1.06 (2H, m), 1.28-1.36 (5H, m), 1.45 (3H, s), 2.07 (2H, brs), 2.56-2.59 (2H, m), 2.65 (3H, m), 2.90-2.99 (2H, m), 3.56 (3H, s), 3.74-3.79 (1H, m), 4.03-4.07 (1H, m), 4.14-4.18 (2H, m), 4.38-4.42 (1H, m), 4.87 (1H, s), 4.90-.4.95 (11H, m), 6.01 (1H, s), 6.80 (2H, d, J=7.7 Hz), 6.95 (2H, d, J=7.7 Hz), 7.08-7.09 (1H, m), 7.18 (2H, d, J=8.6 Hz), 7.39 (1H, d, J=8.7 Hz). MS m/z 551.31 [M+H$^+$].

F) 2-methyl-2-[32-methyl-20-oxo-8,9,10,21-tetrazahexacyclo[19.5.3.2$^{16,19}$.1$^{3,7}$.0$^{6,10}$.0$^{24,28}$]dotriaconta-1(27),3(32),4,6,8,16(31),17,19(30),24(28),25-decaen-2-yl]propanoic acid<Synthesis from chiral methyl 2-methyl-2-[32-methyl-20-oxo-8,9,10,21-tetrazahexacyclo[19.5.3.2$^{16,19}$.1$^{3,7}$.0$^{6,10}$.0$^{24,28}$]dotriaconta-1(27),3(32),4,6,8,16(31),17,19(30),24(28),25-decaen-2-yl)propanoate (retention time short)>

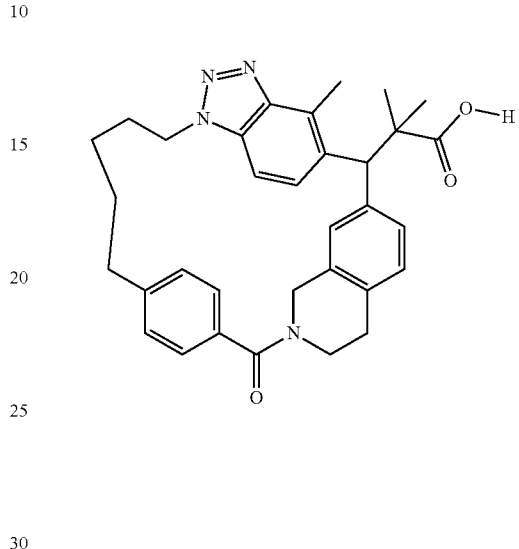

methyl 2-methyl-2-[32-methyl-20-oxo-8,9,10,21-tetrazahexacyclo[19.5.3.2$^{16,19}$.1$^{3,7}$.0$^{6,10}$.0$^{24,28}$]dotriaconta-1(27),3(32),4,6,8,16(31),17,19(30),24(28),25-decaen-2-yl]propanoate (racemate) was subjected to chiral HPLC purification (method D) to obtain chiral methyl 2-methyl-2-[32-methyl-20-oxo-8,9,10,21-tetrazahexacyclo[19.5.3.2$^{16,19}$.1$^{3,7}$.0$^{6,10}$.0$^{24,28}$]dotriaconta-1(27),3(32),4,6,8,16(31),17,19(30),24(28),25-decaen-2-yl]propanoate (retention time short) and chiral methyl 2-methyl-2-[32-methyl-20-oxo-8,9,10,21-tetrazahexacyclo[19.5.3.2$^{16,19}$.1$^{3,7}$.0$^{6,10}$.0$^{24,28}$]dotriaconta-1(27),3(32),4,6,8,16(31),17,19(30),24(28),25-decaen-2-yl]propanoate (retention time long), which were individually taken forward to the next step.

To a solution of chiral methyl 2-methyl-2-[32-methyl-20-oxo-8,9,10,21-tetrazahexacyclo[19.5.3.2$^{16,19}$.1$^{3,7}$.0$^{6,10}$.0$^{24,28}$]dotriaconta-1(27),3(32),4,6,8,16(31),17,19(30),24(28),25-decaen-2-yl]propanoate (retention time short, 0.080 g) in THF (8 ml), TMSOK (0.37 g) was added at room temperature and the mixture was stirred at 60° C. for 16 h. The mixture was, then, cooled to room temperature, diluted with ethyl acetate, neutralized with 1N HCl, and extracted with ethyl acetate. The combined organic extract was washed with water and brine, dried over anhydrous Na$_2$SO$_4$, filtered and solvent evaporated from the filtrate under reduced pressure. The residue was purified by using preparative TLC to obtain title compound (0.028 g) as white solid. $^1$H NMR (400 MHz, CDCl$_3$) δ ppm 1.05-1.12 (2H, m), 1.29 (3H, s), 1.48 (3H, s), 1.64 (1H, brs), 2.07 (2H, brs), 2.51-2.58 (2H, m), 2.65 (3H, s), 2.89-2.99 (2H, m), 3.74-3.78 (2H, m), 4.03-4.18 (3H, m), 4.38-4.42 (1H, m), 4.88-4.95 (2H, m), 6.01 (1H, s), 6.80 (2H, d, J=7.6 Hz), 6.95 (2H, d, J=7.6 Hz), 7.08 (1H, d, J=7.8 Hz), 7.18-7.26 (2H, m), 7.44 (1H, d, J=8.6 Hz). MS m/z 537.30 [M+H$^+$].

Example 63

2-methyl-2-[32-methyl-20-oxo-8,9,10,21-tetrazahexacyclo [19.5.3.2$^{16,19}$.1$^{3,7}$.0$^{6,10}$.0$^{24,28}$]dotriaconta-1(27),3(32),4,6,8,16(31),17,19(30),24(28),25-decaen-2-yl]propanoic acid Chiral, Synthesis from Chiral methyl 2-methyl-2-[32-methyl-20-oxo-8,9,10,21-tetrazahexacyclo [19.5.3.2$^{16,19}$.1$^{3,7}$.0$^{6,10}$.0$^{24,28}$]dotriaconta-1(27),3(32),4,6,8,16(31),17,19(30),24(28),25-decaen-2-yl] propanoate (Retention Time Long)

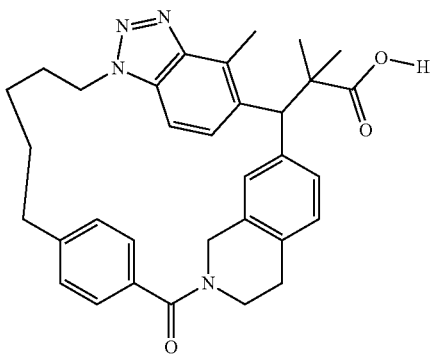 [SMILES: Cc1c2ccc3c1nnn3CCCCCc1ccc(cc1)C(=O)N1CCc3ccc(cc3C1)C2C(C)(C)C(=O)O]

To a solution of chiral methyl 2-methyl-2-[32-methyl-20-oxo-8,9,10,21-tetrazahexacyclo[19.5.3.2$^{16,19}$.1$^{3,7}$. 0$^{6,10}$.0$^{24,28}$] dotriaconta-1(27),3(32),4,6,816(31),17,19(30), 24(28),25-decaen-2-yl]propanoate (retention time long) (0.070 g) in THF (8 ml) TMSOK (0.32 g, 2.50 mmol) was added at room temperature and the mixture was stirred at 60° C. for 16 h. The mixture was, then, cooled to room temperature, diluted with ethyl acetate, neutralized with 1N HCl, and extracted with ethyl acetate. The combined organic extract was washed with water and brine, dried over anhydrous Na$_2$SO$_4$, filtered and solvent evaporated from the filtrate under reduced pressure. The residue was purified by using preparative TLC to obtain title compound (0.020 g) as white solid.

$^1$H NMR (400 MHz, CDCl$_3$)*1.05-1.12 (2H, m), 1.29 (3H, s), 1.48 (3H, s), 1.64 (1H, brs), 2.07 (2H, brs), 2.51-2.58 (2H, m), 2.65 (3H, s), 2.88-2.98 (2H, m), 3.73-3.77 (2H, m), 4.03-4.18 (3H, m), 4.38-4.42 (1H, m), 4.88-4.94 (2H, m), 6.01 (1H, s), 6.80 (2H, d, J=7.6 Hz), 6.95 (2H, d, J=7.6 Hz), 7.08 (1H, d, J=7.8 Hz), 7.18-7.26 (2H, m), 7.44 (1H, d, J=8.6 Hz). MS m/z 537.37 [M+H$^+$].

Example 64

[2-[18,30-dichloro-32-methyl-20-oxo-8,9,10,21-tetrazahexacyclo[19.5.3.2$^{16,19}$.1$^{3,7}$.0$^{6,10}$.0$^{24,28}$]dotriaconta-1(27),3(32),4,6,8,16(31),17,19(30),24(28), 25-decaen-2-yl]acetyl]oxysodium

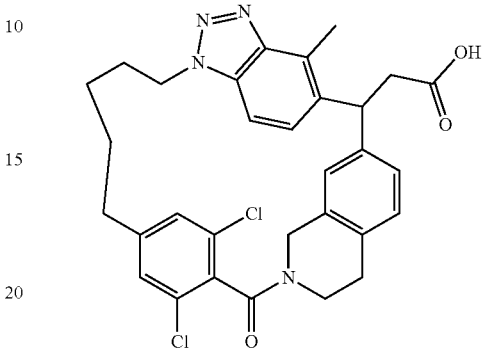

The compounds of Examples 64 could be produced according to the production methods described in the present specification, a method shown in the Examples, or a method analogous thereto.

Example 65

2-[18,30-dichloro-32-methyl-20-oxo-15-oxa-8,9,10, 21-tetrazahexacyclo[19.5.3.2$^{16,19}$.1$^{3,7}$.0$^{6,10}$.0$^{24,28}$] dotriaconta-1(27),3(32),4,6,8,16(31),17,19(30),24 (28),25-decaen-2-yl]-2-methylpropanoic acid (Chiral, Retention Time Short)

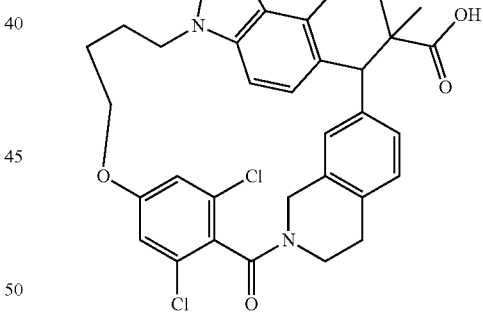

A) 4-[[4-bromo-3-methyl-2-nitrophenyl]amino]butan-1-ol

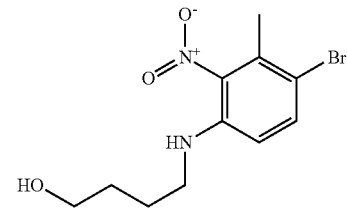 [SMILES: Cc1c(Br)ccc(NCCCCO)c1[N+](=O)[O-]]

To a solution of 1-bromo-4-fluoro-2-methyl-3-nitrobenzene (33 g) in DMF (450 mL) were added K₂CO₃ (39.259 g) followed by 4-amino butanol (17.162 ml) at 25° C. and the mixture was stirred at 80° C. for 16 h. After completion of reaction (as jugged by TLC and LC/MS), the reaction mixture was quenched with ice-cold water. The precipitate thus formed was filtrated and washed with water and finally dried under high vacuum to afford title compound (40 g) as orange solid, which was used to next step without further purification.

¹H NMR (400 MHz, DMSO-d₆): δ 1.43-1.53 (4H, m), 2.24 (3H, s), 3.12 (2H, d, J=5.7 Hz), 3.39 (2H, s), 4.40 (1H, s), 6.13 (1H, s), 6.72 (1H, d, J=8.9 Hz), 7.52 (1H, d, J=8.9 Hz).

B) 4-[[2-amino-4-bromo-3-methylphenyl]amino]butan-1-ol

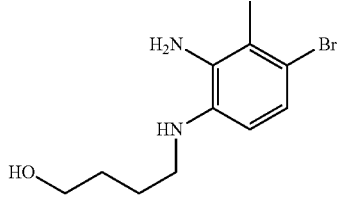

To a stirred solution of 4-[[4-bromo-3-methyl-2-nitrophenyl]amino]butan-1-ol (23 g) in a mixture of ethanol (230 ml) and water (115 m) were added iron powered (21.197 g) followed by NH₄Cl (40.299 g) at 25° C. and reaction mixture was refluxed for 4 h. After completion of reaction (as jugged by TLC), the insoluble material was filtered through celite bed and solvent was evaporated under reduced pressure. Residue was dissolved in sat NaHCO₃ soln. The aqueous layer was extracted with ethyl acetate (50 ml×3), the combined organic layer was washed with brine, dried over anhydrous Na₂SO₄ and evaporated under reduced pressure to afford title compound (11.8 g) as brown solid, which was used to next step without further purification.

¹H NMR (400 MHz, DMSO-d₆): δ 1.48-1.63 (4H, m), 2.16 (3H, s), 2.96 (2H, q, J=6.4 Hz), 3.40 (2H, q, J=6.0 Hz), 4.40 (1H, t, J=5.0 Hz), 4.53 (1H, t, J=4.9 Hz), 4.59 (2H, s), 6.24 (1H, d, J=8.5 Hz), 6.70 (1H, d, J=8.4 Hz). MS m/z 275.1 [M+H]⁺.

C) 4-[5-bromo-4-methyl-1H-1,2,3-benzotriazol-1-yl]butan-1-ol

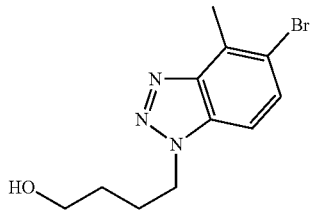 [SMILES: Cc1c(Br)ccc2c1nnn2CCCCO]

To a stirred solution of 4-[[²-amino-4-bromo-3-methylphenyl]amino]butan-1-ol (20 g) in 6N HCl (265 mL) was slowly added a solution of NaNO₂ (10.11 g) in water (87 mL) at 0° C. and the reaction mixture was stirred at 25° C. for 2 h. After (completion of reaction as jugged by TLC and LC/MS), the reaction mixture was neutralized with 4N NaOH at 0° C. The aqueous layer was extracted with EtOAc, combined organics were washed with brine; dried over anhydrous Na₂SO₄ and concentrated under reduced pressure. The crude thus obtained was purified by silica gel column (SiO₂, 120 g, 60% EtOAc/Hexane) to title compound (14 g) as brown solid.

¹H NMR (400 MHz, DMSO-d₆): δ 1.32-1.40 (2H, m), 1.88-1.96 (2H, m), 2.71 (3H, s), 3.38 (2H, t, J=6.3 Hz), 4.70 (2H, t, J=7.0 Hz), 7.69 (2H, t, J=8.9 Hz). MS m/z 286.1 [M+H]⁺.

D) 4-(5-ethenyl-4-methyl-1⁷/-1,2,3-benzotriazol-1-yl)butan-1-ol

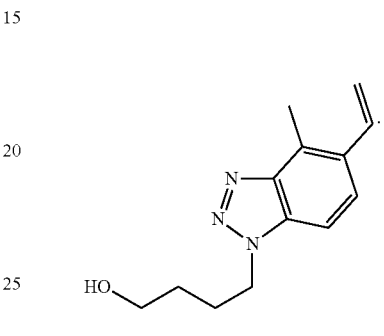

To a degassed solution of 4-[5-bromo-4-methyl-1H-1,2,3-benzotriazol-1-yl]butan-1-ol (5 g) in mixture of THF (50 ml) and n-propanol (100 ml) were added potassium vinyltrifluoroborate (9 g) followed by TEA (10 ml, 70.423 mmol) at 25° C. and the reaction mixture was degassed with argon for 10 min. To this was added PdCl₂(dppf)-DCM (1.5 g) and the reaction mixture was heated at 100° C. for 2 h. After completion of reaction (as jugged by LC/MS), the volatiles were removed under reduced pressure. The residue was dissolved with water, the aqueous layer was extracted with EtOAc, combined organics were washed with brine, dried over anhydrous Na₂SO₄ and concentrated under reduced pressure. The crude thus obtained was purified by silica gel column chromatography (SiO₂, 40 g, 60% EtOAc/Hexane) to give title compound (3 g) as brown liquid.

¹H NMR (400 MHz, DMSO-d₆): δ 1.33-1.40 (2H, m), 1.88-1.96 (2H, m), 2.70 (3H, s), 3.36 (2H, q, J=5.9 Hz), 4.43 (1H, t, J=4.9 Hz), 4.68 (2H, t, J=6.9 Hz), 5.38 (1H, d, J=11.2 Hz), 5.81 (1H, d, J=17.4 Hz), 7.08 (1H, q, J=11.1 Hz), 7.68 (1H, t, J=8.7 Hz), 7.75 (1H, d, J=8.6 Hz).

MS m/z 232.0 [M+H]⁻.

E) tert-butyl 2,6-dichloro-4-[4-(5-ethenyl-4-methyl-1H-1,2,3-benzotriazol-1-yl)butoxy]benzoate

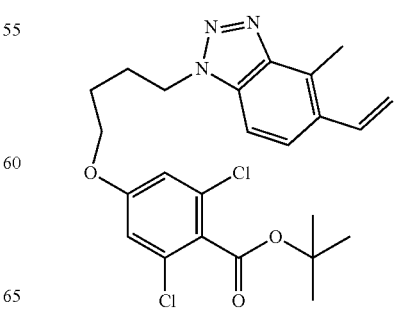

To a stirred solution of 4-[5-ethenyl-4-methyl-1H-1,2,3-benzotriazol-1-yl]butan-1-ol (3 g) in THF (40 ml) were added tert-butyl 2,6-dichloro-4-hydroxybenzoate (3.4 g) and PPh₃ (8.5 g) at 25° C. To this was added DEAD (4 ml) in THF (10 ml) at 0° C. and the reaction mixture was stirred at 25° C. for 3 h. After completion of reaction (as jugged by TLC and LC/MS), the volatiles were removed under reduced pressure. The crude thus obtained was purified by silica gel column chromatography (SiO₂, 40 g, 20% EtOAc/Hexane) to give title compound (4.9 g) as colorless liquid.

¹H NMR (400 MHz, DMSO-d₆) δ 1.53 (9H, s), 1.65-1.70 (2H, m), 2.05-2.03 (2H, m), 2.70 (3H, s), 4.04 (2H, t, J=6.2 Hz), 4.75 (2H, t, J=6.8 Hz), 5.38 (1H, d, J=11.9 Hz), 5.76-5.83 (2H, m), 7.06-7.08 (1H, m), 7.10-7.15 (1H, m), 7.69 (1H, d, J=8.7 Hz), 7.76 (1H, d, J=9.4 Hz). MS m/z 276.0 [M+H]⁺.

F) tert-butyl 2,6-dichloro-4-[4-[5-(hydroxymethyl)-4-methyl-1H-1,2,3-benzotriazol-1-yl]butoxy]benzoate

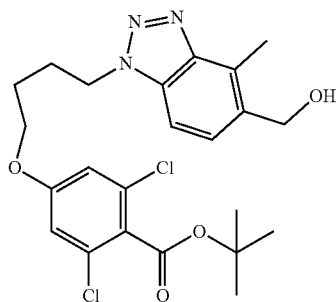 [SMILES: Cc1c(CO)ccc2c1nnn2CCCCOc1cc(Cl)c(C(=O)OC(C)(C)C)c(Cl)c1]

To a stirred solution of tert-butyl 2,6-dichloro-4-[4-[5-ethenyl-4-methyl-1H-1,2,3-benzotriazol-1-yl]butoxy] benzoate (5 g) in mixture of MeOH (50 ml) and DCM (50 ml) was added NaHCO₃ (1.1 g) at 25° C. To this, ozone gas was passed at −78° C. for 2 h. After completion of reaction (as judged by TLC), the reaction mixture was warmed to 0° C. To this was added NaBH₄ (0.796 g) at 0° C. and the reaction mixture was stirred at that temperature for 1 h. After completion of the reaction (as jugged by TLC), the volatiles were removed under reduced pressure. The residue was diluted with ice cold water. The aqueous layer was extracted with DCM, combined organics were washed with brine; dried over anhydrous Na₂SO₄ and concentrated under reduced pressure. The crude thus obtained was purified by silica gel column (SiO₂, 12 g, 30% EtOAc/Hexane) to give title compound (3.5 g) as colorless sticky liquid.

¹H NMR (400 MHz, DMSO-d₆) δ 1.53 (9H, s), 1.66-1.69 (2H, m), 2.03 (2H, t, J=7.2 Hz), 2.64 (3H, s), 4.03 (2H, t, J=6.3 Hz), 4.63 (2H, d, J=5.4 Hz), 4.74 (2H, t, J=6.8 Hz), 5.13 (1H, t, J=5.3 Hz), 7.06 (2H, s), 7.55 (1H, d, J=8.5 Hz), 7.65 (1H, d, J=8.4 Hz). MS m/z 480.1 [M+H]⁺.

G) tert-butyl 2,6-dichloro-4-[4-(5-formyl-4-methyl-1H-1,2,3-benzotriazol-1-yl)butoxy]benzoate

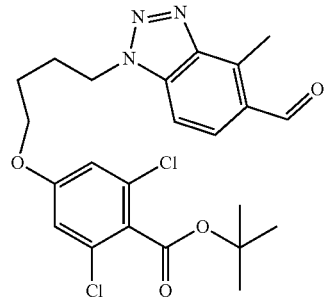 [SMILES: Cc1c(C=O)ccc2c1nnn2CCCCOc1cc(Cl)c(C(=O)OC(C)(C)C)c(Cl)c1]

To a stirred solution of tert-butyl 2,6-dichloro-4-[4-[5-(hydroxymethyl)-4-methyl-1H-1,2,3-benzotriazol-1-yl]butoxy]benzoate (3.3 g) in DCM (50 ml) was added activated MnO₂ (10 g) at 25° C. and the reaction mixture was stirred at 25° C. for 4 h. After completion of starting (jugged by TLC), the insoluble material was filtered through celite bed and residue was dissolved with DCM. Filtrate was evaporated under reduced pressure to give title (3 g) as off white solid, which was used to next step without further purification.

¹H NMR (400 MHz, DMSO-d₆) δ 1.53 (9H, s), 1.71 (2H, t, J=7.2 Hz), 2.07 (2H, t, J=7.6 Hz), 3.06 (3H, s), 4.03 (2H, t, J=6.4 Hz), 4.81 (2H, t, J=6.7 Hz), 7.02 (2H, s), 7.86 (1H, d, J=8.7 Hz), 7.97 (1H, d, J=8.6 Hz), 10.45 (1H, s). MS m/z 478.4 [M+H]⁺.

H) tert-butyl 7-[[1-[4-[4-[[tert-butoxy]carbonyl]-3,5-dichlorophenoxy]butyl]-4-methyl-H-1,2,3-benzotriazol-5-yl][hydroxy]methyl]-1,2,3,4-tetrahydroisoquinoline-2-carboxylate

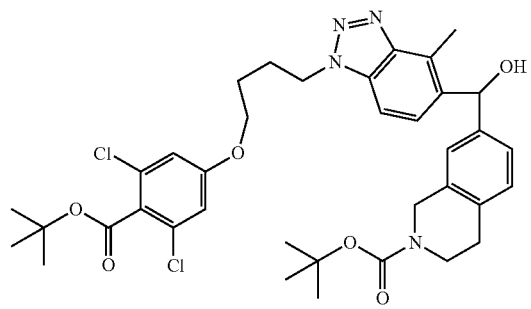 [SMILES: Cc1c(C(O)c2ccc3c(c2)CN(C(=O)OC(C)(C)C)CC3)ccc2c1nnn2CCCCOc1cc(Cl)c(C(=O)OC(C)(C)C)c(Cl)c1]

To a degassed solution of tert-butyl 2,6-dichloro-4-[4-(5-formyl-4-methyl-1H-1,2,3-benzotriazol-1-yl)butoxy]benzoate (360 mg) in mixture of CPME (10 ml) and water (5 ml) were added [2-[[tert-butoxy)carbonyl]-1,2,3,4-tetrahydroisoquinolin-7-yl]boronic acid (627 mg) followed by K₃PO₄ (480 mg) at 25° C. To this was added [RhCl(COD)]₂ (74 mg) at 25° C. and reaction mixture was stirred at 25° C. for 4 h under blue LED light. The reaction mixture was quenched with sat NH₄Cl. The aqueous layer was extracted with EtOAc, combined organics were washed with water, brine, dried over anhydrous Na₂SO₄, filtered and filtrate was concentrated under reduced pressure. The crude thus obtained was purified by silica gel column chromatography (SiO$_2$, 12 g, 25% EtOAc/Hexane) to give title compound (300 mg) as light yellow solid.

$^1$H NMR (400 MHz, DMSO-d$_6$) δ 1.40 (9H, s), 1.52 (9H, s), 1.67 (2H, t, J=6.8 Hz), 2.01 (2H, t, J=7.3 Hz), 2.65-2.71 (5H, m), 3.50 (2H, t, J=5.7 Hz), 4.06 (2H, t, J=8.0 Hz), 4.43 (2H, s), 4.72 (2H, t, J=6.7 Hz), 5.86 (1H, d, J=4.0 Hz), 6.03 (1H, d, J=4.0 Hz), 7.06-7.13 (5H, m), 7.59 (2H, q, J=8.6 Hz). MS m/z 711.6 [M+H]$^+$.

I) tert-butyl 7-[1-[1-[4-[4-[[tert-butoxy]carbonyl]-3,5-dichlorophenoxy]butyl]-4-methyl-1H-1, 2, 3-benzotriazol-5-yl]-3-methoxy-2,2-dimethyl-3-oxopropyl]-1,2,3,4-tetrahydroisoquinoline-2-carboxylate

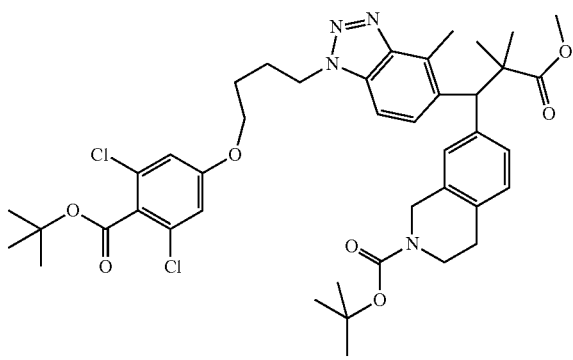 [SMILES: COC(=O)C(C)(C)C(c1ccc2c(c1)CN(C(=O)OC(C)(C)C)CC2)c1ccc2c(nnn2CCCCOc2cc(Cl)c(C(=O)OC(C)(C)C)c(Cl)c2)c1C]

To a stirred solution of tert-butyl 7-[[1-[4-[4-[[tert-butoxy]carbonyl]-3,5-dichlorophenoxy]butyl]-4-methyl-1H-1,2,3-benzotriazol-5-yl][hydroxy]methyl]-1,2,3,4-tetrahydroisoquinoline-2-carboxylate (1.2 g) in DCM (100 ml) were added [[1-methoxy-2-methylprop-1-en-1-yl]oxy]trimethylsilane (1.8 ml) followed by TiCl$_4$ (1M in DCM, 3.7 ml) at 0° C. and the reaction mixture was stirred at 0° C. for 5 min. After completion of reaction (as jugged by LCMS and TLC), the reaction mixture was quenched with water. Aqueous layer was basified with saturated NaHCO$_3$ solution (pH ~8) and filtered through celite bed. The aqueous layer was extracted with 10% MeOH/DCM (3×50 mL), the combined organic layer was washed with brine, dried over anhydrous Na$_2$SO$_4$ and evaporated under reduced pressure to give a compound (1 g, crude) as light grey solid, which was used to next step without further purification.

MS m/z 795.8 [M+H]$^-$.

J) 2,6-dichloro-4-(4-[5-[3-methoxy-2,2-dimethyl-3-oxo-1-[1,2,3,4-tetrahydroisoquinolin-7-yl]propyl]-4-methyl-1H-1,2,3-benzotriazol-1-yl]butoxy)benzoic acid

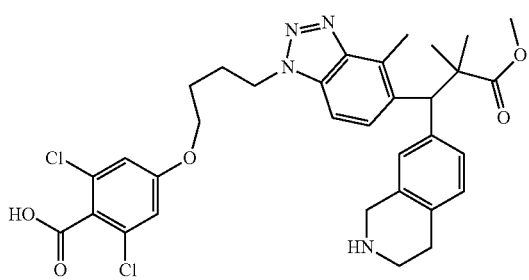 [SMILES: COC(=O)C(C)(C)C(c1ccc2c(c1)CNCC2)c1ccc2c(nnn2CCCCOc2cc(Cl)c(C(=O)O)c(Cl)c2)c1C]

To a stirred solution of tert-butyl 7-[1-[1-[4-[4-[[tert-butoxy]carbonyl]-3,5-dichlorophenoxy]butyl]-4-methyl-1H-1,2,3-benzotriazol-5-yl]-3-methoxy-2,2-dimethyl-3-oxopropyl]-1,2,3,4-tetrahydro isoquinoline-2-carboxylate (1.3 g, crude) in dioxane (13 ml) was added HCl (4M in dioxane, 13 ml) dropwise at 25° C. and the reaction mixture was stirred at that temperature for 2 h. After completion of reaction (as judged by LC/MS), the volatiles were removed under reduced pressure and crude thus obtained was purified by reverse phase prep-HPLC (method A) to give title compound (320 mg) as white solid.

$^1$H NMR (400 MHz, DMSO-d$_6$) δ 1.03 (3H, d, J=5.9 Hz), 1.27 (6H, d, J=21.0 Hz), 1.50-1.60 (2H, m), 2.03 (2H, t, J=6.1 Hz), 2.73 (3H, s), 3.22-3.25 (2H, m), 3.43 (3H, s), 3.83-3.93 (3H, m), 4.70-4.75 (3H, m), 6.62 (2H, s), 6.98 (1H, s), 7.07 (1H, d, J=7.8 Hz), 7.27 (1H, d, J=7.7 Hz), 7.58 (1H, d, J=7.5 Hz), 7.65 (1H, d, J=8.7 Hz), 9.70-9.80 (1H, m). MS m/z 639.4 [M+H]$^+$.

K) methyl 2-[18,30-dichloro-32-methyl-20-oxo-15-oxa-8,9,10,21-tetraazahexacyclo[19.5.3.2$^{16,19}$.1$^{3,7}$.0$^{6,10}$.0$^{24,28}$] dotriacontal(27),(32),4,6,8,16,18,24 (28),25,30-decaen-2-yl]-2-methyl propanoate

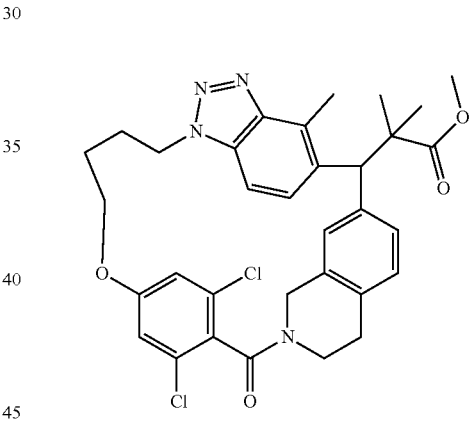

To a solution of HATU (301 mg) in DMF (10 ml) was added a mixture of 2,6-dichloro-4-[4-[5-[3-methoxy-2,2-dimethyl-3-oxo-1-[1,2,3,4-tetrahydro isoquinolin-7-yl]propyl]-4-methyl-1H-1,2,3-benzotriazol-1-yl]butoxy]benzoic acid (390 mg) and N,N-diisopropylethylamine (0.5 ml) in DMF (30 ml) by syringe pump within 1 h at 25° C. and the reaction mixture was stirred at that temperature for 3 h. After completion of reaction (as judged by LC/MS); reaction mixture was diluted with saturated NaHCO$_3$ solution. The aqueous layer was extracted with EtOAc, the combined organic layer was washed with brine, dried over anhydrous Na$_2$SO$_4$ and evaporated under reduced pressure. The crude thus obtained was purified by triturating to give title compound (180 mg) as off white solid which was used to next step without further purification.

MS m/z 621.1 [M+H]$^-$.

L) 2-[18,30-dichloro-32-methyl-20-oxo-15-oxa-8,9,10,21-tetraazahexacyclo[19.5.3.2$^{16,19}$.1$^{3,7}$.0$^{6,10}$.0$^{24,28}$] dotriaconta-1(27),3(32),4,6,8,16(31),17,19(30),24(28),25-decaen-2-yl]-2-methylpropanoic acid (Chiral, Retention Time Short)

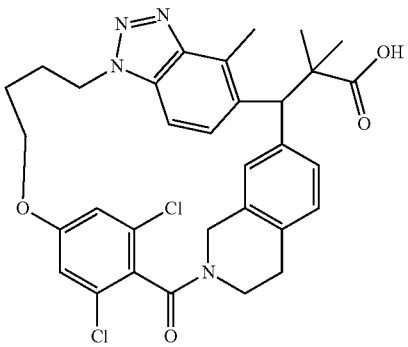 [SMILES: Cc1c2ccc3c1nnn3CCCCOc1cc(Cl)c(c(Cl)c1)C(=O)N1CCc3ccc(cc3C1)C2C(C)(C)C(=O)O]

To a stirred solution of methyl 2-[18,30-dichloro-32-methyl-20-oxo-15-oxa-8,9,10,21-tetraazahexacyclo[19.5.3.2$^{16,19}$.1$^{3,7}$.0$^{6,10}$.0$^{24,28}$] dotriacontal(27),(32),4,6,8,16,18,24(28),25,30-decaen-2-yl]-2-methyl propanoate (180 mg) in mixture of DMSO (4 ml) and MeOH (4 ml) was added KOH (8N, 2 ml) at 25° C. and the reaction mixture was heated at 100° C. for 16 h. After completion of reaction (as jugged by LC/MS), the reaction mass was cooled to 25° C. and the mixture was diluted with EtOAc. The reaction mixture was acidified with 1N HCl (pH ~4-5). The aqueous layer was extracted with EtOAc, the combined organic layer was washed with brine, dried over anhydrous Na$_2$SO$_4$ and evaporated under reduced pressure. The crude thus obtained was purified by reverse phase chiral prep-HPLC (method B) to give 2-[18,30-dichloro-32-methyl-20-oxo-15-oxa-8,9,10,21-tetraazahexacyclo[19.5.3.2$^{16,19}$.1$^{3,7}$.0$^{6,10}$.0$^{24,28}$] dotriaconta-1(27),3(32),4,6,8,16,18,24(28),25,30-decaen-2-yl]-2-methylpropanoic acid (chiral, retention time short, 27.06 mg) as off white sticky solid and 2-[18,30-dichloro-32-methyl-20-oxo-15-oxa-8,9,10,21-tetraazahexacyclo[19.5.3.2$^{16,19}$.1$^{3,7}$.0$^{6,10}$.0$^{24,28}$] dotriaconta-1(27),3(32),4,6,8,16,18,24(28),25,30-decaen-2-yl]-2-methylpropanoic acid (chiral retention time long, 57.59 mg) as off white sticky solid.

2-[18,30-dichloro-32-methyl-20-oxo-15-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]-2-methylpropanoic acid (chiral, retention time short)

$^1$H NMR (400 MHz, DMSO-d$_6$) δ 1.22 (3H, s), 1.33 (3H, s), 1.51-1.60 (2H, m), 2.07 (2H, q, J=6.2 Hz), 2.56 (3H, s), 2.88-2.90 (2H, m), 3.57-3.76 (3H, m), 3.96-4.64 (3H, m), 4.65-4.70 (1H, m), 4.84-5.10 (2H, m), 6.16 (1H, s), 6.20 (1H, s), 6.90 (1H, s), 7.09 (1H, d, J=7.8 Hz), 7.29 (1H, d, J=7.4 Hz), 7.51 (1H, d, J=8.7 Hz), 7.57 (1H, d, J=8.6 Hz), 11.50-11.60 (1H, m). MS m/z 607.5 [M+H]$^+$.

2-[18,30-dichloro-32-methyl-20-oxo-15-oxa-8,9,10,21-tetraazahexacyclo[19.5.3.2$^{16,19}$.1$^{3,7}$.0$^{6,10}$.0$^{24,28}$] dotriaconta-1(27),3(32),4,6,8,16,18,24(28),25,30-decaen-2-yl]-2-methylpropanoic acid (Chiral, Retention Time Long)

$^1$H NMR (400 MHz, DMSO-d$_6$) δ 1.22 (3H, s), 1.33 (3H, s), 1.51-1.60 (2H, m), 2.09 (2H, q, J=5.0 Hz), 2.56 (3H, s), 2.90 (2H, t, J=6.2 Hz), 3.55-3.76 (3H, m), 3.96-4.64 (3H, m), 4.65-4.70 (1H, m), 4.79-4.83 (2H, m), 6.15-6.20 (2H, m), 6.91 (1H, s), 7.09 (1H, d, J=7.8 Hz), 7.29 (1H, d, J=8.0 Hz), 7.50-7.58 (2H, m). MS m/z 605.3 [M−H]$^+$.

Example 66

2-[18,30-dichloro-32-methyl-20-oxo-15-oxa-8,9,10,21-tetraazahexacyclo[19.5.3.2$^{16,19}$.1$^{3,7}$.0$^{6,10}$.0$^{24,28}$] dotriaconta-1(27),3(32),4,6,8,16(31),17,19(30),24(28),25-decaen-2-yl]-2-methylpropanoic acid (Chiral, Retention Time Long)

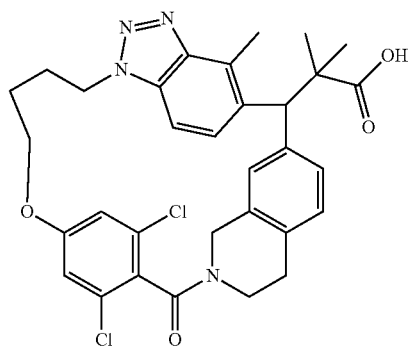 [SMILES: Cc1c2ccc3c1nnn3CCCCOc1cc(Cl)c(c(Cl)c1)C(=O)N1CCc3ccc(cc3C1)C2C(C)(C)C(=O)O]

The compounds of Examples 66 could be produced according to the production methods described in the present specification, a method shown in the Examples, or a method analogous thereto.

Example 67

[18,30,32-trimethyl-20-oxo-14-oxa-8,9,10,21-tetrazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]acetic acid (Chiral, Retention Time Short)

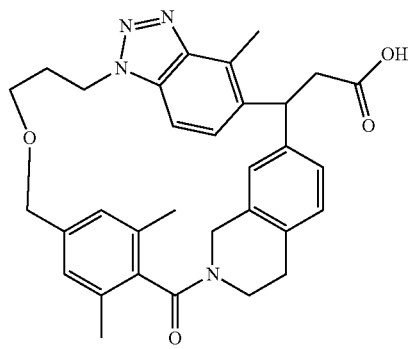 [SMILES: Cc1cc2cc(C)c1C(=O)N1CCc3ccc(cc3C1)C(CC(=O)O)c1ccc3c(nnn3CCCOC2)c1C]

183

A) tert-butyl 7-bromo-1,2,3,4-tetrahydroisoquinoline-2-carboxylate

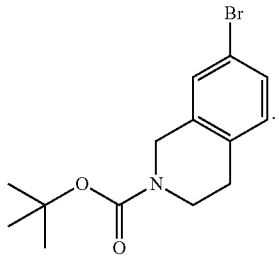 [SMILES: CC(C)(C)OC(=O)N1CCc2ccc(Br)cc2C1]

To a stirred solution of 7-bromo-1,2,3,4-tetrahydroisoquinoline hydrochloride salt (25 g) in THF (400 ml) and H$_2$O (150 ml) were added Na$_2$CO$_3$ (24 g) and Boc$_2$O (39 ml) at 25° C. and reaction mixture was stirred at this temperature for another 16 h. After completion of reaction (as judged by TLC), the reaction mixture was quenched with ice. The aqueous layer was extracted with EtOAc, combined organics were washed with brine; dried over anhydrous Na$_2$SO$_4$ and concentrated under reduced pressure. The crude thus obtained was purified by silica gel column chromatography (SiO$_2$, 5% EtOAc/Hexane) to give title compound (30 g) as white solid.

$^1$H NMR (400 MHz, DMSO-d$_6$): δ 1.42 (9H, s), 2.72 (2H, t, J=5.8 Hz), 3.52 (2H, t, J=5.8 Hz), 4.49 (2H, s), 7.12 (1H, d, J=8.1 Hz), 7.34 (1H, d, J=8.0 Hz), 7.42 (1H, s).

B) tert-butyl 7-(tetramethyl-1,3,2-dioxaborolan-2-yl)-1,2,3,4-tetrahydroisoquinoline-2-carboxylate

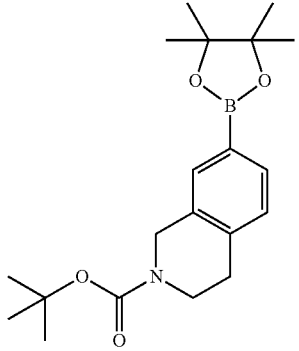 [SMILES: CC(C)(C)OC(=O)N1CCc2ccc(B3OC(C)(C)C(C)(C)O3)cc2C1]

To a degassed solution of give tert-butyl 7-bromo-1,2,3,4-tetrahydroisoquinoline-2-carboxylate (20 g) in DME (90 ml) was added bis(pinacolato)diboron (19 g) and potassium acetate (19 g) at 25° C. and the reaction mixture was degassed with argon for 15 min. To this was added Pd(dppf)$_2$Cl$_2$.DCM (2.6 g) at 25° C. and the reaction mixture was stirred at 90° C. for 4 h. The mixture was filtrated, and filtrate was concentrated in vacuo. The residue was purified by column chromatography (SiO$_2$, 10-20% EtOAc in Hexane) to give title compound (16 g) as white solid.

$^1$H NMR (400 MHz, DMSO-d$_6$) δ 1.28 (12H, s), 1.42 (9H, s), 2.78 (2H, t, J=5.4 Hz), 3.53 (2H, t, J=5.4 Hz), 4.50 (2H, s), 7.16 (1H, d, J=7.4 Hz), 7.45 (2H, m).

184

C) {2-[(tert-butoxy)carbonyl]-1,2,3,4-tetrahydroisoquinolin-7-yl}boronic acid

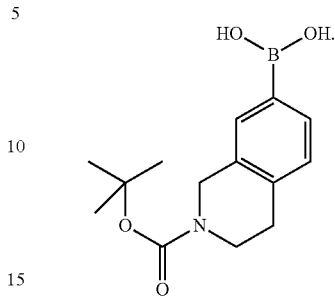

To a stirred solution of tert-butyl 7-(tetramethyl-1,3,2-dioxaborolan-2-yl)-1,2,3,4-tetrahydroisoquinoline-2-carboxylate (2.00 g) in acetone (40 mL) was added NaIO$_4$ (3.57 g) followed by ammonium acetate (1.0 M in water, 27.8 mL) at 25° C. and reaction mixture was stirred at 25° C. for 16 h. After completion of reaction (as jugged by TLC), solvent was evaporated. Residue was diluted with water. The aqueous layer was extracted with EtOAc, combined organics were washed with brine; dried over anhydrous Na$_2$SO$_4$ and concentrated under reduced pressure. The crude thus obtained was purified by silica gel column chromatography (SiO$_2$, 12 g, 50% EtOAc/Hexane) to give title compound (760 mg) as white solid.

$^1$H NMR (400 MHz, DMSO-d$_6$): δ 1.42 (9H, s), 2.75-2.78 (2H, m), 3.52-3.55 (2H, m), 4.48-4.54 (2H, m), 7.10-7.16 (1H, m), 7.54-7.67 (2H, m), 7.94 (2H, s).

D) tert-butyl-4-[[3-[5-[(1E)-3-ethoxy-3-oxoprop-1-en-1-yl]-4-methyl-H-1, 2, 3-benzotriazol-1-yl] propoxy] methyl]-2,6-dimethylbenzoate

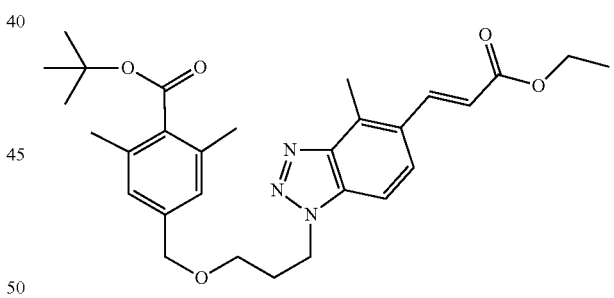

To a degassed solution of tert-butyl 4-[3-[5-bromo-4-methyl-H-1,2,3-benzotriazol-1-yl]propoxy]methyl]-2,6-dimethylbenzoate (3.7 g) in DMF (25 ml) were added ethyl acrylate (8.0 ml; 75.82 mmol) followed by DIPEA (7 ml, 37.9 mmol) at 25° C. and the reaction mixture was degassed with argon for 10 min. To this was added tri-o-tolylphosphine (700 mg) and Pd(OAc)$_2$ (255 mg) at 25° C. and the reaction mixture was heated at 120° C. for 4 h. After completion of reaction (as judged by TLC and LC/MS), the reaction mixture was cooled to 25° C. and quenched with ice-water. The aqueous layer was extracted with EtOAc, combined organics were washed with brine; dried over anhydrous Na$_2$SCO$_4$ and concentrated under reduced pressure. The crude thus obtained was purified by silica gel column chromatography (SiO$_2$; 40 g; 30% EtOAc/Hexane) to afford title compound (3 g) as brown sticky liquid.

¹H NMR (400 MHz, DMSO-d₆): δ 1.28 (3H, t, J=7.0 Hz), 1.53 (9H, s), 2.17-2.20 (8H, m), 2.78 (3H, s), 3.39 (2H, t, J=5.5 Hz), 4.19 (2H, q, J=7.0 Hz), 4.30 (2H, s), 4.78 (2H, t, J=6.4 Hz), 6.63 (1H, d, J=15.8 Hz), 6.89 (2H, s), 7.65 (1H, d, J=8.7 Hz), 7.93 (1H, d, J=8.8 Hz), 8.00 (1H, d, J=12.0 Hz). MS m/z 508.2 [M+H]⁺.

E) tert-butyl-7-[1-[1-[3-[[4-[[tert-butoxy] carbonyl]-3,5-dimethylphenyl]methoxy]propyl]-4-methyl-1H-1,2,3-benzotriazol-5-yl]-3-ethoxy-3-oxopropyl]-1,2,3,4-tetrahydroisoquinoline-2-carboxylate

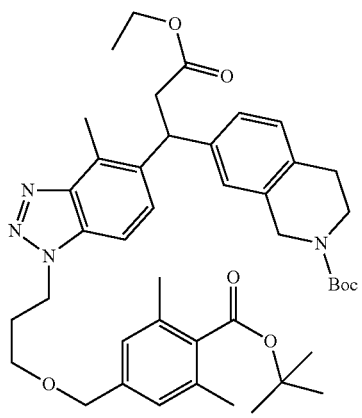 [SMILES: CCOC(=O)CC(c1ccc2c(c1)CN(C(=O)OC(C)(C)C)CC2)c1ccc2c(nnn2CCCOCc2cc(C)c(C(=O)OC(C)(C)C)c(C)c2)c1C]

To a degassed solution of tert-butyl-4-[(3-[5-[(1E)-3-ethoxy-3-oxoprop-1-en-1-yl]-4-methyl-H-1,2,3-benzotriazol-1-yl]propoxy]methyl]-2,6-dimethylbenzoate (500 mg) in mixture of dioxane (12 ml) and water (1.2 ml) were added [²-[[tert-butoxy]carbonyl]-1,2,3,4-tetrahydroisoquinolin-7-yl]boronic acid (821.5 mg) followed by K₃PO₄ (626.45 mg) at 25° C. To this was added [RhCl(COD)]₂ (48.56 mg) at 25° C. and reaction mixture was stirred at 25° C. for 4 h under blue LED light. The reaction mixture was quenched with sat NH₄Cl aqueous solution. The aqueous layer was extracted with EtOAc, combined organics were washed with water, brine, dried over anhydrous Na₂SO₄, filtered and filtrate was concentrated under reduced pressure. The crude thus obtained was purified by silica gel column chromatography (SiO₂, 12 g, 40% EtOAc/Hexane) to give title compound (450 mg) as brown sticky solid.

¹H NMR (400 MHz, DMSO-d₆): δ 0.99 (3H, t, J=6.8 Hz), 1.40 (9H, s), 1.53 (9H, s), 2.14 (2H, t, J=6.6 Hz), 2.20 (6H, s), 2.65-2.70 (2H, m), 2.77 (3H, s), 3.12-3.14 (2H, m), 3.37 (2H, t, J=5.5 Hz), 3.45-3.49 (2H, m), 3.89 (2H, q, J=6.5 Hz), 4.33 (2H, s), 4.41 (2H, s), 4.70 (2H, t, J=6.2 Hz), 4.81 (1H, t, J=7.5 Hz), 6.94 (2H, s), 7.03 (1H, d, J=7.5 Hz), 7.10-7.14 (2H, m), 7.49 (1H, d, J=8.9 Hz), 7.55 (1H, d, J=8.7 Hz). MS m/z 741.0 [M+H]⁺.

F) 4-[[3-[5-[3-ethoxy-3-oxo-1-[1,2,3,4-tetrahydroisoquinolin-7-yl]propyl]-4-methyl-1H-1,2,3-benzotriazol-1-yl]propoxy]methyl]-2,6-dimethylbenzoic acid

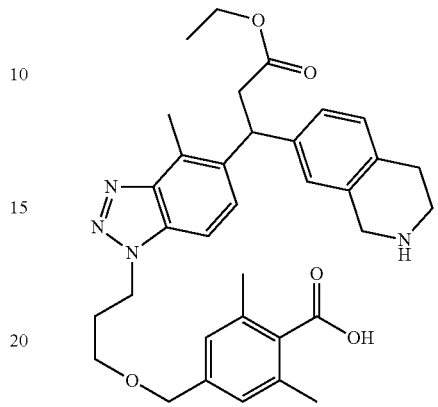

To a stirred solution of tert-butyl-7-[1-[1-[3-[[4-[[tert-butoxy]carbonyl]-3,5-dimethylphenyl]methoxy]propyl]-4-methyl-1H-1,2,3-benzotriazol-5-yl]-3-ethoxy-3-oxopropyl]-1,2,3,4-tetrahydroisoquinoline-2-carboxylate (1.2 g) in DCM (40 ml) was added TFA (1.2 ml) at 25° C. The reaction mixture was stirred at 25° C. for 2 h. After completion of reaction (as jugged by LC/MS), the reaction mixture was concentrated under reduced pressure and crude was purified by reverse phase prep-HPLC (method A) to give title compound (320 mg) as off white solid.

MS m/z 585.4 [M+H]⁻.

G) ethyl-2-[18,30,32-trimethyl-20-oxo-14-oxa-8,9,10,21-tetraazahexacyclo[19.5.3.2¹⁶,¹⁹.1³,⁷.0⁶,¹⁰.0²⁴,²⁸] dotriaconta-1(27),3(32),4,6,8,16,18,24(28),25,30-decaen-2-yl]acetate

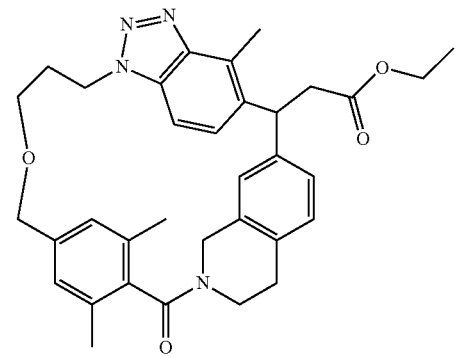 [SMILES: CCOC(=O)CC1c2ccc3c(c2)CN(CC3)C(=O)c2c(C)cc(cc2C)COCCCn2nnc3c(C)c1ccc32]

To a solution of TBTU (100.069 mg) in DMF (10 ml) was added a mixture 4-[[[3-[5-[3-ethoxy-3-oxo-1-[1,2,3,4-tetrahydroisoquinolin-7-yl]propyl]-4-methyl-1H-1,2,3-benzotriazol-1-yl]propoxy] methyl]-2,6-dimethylbenzoic acid (140 mg) in DMF (10 ml) and N,N-diisopropylethylamine (0.215 ml) by syringe pump over 1 h at 25° C. and the reaction mixture was stirred at 25° C. for 3 h. After completion of reaction (as judged by LC/MS), reaction mixture was diluted with saturated NaHCO₃ aqueous solution. The aqueous layer was extracted with EtOAc, the combined organic layer was washed with brine, dried over anhydrous $Na_2SO_4$ and evaporated under reduced pressure to give title compound (120 mg, crude) which was used directly for next step without further purification. MS m/z 567.4 $[M+H]^+$.

H) [18,30,32-trimethyl-20-oxo-14-oxa-8,9,10,21-tetrazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]acetic acid (retention time short) and [18,30,32-trimethyl-20-oxo-14-oxa-8,9,10,21-tetrazahexacyclo [19.5.3.2$^{16,19}$.1$^{3,7}$.0$^{6-10}$.0$^{24,28}$] dotriaconta-(27),3(32),4,6,8,16,18,24(28),25,30-decaen-2-yl]acetic acid (Retention Time Long)

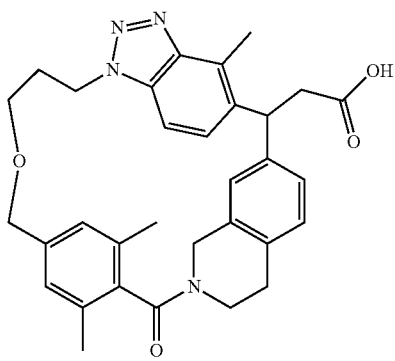 [SMILES: Cc1cc2cc(C)c1C(=O)N1CCc3ccc(cc3C1)C(CC(=O)O)c1ccc3c(nnn3CCCOC2)c1C]

To a stirred solution of ethyl-2-[18,30,32-trimethyl-20-oxo-14-oxa-8,9,10,21-tetraazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]acetate (150 mg) in a mixture of THF (3 ml) and MeOH (1.5 ml) was added 1N NaOH (1.2 ml) at 25° C. and the reaction mixture was stirred at 25° C. for 2 h. After completion of reaction (as judged by TLC and LC/MS), the volatiles were removed under reduced pressure. The crude was dissolved in $H_2O$ and aqueous layer was acidified with 1N HCl. The solid thus formed was filtered and finally purified by reverse phase chiral prep-HPLC (method B) to give [18,30,32-trimethyl-20-oxo-14-oxa-8,9,10,21-tetrazahexacyclo [19.5.3.2$^{16,19}$.1$^{3,7}$.0$^{6,10}$.0$^{24,28}$]dotriaconta-1(27),3(32),4,6,8,16,18,24(28),25,30-decaen-2-yl] acetic acid (retention time short, 30 mg) as grey sticky solid and [18,30,32-trimethyl-20-oxo-14-oxa-8,9,10,21-tetrazahexacyclo [19.5.3.2$^{16,19}$.1$^{3,7}$.0$^{6,10}$.0$^{24,28}$]dotriaconta-1(27),3 (32),4,6,8,16,18,24(28),25,30-decaen-2-yl]acetic acid (retention time long, 30 mg) as grey sticky solid

[18,30,32-trimethyl-20-oxo-14-oxa-8,9,10,21-tetrazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]acetic acid (Retention Time Short)

$^1$H NMR (400 MHz, DMSO-de): δ 1.42 (3H, s), 1.85 (3H, s), 2.38 (2H, q, J=8.0 Hz), 2.93-3.08 (5H, m), 3.34 (2H, q, J=8.0 Hz), 3.64-3.68 (1H, m), 3.77-3.92 (5H, m), 4.17 (1H, d, J=12.0 Hz), 4.30 (1H, d, J=12.0 Hz), 4.68-4.85 (3H, m), 5.81 (1H, s), 6.15 (1H, s), 6.73 (1H, s), 7.17 (1H, d, J=8.0 Hz), 7.28 (1H, d, J=8.0 Hz), 7.37 (1H, d, J=8.0 Hz), 7.54 (1H, d, J=8.0 Hz), 11.54 (brs, 1H). MS m/z 539.4 $[M+H]^+$.

[18,30,32-trimethyl-20-oxo-14-oxa-8,9,10,21-tetrazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]acetic acid (Retention Time Long)

$^1$H NMR (400 MHz, DMSO-d$_6$): δ 1.42 (3H, s), 1.85 (3H, s), 2.38 (2H, q, J=8.0 Hz), 2.93-3.08 (5H, m), 3.34 (2H, q, J=8.0 Hz), 3.64-3.68 (1H, m), 3.77-3.92 (5H, m), 4.17 (1H, d, J=12.0 Hz), 4.30 (1H, d, J=12.0 Hz), 4.68-4.85 (3H, m), 5.81 (11H, s), 6.15 (1H, s), 6.73 (11H, s), 7.17 (1H, d, J=8.0 Hz), 7.28 (1H, d, J=8.0 Hz), 7.37 (1H, d, J=8.0 Hz), 7.54 (1H, d, J=8.0 Hz), 11.49 (bs, 1H). MS m/z 539.4 $[M+H]^+$.

Example 68

[18,30,32-trimethyl-20-oxo-14-oxa-8,9,10,21-tetrazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]acetic acid (Chiral, Retention Time Long)

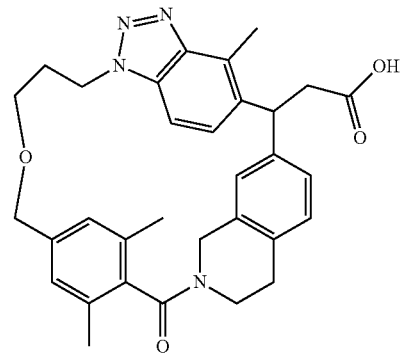 [SMILES: Cc1cc2cc(C)c1C(=O)N1CCc3ccc(cc3C1)C(CC(=O)O)c1ccc3c(nnn3CCCOC2)c1C]

The compounds of Examples 68 could be produced according to the production methods described in the present specification, a method shown in the Examples, or a method analogous thereto.

Structures of Examples 1 to 68 are shown in Table 2.

| EXP | Name | Chemical Structure | Stereo chemistry | MS |
|---|---|---|---|---|
| 1 | [32-methyl-20-oxo-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18,24,27,30-decaen-2-yl]acetic acid | 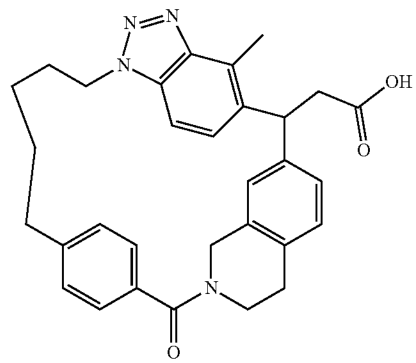 [SMILES: Cc1c2ccc3c1nnn3CCCCCc1ccc(cc1)C(=O)N1CCc3ccc(cc3C1)C2CC(=O)O] | Racemate | 509.3 |
| 2 | [20-oxo-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18,24,27,30-decaen-2-yl]acetic acid | 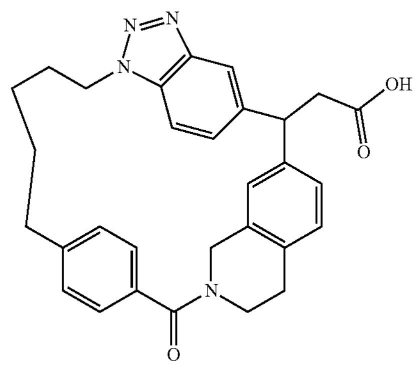 [SMILES: O=C(O)CC1c2ccc3c(c2)CN(CC3)C(=O)c2ccc(cc2)CCCCCn2nnc3cc1ccc32] | Racemate | 495.4 |
| 3 | 2-(18-ethyl-32-methyl-20-oxo-8,9,10,21-tetrazahexacyclo [19.5.3.216,19.13,7.06,10.024,28] dotriaconta-1(27),3(32),4,6,8,16(31),17,19(30),24(28),25-decaen-2-yl)acetic acid | 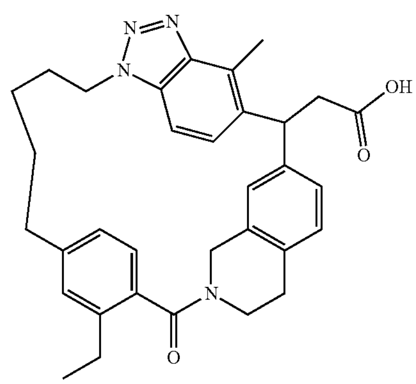 [SMILES: CCc1cc2ccc1C(=O)N1CCc3ccc(cc3C1)C(CC(=O)O)c1ccc3c(nnn3CCCCC2)c1C] | Racemate | 537.4 |
| 4 | [33-methyl-2-oxo-7-oxa-1,15,16,17-tetrazaheptacyclo [22.5.3.2$^{3,9}$.1$^{18,22}$.0$^{4,8}$.0$^{15,19}$.0$^{27,31}$] pentatriaconta-3,8,16,18(33),19,21,24,26,31,34-decaen-23-yl]acetic acid | 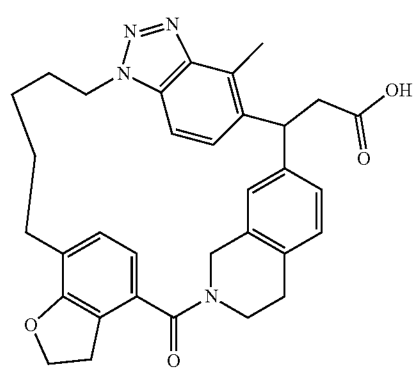 [SMILES: Cc1c2ccc3c1nnn3CCCCCc1ccc(c3c1OCC3)C(=O)N1CCc3ccc(cc3C1)C2CC(=O)O] | Racemate | 551.4 |

-continued

| EXP | Name | Chemical Structure | Stereo chemistry | MS |
|---|---|---|---|---|
| 5 | [6,6,33-trimethyl-2-oxo-5-oxa-1,15,16,17-[22.5.3.2$^{3,9}$.1$^{18,22}$.0$^{4,8}$.0$^{15,19}$.0$^{27,31}$] pentatriaconta-3,8,16,18(33),19,21,24,26,31,34-decaen-23-yl]acetic acid | 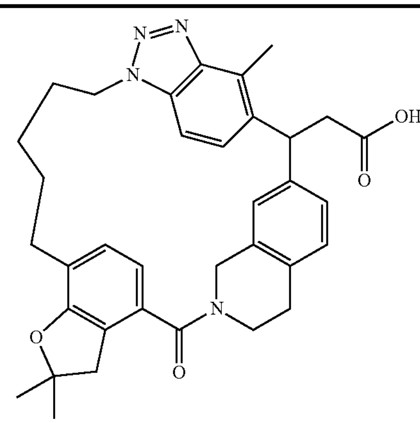 | Racemate | 579.4 |
| 6 | [32-methyl-20-oxo-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18,24,27,30-decaen-2-yl]propanoic acid | 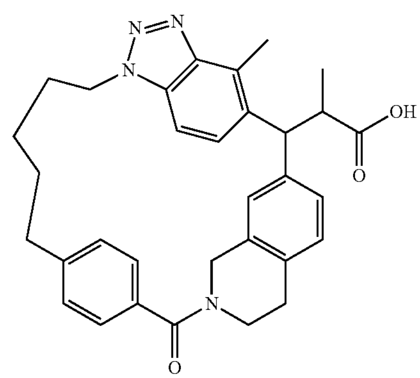 [SMILES: Cc1c2ccc3c1nnn3CCCCCc1ccc(cc1)C(=O)N1CCc3ccc(cc3C1)C2C(C)C(=O)O] | Diastereomer Mixture | 523.3 |
| 7 | [33-methyl-2-oxo-5-oxa-1,15,16,17-tetrazaheptacyclo [22.5.3.2$^{3,9}$.1$^{18,22}$.0$^{4,8}$.0$^{15,19}$.0$^{27,31}$] pentatriaconta-3,8,16,18(33),19,21,24,26,31,34-decaen-23-yl]acetic acid | 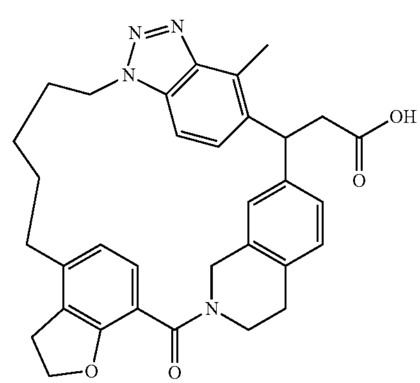 [SMILES: Cc1c2ccc3c1nnn3CCCCCc1ccc(c3c1CCO3)C(=O)N1CCc3ccc(cc3C1)C2CC(=O)O] | Racemate | 551.4 |
| 8 | [6,6,33-trimethyl-2-oxo-5-oxa-1,15,16,17-tetrazaheptacyclo [22.5.3.2$^{3,9}$.1$^{18,22}$.0$^{4,8}$.0$^{15,19}$.0$^{27,31}$] pentatricontal-3,8,16,18(33),19,21,24,26,31,34-decaen-23-yl]acetic acid | 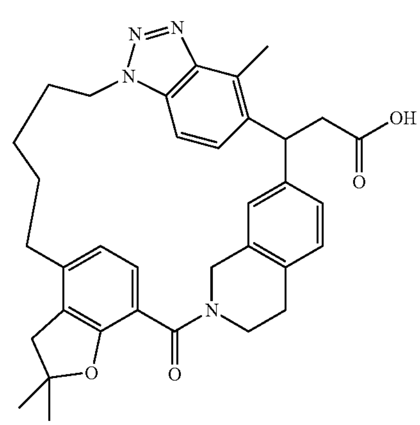 [SMILES: Cc1c2ccc3c1nnn3CCCCCc1ccc(c3c1CC(C)(C)O3)C(=O)N1CCc3ccc(cc3C1)C2CC(=O)O] | Racemate | 579.4 |

-continued

| EXP | Name | Chemical Structure | Stereo chemistry | MS |
|---|---|---|---|---|
| 9 | [18-chloro-32-methyl-20-oxo-8,9,10,21-tetrazahexacyclo[19.5.3.2$^{16,19}$.1$^{3,7}$.0$^{6,10}$.0$^{24,28}$]dotriaconta-1(26),3(32),4,6,8,16,18-24,27,30-decaen-2-yl]acetic acid | 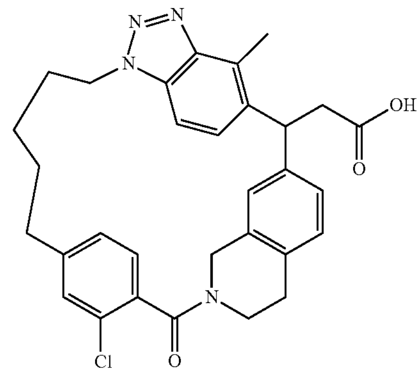 [SMILES: Cc1c2ccc3c1nnn3CCCCCc1ccc(c(Cl)c1)C(=O)N1CCc3ccc(cc3C1)C2CC(=O)O] | Racemate | 543.3 |
| 10 | [18-fluoro-32-methyl-20-oxo-8,9,10,21-tetrazahexacyclo[19.5.3.2$^{16,19}$.1$^{3,7}$.0$^{6,10}$.0$^{24,28}$]dotriaconta-1(26),3(32),4,6,8,16,18,24,27,30,25-decaen-2-yl]acetic acid | 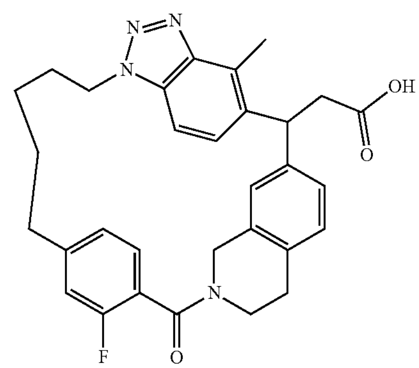 | Racemate | 527.3 |
| 11 | [32-methyl-20-oxo-8,9,10,21-tetrazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetic acid <Synthesis from chiral ethyl [32-methyl-20-oxo-8,9,10,21-tetrazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Chiral, retention time short)> | 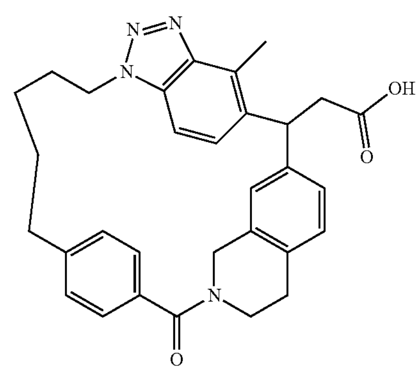 [SMILES: Cc1c2ccc3c1nnn3CCCCCc1ccc(cc1)C(=O)N1CCc3ccc(cc3C1)C2CC(=O)O] | Chiral | 509.4 |
| 12 | [32-methyl-20-oxo-8,9,10,21-tetrazahexacyclo[19.5.3.2$^{16,19}$.1$^{3,7}$.0$^{16,19}$.0$^{24,28}$]dotriaconta-1(26),3(32),4,6,8,16,18,24,27,30-decaen-2-yl]acetic acid <Synthesis from Chiral, Ethyl [32-methyl-20-oxo-8,9,10,21-tetrazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Chiral, retention time long)> | 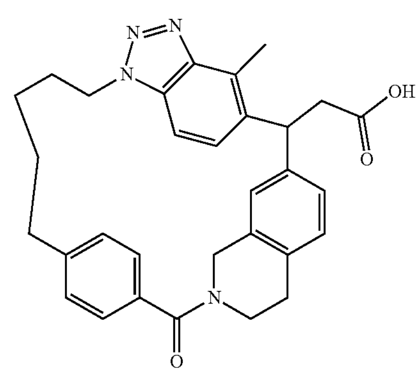 [SMILES: Cc1c2ccc3c1nnn3CCCCCc1ccc(cc1)C(=O)N1CCc3ccc(cc3C1)C2CC(=O)O] | Chiral | 509.3 |

-continued

| EXP | Name | Chemical Structure | Stereo chemistry | MS |
|---|---|---|---|---|
| 13 | [31-methyl-19-oxo-8,9,10,20-tetrazahexacyclo [18.5.3.2$^{15,18}$.1$^{3,7}$.0$^{6,10}$.0$^{23,27}$] hentriaconta-1(25),3(31),4,6,8,15,17, 23,26,29-decaen-2-yl)acetic acid | 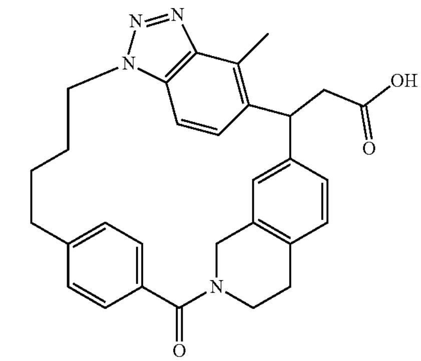 [SMILES: Cc1c2ccc3c1nnn3CCCCc1ccc(cc1)C(=O)N1CCc3ccc(cc3C1)C2CC(=O)O] | Racemate | 495.3 |
| 14 | [(13Z)-33-methyl-21-oxo-8,9,10,22-tetrazahexacyclo [20.5.3.2$^{17,20}$.1$^{3,7}$.0$^{6,10}$.0$^{25,29}$] tritriaconta-1(27),3(33),4,6,8,13,17, 19,25,28,31-undecaen-2-yl]acetic acid | 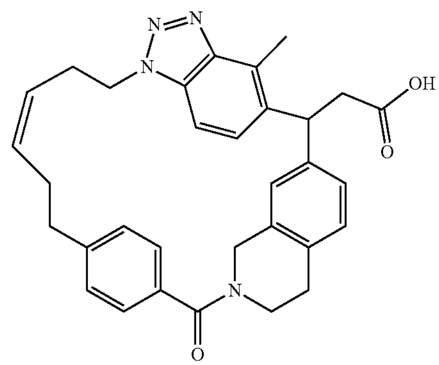 [SMILES: Cc1c2ccc3c1nnn3CC/C=C\CCc1ccc(cc1)C(=O)N1CCc3ccc(cc3C1)C2CC(=O)O] | Racemate | 521.3 |
| 15 | [33-methyl-21-oxo-8,9,10,22-tetrazahexacyclo [20.5.3.2$^{17,20}$.1$^{3,7}$.0$^{6,10}$.0$^{25,29}$] tritriaconta-1(27),3(33),4,6,8,17,19, 25,28,31-decaen-2-yl)acetic acid | 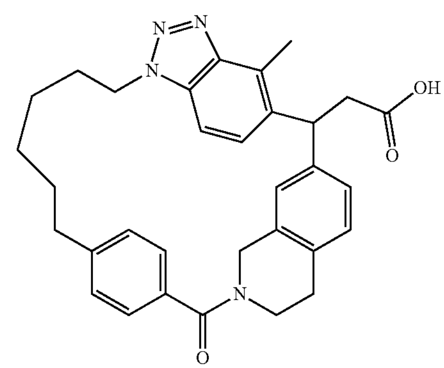 [SMILES: Cc1c2ccc3c1nnn3CCCCCCc1ccc(cc1)C(=O)N1CCc3ccc(cc3C1)C2CC(=O)O] | Racemate | 523.3 |
| 16 | [32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18, 24,27,30-decaen-2-yl]acetic acid | 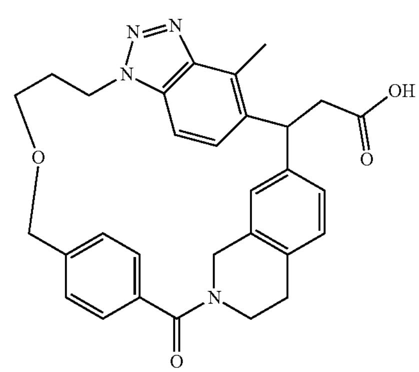 [SMILES: Cc1c2ccc3c1nnn3CCCOCc1ccc(cc1)C(=O)N1CCc3ccc(cc3C1)C2CC(=O)O] | Racemate | 511.4 |

| EXP | Name | Chemical Structure | Stereo chemistry | MS |
|---|---|---|---|---|
| 17 | [18,32-dimethyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18,24,27,30-decaen-2-yl]acetic acid | 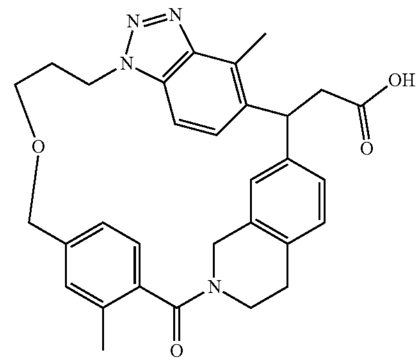 [SMILES: Cc1cc2ccc1C(=O)N1CCc3ccc(cc3C1)C(CC(=O)O)c1ccc3c(nnn3CCCOC2)c1C] | Racemate | 525.3 |
| 18 | [18-ethyl-32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18,24,27,30-decaen-2-yl]acetic acid | 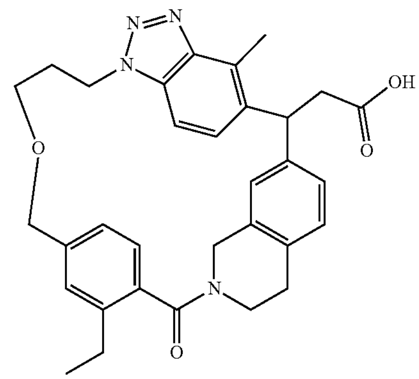 [SMILES: CCc1cc2ccc1C(=O)N1CCc3ccc(cc3C1)C(CC(=O)O)c1ccc3c(nnn3CCCOC2)c1C] | Racemate | 539.3 |
| 19 | [18-cyclopropyl-32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18,24,27,30-decaen-2-yl]acetic acid | 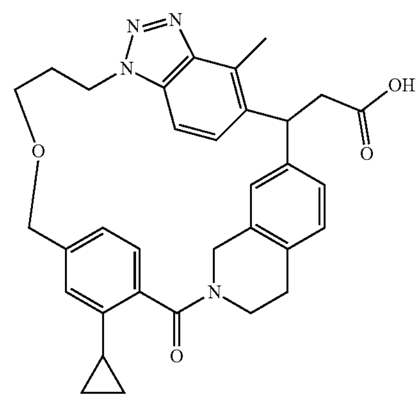 [SMILES: Cc1c2ccc3c1nnn3CCCOCc1ccc(c(C3CC3)c1)C(=O)N1CCc3ccc(cc3C1)C2CC(=O)O] | Racemate | 551.3 |
| 20 | [32-methyl-20-oxo-18-(trifluoromethoxy)-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18,24,27,30-decaen-2-yl]acetic acid | 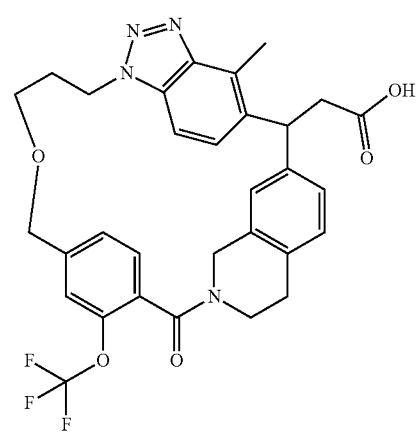 [SMILES: Cc1c2ccc3c1nnn3CCCOCc1ccc(c(OC(F)(F)F)c1)C(=O)N1CCc3ccc(cc3C1)C2CC(=O)O] | Racemate | 595.3 |

| EXP | Name | Chemical Structure | Stereo chemistry | MS |
|---|---|---|---|---|
| 21 | [18-fluoro-32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18, 24,27,30-decaen-2-yl]acetic acid | 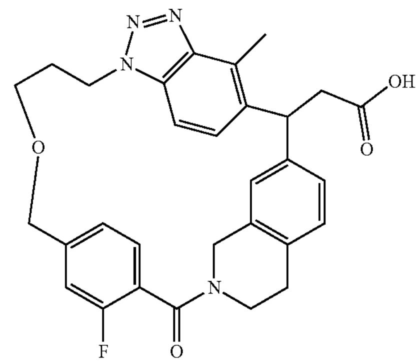 | Racemate | 529.3 |
| 22 | [18-methoxy-32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18, 24,27,30-decaen-2-yl]acetic acid | 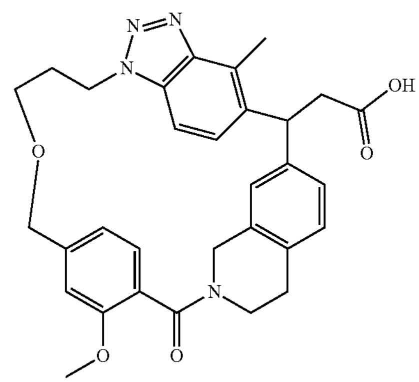 [SMILES: COc1cc2ccc1C(=O)N1CCc3ccc(cc3C1)C(CC(=O)O)c1ccc3c(nnn3CCCOC2)c1C] | Racemate | 541.3 |
| 23 | [32-methyl-20-oxo-18-(trifluoromethyl)-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18, 24,27,30-decaen-2-yl]acetic acid | 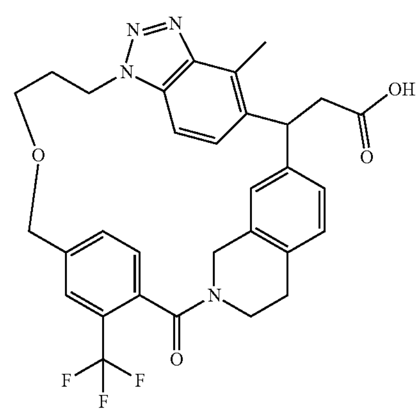 [SMILES: Cc1c2ccc3c1nnn3CCCOCc1ccc(c(C(F)(F)F)c1)C(=O)N1CCc3ccc(cc3C1)C2CC(=O)O] | Racemate | 579.3 |
| 24 | [18-chloro-32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18, 24,27,30-decaen-2-yl]acetic acid | 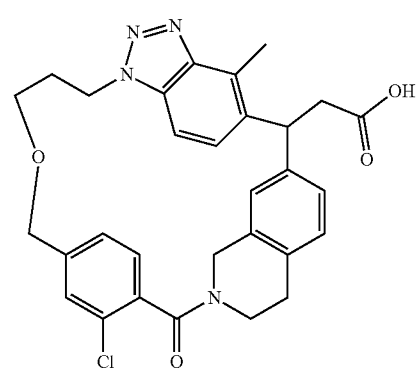 [SMILES: Cc1c2ccc3c1nnn3CCCOCc1ccc(c(Cl)c1)C(=O)N1CCc3ccc(cc3C1)C2CC(=O)O] | Racemate | 545.3 |

| EXP | Name | Chemical Structure | Stereo chemistry | MS |
|---|---|---|---|---|
| 25 | [32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18, 24,27,30-decaen-2-yl]acetic acid <Synthesis from chiral ethyl [32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18, 24,27,30-decaen-2-yl]acetate (Chiral, retention time short)> | 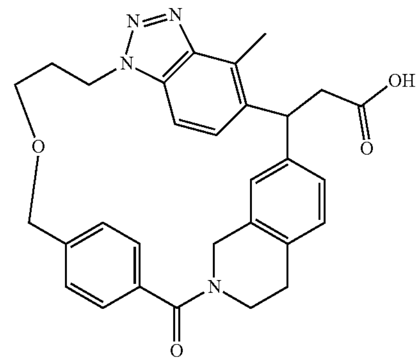 [SMILES: Cc1c2ccc3c1nnn3CCCOCc1ccc(cc1)C(=O)N1CCc3ccc(cc3C1)C2CC(=O)O] | Chiral | 511.3 |
| 26 | [32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18, 24,27,30-decaen-2-yl]acetic acid <Synthesis from chiral ethyl [32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18, 24,27,30-decaen-2-yl]acetate (Chiral, retention time long)> | 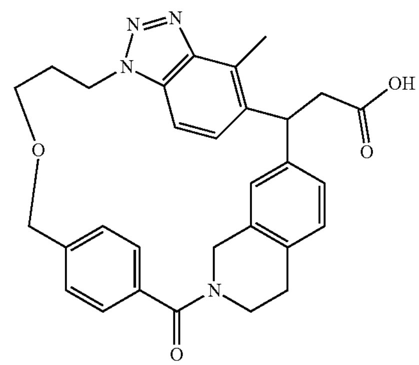 [SMILES: Cc1c2ccc3c1nnn3CCCOCc1ccc(cc1)C(=O)N1CCc3ccc(cc3C1)C2CC(=O)O] | Chiral | 511.3 |
| 27 | ethyl 2-[32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18, 24,27,30-decaen-2-yl]acetate | 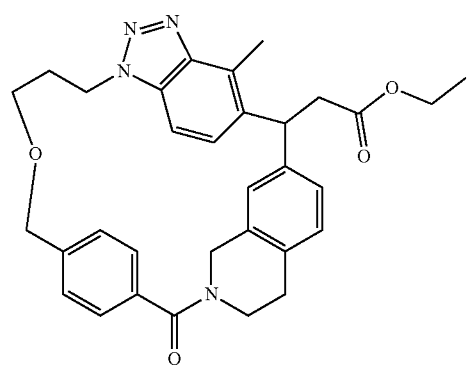 [SMILES: CCOC(=O)CC1c2ccc3c(c2)CN(CC3)C(=O)c2ccc(cc2)COCCCn2nnc3c(C)c1ccc32] | Racemate | 539.3 |
| 28 | 2-methyl-2-[32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18, 24,27,30-decaen-2-yl]propanoic acid | 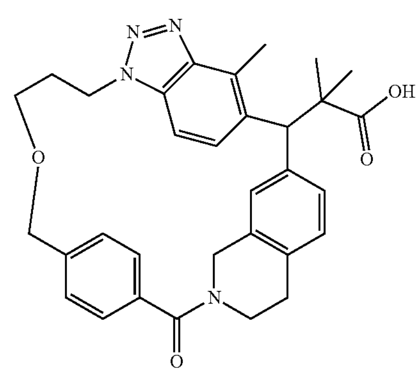 [SMILES: Cc1c2ccc3c1nnn3CCCOCc1ccc(cc1)C(=O)N1CCc3ccc(cc3C1)C2C(C)(C)C(=O)O] | Racemate | 539.3 |

| EXP | Name | Chemical Structure | Stereo chemistry | MS |
|---|---|---|---|---|
| 29 | [32-methyl-20-oxo-13-oxa-8,9,10,21-tetrazahexacyclo [19.5.3.2^{16,19}.1^{3,7}.0^{6,10}.0^{24,28}] dotriaconta-1(26),3(32),4,6,8,16,18,24,27,30-decaen-2-yl]acetic acid | 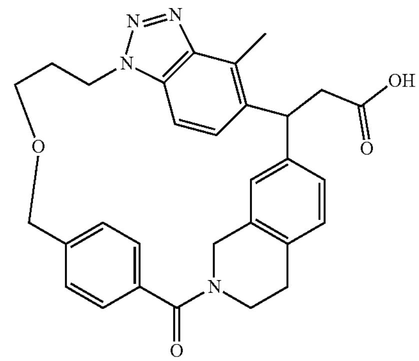 [SMILES: Cc1c2ccc3c1nnn3CCCOCc1ccc(cc1)C(=O)N1CCc3ccc(cc3C1)C2CC(=O)O] | Racemate | 511.3 |
| 30 | [32-methyl-20-oxo-15-oxa-8,9,10,21-tetrazahexacyclo [19.5.3.2^{16,19}.1^{3,7}.0^{6,10}.0^{24,28}] dotriaconta-1(26),3(32),4,6,8,16,18,24,27,30-decaen-2-yl]acetic acid | 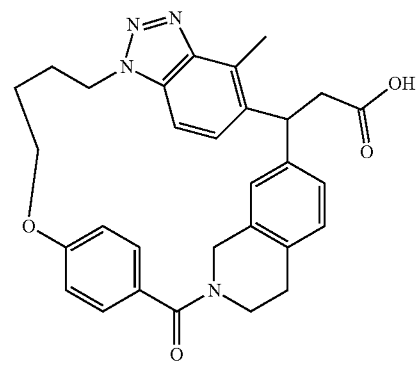 [SMILES: Cc1c2ccc3c1nnn3CCCCOc1ccc(cc1)C(=O)N1CCc3ccc(cc3C1)C2CC(=O)O] | Racemate | 511.3 |
| 31 | [18-fluoro-32-methyl-20-oxo-15-oxa-8,9,10,21-tetrazahexacyclo [19.5.3.2^{16,19}.1^{3,7}.0^{6,10}.0^{24,28}] dotriaconta-1(26),3(32),4,6,8,16,18,24,27,30-decaen-2-yl]acetic acid | 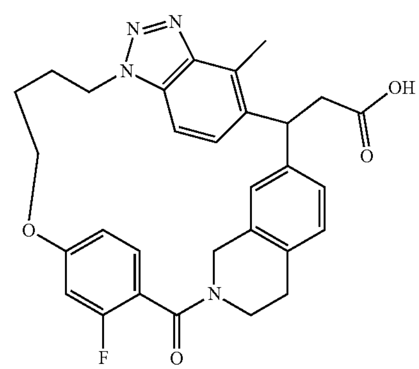 [SMILES: Cc1c2ccc3c1nnn3CCCCOc1ccc(c(F)c1)C(=O)N1CCc3ccc(cc3C1)C2CC(=O)O] | Racemate | 592.4 |
| 32 | [18,30-difluoro-32-methyl-20-oxo-15-oxa-8,9,10,21-tetrazahexacyclo [19.5.3.2^{16,19}.1^{3,7}.0^{6,10}.0^{24,28}] dotriaconta-1(26),3(32),4,6,8,16,18,24,27,30-decaen-2-yl]acetic acid | 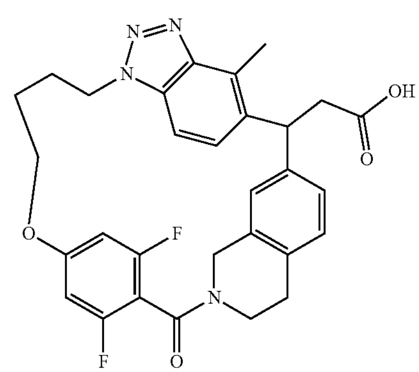 [SMILES: Cc1c2ccc3c1nnn3CCCCOc1cc(F)c(c(F)c1)C(=O)N1CCc3ccc(cc3C1)C2CC(=O)O] | Racemate | 547.4 |

-continued

| EXP | Name | Chemical Structure | Stereo chemistry | MS |
|---|---|---|---|---|
| 33 | [6,6,33-trimethyl-2-oxo-7,10-dioxa-1,15,16,17-tetrazaheptacyclo[22.5.3.2$^{3,9}$.1$^{18,22}$.0$^{4,8}$.0$^{15,19}$.0$^{27,31}$]pentatriaconta-3,8,16,18(33),19,21,24,26,31,34-decaen-23-yl]acetic acid | 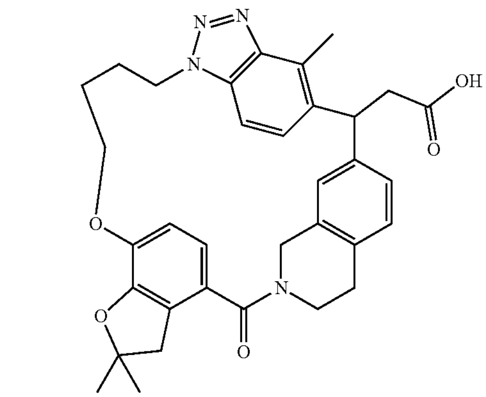 [SMILES: Cc1c2ccc3c1nnn3CCCCOc1ccc(c3c1OC(C)(C)C3)C(=O)N1CCc3ccc(cc3C1)C2CC(=O)O] | Racemate | 581.4 |
| 34 | [5-methyl-2-oxo-2H-1,3-dioxol-4-yl]methyl[32-methyl-20-oxo-14-oxa-8,9,10,21-tetrazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]actate <Synthesis from Chiral, Ethyl [32-methyl-20-oxo-14-oxa-8,9,10,21-tetrazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Chiral, retention time short)> | 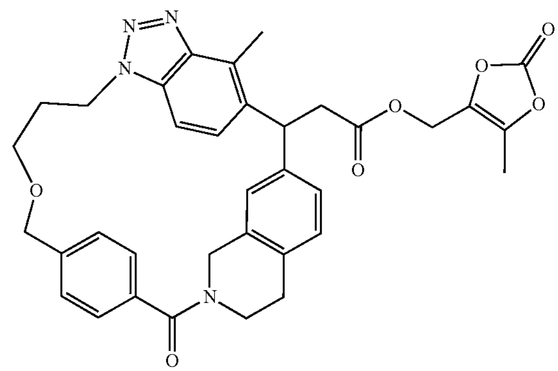 [SMILES: Cc1oc(=O)oc1COC(=O)CC1c2ccc3c(c2)CN(CC3)C(=O)c2ccc(cc2)COCCCn2nnc3c(C)c1ccc32] | Chiral | 623.3 |
| 35 | [5-methyl-2-oxo-2H-1,3-dioxol-4-yl]methyl[32-methyl-20-oxo-14-oxa-8,9,10,21-tetrazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]actate <Synthesis from Chiral, Ethyl [32-methyl-20-oxo-14-oxa-8,9,10,21-tetrazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]acetate (Chiral, retention time long)> | 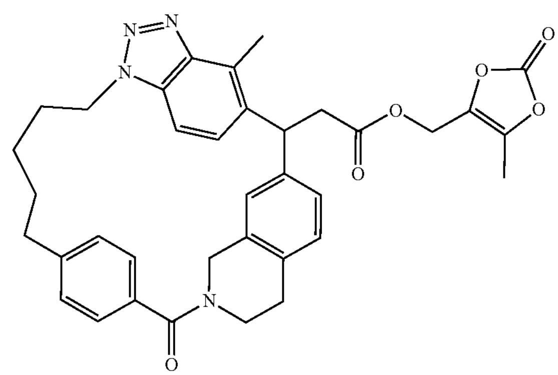 [SMILES: Cc1oc(=O)oc1COC(=O)CC1c2ccc3c(c2)CN(CC3)C(=O)c2ccc(cc2)CCCCCn2nnc3c(C)c1ccc32] | Chiral | 621.4 |
| 36 | ethyl [32-methyl-20-oxo-14-oxa-8,9,10,21-tetrazahexacyclo[19.5.3.2$^{16,19}$.1$^{3,7}$.0$^{6,10}$.0$^{24,28}$]dotriaconta-1(26),3(32),4,6,8,16,18,24,27,30-dacaen-2-yl]acetate (Chiral,retention time short) | 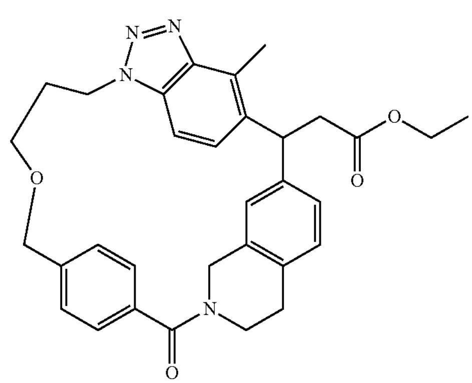 [SMILES: CCOC(=O)CC1c2ccc3c(c2)CN(CC3)C(=O)c2ccc(cc2)COCCCn2nnc3c(C)c1ccc32] | Chiral | 539.3 |

-continued

| EXP | Name | Stereo chemistry | MS |
|-----|------|------------------|-----|
| 37 | ethyl [32-methyl-20-oxo-8,9,10,21-tetrazahexacyclo [19.5.3.2^16,19.1^3,7.0^6,10.0^24,28] dotriaconta-1(26),3(32),4,6,8,16,18,24,27,30-decaen-2-yl]acetate (Chiral, retention time short) | Chiral | 537.4 |
| 38 | 2-[32-methyl-20-oxo-8,9,10,21-tetrazahexacyclo [19.5.3.2^16,19.1^3,7.0^6,10.0^24,28] dotriaconta-1(26),3(32),4,6,8,16,18,24,27,30-decaen-2-yl]-N-[6-methylpyridin-3-yl]acetamide <Synthesis from Chiral, Ethyl [32-methyl-20-oxo-8,9,10,21-tetrazahexacyclo [19.5.3.2^16,19.1^3,7.0^6,10.0^24,28] dotriaconta-1(26),3(32),4,6,8,16,18,24,27,30-decaen-2-yl]acetate (Chiral, retention time short)> | Chiral | 599.4 |
| 39 | 2-[32-methyl-20-oxo-8,9,10,21-tetrazahexacyclo [19.5.3.2^16,19.1^3,7.0^6,10.0^24,28] dotriaconta-1(26),3(32),4,6,8,16,18,24,27,30-decaen-2-yl]-N-[pyridin-3-yl]acetamide <Synthesis from Chiral, Ethyl [32-methyl-20-oxo-8,9,10,21-tetrazahexacyclo [19.5.3.2^16,19.1^3,7.0^6,10.0^24,28] dotriaconta-1(26),3(32),4,6,8,16,18,24,27,30-decaen-2-yl]acetate (Chiral, retention time short)> | Chiral | 585.4 |
| 40 | 1-[[[cyclohexyloxy]carbonyl]oxy]ethyl [32-methyl-20-oxo-14-oxa-8,9,10,21-tetrazahexacyclo [19.5.3.2^16,19.1^3,7.0^6,10.0^24,28] dotriaconta-1(26),3(32),4,6,8,16,18,24,27,30-decaen-2-yl]acetate <Synthesis from Chiral, Ethyl [32-methyl-20-oxo-14-oxa-8,9,10,21-tetrazahexacyclo [19.5.3.2^16,19.1^3,7.0^6,10.0^24,28] dotriaconta-1(26),3(32),4,6,8,16,18,24,27,30-decaen-2-yl]acetate (Chiral, retention time short)> | Chiral | 681.4 |

| EXP | Name | Stereo chemistry | MS |
|---|---|---|---|
| 41 | sodium [32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18,24,27,30-decaen-2-yl]acetate <Synthesis from Chiral, Ethyl [32-methyl-20-oxo-14-oxa8,9,10,21-tetrazahexacyclo [19.5.3.2$^{16,19}$.1$^{3,7}$.0$^{6,10}$.0$^{24,28}$] dotriaconta-1(26),3(32),4,6,8,16,18,24,27,30-decaen-2-yl]acetate (Chiral, retention time short)> | Chiral | 511.3 |
| 42 | 2-[32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18,24,27,30-decaen-2-yl]-N-[6-methylpyridin-3-yl]acetamide | Chiral | 601.4 |
| 43 | 2-[18,30-dichloro-32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18,24,27,30-decaen-2-yl]-2-methylpropanoic acid | Racemate | |
| 44 | 2-methyl-2-[32-methyl-20-oxo-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18,24,27,30-decaen-2-yl]propanoic acid | Racemate | |

| EXP | Name | Chemical Structure | Stereo chemistry | MS |
|---|---|---|---|---|
| 45 | 2-methyl-2-[18,30,32-trimethyl-20-oxo-14-oxa-8,9,10,21-tetrazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]propanoic acid | 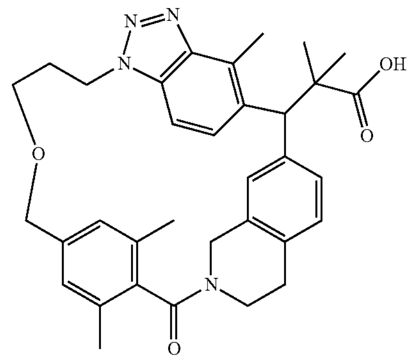 [SMILES: Cc1cc2cc(C)c1C(=O)N1CCc3ccc(cc3C1)C(C(C)(C)C(=O)O)c1ccc3c(nnn3CCCOC2)c1C] | Racemate | |
| 46 | 2-[18,30-dichloro-32-methyl-20-oxo-15-oxa-8,9,10,21-tetrazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]-2-methylpropanoic acid | 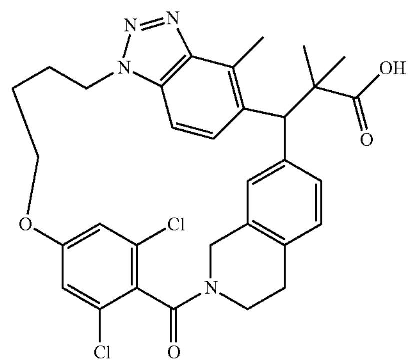 [SMILES: Cc1c2ccc3c1nnn3CCCCOc1cc(Cl)c(c(Cl)c1)C(=O)N1CCc3ccc(cc3C1)C2C(C)(C)C(=O)O] | Racemate | |
| 47 | 2-methyl-2-[18,30,32-trimethyl-20-oxo-14-oxa-8,9,10,21-tetrazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]propanoic acid | 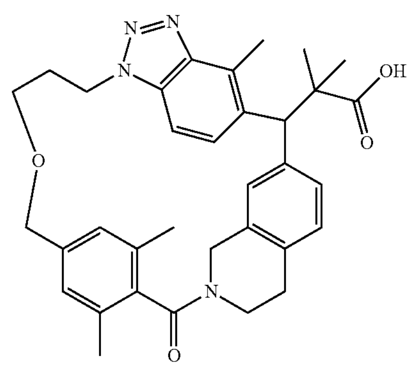 [SMILES: Cc1cc2cc(C)c1C(=O)N1CCc3ccc(cc3C1)C(C(C)(C)C(=O)O)c1ccc3c(nnn3CCCOC2)c1C] | Racemate | |
| 48 | 2-[18,30-dichloro-25,32-dimethyl-20-oxo-14-oxa-8,9,10,21-tetrazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]-2-methylpropanoic acid | 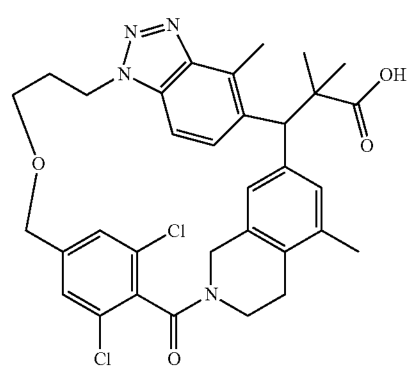 [SMILES: Cc1cc2cc3c1CCN(C3)C(=O)c1c(Cl)cc(cc1Cl)COCCCn1nnc3c(C)c(ccc31)C2C(C)(C)C(=O)O] | Racemate | |

| EXP | Name | Chemical Structure | Stereo chemistry | MS |
|---|---|---|---|---|
| 49 | 2-methyl-2-[18,25,30-trichloro-32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18,24,27,30-decaen-2-yl]propanoic acid | 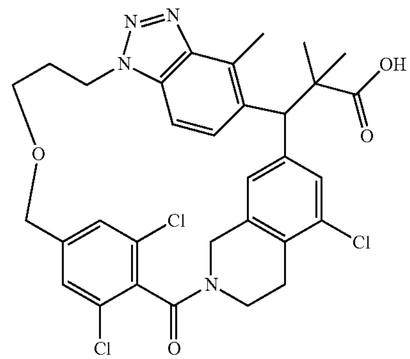 [SMILES: Cc1c2ccc3c1nnn3CCCOCc1cc(Cl)c(c(Cl)c1)C(=O)N1CCc3c(Cl)cc(cc3C1)C2C(C)(C)C(=O)O] | Racemate | |
| 50 | 2-[18,30-dichloro-32-methyl-20-oxo-25-[trifluoromethyl]-14-tetrazahexacyclo [19.5.3.2$^{16,19}$.1$^{3,7}$.0$^{6,10}$.0$^{24,28}$] dotriaconta-1(26),3(32),4,6,8,16,18,24,27,30-decaen-2-yl]-2-methyl propanoic acid | 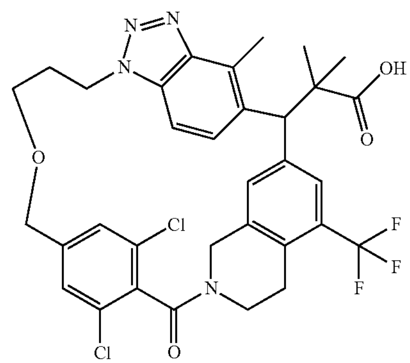 [SMILES: Cc1c2ccc3c1nnn3CCCOCc1cc(Cl)c(c(Cl)c1)C(=O)N1CCc3c(cc(cc3C(F)(F)F)C2C(C)(C)C(=O)O)C1] | Racemate | |
| 51 | 2-[8-[cyclopropylmethyl]-34-methyl-2,7-dioxo-5-oxa-1,8,16,17,18-pentazaheptacyclo [23.5.3.2$^{3,10}$.1$^{19,23}$.0$^{4,9}$.0$^{16,20}$.0$^{28,32}$] hexatriaconta-3,9,17,19(34),20,22,25,27,32,35-decaen-24-yl]-2-methylpropanoic acid | 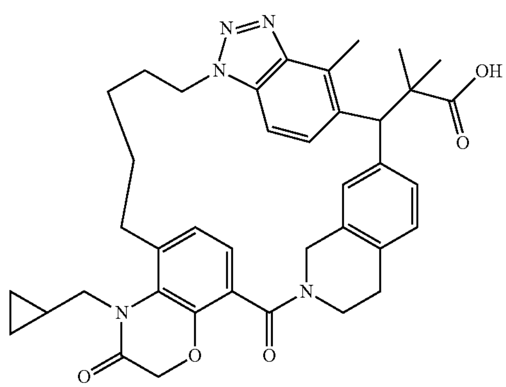 [SMILES: Cc1c2ccc3c1nnn3CCCCCc1ccc(c3c1N(CC1CC1)C(=O)CO3)C(=O)N1CCc3ccc(cc3C1)C2C(C)(C)C(=O)O] | Racemate | |
| 52 | 2-[18,30-dichloro-32-methyl-20-oxo-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18,24,27,30-decaen-2-yl]-2-methylpropanoic acid | 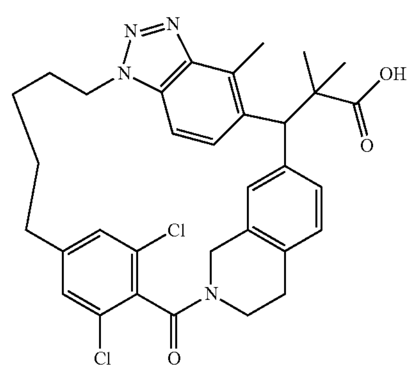 [SMILES: Cc1c2ccc3c1nnn3CCCCCc1cc(Cl)c(c(Cl)c1)C(=O)N1CCc3ccc(cc3C1)C2C(C)(C)C(=O)O] | Racemate | |

-continued

| EXP | Name | Chemical Structure | Stereo chemistry | MS |
|---|---|---|---|---|
| 53 | 2-[18,30-dichloro-5-methoxy-20-oxo-14-tetrazahexacyclo [19.5.3.2$^{16,19}$.1$^{3,7}$.0$^{6,10}$.0$^{24,28}$] dotriaconta-1(26),3(32),4,6,8,16,18, 24,27,30-decaen-2-yl]-2-methylpropanoic acid | 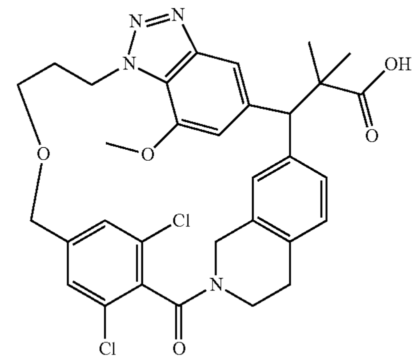 [SMILES: COc1cc2cc3nnn(c13)CCCOCc1cc(Cl)c(c(Cl)c1)C(=O)N1CCc3ccc(cc3C1)C2C(C)(C)C(=O)O] | Racemate | |
| 54 | 2-[18,30-dichloro-5-methoxy-32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18, 24,27,30-decaen-2-yl]-2-methylpropanoic acid | 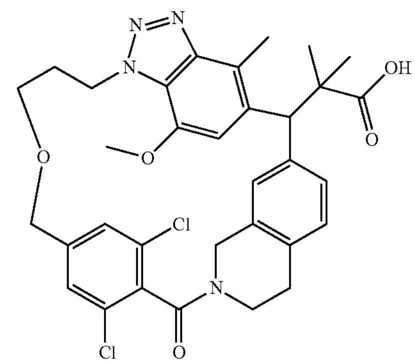 [SMILES: COc1cc2c(C)c3nnn(c13)CCCOCc1cc(Cl)c(c(Cl)c1)C(=O)N1CCc3ccc(cc3C1)C2C(C)(C)C(=O)O] | Racemate | |
| 55 | 2-methyl-2-[32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(27),3(32),4,6,8,16,18, 24(28),25,30-decaen-2-yl]propanoic acid <Chiral, synthesis from chiral methyl 2-methyl-2-[32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(27),3(32),4,6, 8,16,18,24(28),25,30-decaen-2-yl]propanoate (retention time short)> | 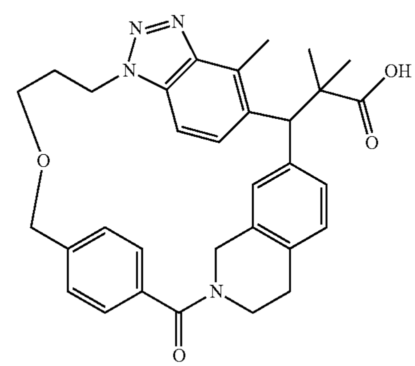 [SMILES: Cc1c2ccc3c1nnn3CCCOCc1ccc(cc1)C(=O)N1CCc3ccc(cc3C1)C2C(C)(C)C(=O)O] | Chiral | 539.4 |
| 56 | 2-methyl-2-[32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(27),3(32),4,6,8,16,18, 24(28),25,30-decaen-2-yl]propanoic acid <Chiral, synthesis from chiral methyl 2-methyl-2-[32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(27),3(32),4,6, 8,16,18,24(28),25, 30-decaen-2-yl] propanoate (retention time long)> | 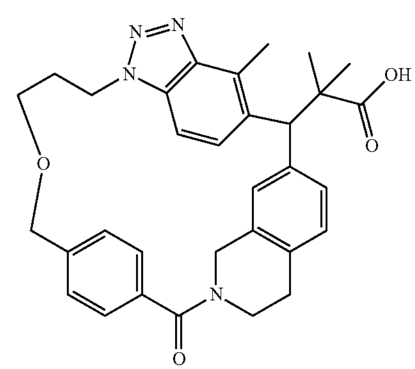 [SMILES: Cc1c2ccc3c1nnn3CCCOCc1ccc(cc1)C(=O)N1CCc3ccc(cc3C1)C2C(C)(C)C(=O)O] | Chiral | 539.4 |

-continued

| EXP | Name | Chemical Structure | Stereo chemistry | MS |
|---|---|---|---|---|
| 57 | 2-[18,30-dichloro-32-methyl-20-oxo-8,9,10,21-tetrazahexacyclo [19.5.3.2$^{16,19}$.1$^{3,7}$.0$^{6,10}$.0$^{24,28}$] dotriaconta-1(26),3(32),4,6,8,16,18, 24,27,30-decaen-2-yl]-2-methylpropanoic acid | 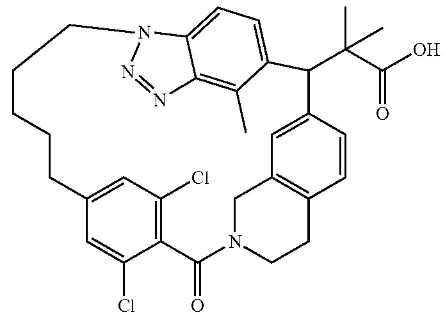 [SMILES: Cc1c2ccc3c1nnn3CCCCCc1cc(Cl)c(c(Cl)c1)C(=O)N1CCc3ccc(cc3C1)C2C(C)(C)C(=O)O] | Racemate | 605.4 |
| 58 | 2-methyl-2-[18,30,32-trimethyl-20-oxo-14-oxa-8,9,10,21-tetrazahexacyclo [19.5.3.2$^{16,19}$.1$^{3,7}$.0$^{6,10}$.0$^{24,28}$] dotriaconta-1(27),3(32),4,6,8,16(31), 17,19(30),24(28),25-decaen-2-yl]propanoic acid <Chiral, synthesis from chiral methyl 2-methyl-2-[18,30,32-trimethyl-20-oxo-14-oxa-8,9, 10,21-tetrazahexacyclo [19.5.3.2$^{16,19}$.1$^{3,7}$.0$^{6,10}$.0$^{24,28}$] dotriaconta-1(27),3(32),4,6,8, 16,18,24(28),25,30-decaen-2-yl]propanoate (retention time short)> | 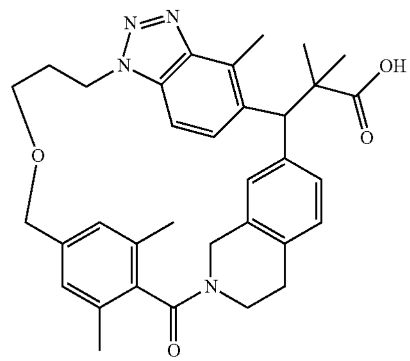 [SMILES: Cc1cc2cc(C)c1C(=O)N1CCc3ccc(cc3C1)C(C(C)(C)C(=O)O)c1ccc3c(nnn3CCCOC2)c1C] | Chiral | 567.5 |
| 59 | 2-methyl-2-[18,30,32-trimethyl-20-oxo-14-oxa-8,9,10,21-tetrazahexacyclo [19.5.3.2$^{16,19}$.1$^{3,7}$.0$^{6,10}$.0$^{24,28}$] dotriaconta-1(27),3(32),4,6,8,16(31), 17,19(30),24(28),25-decaen-2-yl]propanoic acid <Chiral, synthesis from chiral methyl 2-methyl-2-[18,30,32-trimethyl-20-oxo-14-oxa-8,9, 10,21-tetrazahexacyclo [19.5.3.2$^{16,19}$.1$^{3,7}$.0$^{6,10}$.0$^{24,28}$] dotriaconta-1(27),3(32),4,6,8,16, 18,24(28),25,30-decaen-2-yl]propanoate (retention time long)> | 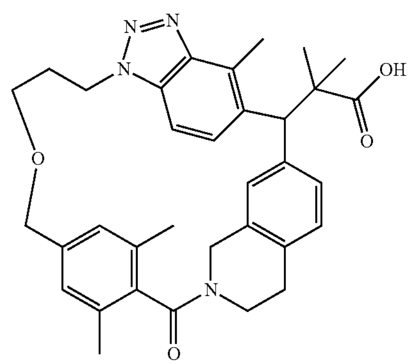 [SMILES: Cc1cc2cc(C)c1C(=O)N1CCc3ccc(cc3C1)C(C(C)(C)C(=O)O)c1ccc3c(nnn3CCCOC2)c1C] | Chiral | 567.5 |
| 60 | 2-[18,30-dichloro-32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(27),3(32),4,6,8,16,18, 24(28),25,30-decaen-2-yl]-2-methylpropanoic acid <Chiral, synthesis from chiral methyl 2-[18,30-dichloro-32-methyl-20-oxo-14-oxa-8,9, 10,21-tetrazahexacyclo [19.5.3.2$^{16,19}$.1$^{3,7}$.0$^{6,10}$.0$^{24,28}$] dotriaconta-1(27),3(32),4,6,8,16, 18,24(28),25,30-decaen-2-yl]-2-methylpropanoate (retention time short)> | 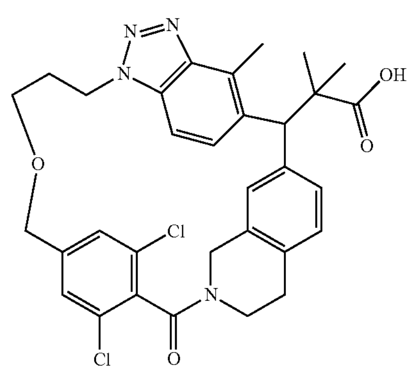 [SMILES: Cc1c2ccc3c1nnn3CCCOCc1cc(Cl)c(c(Cl)c1)C(=O)N1CCc3ccc(cc3C1)C2C(C)(C)C(=O)O] | Chiral | 607.5 |

-continued

| EXP | Name | Chemical Structure | Stereo chemistry | MS |
|---|---|---|---|---|
| 61 | 2-[18,30-dichloro-32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(27),3(32),4,6,8,16, 18,24(28),25,30-decaen-2-yl]-2-methylpropanoic acid <Chiral, synthesis from chiral methyl 2-[18,30-dichloro-32-methyl-20-oxo-14-oxa-8,9,10,21-tetrazahexacyclo [19.5.3.2$^{16,19}$.1$^{3,7}$.0$^{6,10}$.0$^{24,28}$] dotriaconta-1(27),3(32),4,6,8,16,18,24(28),25, 30-decaen-2-yl]-2-methylpropanoate (retention time long)> | 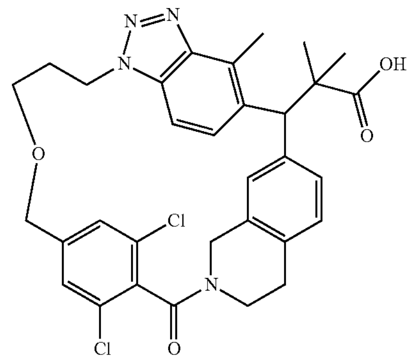 [SMILES: Cc1c2ccc3c1nnn3CCCOCc1cc(Cl)c(c(Cl)c1)C(=O)N1CCc3ccc(cc3C1)C2C(C)(C)C(=O)O] | Chiral | 607.5 |
| 62 | 2-methyl-2-[32-methyl-20-oxo-8,9,10,21-tetrazahexacyclo [19.5.3.2$^{16,19}$.1$^{3,7}$.0$^{6,10}$.0$^{24,28}$] dotriaconta-1(27),3(32),4,6,8,16(31), 17,19(30),24(28),25-decaen-2-yl]propanoic acid <Chiral, synthesis from chiral methyl 2-methyl-2-[32-methyl-20-oxo-8,9,10,21-tetrazahexacyclo [19.5.3.2$^{16,19}$.1$^{3,7}$.0$^{6,10}$.0$^{24,28}$] dotriaconta-1(27),3(32),4,6,8,16(31), 17,19(30),24(28),25-decaen-2-yl]propanoate (retention time short)> | 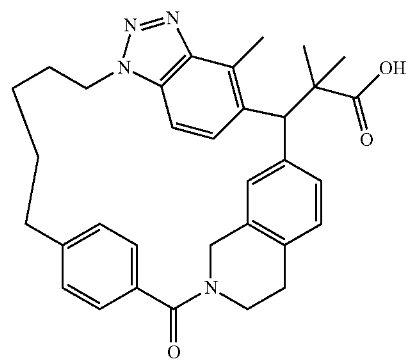 [SMILES: Cc1c2ccc3c1nnn3CCCCCc1ccc(cc1)C(=O)N1CCc3ccc(cc3C1)C2C(C)(C)C(=O)O] | Chiral | 537.3 |
| 63 | 2-methyl-2-[32-methyl-20-oxo-8,9,10,21-tetrazahexacyclo [19.5.3.2$^{16,19}$.1$^{3,7}$.0$^{6,10}$.0$^{24,28}$] dotriaconta-1(27),3(32),4,6,8,16(31), 17,19(30),24(28),25-decaen-2-yl]propanoic acid <Chiral, synthesis from chiral methyl-2-methyl-2-[32-methyl-20-oxo-8,9,10,21-tetrazahexacyclo [19.5.3.2$^{16,19}$.1$^{3,7}$.0$^{6,10}$.0$^{24,28}$] dotriaconta-1(27),3(32),4,6,8,16(31), 17,19(30),24(28),25-decaen-2-yl]propanoate (retention time long)> | 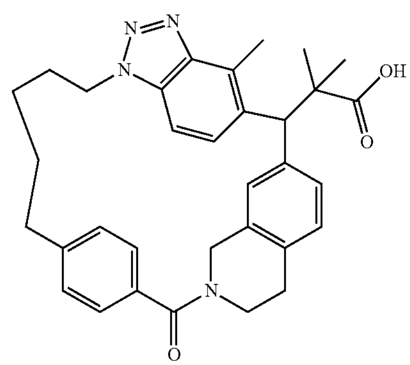 [SMILES: Cc1c2ccc3c1nnn3CCCCCc1ccc(cc1)C(=O)N1CCc3ccc(cc3C1)C2C(C)(C)C(=O)O] | Chiral | 537.4 |
| 64 | [2-[18,30-dichloro-32-methyl-20-oxo-8,9,10,21-tetrazahexacyclo [19.5.3.2$^{16,19}$.1$^{3,7}$.0$^{6,10}$.0$^{24,28}$] dotriaconta-1(27),3(32),4,6,8,16(31), 17,19(30),24(28),25-decaen-2-yl]acetyl]oxysodium | 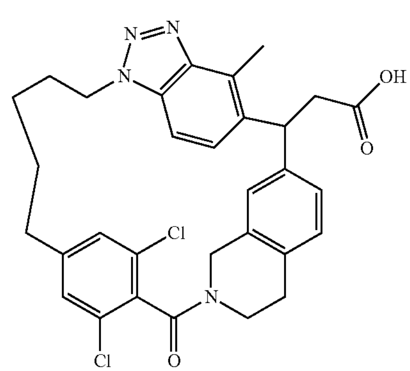 [SMILES: Cc1c2ccc3c1nnn3CCCCCc1cc(Cl)c(c(Cl)c1)C(=O)N1CCc3ccc(cc3C1)C2CC(=O)O] | Racemate | 577.4 |

-continued

| EXP | Name | Chemical Structure | Stereo chemistry | MS |
|---|---|---|---|---|
| 65 | 2-[18,30-dichloro-32-methyl-20-oxo-15-oxa-8,9,10,21-tetrazahexacyclo[19.5.3.2$^{16,19}$.1$^{3,7}$.0$^{6,10}$.0$^{24,28}$]dotriaconta-1(27),3(32),4,6,8,16(31),17,19(30),24(28),25-decaen-2-yl]-2-methylpropanoic acid (Chiral, retention time short | 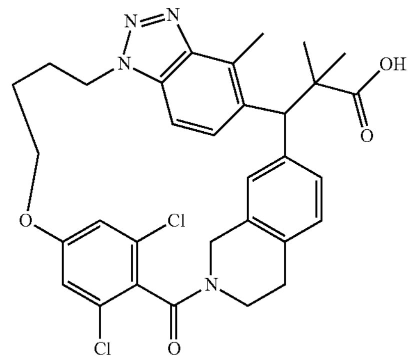 [SMILES: Cc1c2ccc3c1nnn3CCCCOc1cc(Cl)c(c(Cl)c1)C(=O)N1CCc3ccc(cc3C1)C2C(C)(C)C(=O)O] | Chiral | 607.5 |
| 66 | 2-[18,30-dichloro-32-methyl-20-oxo-15-oxa-8,9,10,21-tetrazahexacyclo[19.5.3.2$^{16,19}$.1$^{3,7}$.0$^{6,10}$.0$^{24,28}$]dotriaconta-1(27),3(32),4,6,8,16(31),17,19(30),24(28),25-decaen-2-yl]-2-methylpropanoic acid (Chiral, retention time long) | 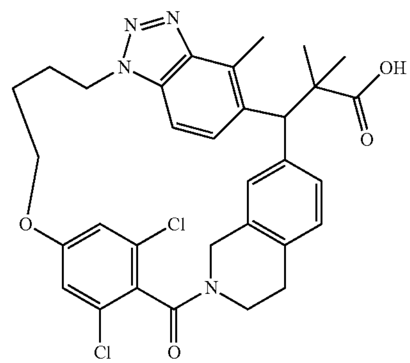 [SMILES: Cc1c2ccc3c1nnn3CCCCOc1cc(Cl)c(c(Cl)c1)C(=O)N1CCc3ccc(cc3C1)C2C(C)(C)C(=O)O] | Chiral | 605.3 |
| 67 | [18,30,32-trimethyl-20-oxo-14-oxa-8,9,10,21-tetrazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]acetic acid (Chiral, retention time short) | 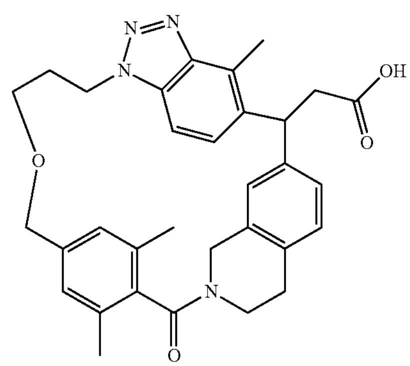 [SMILES: Cc1cc2cc(C)c1C(=O)N1CCc3ccc(cc3C1)C(CC(=O)O)c1ccc3c(nnn3CCCOC2)c1C] | Chiral | 539.4 |
| 68 | [18,30,32-trimethyl-20-oxo-14-oxa-8,9,10,21-tetrazahexacyclo[19.5.3.2$^{16,19}$.1$^{3,7}$.0$^{6,10}$.0$^{24,28}$]dotriaconta-1(27),3(32),4,6,8,16,18,24(28),25,30-decaen-2-yl]acetic acid (Chiral, retention time long) | 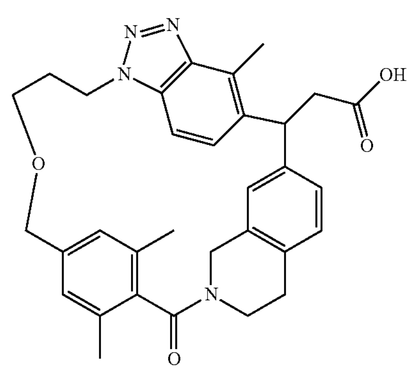 [SMILES: Cc1cc2cc(C)c1C(=O)N1CCc3ccc(cc3C1)C(CC(=O)O)c1ccc3c(nnn3CCCOC2)c1C] | Chiral | 539.4 |

Test Example 1: Measurement of Activity of Inhibiting NRF2 Binding

The inhibitory activity of test compounds against the binding between NRF2 and KEAP1 was measured by Time Resolved Fluorescence Resonance Energy Transfer (TR-FRET) method. Into a 384 well plate, 2 μL of a compound, 2 μL of 2 nM solution of biotinylated human KEAP1 protein (Kelch domain), 2 μL of 14 nM solution of TAMRA-labeled NRF2 peptide (TAMRA-Abu(4)-VWYTDIRMRDWM-OH), and 2 μL of 2 nM solution of Tb-labeled streptavidin, all solutions diluted with assay buffer (25 mM HEPES, pH7.5, 150 mM NaCl, 0.01% Tween-20), were added. For some wells, the KEAP1 protein was not added to define control wells. The plate was incubated at room temperature for 60 minutes, and time-resolved fluorescence was measured with a plate reader Envision (manufactured by PerkinElmer). The inhibitory activity for each compound at a compound concentration of 100 nM were calculated as a relative activity value by setting the fluorescence intensity of control wells to which the KEAP1 protein was not added as 100% inhibition, and the fluorescence intensity of wells to which no compound was added as 0%.

The measurement results according to the method described above (inhibition rate of signal value relative to control at 100 nM of test compound) are shown in Table 3.
[Table 3]

TABLE 3

| EXP | NRF2 binding inhibitory activity (at 100 nM) |
|---|---|
| 1 | 100% |
| 2 | 100% |
| 3 | 100% |
| 4 | 100% |
| 5 | 100% |
| 6 | 100% |
| 7 | 100% |
| 8 | 100% |
| 9 | 100% |
| 10 | 100% |
| 11 | 100% |
| 12 | 100% |
| 13 | 99% |
| 14 | 79% |
| 15 | 100% |
| 16 | 100% |
| 17 | 100% |
| 18 | 100% |
| 19 | 100% |
| 20 | 100% |
| 21 | 100% |
| 22 | 100% |
| 23 | 100% |
| 24 | 100% |
| 25 | 100% |
| 26 | 99% |
| 27 | 6% |
| 28 | 100% |
| 29 | 100% |
| 30 | 100% |
| 31 | 100% |
| 32 | 100% |
| 33 | 100% |
| 34 | 99% |
| 35 | 99% |
| 36 | 15% |
| 37 | 29% |
| 38 | 79% |
| 39 | 97% |
| 40 | 82% |
| 41 | 100% |
| 42 | 60% |
| 55 | 100% |

TABLE 3-continued

| EXP | NRF2 binding inhibitory activity (at 100 nM) |
|---|---|
| 56 | 99% |
| 57 | 100% |
| 58 | 100% |
| 59 | 100% |
| 60 | 100% |
| 61 | 99% |
| 62 | 100% |
| 63 | 46% |
| 64 | 100% |
| 65 | 100% |
| 66 | 94% |
| 67 | 99% |
| 68 | 93% |

Test Example 2: Activity of Compound on Expression of NRF2-Downstream Gene in Rat Kidney and Liver For the NRF2-downstream gene, Nqo1 mRNA was examined in regard to the expression level in kidney. Compounds were prepared into 0.5% methylcellulose (MC, METOLOSE, Shin-Etsu Chemical Co., Ltd.) suspensions, and were orally administered to male SD rats (CLEA Japan, Inc.) in a dose of 5 mL/kg. About 17 hours after the administration, the rats were euthanized under anesthesia, and their kidneys and livers were collected. By using an extraction kit, QIAsymphony RNA kit (QIAGEN, catalog number 931636) or RNeasy 96 Kit (QIAGEN, catalog number 74182), total RNA was extracted. From the total RNA thus obtained, cDNA was produced by using a cDNA synthesis kit, Superscript IV VIVO Master Mix (Thermo Fisher Scientific, catalog number 11754-250). By using the cDNA thus obtained with Taqman Fast Advanced Master Mix (Thermo Fisher Scientific, catalog number 4444557) or Platinum Quantitative PCR SuperMix (Thermo Fisher Scientific, catalog number 11743-500), and primers and a probe, the sequences of SEQ ID NO:1. SEQ ID NO:2, and SEQ ID NO: 3, which are shown in Table 4, real-time quantitative PCR was conducted with 7900HT Fast Real-Time PCR Systems or ViiA7 Fast Real-Time PCR Systems (Applied Biosystems). The expression level of Nqo1 mRNA in each organ of the rat to which the vehicle, 0.5% MC solution, was administered is defined as 1, and the variation is shown in Table 5.

TABLE 4

Probe and Primer Sequences for Rat Nqo1

| Probe | TCTGCGCTTCTGTGGCTTCCAGGTCT |
|---|---|
| Primer_F | GGGGACATGAACGTCATTCTCTG |
| Primer_R | GCCAATGCTGTACACCAGTTG |

TABLE 5

| Example | dose (mg/kg) | tissue | Nqo1 mRNA expression (fold change vs vehicle) |
|---|---|---|---|
| 3 | 3 | Kidney | 4.7 |
| 4 | 3 | Kidney | 6.8 |
| 5 | 3 | Kidney | 3.3 |
| 7 | 3 | Kidney | 4.3 |
| 9 | 3 | Kidney | 5.5 |
| 10 | 3 | Kidney | 5.9 |

TABLE 5-continued

| Example | dose (mg/kg) | tissue | Nqo1 mRNA expression (fold change vs vehicle) |
|---|---|---|---|
| 11 | 3 | Kidney | 8 |
| 21 | 3 | Kidney | 5 |
| 25 | 3 | Kidney | 6.5 |
|  |  | Liver | 22.2 |
| 29 | 3 | Kidney | 5.9 |
| 55 | 3 | Kidney | 6.3 |
| 58 | 3 | Kidney | 4.8 |
| 60 | 3 | Kidney | 2.9 |
| 62 | 3 | Kidney | 6.9 |
| 65 | 3 | Kidney | 3.6 |

Formulation Examples

A medicament containing the inventive compound as an active ingredient can be produced in accordance with, for example, the following formulation.

1. Capsule

| (1) Compound obtained in Example 1 | 10 mg |
|---|---|
| (2) Lactose | 90 mg |
| (3) Microcrystalline cellulose | 70 mg |
| (4) Magnesium stearate | 10 mg |
| 1 capsule | 180 mg |

The whole amount of (1), (2) and (3), and 5 mg of (4) are admixed and then granulated. To this, the remaining 5 mg of (4) is added, and the whole is encapsulated in a gelatin capsule.

2. Tablet

| (1) Compound obtained in Example 1 | 10 mg |
|---|---|
| (2) Lactose | 35 mg |
| (3) Corn starch | 150 mg |
| (4) Microcrystalline cellulose | 30 mg |
| (5) Magnesium stearate | 5 mg |
| 1 tablet | 230 mg |

The whole amount of (1), (2) and (3), and 20 mg of (4) and 2.5 mg of (5) are admixed and then granulated. To this granule, the remaining 10 mg of (4) and 2.5 mg of (5) are added, and the granule is pressure-molded into a tablet.

The present invention can provide a compound that has an excellent NRF2 activating activity, and is expected to be useful as a preventive or therapeutic agent for diseases associated with oxidative stress, in particular, hepatic disease (for example, non-alcoholic steatohepatitis (NASH)), bile duct disease (for example, primary sclerosing cholangitis (PSC)), cardiovascular disease (for example, heart failure or pulmonary arterial hypertension), lung disease (for example, chronic obstructive pulmonary disease (COPD)), kidney disease (for example, chronic kidney disease (CKD) or acute kidney injury (AKI)), central nervous system disease (for example, Parkinson's disease, Alzheimer's disease, cerebral stroke), mitochondrial disease (for example, Friedreich motor ataxia, mitochondrial myopathy), inflammatory disease (for example, multiple sclerosis (MS), inflammatory bowel disease (IBD)), sickle cell disease, cancer, or the like.

The invention claimed is:
1. A compound represented by the following formula (I):

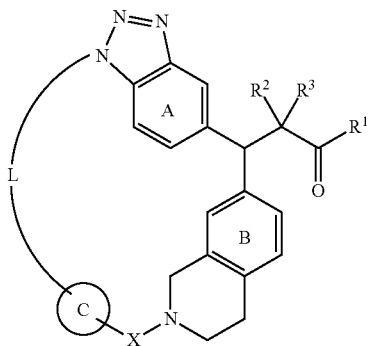

(I)

wherein
R$^1$ is OH, ORy or NHRy;
Ry is an optionally substituted C$_{1-6}$ alkyl group or an optionally substituted cyclic group;
R$^2$ and R$^3$, which may be the same or different, are a hydrogen atom or an optionally substituted C$_{1-6}$ alkyl group, or R$^2$ and R$^3$ are joined together to form a C$_{3-6}$ cycloalkyl group;
X is C(=O), SO$_2$ or CR$^{x1}$R$^{x2}$;
R$^{x1}$ and R$^{x2}$, which may be the same or different, are a hydrogen atom or an optionally substituted C$_{1-6}$ alkyl group;
ring A is a benzene ring which may have an additional substituent(s);
ring B is a benzene ring which may have an additional substituent(s);
ring C is an optionally substituted 5- or 6-membered aromatic ring which may contain a heteroatom(s); and
L is optionally substituted, saturated or unsaturated linear C$_{4-8}$ alkylene optionally inserted by a heteroatom,
or a salt thereof.

2. The compound according to claim 1 or a salt thereof, wherein in formula (I),
L is —(CR$^4$R$^5$)n-Y$^1$—(CR$^6$R$^7$)m-Y$^2$—*
wherein * represents attachment to ring C;
n is an integer of 2 or more and 4 or less;
m is an integer of 1 or more and 4 or less;
R$^4$ and R$^5$ are the same as or different from each other, and are each a hydrogen atom, a halogen atom, OH, an optionally substituted C$_{1-6}$ alkyl group or an optionally substituted C$_{1-6}$ alkoxy group, or R$^4$ and R$^5$ are joined together to form an optionally substituted C$_{3-6}$ cycloalkyl group, and a plurality of R$^4$ or a plurality of R$^5$ may be the same as or different from each other, and the adjacent R$^4$ or R$^5$ may be joined together to form a double bond;
R$^6$ and R$^7$ are the same as or different from each other, and are each a hydrogen atom, a halogen atom, OH, an optionally substituted C$_{1-6}$ alkyl group or an optionally substituted C$_{1-6}$ alkoxy group, or R$^6$ and R$^7$ are joined together to form an optionally substituted C$_{3-6}$ cycloalkyl group, and when m is 2 or more, a plurality of R$^6$ or a plurality of R$^7$ may be the same as or different from each other, and the adjacent R$^6$ or R$^7$ may be joined together to form a double bond;
Y$^1$ and Y$^2$, which may be the same or different, are a bond, an oxygen atom, a sulfur atom, SO, SO$_2$ or NR$^8$,
provided that when Y$^1$ is a bond, m is 1 or 4; and R$^8$ is a hydrogen atom or an optionally substituted C$_{1-6}$ alkyl group, provided that when a plurality of R$^8$ is present, the plurality of R$^8$ may be the same as or different from each other.

3. The compound according to claim 1, or a salt thereof, wherein in formula (I),
L is selected from the group consisting of the following formulas:
—CR$^4$R$^5$—CR$^4$R$^5$—CR$^6$R$^7$—CR$^6$R$^7$—CR$^6$R$^7$—CR$^6$R$^7$—*;
—CR$^4$R$^5$—CR$^4$R$^5$—CR$^4$R$^5$—CR$^4$R$^5$—CR$^6$R$^7$—*;
—CR$^4$R$^5$—CR$^4$R$^5$—CR$^4$R$^5$—CR$^6$R$^7$—O—*;
—CR$^4$R$^5$—CR$^4$R$^5$—CR$^4$R$^5$—O—CR$^6$R$^7$—*; and
—CR$^4$R$^5$—CR$^4$R$^5$—O—CR$^6$R$^7$—CR$^6$R$^7$—*.

4. The compound according to claim 1, or a salt thereof, wherein in formula (I),
R$^1$ is OH or ORy;
Ry is a C$_{1-6}$ alkyl group;
R$^2$ and R$^3$, which may be the same or different, are a hydrogen atom or a C$_{1-3}$ alkyl group;
X is C(=O);
ring A is a benzene ring which may have an additional substituent(s) of a fluorine atom, a chlorine atom, a C$_{1-3}$ alkyl group optionally substituted with 1 to 3 substituents (selected from a halogen atom and a C$_{1-3}$ alkoxy group), or a C$_{1-3}$ alkoxy group optionally substituted with 1 to 3 substituents (selected from a halogen atom and a C$_{1-3}$ alkoxy group);
ring B is a benzene ring which may have an additional substituent(s) of a fluorine atom, a chlorine atom, a cyano group, a C$_{1-3}$ alkyl group optionally substituted with 1 to 3 substituents (selected from a halogen atom and a C$_{1-3}$ alkoxy group), or a C$_{1-3}$ alkoxy group optionally substituted with 1 to 3 substituents (selected from a halogen atom and a C$_{1-3}$ alkoxy group); and
ring C is a group represented by the following formula:

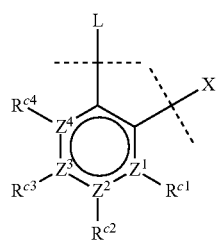

(C-3)

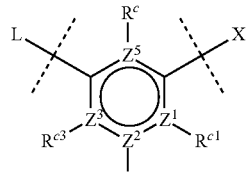

(C-4)

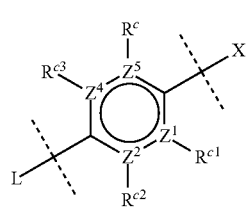

(C-5)

wherein $Z^1$, $Z^2$, $Z^3$, $Z^4$ and $Z^5$ which may be the same or different, are a carbon atom or a nitrogen atom;

$R^c$ is a hydrogen atom, a halogen atom, a nitro group, a cyano group, a hydroxy group, an optionally halogenated $C_{1-6}$ alkyl group, an optionally halogenated $C_{1-6}$ alkoxy group, or a $C_{3-10}$ cycloalkyl group; and $R^{c1}$, $R^{c2}$, $R^{c3}$ and $R^{c4}$, which may be the same or different, are a hydrogen atom, a halogen atom, a nitro group, a cyano group, a hydroxy group, an optionally halogenated $C_{1-6}$ alkyl group, an optionally halogenated $C_{1-6}$ alkoxy group, or a $C_{3-10}$ cycloalkyl group; or adjacent two of $R^{c1}$, $R^{c2}$, $R^{c3}$ and $R^{c4}$ may be joined together to form an optionally substituted ring, provided that when $Z^1$, $Z^2$, $Z^3$, $Z^4$ or $Z^5$ is a nitrogen atom, $R^1$, $R^{c1}$, $R^{c2}$, $R^{c3}$ or $R^{c4}$ is not present.

5. The compound according to claim 1, or a salt thereof, wherein in formula (I), $R^1$ is OH $R^2$ and $R^3$, which may be the same or different, are a hydrogen atom or a $C_{1-3}$ alkyl group;

X is C(=O);

ring A is a benzene ring which may have an additional substituent(s) of a $C_{1-3}$ alkyl group;

ring B is a benzene ring which does not have an additional substituent(s); and ring C is a group represented by the following formula:

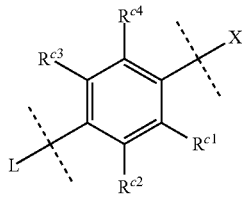

wherein $R^{c1}$ and $R^{c4}$, which may be the same or different, are a hydrogen atom, an optionally halogenated $C_{1-6}$ alkyl group, an optionally halogenated $C_{1-6}$ alkoxy group, a chlorine atom, or a fluorine atom, and $R^{c2}$ and $R^{c3}$ are each a hydrogen atom; and L is —CH$_2$—CH$_2$—CH$_2$—CH$_2$—CH$_2$—*, —CH$_2$—CH$_2$—CH$_2$—CH$_2$—O—*, —CH$_2$—CH$_2$—CH$_2$—O—CH$_2$—*, or —CH$_2$—CH$_2$—O—CH$_2$—CH$_2$—*.

6. The compound according to claim 1, or a salt thereof, wherein in formula (I), $R^1$ is OH $R^2$ and $R^3$, which may be the same or different, are a hydrogen atom or a methyl group;

X is C(=O);

ring A is a substructure represented by the following formula:

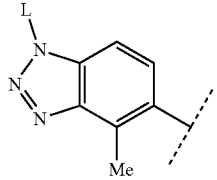

ring B: a benzene ring which does not have an additional substituent;

ring C: a group represented by the following formula:

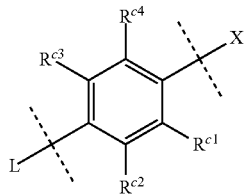

wherein $R^{c1}$ and $R^{c4}$, which may be the same or different, are a hydrogen atom, a chlorine atom, or a methyl group, and $R^{c2}$ and $R^{c3}$ are each a hydrogen atom; and L is —CH$_2$—CH$_2$—CH$_2$—CH$_2$—CH$_2$—*, —CH$_2$—CH$_2$—CH$_2$—CH$_2$—O—*, —CH$_2$—CH$_2$—CH$_2$—O—CH$_2$—*, or —CH$_2$—CH$_2$—O—CH$_2$—CH$_2$—*.

7. A compound of the following formula:

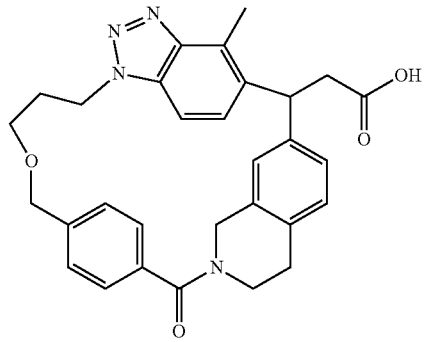 [SMILES: Cc1c2ccc3c1nnn3CCCOCc1ccc(cc1)C(=O)N1CCc3ccc(cc3C1)C2CC(=O)O]

or a salt thereof.

8. A medicament comprising the compound according to claim 1 or a salt thereof.

9. The medicament according to claim 8, wherein the medicament is an NRF2 activator.

10. A pharmaceutical composition comprising the compound according to claim 1 or a pharmaceutically acceptable salt thereof for use in prevention or treatment for hepatic and bile duct disease, cardiovascular disease, lung disease, kidney disease, central nervous system disease, cancer, sickle cell disease, mitochondrial disease, or inflammatory disease.

11. A method of activating NRF2 in a mammal comprising administering the compound according to claim 1 or a salt thereof to the mammal in an effective amount.

12. The compound according to claim 1 or a salt thereof, wherein in formula (I), $R^1$ is OH $R^2$ and $R^3$, which may be the same or different, are a hydrogen atom or a methyl group;

X is C(=O);

ring A is a substructure represented by the following formula:

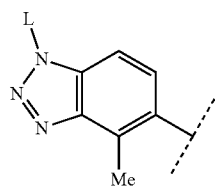

ring B is a benzene ring which does not have an additional substituent; and ring C is a group represented by the following formula:

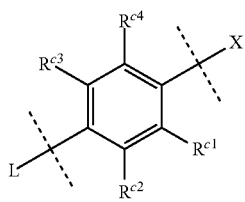

wherein $R^{c1}$ and $R^{c4}$, which may be the same or different, are a hydrogen atom or a methyl group, and $R^{c2}$ and $R^{c3}$ are each a hydrogen atom; and L is —CH$_2$—CH$_2$—CH$_2$—O—CH$_2$*.

13. A compound of the following formula:

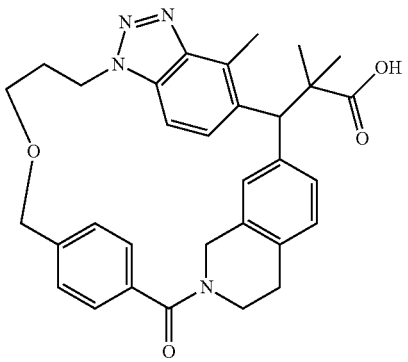 [SMILES: Cc1c2ccc3c1nnn3CCCOCc1ccc(cc1)C(=O)N1CCc3ccc(cc3C1)C2C(C)(C)C(=O)O]

or a salt thereof.

14. A compound of the following formula:

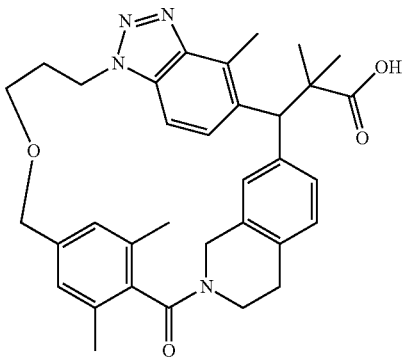 [SMILES: Cc1cc2cc(C)c1C(=O)N1CCc3ccc(cc3C1)C(C(C)(C)C(=O)O)c1ccc3c(nnn3CCCOC2)c1C]

or a salt thereof.

* * * * *

UNITED STATES PATENT AND TRADEMARK OFFICE
CERTIFICATE OF CORRECTION

PATENT NO. : 11,518,763 B2
APPLICATION NO. : 17/299659
DATED : December 6, 2022
INVENTOR(S) : Matsumoto et al.

It is certified that error appears in the above-identified patent and that said Letters Patent is hereby corrected as shown below:

In the Specification

Column 10, Lines 24-26, "[32-methyl-20-oxo-14-oxa-8,9,10,21-tetraazahexacyclo [19.5.3.216,19.13,7.06,10.024,28] dotriaconta-1(26),3(32),4,6,8,16,18,24,27,30-decaen-2-yl]acetic" should read as --[32-methyl-20-oxo-14-oxa-8,9,10,21-tetraazahexacyclo[19.5.3.2$^{16,19}$.1$^{3,7}$.0$^{6,10}$.0$^{24,28}$] dotriaconta-1(26),3(32),4,6,8,16,18,24,27,30-decaen-2-yl]acetic--.

Column 16, Line 3, "C4-8" should read as --C$_{4-8}$--.

Column 17, Table 1, Line 43, "CR6R7NR8--*" should read as --CR6R7-NR8--*--.

Column 16, Line 40, ""the" should read as --"The--.

Column 21, Line 65, "tetrahydroacridiny]," should read as --tetrahydroacridinyl,--.

Column 22, Line 55, "mehtylsulfonylamino," should read as --methylsulfonylamino,--.

Column 24, Line 13, "di-C6-i4 aryl-carbonyl-sulfamoyl" should read as --di-C$_{6-14}$ aryl-carbonyl-sulfamoyl--.

Column 24, Line 16, "pyridylsulfamoyl 1)." should read as --pyridylsulfamoyl).--.

Column 24, Line 52, "mehtylsulfonyloxy," should read as --methylsulfonyloxy,--.

Column 36, Lines 32-33, "0-(7-azabenzotriazol-1-yl)-N,N,N′,N′-tetramethyluronium" should read as --O-(7-azabenzotriazol-1-yl)-N,N,N′,N′-tetramethyluronium--.

Column 52, Line 9, "al-antitrypsin" should read as --α1-antitrypsin--.

Column 52, Line 48, "vims)," should read as --virus),--.

Signed and Sealed this
Fourth Day of April, 2023

Katherine Kelly Vidal
*Director of the United States Patent and Trademark Office*

Column 54, Line 38, "V-tocopherol" should read as --α-tocopherol--.

Column 56, Line 60, "V-tocopherol" should read as --α-tocopherol--.

Column 62, Line 44, "[M+H]⁻." should read as --[M+H]$^{+}$.--.

Column 63, Line 16, "[M+H]⁻." should read as --[M+H]$^{+}$.--.

Column 63, Line 67, "[M+H]⁻." should read as --[M+H]$^{+}$.--.

Column 64, Line 46, "[M+H]⁻." should read as --[M+H]$^{+}$.--.

Column 65, Line 22, "[M+H]⁻." should read as --[M+H]$^{+}$.--.

Column 68, Line 5, "[M+H]⁻." should read as --[M+H]$^{+}$.--.

Column 68, Line 32, "[M+H]⁻." should read as --[M+H]$^{+}$.--.

Column 68, Line 67, "[M+H]⁻." should read as --[M+H]$^{+}$.--.

Column 69, Line 26, "[M+H]⁻." should read as --[M+H]$^{+}$.--.

Column 70, Line 50, "[M+H]⁻." should read as --[M+H]$^{+}$.--.

Column 71, Line 9, "[M+H]⁻." should read as --[M+H]$^{+}$.--.

Column 71, Line 38, "[M+H]⁻." should read as --[M+H]$^{+}$.--.

Column 71, Line 67, "[M+H]⁻." should read as --[M+H]$^{+}$.--.

Column 72, Line 22, "[M+H]⁻." should read as --[M+H]$^{+}$.--.

Column 72, Line 40, "[M+H]⁻." should read as --[M+H]$^{+}$.--.

Column 73, Line 50, "[M+H]⁻." should read as --[M+H]$^{+}$.--.

Column 74, Line 10, "[M+H]⁻." should read as --[M+H]$^{+}$.--.

Column 74, Line 41, "[M+H]⁻." should read as --[M+H]$^{+}$.--.

Column 74, Line 67, "[M+H]⁻." should read as --[M+H]$^{+}$.--.

Column 76, Line 67, "[M+H]⁻." should read as --[M+H]$^{+}$.--.

Column 77, Line 30, "[M+H]⁻." should read as --[M+H]$^{+}$.--.

Column 77, Line 67, "[M+H]⁻." should read as --[M+H]⁺.--.

Column 78, Line 18, "[M+H]⁻." should read as --[M+H]⁺.--.

Column 78, Line 38, "[M+H]⁻." should read as --[M+H]⁺.--.

Column 80, Line 3, "[M+H]⁻." should read as --[M+H]⁺.--.

Column 80, Line 24, "[M+H]⁻." should read as --[M+H]⁺.--.

Column 80, Line 43, "[M+H]⁻." should read as --[M+H]⁺.--.

Column 84, Line 21, "[M+H]⁻." should read as --[M+H]⁺.--.

Column 85, Line 3, "[M+H]⁻." should read as --[M+H]⁺.--.

Column 87, Line 14, "THE" should read as --THF--.

Column 87, Line 20, "THE" should read as --THF--.

Column 89, Line 8, "[M+H]⁻." should read as --[M+H]⁺.--.

Column 91, Lines 57-60, "2-(32-methyl-20-oxo-8,9,10,21-tetraazahexacyclo[19.5.3.2$^{16,19}$.13,7.06,10.024,28]dotriaconta-1(26),3,5,7(32),8,16(31),17,19(30),24,27-decaen-2-yl]acetate" should read as --2-(32-methyl-20-oxo-8,9,10,21-tetraazahexacyclo[19.5.3.2$^{16,19}$.1$^{3,7}$.0$^{6,10}$.0$^{24,28}$]dotriaconta-1(26),3,5,7(32),8,16(31),17,19(30),24,27-decaen-2-yl]acetate--.

Column 100, Line 4, "[M+H]⁻." should read as --[M+H]⁺.--.

Column 100, Line 43, "[M+H]⁻." should read as --[M+H]⁺.--.

Column 102, Line 10, "[M+H]⁻." should read as --[M+H]⁺.--.

Column 102, Line 67, "[M+H]⁻." should read as --[M+H]⁺.--.

Column 104, Line 67, "[M+H]⁻." should read as --[M+H]⁺.--.

Column 107, Line 26, insert paragraph break between "Hz)>" and "G)".

Column 117, Line 10, "[M+H]$^y$." should read as --[M+H]⁺.--.

Column 117, Line 11, "[4-(/er/-" should read as --[4-(tert- --.

CERTIFICATE OF CORRECTION (continued)
U.S. Pat. No. 11,518,763 B2

Column 117, the structure from Lines 15 to 35, 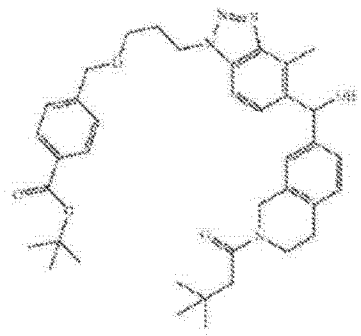 should be,

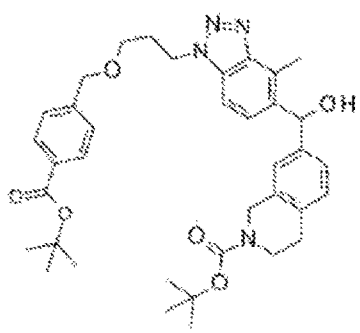

Column 120, Line 50, "[M+Na]⁻." should read as --[M+Na]$^+$.--.

Column 124, Line 3, "[M+H]⁻." should read as --[M+H]$^+$.--.

Column 124, Line 45, "[M+H]⁻." should read as --[M+H]$^+$.--.

Column 125, Line 30, "[M+H]⁻." should read as --[M+H]$^+$.--.

Column 128, Line 46, "[M+H]⁻." should read as --[M+H]$^+$.--.

Column 128, Line 67, "[M+H]⁻." should read as --[M+H]$^+$.--.

Column 137, Lines 4-7, "2-[18,30-Dichloro-25,32-dimethyl-20-oxo-14-oxa-8,9,10,21-tetraazahexacyclo[19.5.3.216, 19.13,7.06,10.024,28]dotriaconta-1(26),3(32),4,6,8,16,18,24,27,30-decaen-2-yl]-2-methylpropanoic acid" should read as --2-[18,30-Dichloro-25,32-dimethyl-20-oxo-14-oxa-8,9,10,21-tetraazahexacyclo[19.5.3.2$^{16,19}$.1$^{3,7}$.0$^{6,10}$.0$^{24,28}$]dotriaconta-1(26),3(32),4,6,8,16,18,24,27,30-decaen-2-yl]-2-methylpropanoic acid--.

Column 143, Line 39, "S1O2," should read as --SiO$_2$--.

Column 145, Line 67, "[M+H]⁻." should read as --[M+H]$^+$.--

Column 151, Line 16, "THE" should read as --THF--.

Column 154, Line 37, "MeO/DCM" should read as --MeOH/DCM--.

Column 154, Line 42, "[M+H]$^-$." should read as --[M+H]$^+$.--.

Column 155, Lines 50-53, "4-[[3-[5-[3-methoxy-2,2-dimethyl-3-oxo-1-[1,2,3,4-tetrahydro isoquinolin-7-yl] propyl]-4-methyl-1H-1,2,3-benzotriazol-1-yl]propoxy]methyl]benzoic" should read as --4-[[3-[5-[3-methoxy-2,2-dimethyl-3-oxo-1-[1,2,3,4-tetrahydroisoquinolin-7-yl] propyl]-4-methyl-1H-1,2,3-benzotriazol-1-yl]propoxy]methyl]benzoic--.

Column 156, Line 12, "[M+H]$^-$." should read as --[M+H]$^+$.--.

Column 157, Line 5, "[M+H]$^-$." should read as --[M+H]$^+$.--.

Column 159, Line 2, "THE" should read as --THF--.

Column 162, Line 1, "[M+H]$^-$." should read as --[M+H]$^+$.--.

Column 163, Line 67, "[M+H]$^-$." should read as --[M+H]$^+$.--.

Column 169, Lines 37-40, "C) tert-butyl 7-[[I-[5-[4-[tert-butoxyca rbonyl]phenyl]pentyl]-4-methyl-1H-benzo[d][1,2,3]triazol-5-yl][hydroxy]methyl]-3,4-dihydroisoquinoline-2(1H)-carboxylate" should read as --C) tert-butyl 7-[[1-[5-[4-[tert-butoxycarbonyl]phenyl]pentyl]-4-methyl-1H-benzo[d][1,2,3] triazol-5-yl][hydroxy]methyl]-3,4-dihydroisoquinoline-2(1H)-carboxylate--.

Column 175, Lines 63-64, "4-[[$^2$-amino-4-bromo-3-methylphenyl]amino]butan-1-ol (20 g)" should read as --4-[[2-amino-4-bromo-3-methylphenyl]amino]butan-1-ol (20 g)--.

Column 176, Line 48, "[M+H]$^-$." should read as --[M+H]$^+$.--.

Column 177, Line 2, "THE" should read as --THF--.

Column 179, Line 47, "[M+H]$^-$." should read as --[M+H]$^+$.--.

Column 180, Lines 1-4, "tert-butyl 7-[1-[1-[4-[4-[[tert-butoxy]carbonyl]-3,5-dichlorophenoxy] butyl]-4-methyl-1H-1,2,3-benzotriazol-5-yl]-3-methoxy-2,2-dimethyl-3-oxopropyl]-1,2,3,4-tetrahydro isoquinoline-2-carboxylate" should read as --tert-butyl 7-[1-[1-[4-[4-[[tert-butoxy]carbonyl]-3,5-dichlorophenoxy] butyl]-4-methyl-1H-1,2,3-benzotriazol-5-yl]-3-methoxy-2,2-dimethyl-3-oxopropyl]-1,2,3,4-tetra--.

Column 180, Line 20, remove paragraph break after 639.4.

Column 180, Lines 51-55, "2,6-dichloro-4-[4-[5-[3-methoxy-2,2-dimethyl-3-oxo-1-[1,2,3,4-tetrahydro isoquinolin-7-yl] propyl]-4-methyl-1H-1,2,3 -benzotriazol-1-yl]butoxy]benzoic" should read as --2,6-dichloro-4-[4-[5-[3-methoxy-2,2-dimethyl-3-oxo-1-[1,2,3,4-tetrahydroisoquinolin-7-yl] propyl]-4-methyl-1H-1,2,3-benzotriazol-1-yl]butoxy]benzoic--.

Column 180, Line 67, "[M+H]$^-$." should read as --[M+H]$^+$.--.

CERTIFICATE OF CORRECTION (continued)
U.S. Pat. No. 11,518,763 B2

Column 185, Lines 47-48, "[$^2$-[[tert-butoxy]carbonyl]-1,2,3,4-tetrahydroisoquinolin-7-yl]boronic" should read as --[2-[[tert-butoxy]carbonyl]-1,2,3,4-tetrahydroisoquinolin-7-yl]boronic--.

Column 186, Line 35, "[M+H]$^-$." should read as --[M+H]$^+$.--.

Column 189, in "EXP 3," Line 3, "[19.5 .3 .216,19.13 ,7.06,10.024,28]" should read as --"[$19.5.3.2^{16,19}.1^{3,7}.0^{6,10}.0^{24,28}$]"--.